United States Patent
Li et al.

(10) Patent No.: US 11,214,802 B2
(45) Date of Patent: *Jan. 4, 2022

(54) RNAI AGENTS FOR INHIBITING EXPRESSION OF ALPHA-ENAC AND METHODS OF USE

(71) Applicant: Arrowhead Pharmaceuticals, Inc., Pasadena, CA (US)

(72) Inventors: Zhen Li, Westfield, NJ (US); Rui Zhu, Middleton, WI (US); Tao Pei, Middleton, WI (US); Anthony Nicholas, Oregon, WI (US); Erik W Bush, Verona, WI (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/778,582

(22) Filed: Jan. 31, 2020

(65) Prior Publication Data
US 2020/0299691 A1 Sep. 24, 2020

Related U.S. Application Data

(63) Continuation of application No. 16/028,006, filed on Jul. 5, 2018, now Pat. No. 10,590,416.

(60) Provisional application No. 62/679,549, filed on Jun. 1, 2018, provisional application No. 62/631,683, filed on Feb. 17, 2018, provisional application No. 62/529,132, filed on Jul. 6, 2017.

(51) Int. Cl.
*C12N 15/113* (2010.01)
*A61P 5/40* (2006.01)

(52) U.S. Cl.
CPC .............. *C12N 15/113* (2013.01); *A61P 5/40* (2018.01); *C12N 15/1138* (2013.01); *C12N 2310/14* (2013.01); *C12N 2310/315* (2013.01); *C12N 2310/333* (2013.01); *C12N 2310/335* (2013.01); *C12N 2310/343* (2013.01); *C12N 2310/346* (2013.01); *C12N 2310/351* (2013.01); *C12N 2320/32* (2013.01)

(58) Field of Classification Search
None
See application file for complete search history.

(56) References Cited

U.S. PATENT DOCUMENTS

| | | |
|---|---|---|
| 4,426,330 A | 1/1984 | Sears et al. |
| 4,522,811 A | 6/1985 | Eppstein et al. |
| 4,534,899 A | 8/1985 | Sears et al. |
| 4,837,028 A | 6/1989 | Allen et al. |
| 5,013,556 A | 5/1991 | Woodle et al. |
| 5,213,804 A | 5/1993 | Martin et al. |
| 5,225,212 A | 7/1993 | Martin et al. |
| 5,264,221 A | 11/1993 | Tagawa et al. |
| 5,328,470 A | 7/1994 | Nabel et al. |
| 5,356,633 A | 10/1994 | Woodle et al. |
| 5,540,935 A | 7/1996 | Miyazaki et al. |
| 5,543,152 A | 8/1996 | Webb et al. |
| 5,556,948 A | 9/1996 | Tagawa et al. |
| 5,665,710 A | 9/1997 | Rahman et al. |
| 5,705,188 A | 1/1998 | Junichi et al. |
| 5,998,203 A | 12/1999 | Matulic-adamic et al. |
| 6,218,108 B1 | 4/2001 | Kool et al. |
| 6,887,906 B1 | 5/2005 | Teng et al. |
| 7,718,632 B2 | 5/2010 | Van Heeke et al. |
| 7,939,508 B2 | 5/2011 | Van Heeke et al. |
| 7,943,592 B2 | 5/2011 | Van Heeke et al. |
| 8,119,612 B2 | 2/2012 | Van Heeke et al. |
| 8,168,606 B2 | 5/2012 | Van Heeke et al. |
| 9,074,212 B2 | 7/2015 | Van Heeke et al. |
| 10,590,416 B2 * | 3/2020 | Li ................ C12N 15/1138 |
| 2004/0259247 A1 | 12/2004 | Tuschl et al. |
| 2005/0255487 A1 | 11/2005 | Khvorova et al. |
| 2005/0256069 A1 | 11/2005 | Manoharan et al. |
| 2007/0031844 A1 | 2/2007 | Khvorova et al. |
| 2007/0135372 A1 | 6/2007 | Machlachlan et al. |

(Continued)

FOREIGN PATENT DOCUMENTS

| | | |
|---|---|---|
| EP | 1394274 A2 | 3/2004 |
| EP | 2171059 A2 | 4/2010 |

(Continued)

OTHER PUBLICATIONS

Amosova, et al. "Effect of the 1-(2'-deoxy-b-D-ribofuranosyl)-3-nitropyrrole residue on the stability of DNA duplexes and triplexes" Nucleic Acids Research, (1997), vol. 25, No. 10, pp. 1930-1934.
Baker, et al. "Abnormalities of Nasal Potential Difference Measurement in Liddle's Syndrome" J. Clin. Invest. 102 (1):10-14 (1998).
Berger, et al. "Universal bases for hybridization, replication ad chain termination" Nucleic Acids Research, (2000), vol. 28, No. 15, pp. 2911-2914.
Boucher, "Relationship of Airway Epithelial Ion Transport to Chronic Bronchitis" Proc. Am. Thorac. Soc. 1:66-70 (2004).
Chaudhuri, et al. "Very High Affinity DNA Recognition by Bicyclic and Cross-Linked Oligonucleotides" J. Am. Chem. Soc. (1995), vol. 117, p. 10434-10442.
Chen, et al. "Gene therapy for brain tumors: Regression of experimental gliomas by adenovirus-mediated gene transfer in vivo" Proc. Natl. Acad. Sci., (1994) vol. 91, pp. 3054-3057.

(Continued)

*Primary Examiner* — Brian Whiteman
(74) *Attorney, Agent, or Firm* — Robert Teigen; Paul VanderVelde; Meibo Chen

(57) ABSTRACT

Described are RNAi agents, compositions that include RNAi agents, and methods for inhibition of an alpha-ENaC (SCNN1A) gene. The alpha-ENaC RNAi agents and RNAi agent conjugates disclosed herein inhibit the expression of an alpha-ENaC gene. Pharmaceutical compositions that include one or more alpha-ENaC RNAi agents, optionally with one or more additional therapeutics, are also described. Delivery of the described alpha-ENaC RNAi agents to epithelial cells, such as pulmonary epithelial cells, in vivo, provides for inhibition of alpha-ENaC gene expression and a reduction in ENaC activity, which can provide a therapeutic benefit to subjects, including human subjects.

42 Claims, 31 Drawing Sheets

Specification includes a Sequence Listing.

(56) References Cited

U.S. PATENT DOCUMENTS

| | | |
|---|---|---|
| 2008/0015141 A1 | 1/2008 | Lang et al. |
| 2008/0113351 A1 | 5/2008 | Naito et al. |
| 2011/0288154 A1 | 11/2011 | Strapps et al. |
| 2015/0284726 A1 | 10/2015 | Van Heeke et al. |
| 2018/0148726 A1 | 5/2018 | Van Heeke et al. |

FOREIGN PATENT DOCUMENTS

| | | |
|---|---|---|
| EP | 2223692 B1 | 7/2013 |
| WO | 1988004924 A1 | 7/1988 |
| WO | 1990004384 A1 | 5/1990 |
| WO | 1991005545 A1 | 5/1991 |
| WO | 1994020073 A1 | 9/1994 |
| WO | 1996010391 A1 | 4/1996 |
| WO | 1996040062 A1 | 12/1996 |
| WO | 1997004787 A1 | 2/1997 |
| WO | 1997013499 A1 | 4/1997 |
| WO | 1997030731 A2 | 8/1997 |
| WO | 1998040516 A1 | 9/1998 |
| WO | 1999040201 A1 | 8/1999 |
| WO | 2000053722 A2 | 9/2000 |
| WO | 2002092854 A2 | 11/2002 |
| WO | 2003057847 A2 | 7/2003 |
| WO | 2004011647 A1 | 2/2004 |
| WO | 2004050894 A2 | 6/2004 |
| WO | 2004070057 A2 | 8/2004 |
| WO | 2004089423 A2 | 10/2004 |
| WO | 2004094636 A1 | 11/2004 |
| WO | 2006066158 A2 | 6/2006 |
| WO | 2006071410 A2 | 7/2006 |
| WO | 2006081546 A2 | 8/2006 |
| WO | 2008022309 A2 | 2/2008 |
| WO | 2008043561 A2 | 4/2008 |
| WO | 2008152131 A2 | 12/2008 |
| WO | 2011104169 A1 | 9/2011 |
| WO | 2012083185 A2 | 6/2012 |
| WO | 2013032829 A1 | 3/2013 |
| WO | 2013158141 A1 | 10/2013 |
| WO | 2018085415 A1 | 5/2018 |
| WO | 2019089765 A1 | 5/2019 |
| WO | 2019161213 A1 | 8/2019 |

OTHER PUBLICATIONS

Czauderna, F.; Nucleic Acids Res., 2003, 31(11), 2705-16.
Du Plessis, et al. "The influence of particle size of liposomes on the deposition of drug into skin" International Journal of Pharmaceutics, (1994) vol. 103, p. 277-282.
Elbashir et al., Nature, 411:494-498 (2001).
Elbashir et al., Embo J., 20(23):6877-6888 (2001).
Gibson, et al. "Pathophysiology and Management of Pulmonary Infections in Cystic Fibrosis" Am. J. Respir. Crit. Care Med. 169:918-951 (2003).
Griesenbach, et al. "Inefficient cationic lipid-mediated siRNA and antisense oligonucleotide transfer to airway epithelial cells in vivo" Respiratory Research (2006), vol. 7, No. 1 doi: 10.1186/1465-9921-7-26.
Guckian, et al. "Experimental Measurement of Aromatic Stacking Affinities in the Context of Duplex DNA" J. Am. Chem. Soc. (1996) vol. 118, pp. 8182-8183.
Guckian, et al. "Structure and Base Pairing Properties of a Replicable Nonpolar Isostere for Deoxyadenosine" J. Org. Chem. (1998) vol. 63, pp. 9652-9656.
Han, et al. "Effect of amiloride on the pathology of a rat model of chronic obstructive pulmonary disease" Zhonghua Jie He He Hu Xi Za Zhi 30(5): 363-367 (May 2007)—English Abstract.
Hironaka, et al. "Pulmonary Fibrosis and Lung Carcinoma: A Comparative Study of Metaplastic Epithelia in Honeycombed Areas of Usual Interstitial Pneumonia With or Without Lung Carcinoma" Pathology International 49:1060-1066 (1999).
Hirsh, "Altering Airway Surface Liquid Volume: Inhalation Therapy with Amiloride and Hyperosmotic Agents" Advanced Drug Delivery Reviews. 54:1445-1462 (2002).
Hirsh, et al. "Design, Synthesis, and Structure—Activity Relationships of Novel 2-Substituted Pyrazinoylguanidine Epithelial Sodium Channel Blockers: Drugs for Cystic Fibrosis and Chronic Bronchitis" J. Med. Chem. 49:4098-4115 (2006).
Ho, et al. "Preparation of Microemulsions Using Polyglycerol Fatty Acid Esters as Surfactant for the Delivery of Protein Drugs" Journal of Pharmaceutical Sciences. (1996) vol. 85 No. 2, pp. 138-143.
Kraynack et al., RNA, 12:163-176 (2006).
Li T, Folkesson H. "RNA interference for alpha-ENaC inhibits rat lung fluid absorption in vivo" American Journal of Physiology. Lung Cellular and Molecular Physiology (2006) 290, pp. L649-L660.
Loakes, et al. "Stability and Structure of DNA Oligonucleotides Containing Non-specific Base Analogues" J. Mol. Biol. (1997) vol. 70, pp. 426-435.
Loakes, et al. "The applications of universal DNA base analogues" Nucleic Acids Research (2001), vol. 29 No. 12, pp. 2437-2447.
Mall, et al. "Increased Airway Epithelial Na+Absorption Produces Cystic Fibrosis-like Lung Disease in Mice" Nature Medicine 10(5): 487-493 (2004).
McMinn, et al. "Efforts toward Expansion of the Genetic Alphabet: DNA Polymerase Recognition of a Highly Stable, Self-Pairing Hydrophobic Base" J. Am. Chem. Soc. (1999) vol. 121, pp. 11585-11586.
MRC Working Party, "Medical Research Council Trial of Treatment of Hypertension in Older Adults: Principal Results" BMJ 304:405-412 (1992).
Morales, et al. "Minor Groove Interactions between Polymerase and DNA: More Essential to Replication than Watson-Crick Hydrogen Bonds?" J. Am. Chem. Soc. (1999) vol. 121, pp. 2323-2324.
Moran, et al. "Difluorotoluene, a Nonpolar Isostere for Thymine, Codes Specifically and Efficiently for Adenine in DNA Replication" J. Am. Chem. Soc. (1997) vol. 199, pp. 2056-2057.
Moran, et al. "A Thymidine triphosphate shape analog lacking Watson-Crick pairing ability is replicated with high sequence selectivity" Proc. Natl. Acad. Sci. (1997), vol. 94, pp. 10506-10511.
Oliver, et al. "Effect of the Universal Base 3-Nitropyrrole on the Selectivity of Neighboring Natural Bases" Organic Letters. (2001), vol. 3 No. 13, pp. 1977-1980.
O'Neill, et al. "A Highly Effective Nonpolar Isostere of Deoxyguanosine: Synthesis, Structure, Stacking, and Base Pairing" J. Org. Chem. (2002), vol. 67, pp. 5869-5875.
O'Riordan et al., 27 J. Aerosol Med. & Pulmonary Drug Dev., 200-208 (2014).
Rezaiguia, et al. "Acute Bacterial Pneumonia in Rats Increases Alveolar Epithelial Fluid Clearance by a Tumor Necrosis Factor-Alpha-dependent Mechanism" J.Clin. Invest. 99(2): 325-335 (1997).
Saetrom et al., BioInformatics, 20(17):3055-3063 (2004).
Scherer, "Approaches for the sequence-specific knockdown of mRNA" Nature Biotechnology, 21(12): 1457-1465 (2003).
Schweitzer, et al. "Aromatic Nonpolar Nucleosides at Hydrophobic Isosteres of Pyrimidine and Purine Nucleosides" J. Org. Chem. (1994), vol. 59, pp. 7238-7242.
Shankar, et al. "The prospect of Silencing Disease Using RNA Interference" JAMA, (2005), vol. 293, No. 11, pp. 1367-1373.
Takakura, et al. "Uptake Characteristics of Oligonucleotides in the Isolated Rat Liver Perfusion System" Antisense & Nucleic Acid Drug Development, (1996), vol. 6, pp. 177-183.
Tarran, et al., "Soluble Mediators, Not Cilia, Determine Airway Surface Liquid Volume in Normal and Cystic Fibrosis Superficial Airway Epithelia" J.Gen. Physiol. 127(5): 591-604 (2006).
Tuschl, et al. "Mechanisms of gene silencing by double-stranded RNA" Nature, (2004), vol. 431, pp. 343-349.
Vallone, et al. "Melting studies of short DNA hairpins containing the universal base 5-nitroindole" Nucleic Acids Research, (1999), vol. 27, No. 17, pp. 3589-3596.
Vickers et al., Journal of Biological Chemistry, 278(9):7108-7118 (2003).
GenBank NM_001038.5; *Homo sapiens* sodium channel epithelial 1 alpha subunit (SCNN1A), transcript variant 1, mRNA; (2018).
International Search Report for corresponding PCT Application No. PCT/US18/40874 dated Sep. 21, 2018.

(56) References Cited

OTHER PUBLICATIONS

European Search Report and European Search Opinion for corresponding Application No. EP18828259.4 dated Feb. 23, 2021 and dated Jun. 7, 2021.
Caci et al.; "Epithelial Sodium Channel Inhibition in Primary Human Bronchial Epithelia by Transfected siRNA"; Am J Respir Cell Mol Biol; 40(2):211-216 (2008) & Supplemental Data (2009).
Clark, Kenneth, et al. "Pharmacological Characterization of a Novel ENaCα siRNA (GSK2225745) With Potential for the Treatment of Cystic Fibrosis"; Molecular Therapy-Nucleic Acids; vol. 2; 2013; p. e65.
Crosby, J. et al. "Inhaled ENaC antisense oligonucleotide ameliorates cystic fibrosis-like lung disease in mice" Journal of Cystic Fibrosis; 16, (2017); 671-680.
Gianotti, et al. "Epithelial Sodium Channel Silencing as a Strategy to Correct the Airway Surface Fluid Deficit in Cystic Fibrosis"; Am J Respir Cell Mol Biol; vol. 49, Issue 3; (2013), pp. 445-452.
Partial European Search Report and Provisional Search Opinion for corresponding Application No. EP18828259.4 dated Feb. 23, 2021.

\* cited by examiner

RNAI AGENTS FOR INHIBITING EXPRESSION OF ALPHA-ENAC AND METHODS OF USE

CROSS REFERENCE TO RELATED APPLICATIONS

This application is a divisional of U.S. patent application Ser. No. 16/028,006, filed Jul. 5, 2018, which claims priority to U.S. Provisional Patent Application Ser. No. 62/679,549, filed on Jun. 1, 2018, U.S. Provisional Patent Application Ser. No. 62/631,683, filed on Feb. 17, 2018, and U.S. Provisional Patent Application Ser. No. 62/529,132, filed on Jul. 6, 2017, the contents of each of which are incorporated herein by reference in its entirety.

SEQUENCE LISTING

This application contains a Sequence Listing which has been submitted in ASCII format and is hereby incorporated by reference in its entirety. The ASCII copy is named 30656-US2_SequenceListing and is 74 kb in size.

FIELD OF THE INVENTION

The present disclosure relates to RNA interference (RNAi) agents, e.g., double stranded RNAi agents, for inhibition of alpha-ENaC gene expression, compositions that include alpha-ENaC RNAi agents, and methods of use thereof.

BACKGROUND

The vertebrate amiloride-sensitive epithelial sodium channel ("ENaC" or "amiloride-sensitive sodium channel") is a member of the degenerin/ENaC channel superfamily, characterized by two membrane-spanning domains, intracellular N- and C-termini, and a large extracellular loop which is a substrate for furin proteases. The channel is a heterotrimeric complex composed of three homologous subunits (alpha ($\alpha$), beta ($\beta$), and gamma ($\gamma$)) encoded by three separate genes: SCNN1A (alpha), SCNN1B (beta), and SCNN1G (gamma). All three subunits are required for full channel activity. A fourth subunit (delta ($\delta$)) encoded by SCNN1D is expressed in testes and ovaries and may be able to functionally substitute for the alpha (a) subunit in those tissues.

ENaC is expressed on the apical membrane of epithelial cells, particularly in the lung, renal distal convoluted tubule, gastrointestinal (GI) tract, reproductive tract, and ocular surface epithelium in the eye. In these epithelia, ENaC channels mediate influx of extracellular sodium ions which are then actively transported from the cell by the basolateral sodium/potassium ATPase, establishing an osmotic gradient and causing epithelial luminal water to be absorbed into the interstitium. In the kidney, ENaC mediates electrolyte balance and blood pressure, and is the target of systemic small molecule diuretics such as amiloride. In the lung, airway epithelial ENaC plays a key role in the regulation of lung hydration and mucociliary clearance.

Type 1 pseudohypoaldosteronism (PHA) patients that carry loss-of-function mutations in SCNN1A, SCNN1B, or SCNN1G, produce excess airway surface liquid and have significantly higher mucociliary clearance rates. Conversely, airway epithelial ENaC activity is significantly elevated in cystic fibrosis (CF) patients of all genotypes. Enhanced ENaC activity, together with reduced cystic fibrosis transmembrane conductance regulator (CFTR) chloride channel activity, is the primary pathogenic mechanism that underlies airway dehydration and mucociliary stasis in CF lung disease patients.

Inhaled small molecule ENaC inhibitors have shown initial promise in the treatment of CF, but their clinical development has been limited by short duration of action in the lung and on-target toxicity (hyperkalemia) associated with inhibition of renal ENaC. (See, e.g., O'Riordan et al., 27 J. Aerosol Med. & Pulmonary Drug Dev., 200-208 (2014)).

Certain RNAi agents capable of inhibiting the expression of an alpha-ENaC gene (i.e., SCNN1A) have been previously identified, such as those disclosed in, for example, U.S. Pat. No. 7,718,632. However, the sequences and modifications of the alpha-ENaC RNAi agents disclosed herein differ from those previously disclosed or known in the art. The alpha-ENaC RNAi agents disclosed herein provide for highly potent and efficient inhibition of the expression of an alpha-ENaC gene.

SUMMARY

There exists a need for novel RNA interference (RNAi) agents (termed RNAi agent, RNAi trigger, or trigger), e.g., double stranded RNAi agents, that are able to selectively and efficiently inhibit the expression of the alpha-ENaC gene (i.e., SCNN1A). Further, there exists a need for compositions of novel alpha-ENaC-specific RNAi agents for the treatment of diseases associated with enhanced ENaC activity.

In general, the present disclosure features alpha-ENaC gene-specific RNAi agents, compositions that include alpha-ENaC RNAi agents, and methods for inhibiting expression of an alpha-ENaC gene in vitro and/or in vivo using the alpha-ENaC RNAi agents and compositions that include alpha-ENaC RNAi agents described herein. The alpha-ENaC RNAi agents described herein are able to selectively and efficiently decrease expression of an alpha-ENaC gene, and thereby reduce ENaC levels in a subject, reduce ENaC activity in a subject, or reduce both ENaC levels and ENaC activity in a subject, e.g., a human or animal subject.

The described alpha-ENaC RNAi agents can be used in methods for therapeutic treatment (including preventative or prophylactic treatment) of symptoms and diseases associated with enhanced or elevated ENaC activity levels, including, but not limited to various respiratory diseases such as cystic fibrosis, chronic bronchitis, chronic obstructive pulmonary disease (COPD), asthma, respiratory tract infections, primary ciliary dyskinesia, and lung carcinoma cystic fibrosis. For example, in subjects suffering from cystic fibrosis (CF), increased ENaC activity is known to contribute to drying mucus in the airway and a reduced ability of the lung to clear toxins and infectious agents. Further, it is also known that CF subjects that have inherited poorly functioning ENaC genes have shown milder lung disease, providing additional evidence that inhibition ENaC levels may be beneficial for certain patient populations. The described alpha-ENaC RNAi agents can also be used, for example, for the therapeutic treatment (including prophylactic or preventative treatment) of symptoms and diseases associated with enhanced or elevated ENaC activity levels in the ocular surface epithelium, such as the conjunctival epithelium, including for the treatment of ocular diseases and disorders such as dry eye syndrome. The alpha-ENaC RNAi agents disclosed herein can selectively reduce alpha-ENaC expression, which can lead to a reduction in ENaC activity. The methods disclosed herein include the administration of one or more alpha-ENaC RNAi agents to a subject, e.g., a human or animal subject, by any suitable means known in the art, such as aerosol inhalation or dry powder inhalation, intranasal administration, intratracheal administration, or oropharyngeal aspiration administration.

In one aspect, the disclosure features RNAi agents for inhibiting expression of an alpha-ENaC gene, wherein the RNAi agent includes a sense strand and an antisense strand. Also described herein are compositions that include or consist of an RNAi agent capable of inhibiting the expression of an alpha-ENaC gene, wherein the RNAi agent includes or consists of a sense strand and an antisense strand, and the composition further comprises at least one pharmaceutically acceptable excipient.

In another aspect, the disclosure features compositions that include one or more of the disclosed alpha-ENaC RNAi agents that are able to selectively and efficiently decrease expression of the alpha-ENaC gene. The compositions that include one or more alpha-ENaC RNAi agents described herein can be administered to a subject, such as a human or animal subject, for the treatment (including prophylactic treatment or inhibition) of symptoms and diseases associated with enhanced or elevated ENaC activity (also referred to herein as enhanced ENaC channel activity levels or elevated ENaC channel activity levels).

Each alpha-ENaC RNAi agent disclosed herein includes a sense strand and an antisense strand. The sense strand and the antisense strand can be partially, substantially, or fully complementary to each other. The length of the RNAi agent sense and antisense strands described herein each can be 16 to 30 nucleotides. In some embodiments, the sense and antisense strands are independently 17 to 26 nucleotides in length. The sense and antisense strands can be either the same length or different lengths. In some embodiments, the sense and antisense strands are independently 21 to 26 nucleotides in length. In some embodiments, the sense and antisense strands are independently 21 to 24 nucleotides in length. In some embodiments, both the sense strand and the antisense strand are 21 nucleotides in length. In some embodiments, the sense and/or antisense strands are independently 16, 17, 18, 19, 20, 21, 22, 23, 24, 25, 26, 27, 28, 29, or 30 nucleotides in length. The RNAi agents described herein, upon delivery to a cell expressing alpha-ENaC, inhibit the expression of one or more alpha-ENaC genes in vivo or in vitro.

An alpha-ENaC RNAi agent described herein includes at least 16 consecutive nucleotides that have at least 85% identity to a core stretch sequence (also referred to herein as a "core stretch" or "core sequence") of the same number of nucleotides in an alpha-ENaC mRNA. In some embodiments, this sense strand core stretch is 16, 17, 18, 19, 20, 21, 22, or 23 nucleotides in length. In some embodiments, this sense strand core stretch is 17 nucleotides in length. In some embodiments, this sense strand core stretch is 19 nucleotides in length.

An antisense strand of an alpha-ENaC RNAi agent described herein includes at least 16 consecutive nucleotides that have at least 85% complementarity to a core stretch of the same number of nucleotides in an alpha-ENaC mRNA and to the corresponding sense strand. In some embodiments, this antisense strand core stretch is 16, 17, 18, 19, 20, 21, 22, or 23 nucleotides in length.

In some embodiments, the alpha-ENaC RNAi agents disclosed herein target a portion of an alpha-ENaC gene having the sequence of any of the sequences disclosed in Table 1.

Examples of alpha-ENaC RNAi agent sense strands and antisense strands that can be used in an alpha-ENaC RNAi agent are provided in Tables 3 and 4. Examples of alpha-ENaC RNAi agent duplexes are provided in Table 5. Examples of 19-nucleotide core stretch sequences that may consist of or may be included in the sense strands and antisense strands of certain alpha-ENaC RNAi agents disclosed herein, are provided in Table 2.

In another aspect, the disclosure features methods for delivering alpha-ENaC RNAi agents to epithelial cells in a subject, such as a mammal, in vivo. Also described herein are compositions for use in such methods. In some embodiments, disclosed herein are methods for delivering alpha-ENaC RNAi agents to pulmonary epithelial cells in vivo to a subject. In some embodiments, disclosed herein are methods for delivering alpha-ENaC RNAi agents to pulmonary epithelial cells of a human subject in vivo. The one or more alpha-ENaC RNAi agents can be delivered to target cells or tissues using any oligonucleotide delivery technology known in the art. Nucleic acid delivery methods include, but are not limited to, by encapsulation in liposomes, by iontophoresis, or by incorporation into other vehicles, such as hydrogels, cyclodextrins, biodegradable nanocapsules, and bioadhesive microspheres, proteinaceous vectors, or Dynamic Polyconjugates™ (DPCs) (see, for example WO 2000/053722, WO 2008/022309, WO 2011/104169, and WO 2012/083185, each of which is incorporated herein by reference).

In some embodiments, an alpha-ENaC RNAi agent is delivered to cells or tissues by covalently linking the RNAi agent to a targeting group. In some embodiments, the targeting group can include a cell receptor ligand, such as an integrin targeting ligand. Integrins are a family of transmembrane receptors that facilitate cell-extracellular matrix (ECM) adhesion. In particular, integrin alpha-v-beta-6 (αvβ6) is an epithelial-specific integrin that is known to be a receptor for ECM proteins and the TGF-beta latency-associated peptide (LAP), and is expressed in various cells and tissues. Integrin αvβ6 is known to be highly unregulated in injured pulmonary epithelium. In some embodiments, the alpha-ENaC RNAi agents described herein are linked to an integrin targeting ligand that has affinity for integrin αvβ6. As referred to herein, an "αvβ6 integrin targeting ligand" is a compound that has affinity for integrin αvβ6, which can be utilized as a ligand to facilitate the targeting and delivery of an RNAi agent to which it is attached to the desired cells and/or tissues (i.e., to cells expressing integrin αvβ6). In some embodiments, multiple αvβ6 integrin targeting ligands or clusters of αvβ6 integrin targeting ligands are linked to an alpha-ENaC RNAi agent. In some embodiments, the alpha-ENaC RNAi agent—αvβ6 integrin targeting ligand conjugates are selectively internalized by lung epithelial cells, either through receptor-mediated endocytosis or by other means.

Examples of targeting groups useful for delivering alpha-ENaC RNAi agents that include $\alpha v\beta 6$ integrin targeting ligands are disclosed, for example, in International Patent Application Publication No. WO 2018/085415 and in U.S. Provisional Patent Application Nos. 62/580,398 and 62/646,739, the contents of each of which are incorporated by reference herein in its entirety.

A targeting group can be linked to the 3' or 5' end of a sense strand or an antisense strand of an alpha-ENaC RNAi agent. In some embodiments, a targeting group is linked to the 3' or 5' end of the sense strand. In some embodiments, a targeting group is linked to the 5' end of the sense strand. In some embodiments, a targeting group is linked internally to a nucleotide on the sense strand and/or the antisense strand of the RNAi agent. In some embodiments, a targeting group is linked to the RNAi agent via a linker.

A targeting group, with or without a linker, can be attached to the 5' or 3' end of any of the sense and/or antisense strands disclosed in Tables 2, 3, and 4. A linker, with or without a targeting group, can be attached to the 5' or 3' end of any of the sense and/or antisense strands disclosed in Tables 2, 3, and 4.

In another aspect, the disclosure features compositions that include one or more alpha-ENaC RNAi agents that have the duplex structures disclosed in Table 5.

In some embodiments, described herein are compositions that include a combination or cocktail of at least two alpha-ENaC RNAi agents having different sequences. In some embodiments, the two or more alpha-ENaC RNAi agents are each separately and independently linked to targeting groups. In some embodiments, the two or more alpha-ENaC RNAi agents are each linked to targeting groups that include or consist of integrin targeting ligands. In some embodiments, the two or more alpha-ENaC RNAi agents are each linked to targeting groups that include or consist of αvβ6 integrin targeting ligands.

In another aspect, the disclosure features methods for inhibiting alpha-ENaC gene expression in a subject, the methods including administering to the subject an amount of an alpha-ENaC RNAi agent capable of inhibiting the expression of an alpha-ENaC gene, wherein the alpha-ENaC RNAi agent comprises a sense strand and an antisense strand. Also described herein are compositions for use in such methods.

In a further aspect, the disclosure features methods of treatment (including prophylactic or preventative treatment) of diseases or symptoms caused by enhanced or elevated ENaC activity, the methods comprising administering to a subject in need thereof an alpha-ENaC RNAi agent that includes an antisense strand comprising the sequence of any of the sequences in Table 2 or Table 3. Also described herein are compositions for use in such methods.

In some embodiments, the described alpha-ENaC RNAi agents are optionally combined with one or more additional (i.e., second, third, etc.) therapeutics. A second therapeutic can be another alpha-ENaC RNAi agent (e.g., an alpha-ENaC RNAi agent that targets a different sequence within the alpha-ENaC gene). An additional therapeutic can also be a small molecule drug, antibody, antibody fragment, and/or aptamer. The alpha-ENaC RNAi agents, with or without the one or more additional therapeutics, can be combined with one or more excipients to form pharmaceutical compositions.

In some embodiments, compositions for delivering an alpha-ENaC RNAi agent to an epithelial cell in vivo are described. In some embodiments, an alpha-ENaC RNAi agent is delivered without being conjugated to a targeting ligand or pharmacokinetic (PK) modulator (referred to as being "naked" or a "naked RNAi agent"). In some embodiments, an alpha-ENaC RNAi agent is conjugated to a targeting group, a linking group, a PK modulator, and/or another non-nucleotide group. In some embodiments, an alpha-ENaC RNAi agent is conjugated to a targeting group wherein the targeting group includes an integrin targeting ligand. In some embodiment, the integrin targeting ligand is an αvβ6 integrin targeting ligand. In some embodiments, a targeting group includes one or more αvβ6 integrin targeting ligands.

In some embodiments, an alpha-ENaC RNAi agent is linked to one or more linking groups or other non-nucleotide groups or compounds, such as pharmacokinetic modulators.

In some embodiments, an alpha-ENaC RNAi agent is conjugated to a polyethylene glycol (PEG) moiety, or to a hydrophobic group having 12 or more carbon atoms, such as a cholesterol or palmitoyl group. In some embodiments, an alpha-ENaC RNAi agent is linked to one or more pharmacokinetic modulators selected from cholesterol or cholesteryl derivatives, alkyl groups, alkenyl groups, alkynyl groups, aryl groups, aralkyl groups, aralkenyl groups, or aralkynyl groups, each of which may be linear, branched, cyclic, and/or substituted or unsubstituted. In some embodiments, the location of attachment for these moieties is at the 5' or 3' end of the sense strand, at the 2' position of the ribose ring of any given nucleotide of the sense strand, and/or attached to the phosphate or phosphorothioate backbone at any position of the sense strand.

In some embodiments, one or more of the described alpha-ENaC RNAi agents are administered to a mammal in a pharmaceutically acceptable carrier or diluent. In some embodiments, the mammal is a human.

The use of alpha-ENaC RNAi agents provides methods for therapeutic (including prophylactic) treatment of diseases or disorders associated with enhanced or elevated ENaC activity. The described alpha-ENaC RNAi agents are capable of inhibiting (e.g., inhibit) the expression of alpha-ENaC. Alpha-ENaC RNAi agents can also be used to treat various respiratory diseases, including cystic fibrosis, chronic bronchitis, non-cystic fibrosis bronchiectasis, chronic obstructive pulmonary disease (COPD), asthma, respiratory tract infections, primary ciliary dyskinesia, and lung carcinoma cystic fibrosis. Alpha-ENaC RNAi agents can further be used to treat, for example, various ocular diseases and disorders, such as dry eye. Such methods of treatment include administration of an alpha-ENaC RNAi agent to a human being or animal having elevated or enhanced ENaC activity levels.

Described herein are compositions for delivery of alpha-ENaC RNAi agents to pulmonary epithelial cells. Furthermore, compositions for delivery of alpha-ENaC RNAi agents to cells, including renal epithelial cells and/or epithelial cells in the GI or reproductive tract and/or and ocular surface epithelial cells in the eye, in vivo, are generally described herein.

The pharmaceutical compositions including one or more alpha-ENaC RNAi agents can be administered in a number of ways depending upon whether local or systemic treatment is desired. Administration can be, but is not limited to, for example, intravenous, intraarterial, subcutaneous, intraperitoneal, subdermal (e.g., via an implanted device), and intraparenchymal administration. In some embodiments, the pharmaceutical compositions described herein are administered by inhalation (such as dry powder or aerosol inhalation), intranasal administration, intratracheal administration, or oropharyngeal aspiration administration.

The described alpha-ENaC RNAi agents and/or compositions that include alpha-ENaC RNAi agents can be used in methods for therapeutic treatment of disease or conditions caused by enhanced or elevated ENaC activity levels. Such methods include administration of an alpha-ENaC RNAi agent as described herein to a subject, e.g., a human or animal subject.

In another aspect, the disclosure provides methods for the treatment (including prophylactic treatment) of a pathological state (such as a condition or disease) mediated at least in part by alpha-ENaC expression, wherein the methods include administering to a subject a therapeutically effective amount of an RNAi agent that includes an antisense strand comprising the sequence of any of the sequences in Table 2 or Table 3.

In some embodiments, methods for inhibiting expression of an alpha-ENaC gene are disclosed herein, wherein the methods include administering to a cell an RNAi agent that includes an antisense strand comprising the sequence of any of the sequences in Table 2 or Table 3.

In some embodiments, methods for the treatment (including prophylactic treatment) of a pathological state mediated at least in part by alpha-ENaC expression are disclosed herein, wherein the methods include administering to a subject a therapeutically effective amount of an RNAi agent that includes a sense strand comprising the sequence of any of the sequences in Table 2 or Table 4.

In some embodiments, methods for inhibiting expression of an alpha-ENaC gene are disclosed herein, wherein the methods comprise administering to a cell an RNAi agent that includes a sense strand comprising the sequence of any of the sequences in Table 2 or Table 4.

In some embodiments, methods for the treatment (including prophylactic treatment) of a pathological state mediated at least in part by alpha-ENaC expression are disclosed herein, wherein the methods include administering to a subject a therapeutically effective amount of an RNAi agent that includes a sense strand comprising the sequence of any of the sequences in Table 4, and an antisense strand comprising the sequence of any of the sequences in Table 3.

In some embodiments, methods for inhibiting expression of an alpha-ENaC gene are disclosed herein, wherein the methods include administering to a cell an RNAi agent that includes a sense strand comprising the sequence of any of the sequences in Table 4, and an antisense strand comprising the sequence of any of the sequences in Table 3.

In some embodiments, methods of inhibiting expression of an alpha-ENaC gene are disclosed herein, wherein the methods include administering to a subject an alpha-ENaC RNAi agent that includes a sense strand consisting of the nucleobase sequence of any of the sequences in Table 4, and the antisense strand consisting of the nucleobase sequence of any of the sequences in Table 3. In other embodiments, disclosed herein are methods of inhibiting expression of an alpha-ENaC gene, wherein the methods include administering to a subject an alpha-ENaC RNAi agent that includes a sense strand consisting of the modified sequence of any of the modified sequences in Table 4, and the antisense strand consisting of the modified sequence of any of the modified sequences in Table 3.

In some embodiments, methods for inhibiting expression of an alpha-ENaC gene in a cell are disclosed herein, wherein the methods include administering one or more alpha-ENaC RNAi agents having a duplex structure of one of the duplexes set forth in Table 5.

The alpha-ENaC RNAi agents disclosed herein are designed to target specific positions on an alpha-ENaC gene (SEQ ID NO:1). As defined herein, an antisense strand sequence is designed to target an alpha-ENaC gene at a given position on the gene when the 5' terminal nucleobase of the antisense strand is aligned with a position that is 19 nucleotides downstream (towards the 3' end) from the position on the gene when base pairing to the gene. For example, as illustrated in Tables 1 and 2 herein, an antisense strand sequence designed to target an alpha-ENaC gene at position 972 requires that when base pairing to the gene, the 5' terminal nucleobase of the antisense strand is aligned with position 990 of the alpha-ENaC gene.

As provided herein, an alpha-ENaC RNAi agent does not require that the nucleobase at position 1 (5'→3') of the antisense strand be complementary to the gene, provided that there is at least 85% complementarity (e.g., at least 85, 86, 87, 88, 89, 90, 91, 92, 93, 94, 95, 96, 97, 98, 99, or 100% complementarity) of the antisense strand and the gene across a core stretch sequence of at least 16 consecutive nucleotides. For example, for an alpha-ENaC RNAi agent disclosed herein that is designed to target position 972 of an alpha-ENaC gene, the 5' terminal nucleobase of the antisense strand of the of the alpha-ENaC RNAi agent must be aligned with position 990 of the gene; however, the 5' terminal nucleobase of the antisense strand may be, but is not required to be, complementary to position 990 of an alpha-ENaC gene, provided that there is at least 85% complementarity (e.g., at least 85, 86, 87, 88, 89, 90, 91, 92, 93, 94, 95, 96, 97, 98, 99, or 100% complementarity) of the antisense strand and the gene across a core stretch sequence of at least 16 consecutive nucleotides. As shown by, among other things, the various examples disclosed herein, the specific site of binding of the gene by the antisense strand of the alpha-ENaC RNAi agent (e.g., whether the alpha-ENaC RNAi agent is designed to target an alpha-ENaC gene at position 972, at position 1291, at position 1000, or at some other position) is a important factor for the level of inhibition achieved by the alpha-ENaC RNAi agent.

In some embodiments, an alpha-ENaC RNAi agent disclosed herein includes an antisense strand that consists of, consists essentially of, or comprises a nucleobase sequence differing by 0 or 1 nucleobases from the nucleotide sequence (5'→3') UAUUUGUUCUGGUUGCACAGG (SEQ ID NO:3). In some embodiments, an alpha-ENaC RNAi agent disclosed herein includes an antisense strand that consists of, consists essentially of, or comprises a nucleotide sequence differing by no more than 1 nucleotide from the nucleotide sequence (5'→3') UAUUUGUUCUGGUUGCACAGG (SEQ ID NO:3), wherein all or substantially all of the nucleotides are modified nucleotides. In some embodiments, an alpha-ENaC RNAi agent disclosed herein includes an antisense strand that consists of, consists essentially of, or comprises a nucleobase sequence differing by 0 or 1 nucleobases from the nucleotide sequence (5'→3') UAUUU-GUUCUGGUUGCACAGG (SEQ ID NO:3), wherein SEQ ID NO:3 is located at positions 1-21 (5'→3') of the antisense strand.

In some embodiments, an alpha-ENaC RNAi agent disclosed herein includes an antisense strand that consists of, consists essentially of, or comprises a modified nucleotide sequence differing by no more than 1 nucleotide from the nucleotide sequence (5'→3') usAfsusUfuGfuUf-cUfgGfuUfgCfaCfaGfsg (SEQ ID NO:2), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 12A through 12G showing all internucleoside linkages).

In some embodiments, an alpha-ENaC RNAi agent disclosed herein includes an antisense strand that consists of, consists essentially of, or comprises the nucleotide sequence (5'→3') usAfsusUfuGfuUfcUfgGfuUfgCfaCfaGfsg (SEQ ID NO:2), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an alpha-ENaC RNAi agent disclosed herein includes a sense strand that consists of, consists essentially of, or comprises a nucleobase sequence differing by 0 or 1 nucleobases from the nucleotide sequence (5'→3') CCUGUGCAACCAGAACAAAUA (SEQ ID NO:5). In some embodiments, an alpha-ENaC RNAi agent disclosed herein includes a sense strand that consists of, consists essentially of, or comprises a nucleotide sequence differing by no more than 1 nucleotide from the nucleotide sequence (5'→3') CCUGUGCAACCAGAACAAAUA (SEQ ID NO:5), wherein all or substantially all of the nucleotides are modified nucleotides. In some embodiments, an alpha-ENaC RNAi agent disclosed herein includes an antisense strand that consists of, consists essentially of, or comprises a nucleobase sequence differing by 0 or 1 nucleobases from the nucleotide sequence (5'→3') CCUGUGCAACCAGAACAAAUA (SEQ ID NO:5), wherein SEQ ID NO:5 is located at positions 1-21 (5'→3') of the antisense strand.

In some embodiments, an alpha-ENaC RNAi agent disclosed herein includes a sense strand that consists of, consists essentially of, or comprises a modified nucleotide sequence differing by no more than 1 nucleotide from the nucleotide sequence (5'→3') cscugugcaAfCfCfagaacaaaua (SEQ ID NO:4), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the antisense strand is at least substantially complementary to the sense strand. In some embodiments, an alpha-ENaC RNAi agent disclosed herein includes a sense strand that consists of, consists essentially of, or comprises the modified nucleotide sequence (5'→3') cscugugcaAfCfCfagaacaaaua (SEQ ID NO:4), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the antisense strand is at least substantially complementary to the sense strand. In some embodiments, one or more inverted abasic residues are added to the 5' end of the sense strand, to the 3' end of the sense strand, or to both the 5' and the 3' end of the sense strand of SEQ ID NO:4. In some embodiments, a targeting ligand, such as an αvβ6 integrin targeting ligand, may be covalently linked to the 5' end of the sense strand, to the 3' end of the sense strand, or to both the 5' and the 3' end of the sense strand of SEQ ID NO:4.

In some embodiments, an alpha-ENaC RNAi agent disclosed herein includes an antisense strand that consists of, consists essentially of, or comprises a nucleobase sequence differing by 0 or 1 nucleobases from the nucleotide sequence (5'→3') UAUUUGUUCUGGUUGCACAGG (SEQ ID NO:3) and a sense strand that consists of, consists essentially of, or comprises a nucleobase sequence differing by 0 or 1 nucleobases from the nucleotide sequence (5'→3') CCUGUGCAACCAGAACAAAUA (SEQ ID NO:5). In some embodiments, an alpha-ENaC RNAi agent disclosed herein includes an antisense strand that consists of, consists essentially of, or comprises a nucleotide sequence differing by no more than 1 nucleotide from the nucleotide sequence (5'→3') UAUUUGUUCUGGUUGCACAGG (SEQ ID NO:3), wherein all or substantially all of the nucleotides are modified nucleotides, and a sense strand that consists of, consists essentially of, or comprises a nucleotide sequence differing by no more than 1 nucleotide from the nucleotide sequence (5'→3') CCUGUGCAACCAGAACAAAUA (SEQ ID NO:5), wherein all or substantially all of the nucleotides are modified nucleotides.

In some embodiments, an alpha-ENaC RNAi agent disclosed herein includes an antisense strand that consists of, consists essentially of, or comprises the modified nucleotide sequence (5'→3') usAfsusUfuGfuUfcUfgGfuUfgCfaCfaGfsg (SEQ ID NO:2), and a sense strand that consists of, consists essentially of, or comprises the modified nucleotide sequence (5'→3') cscugugcaAfCfCfagaacaaaua (SEQ ID NO:4), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage. In some embodiments, an alpha-ENaC RNAi agent disclosed herein includes an antisense strand that consists of, consists essentially of, or comprises the modified nucleotide sequence (5'→3') usAfsusUfuGfuUfcUfgGfuUfgCfaCfaGfsg (SEQ ID NO:2), and a sense strand that consists of, consists essentially of, or comprises the modified nucleotide sequence (5'→3') cscugugcaAfCfCfagaacaaaua (SEQ ID NO:4), and wherein the sense strand further comprises an inverted abasic residue at the 3' terminal end and an αvβ6 integrin targeting ligand covalently linked to the 5' terminal end.

In some embodiments, an alpha-ENaC RNAi agent disclosed herein includes an antisense strand that consists of, consists essentially of, or comprises a nucleobase sequence that differs by 0 or 1 nucleobases from the nucleotide sequence (5'→3') UAUUUGUUCUGGUUGCACAGC (SEQ ID NO:7). In some embodiments, an alpha-ENaC RNAi agent disclosed herein includes an antisense strand that consists of, consists essentially of, or comprises a nucleotide sequence differing by no more than 1 nucleotide from the nucleotide sequence (5'→3') UAUUUGUUCUGGUUGCACAGC (SEQ ID NO:7), wherein all or substantially all of the nucleotides are modified nucleotides. In some embodiments, an alpha-ENaC RNAi agent disclosed herein includes an antisense strand that consists of, consists essentially of, or comprises a nucleobase sequence differing by 0 or 1 nucleobases from the nucleotide sequence (5'→3') UAUUUGUUCUGGUUGCACAGC (SEQ ID NO:7), wherein SEQ ID NO:7 is located at positions 1-21 (5'→3') of the antisense strand.

In some embodiments, an alpha-ENaC RNAi agent disclosed herein includes an antisense strand that consists of, consists essentially of, or comprises a modified nucleotide sequence differing by no more than 1 nucleotide from the modified nucleotide sequence (5'→3') usAfsusUfuGfuUfcUfgGfuUfgCfaCfaCfgfsc (SEQ ID NO:6), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an alpha-ENaC RNAi agent disclosed herein includes a sense strand that consists of, consists essentially of, or comprises a nucleobase sequence differing by 0 or 1 nucleobases from the nucleotide sequence (5'→3') GCUGUGCAACCAGAACAAAUA (SEQ ID NO:9). In some embodiments, an alpha-ENaC RNAi agent disclosed herein includes a sense strand that consists of, consists essentially of, or comprises a nucleotide sequence differing by no more than 1 nucleotide from the nucleotide sequence (5'→3') GCUGUGCAACCAGAACAAAUA (SEQ ID NO:9), wherein all or substantially all of the nucleotides are modified nucleotides. In some embodiments, an alpha-ENaC RNAi agent disclosed herein includes an antisense strand that consists of, consists essentially of, or comprises a nucleobase sequence differing by 0 or 1 nucleobases from the nucleotide sequence (5'→3') GCUGUGCAACCAGAACAAAUA (SEQ ID NO:9), wherein SEQ ID NO:9 is located at positions 1-21 (5'→3') of the antisense strand.

In some embodiments, an alpha-ENaC RNAi agent disclosed herein includes a sense strand that consists of, consists essentially of, or comprises a modified nucleotide sequence that differs by no more than 1 nucleotide from the nucleotide sequence (5'→3') gscugugcaAfCfCfagaacaaaua (SEQ ID NO: 8), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the antisense strand is at least substantially complementary to the sense strand. In some embodiments, one or more inverted abasic residues may be added to the 5' end of the sense strand, to the 3' end of the sense strand, or to both the 5' and the 3' end of the sense strand of SEQ ID NO:8. In some embodiments, a targeting ligand, such as an αvβ6 integrin targeting ligand, may be covalently linked to the 5' end of the sense strand, to the 3' end of the sense strand, or to both the 5' and the 3' end of the sense strand of SEQ ID NO:8.

In some embodiments, an alpha-ENaC RNAi agent disclosed herein includes an antisense strand that consists of, consists essentially of, or comprises a nucleobase sequence differing by 0 or 1 nucleobases from the nucleotide sequence (5'→3') UAUUUGUUCUGGUUGCACAGC (SEQ ID NO:7) and a sense strand that consists of, consists essentially of, or comprises a nucleobase sequence differing by 0 or 1 nucleobases from the nucleotide sequence (5'→3') GCUGUGCAACCAGAACAAAUA (SEQ ID NO:9). In some embodiments, an alpha-ENaC RNAi agent disclosed herein includes an antisense strand that consists of, consists essentially of, or comprises a nucleotide sequence differing by no more than 1 nucleotide from the nucleotide sequence (5'→3') UAUUUGUUCUGGUUGCACAGC (SEQ ID NO:7), wherein all or substantially all of the nucleotides are modified nucleotides, and a sense strand that consists of, consists essentially of, or comprises a nucleotide sequence differing by no more than 1 nucleotide from the nucleotide sequence (5'→3') GCUGUGCAACCAGAACAAAUA (SEQ ID NO:9), wherein all or substantially all of the nucleotides are modified nucleotides.

In some embodiments, an alpha-ENaC RNAi agent disclosed herein includes an antisense strand that consists of, consists essentially of, or comprises a modified nucleotide sequence differing by no more than 1 nucleotide from the nucleotide sequence (5'→3') usAfsusUfuGfuUfcUfgGfuUfgCfaCfaGfsc (SEQ ID NO:6), and a sense strand that consists of, consists essentially of, or comprises a modified nucleotide sequence differing by no more than 1 nucleotide from the nucleotide sequence (5'→3') gscugugcaAfCfCfagaacaaaua (SEQ ID NO:8), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage. In some embodiments, an alpha-ENaC RNAi agent disclosed herein includes an antisense strand that consists of, consists essentially of, or comprises the modified nucleotide sequence (5'→3') usAfsusUfuGfuUfcUfgGfuUfgCfaCfaGfsc (SEQ ID NO:6), and a sense strand that consists of, consists essentially of, or comprises the modified nucleotide sequence (5'→3') gscugugcaAfCfCfagaacaaaua (SEQ ID NO:8), and wherein the sense strand further comprises an inverted abasic residue at the 3' terminal end and an αvβ6 integrin targeting ligand covalently linked to the 5' terminal end.

In some embodiments, an alpha-ENaC RNAi agent disclosed herein includes an antisense strand that consists of, consists essentially of, or comprises a modified nucleotide sequence differing by no more than 1 nucleotide from the nucleotide sequence (5'→3') cPrpusAfsusUfuGfuUfcUfgGfuUfgCfaCfaGfsg (SEQ ID NO:10), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; s represents a phosphorothioate linkage, cPrpu represents a 5'-cyclopropyl phosphonate-2'-O-methyl uridine (see Table 6), and wherein the sense strand is at least substantially complementary to the antisense strand.

In some embodiments, an alpha-ENaC RNAi agent disclosed herein includes an antisense strand that consists of, consists essentially of, or comprises a modified nucleotide sequence differing by no more than 1 nucleotide from the nucleotide sequence (5'→3') cPrpusAfsusUfuGfuUfcUfgGfuUfgCfaCfaGfsg (SEQ ID NO:10), and a sense strand that consists of, consists essentially of, or comprises a modified nucleotide sequence differing by no more than 1 nucleotide from the nucleotide sequence (5'→3') cscugugcaAfCfCfagaacaaaua (SEQ ID NO:4), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; s represents a phosphorothioate linkage, and cPrpu represents a 5'-cyclopropyl phosphonate-2'-O-methyl uridine (see Table 6). In some embodiments, an alpha-ENaC RNAi agent disclosed herein includes an antisense strand that consists of, consists essentially of, or comprises the modified nucleotide sequence (5'→3') cPrpusAfsusUfuGfuUfcUfgGfuUfgCfaCfaGfsg (SEQ ID NO:10), and a sense strand that consists of, consists essentially of, or comprises the modified nucleotide sequence (5'→3') cscugugcaAfCfCfagaacaaaua (SEQ ID NO:4), and wherein the sense strand further comprises an inverted abasic residue at the 3' terminal end and an αvβ6 integrin targeting ligand covalently linked to the 5' terminal end.

In some embodiments, an alpha-ENaC RNAi agent disclosed herein includes an antisense strand that consists of, consists essentially of, or comprises a nucleotide sequence that differs by 0 or 1 nucleotides from one of the following nucleotide sequences (5'→3'):

```
                                  (SEQ ID NO: 3)
            UAUUUGUUCUGGUUGCACAGG;

(SEQ ID NO: 7)
            UAUUUGUUCUGGUUGCACAGC;

(SEQ ID NO: 230)
            UGAUUUGUUCUGGUUGCACAG;
            or (SEQ ID NO: 254)
            AGAAGUCAUUCUGCUCUGCUU;
``` wherein the alpha-ENaC RNAi agent further includes a sense strand that is at least partially complementary to the antisense strand; and wherein the all or substantially all of the nucleotides on both the antisense strand and the sense strand are modified nucleotides.

In some embodiments, an alpha-ENaC RNAi agent disclosed herein includes an antisense strand that consists of, consists essentially of, or comprises a nucleotide sequence that differs by 0 or 1 nucleotides from one of the following nucleotide sequences (5'→3'):

```
                                  (SEQ ID NO: 3)
     UAUUUGUUCUGGUUGCACAGG;

(SEQ ID NO: 7)
     UAUUUGUUCUGGUUGCACAGC;

(SEQ ID NO: 230)
     UGAUUUGUUCUGGUUGCACAG;
     or (SEQ ID NO: 254)
     AGAAGUCAUUCUGCUCUGCUU;
``` wherein the alpha-ENaC RNAi agent further includes a sense strand that is at least partially complementary to the antisense strand; wherein the all or substantially all of the nucleotides on both the antisense strand and the sense strand are modified nucleotides; wherein the sense strand includes an inverted abasic residue at the 3' terminal end; and wherein an αvβ6 integrin targeting ligand is linked to at the 5' terminal end of the sense strand.

In some embodiments, an alpha-ENaC RNAi agent disclosed herein includes an antisense strand that consists of, consists essentially of, or comprises a nucleotide sequence that differs by 0 or 1 nucleotides from one of the following nucleotide sequences (5'→3'):

```
                                  (SEQ ID NO: 3)
     UAUUUGUUCUGGUUGCACAGG;

(SEQ ID NO: 7)
     UAUUUGUUCUGGUUGCACAGC;

(SEQ ID NO: 230)
     UGAUUUGUUCUGGUUGCACAG;
     or (SEQ ID NO: 254)
     AGAAGUCAUUCUGCUCUGCUU;
``` wherein the alpha-ENaC RNAi agent further includes a sense strand that is at least partially complementary to the antisense strand; wherein the all or substantially all of the nucleotides on both the antisense strand and the sense strand are modified nucleotides; wherein the sense strand includes an inverted abasic residue at the 3' terminal end; wherein an αvβ6 integrin targeting ligand is linked to at the 5' terminal end of the sense strand; and wherein the respective antisense strand sequence is located at positions 1-21 of the antisense strand.

In some embodiments, an alpha-ENaC RNAi agent disclosed herein includes an antisense strand and a sense strand, wherein the antisense strand and the sense strand consist of, consist essentially of, or comprise nucleotide sequences that differ by 0 or 1 nucleotides from one of the following nucleotide sequence (5'→3') pairs:

```
                                  (SEQ ID NO: 3)
     UAUUUGUUCUGGUUGCACAGG
     and
                                  (SEQ ID NO: 5)
     CCUGUGCAACCAGAACAAAUA;

(SEQ ID NO: 7)
     UAUUUGUUCUGGUUGCACAGC
     and
                                  (SEQ ID NO: 9)
     GCUGUGCAACCAGAACAAAUA;

(SEQ ID NO: 230)
     UGAUUUGUUCUGGUUGCACAG
     and
                                  (SEQ ID NO: 259)
     CUGUGCAACCAGAACAAAUCA;
     or
                                  (SEQ ID NO: 254)
     AGAAGUCAUUCUGCUCUGCUU
     and
                                  (SEQ ID NO: 289)
     GCAGAGCAGAAUGACUUCUUU;
``` wherein all or substantially all of the nucleotides on both the antisense strand and the sense strand are modified nucleotides.

In some embodiments, an alpha-ENaC RNAi agent disclosed herein includes an antisense strand and a sense strand, wherein the antisense strand and the sense strand consist of, consist essentially of, or comprise nucleotide sequences that differ by 0 or 1 nucleotides from one of the following nucleotide sequences (5'→3') pairs:

```
                                  (SEQ ID NO: 3)
     UAUUUGUUCUGGUUGCACAGG
     and
                                  (SEQ ID NO: 5)
     CCUGUGCAACCAGAACAAAUA;

(SEQ ID NO: 7)
     UAUUUGUUCUGGUUGCACAGC
     and
                                  (SEQ ID NO: 9)
     GCUGUGCAACCAGAACAAAUA;

(SEQ ID NO: 230)
     UGAUUUGUUCUGGUUGCACAG
     and
                                  (SEQ ID NO: 259)
     CUGUGCAACCAGAACAAAUCA;
     or
                                  (SEQ ID NO: 254)
     AGAAGUCAUUCUGCUCUGCUU
     and
                                  (SEQ ID NO: 289)
     GCAGAGCAGAAUGACUUCUUU;
``` wherein all or substantially all of the nucleotides on both the antisense strand and the sense strand are modified nucleotides; wherein the sense strand includes an inverted abasic residue at the 3' terminal end; and wherein an αvβ6 integrin targeting ligand is linked to at the 5' terminal end of the sense strand.

In some embodiments, an alpha-ENaC RNAi agent disclosed herein includes an antisense strand that consists of, consists essentially of, or comprises a modified nucleotide sequence that differs by 0 or 1 nucleotides from one of the following nucleotide sequences (5'→3'):

usAfsusUfuGfuUfcUfgGfuUfgCfaCfaGfsg; (SEQ ID NO: 2)

usAfsusUfuGfuUfcUfgGfuUfgCfaCfaGfsc; (SEQ ID NO: 6)

cPrpusAfsusUfuGfuUfcUfgGfuUfgCfaCfaGfsg; (SEQ ID NO: 10)

usGfsasUfuUfgUfuCfuGfgUfuGfcAfcAfsg; (SEQ ID NO: 107)
or asGfsasAfgUfcAfuUfcUfgCfuCfuGfcusu; (SEQ ID NO: 152)

wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; s represents a phosphorothioate linkage, cPrpu represents a 5'-cyclopropyl phosphonate-2'-O-methyl uridine (see Table 6); wherein the alpha-ENaC RNAi agent further includes the sense strand that is at least partially complementary to the antisense strand; and wherein the all or substantially all of the nucleotides on the sense strand are modified nucleotides.

In some embodiments, an alpha-ENaC RNAi agent disclosed herein includes an antisense strand that consists of, consists essentially of, or comprises a modified nucleotide sequence that differs by 0 or 1 nucleotides from one of the following nucleotide sequences (5'→3'):

usAfsusUfuGfuUfcUfgGfuUfgCfaCfaGfsg; (SEQ ID NO: 2)

usAfsusUfuGfuUfcUfgGfuUfgCfaCfaGfsc; (SEQ ID NO: 6)

cPrpusAfsusUfuGfuUfcUfgGfuUfgCfaCfaGfsg; (SEQ ID NO: 10)

usGfsasUfuUfgUfuCfuGfgUfuGfcAfcAfsg; (SEQ ID NO: 107)
or asGfsasAfgUfcAfuUfcUfgCfuCfuGfcusu; (SEQ ID NO: 152)

wherein the alpha-ENaC RNAi agent further includes the sense strand that is at least partially complementary to the antisense strand; wherein the all or substantially all of the nucleotides on the sense strand are modified nucleotides; wherein the sense strand includes an inverted abasic residue at the 3' terminal end; and wherein an αvβ6 integrin targeting ligand is linked to at the 5' terminal end of the sense strand.

In some embodiments, an alpha-ENaC RNAi agent disclosed herein includes an antisense strand and a sense strand that consists of, consists essentially of, or comprise modified nucleotide sequences that differs by 0 or 1 nucleotides from one of the following nucleotide sequence pairs (5'→3'):

usAfsusUfuGfuUfcUfgGfuUfgCfaCfaGfsg (SEQ ID NO: 2)
and cscugugcaAfCfCfagaacaaaua; (SEQ ID NO: 4)

usAfsusUfuGfuUfcUfgGfuUfgCfaCfaGfsc (SEQ ID NO: 6)
and gscugugcaAfCfCfagaacaaaua; (SEQ ID NO: 8)

cPrpusAfsusUfuGfuUfcUfgGfuUfgCfaCfaGfsg (SEQ ID NO: 10)
and cscugugcaAfCfCfagaacaaaua; (SEQ ID NO: 4)

usGfsasUfuUfgUfuCfuGfgUfuGfcAfcAfsg (SEQ ID NO: 107)
and csugugcaaCfCfAfgaacaaaucas; (SEQ ID NO: 293)
or asGfsasAfgUfcAfuUfcUfgCfuCfuGfcusu (SEQ ID NO: 152)
and gscagagCfAfGfaaugacuucuuu; (SEQ ID NO: 294)

wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; s represents a phosphorothioate linkage, and cPrpu represents a 5'-cyclopropyl phosphonate-2'-O-methyl uridine (see Table 6).

In some embodiments, an alpha-ENaC RNAi agent disclosed herein includes an antisense strand and a sense strand that consists of, consists essentially of, or comprises one of the following nucleotide sequence pairs (5'→3'):

usAfsusUfuGfuUfcUfgGfuUfgCfaCfaGfsg (SEQ ID NO: 2)
and cscugugcaAfCfCfagaacaaaua; (SEQ ID NO: 4)

usAfsusUfuGfuUfcUfgGfuUfgCfaCfaGfsc (SEQ ID NO: 6)
and gscugugcaAfCfCfagaacaaaua; (SEQ ID NO: 8)

cPrpusAfsusUfuGfuUfcUfgGfuUfgCfaCfaGfsg (SEQ ID NO: 10)
and cscugugcaAfCfCfagaacaaaua; (SEQ ID NO: 4)

usGfsasUfuUfgUfuCfuGfgUfuGfcAfcAfsg (SEQ ID NO: 107)
and csugugcaaCfCfAfgaacaaaucas; (SEQ ID NO: 293)
or asGfsasAfgUfcAfuUfcUfgCfuCfuGfcusu (SEQ ID NO: 152)
and gscagagCfAfGfaaugacuucuuu; (SEQ ID NO: 294)

wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; s represents a phosphorothioate linkage, and cPrpu represents a 5'-cyclopropyl phosphonate-2'-O-methyl uridine (see Table 6); wherein the sense strand includes an inverted abasic residue at the 3' terminal end; and wherein an αvβ6 integrin targeting ligand is linked to at the 5' terminal end of the sense strand.

In some embodiments, an alpha-ENaC RNAi agent disclosed herein includes an antisense strand comprises a nucleobase sequence that differs by 0 or 1 nucleobases from the nucleotide sequence (5'→3') UAUUUGUUCUGGUUGCACA (SEQ ID NO:21). In some embodiments, an alpha-ENaC RNAi agent disclosed herein includes an antisense strand that comprises a nucleotide sequence differing by no more than 1 nucleotide from the nucleotide sequence (5'→3') UAUUUGUUCUGGUUGCACA (SEQ ID NO:21), wherein all or substantially all of the nucleotides are modified nucleotides. In some embodiments, an alpha-ENaC RNAi agent disclosed herein includes an antisense strand that comprises a nucleobase sequence differing by 0 or 1 nucleobases from the nucleotide sequence (5'→3') UAUUUGUUCUGGUUGCACA (SEQ ID NO:21), wherein SEQ ID NO:21 is located at positions 1-19 (5'→3') of the antisense strand.

As used herein, the terms "oligonucleotide" and "polynucleotide" mean a polymer of linked nucleosides each of which can be independently modified or unmodified.

As used herein, an "RNAi agent" (also referred to as an "RNAi trigger") means a composition that contains an RNA or RNA-like (e.g., chemically modified RNA) oligonucleotide molecule that is capable of degrading or inhibiting (e.g., degrades or inhibits under appropriate conditions) translation of messenger RNA (mRNA) transcripts of a target mRNA in a sequence specific manner. As used herein, RNAi agents may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action. RNAi agents disclosed herein are comprised of a sense strand and an antisense strand, and include, but are not limited to: short interfering RNAs (siRNAs), double stranded RNAs (dsRNA), micro RNAs (miRNAs), short hairpin RNAs (shRNA), and dicer substrates. The antisense strand of the RNAi agents described herein is at least partially complementary to the mRNA being targeted (i.e. alpha-ENaC mRNA). RNAi agents can include one or more modified nucleotides and/or one or more non-phosphodiester linkages.

As used herein, the terms "silence," "reduce," "inhibit," "down-regulate," or "knockdown" when referring to expression of a given gene, mean that the expression of the gene, as measured by the level of RNA transcribed from the gene or the level of polypeptide, protein, or protein subunit translated from the mRNA in a cell, group of cells, tissue, organ, or subject in which the gene is transcribed, is reduced when the cell, group of cells, tissue, organ, or subject is treated with the RNAi agents described herein as compared to a second cell, group of cells, tissue, organ, or subject that has not or have not been so treated.

As used herein, the terms "sequence" and "nucleotide sequence" mean a succession or order of nucleobases or nucleotides, described with a succession of letters using standard nomenclature.

As used herein, a "base," "nucleotide base," or "nucleobase," is a heterocyclic pyrimidine or purine compound that is a component of a nucleotide, and includes the primary purine bases adenine and guanine, and the primary pyrimidine bases cytosine, thymine, and uracil. A nucleobase may further be modified to include, without limitation, universal bases, hydrophobic bases, promiscuous bases, size-expanded bases, and fluorinated bases. (See, e.g., Modified Nucleosides in Biochemistry, Biotechnology and Medicine, Herdewijn, P. ed. Wiley-VCH, 2008). The synthesis of such modified nucleobases (including phosphoramidite compounds that include modified nucleobases) is known in the art.

As used herein, and unless otherwise indicated, the term "complementary," when used to describe a first nucleobase or nucleotide sequence (e.g., RNAi agent sense strand or targeted mRNA) in relation to a second nucleobase or nucleotide sequence (e.g., RNAi agent antisense strand or a single-stranded antisense oligonucleotide), means the ability of an oligonucleotide or polynucleotide including the first nucleotide sequence to hybridize (form base pair hydrogen bonds under mammalian physiological conditions (or similar conditions in vitro)) and form a duplex or double helical structure under certain standard conditions with an oligonucleotide or polynucleotide including the second nucleotide sequence. Complementary sequences include Watson-Crick base pairs or non-Watson-Crick base pairs and include natural or modified nucleotides or nucleotide mimics, at least to the extent that the above hybridization requirements are fulfilled. Sequence identity or complementarity is independent of modification. For example, a and Af, as defined herein, are complementary to U (or T) and identical to A for the purposes of determining identity or complementarity.

As used herein, "perfectly complementary" or "fully complementary" means that in a hybridized pair of nucleobase or nucleotide sequence molecules, all (100%) of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, "partially complementary" means that in a hybridized pair of nucleobase or nucleotide sequence molecules, at least 70%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, "substantially complementary" means that in a hybridized pair of nucleobase or nucleotide sequence molecules, at least 85%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, the terms "complementary," "fully complementary," "partially complementary," and "substantially complementary" are used with respect to the nucleobase or nucleotide matching between the sense strand and the antisense strand of an RNAi agent, or between the antisense strand of an RNAi agent and a sequence of an alpha-ENaC mRNA.

As used herein, the terms "substantially identical" or "substantial identity," as applied to a nucleic acid sequence means that a nucleotide sequence (or a portion of a nucleotide sequence) has at least about 85% sequence identity or more, e.g., at least 90%, at least 95%, or at least 99% identity, compared to a reference sequence. Percentage of sequence identity is determined by comparing two optimally aligned sequences over a comparison window. The percentage is calculated by determining the number of positions at which the same type of nucleic acid base occurs in both sequences to yield the number of matched positions, dividing the number of matched positions by the total number of positions in the window of comparison and multiplying the result by 100 to yield the percentage of sequence identity. The inventions disclosed herein encompass nucleotide sequences substantially identical to those disclosed herein.

As used herein, the terms "treat," "treatment," and the like, mean the methods or steps taken to provide relief from or alleviation of the number, severity, and/or frequency of one or more symptoms of a disease in a subject. As used herein, "treat" and "treatment" may include preventative treatment, management, prophylactic treatment, and/or inhibition or reduction of the number, severity, and/or frequency of one or more symptoms of a disease in a subject.

As used herein, the phrase "introducing into a cell," when referring to an RNAi agent, means functionally delivering the RNAi agent into a cell. The phrase "functional delivery," means delivering the RNAi agent to the cell in a manner that enables the RNAi agent to have the expected biological activity, e.g., sequence-specific inhibition of gene expression.

Unless stated otherwise, use of the symbol ⌇ as used herein means that any group or groups may be linked thereto that is in accordance with the scope of the inventions described herein.

As used herein, the term "isomers" refers to compounds that have identical molecular formulae, but that differ in the nature or the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images are termed "enantiomers," or sometimes optical isomers. A carbon atom bonded to four non-identical substituents is termed a "chiral center."

As used herein, unless specifically identified in a structure as having a particular conformation, for each structure in which asymmetric centers are present and thus give rise to enantiomers, diastereomers, or other stereoisomeric configurations, each structure disclosed herein is intended to represent all such possible isomers, including their optically pure and racemic forms. For example, the structures disclosed herein are intended to cover mixtures of diastereomers as well as single stereoisomers.

As used in a claim herein, the phrase "consisting of" excludes any element, step, or ingredient not specified in the claim. When used in a claim herein, the phrase "consisting essentially of" limits the scope of a claim to the specified materials or steps and those that do not materially affect the basic and novel characteristic(s) of the claimed invention.

The person of ordinary skill in the art would readily understand and appreciate that the compounds and compositions disclosed herein may have certain atoms (e.g., N, O, or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the environment (such as pH), as would be readily understood by the person of ordinary skill in the art.

As used herein, the term "linked" or "conjugated" when referring to the connection between two compounds or molecules means that two compounds or molecules are joined by a covalent bond. Unless stated, the terms "linked" and "conjugated" as used herein may refer to the connection between a first compound and a second compound either with or without any intervening atoms or groups of atoms.

As used herein, the term "including" is used to herein mean, and is used interchangeably with, the phrase "including but not limited to." The term "or" is used herein to mean, and is used interchangeably with, the term "and/or," unless the context clearly indicates otherwise.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other objects, features, aspects, and advantages of the invention will be apparent from the following detailed description, accompanying figures, and from the claims.

The following abbreviations are used in FIGS. 12A to 12G: a, c, g, and u are 2'-O-methyl modified nucleotides; Af, Cf, Gf, and Uf are 2'-fluoro modified nucleotides; p is a phosphodiester linkage; s is a phosphorothioate linkage; invAb is an inverted abasic residue; cPrp is a 5' terminal cyclopropyl phosphonate group (see Table 6); NH2-C6 is a $C_6$ amino group (see Table 6); and TriAlk14 is a tri-alkyne linker having the structure depicted herein (see Table 6).

Figures 12A, 12B, 12C:
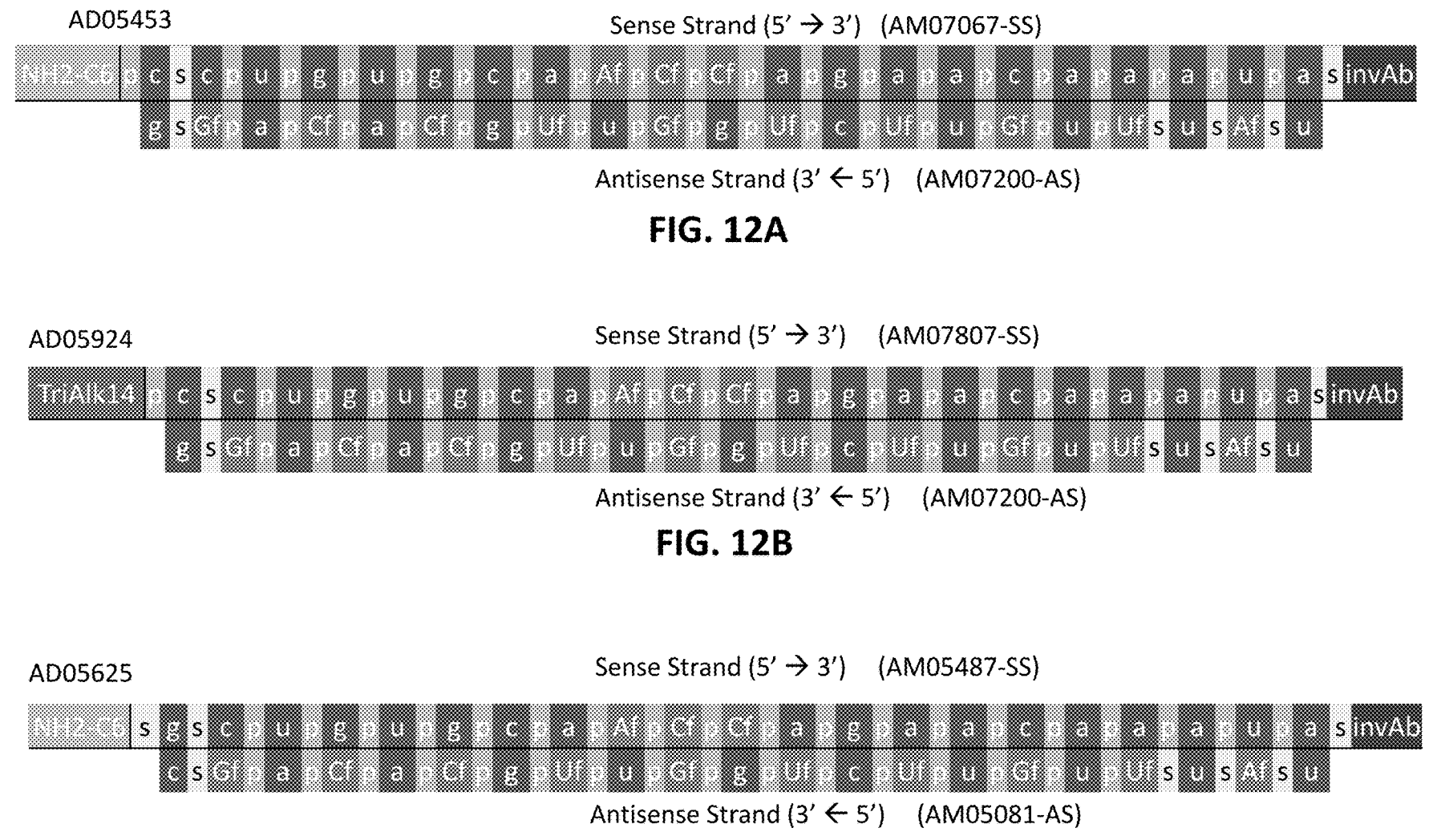

FIG. 12B. Schematic diagram of the modified sense and antisense strands of alpha-ENaC RNAi agent AD05924 (see Tables 3-5), shown functionalized with a tri-alkyne group on the 5' terminal end of the sense strand for facilitating the linkage to targeting ligands. As described herein, AD05453 and AD05924 have the same modified nucleotide sequences, and represent alternative approaches to synthesizing an alpha ENaC-RNAi agent conjugate disclosed herein.

FIG. 12C. Schematic diagram of the modified sense and antisense strands of alpha-ENaC RNAi agent AD05625 (see Tables 3-5), shown functionalized with an amino group on the 5' terminal end of the sense strand for facilitating the linkage to targeting ligands.

Figure 12D:
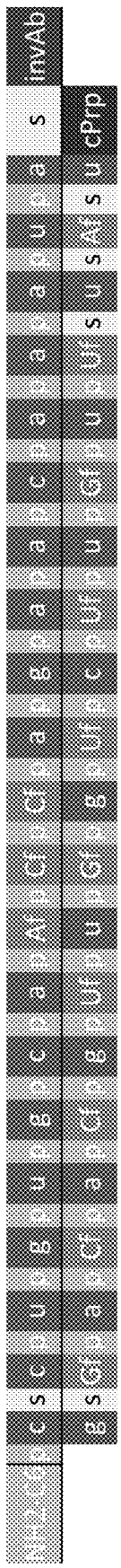
FIG. 12A. Schematic diagram of the modified sense and antisense strands of alpha-ENaC RNAi agent AD05453 (see Tables 3-5), shown with an amino group on the 5' terminal end of the sense strand for facilitating the linkage to targeting ligands.

FIG. 12D. Schematic diagram of the modified sense and antisense strands of alpha-ENaC RNAi agent AD05347 (see Tables 3-5), shown functionalized with an amino group on the 5' terminal end of the sense strand for facilitating the linkage to targeting ligands.

Figure 12E:

FIG. 12E. Schematic diagram of the modified sense and antisense strands of alpha-ENaC RNAi agent AD05831 (see Tables 3-5), shown functionalized with an amino group on the 5' terminal end of the sense strand for facilitating the linkage to targeting ligands.

Figure 12F:
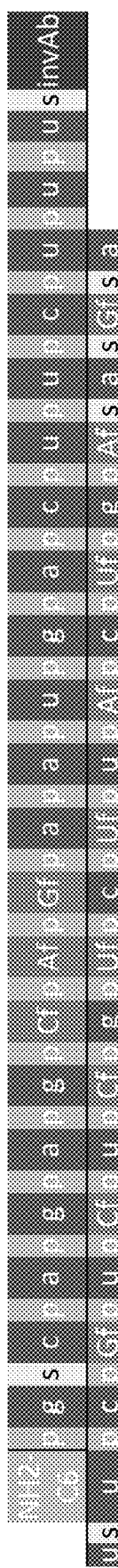

FIG. 12F. Schematic diagram of the modified sense and antisense strands of alpha-ENaC RNAi agent AD05833 (see Tables 3-5), shown functionalized with an amino group on the 5' terminal end of the sense strand for facilitating the linkage to targeting ligands.

Figures 12G, 12H:
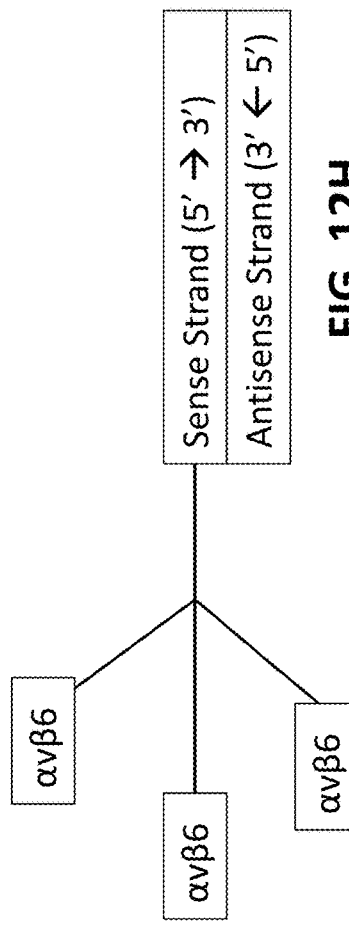
Figure 13A:
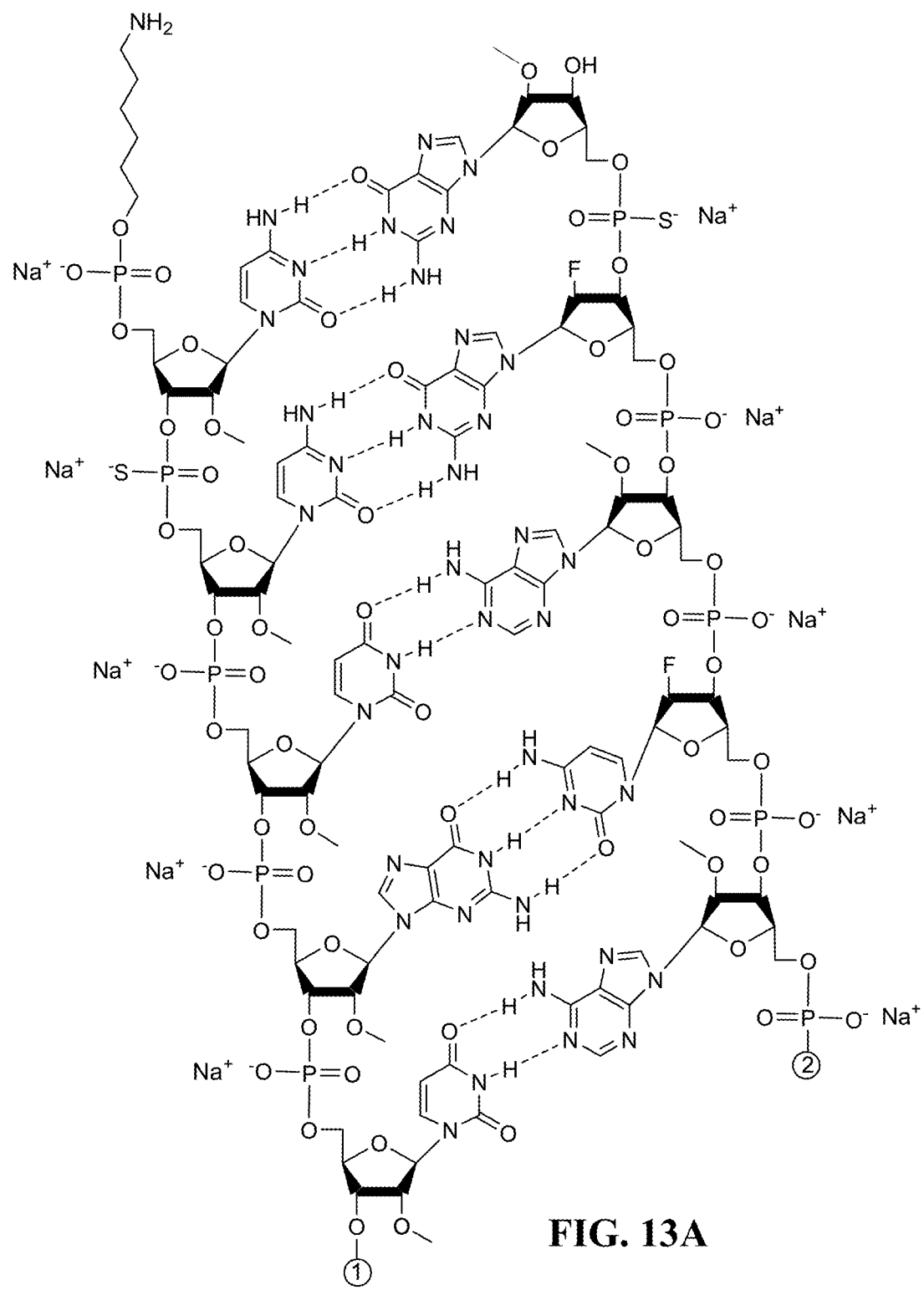
Figure 13B:
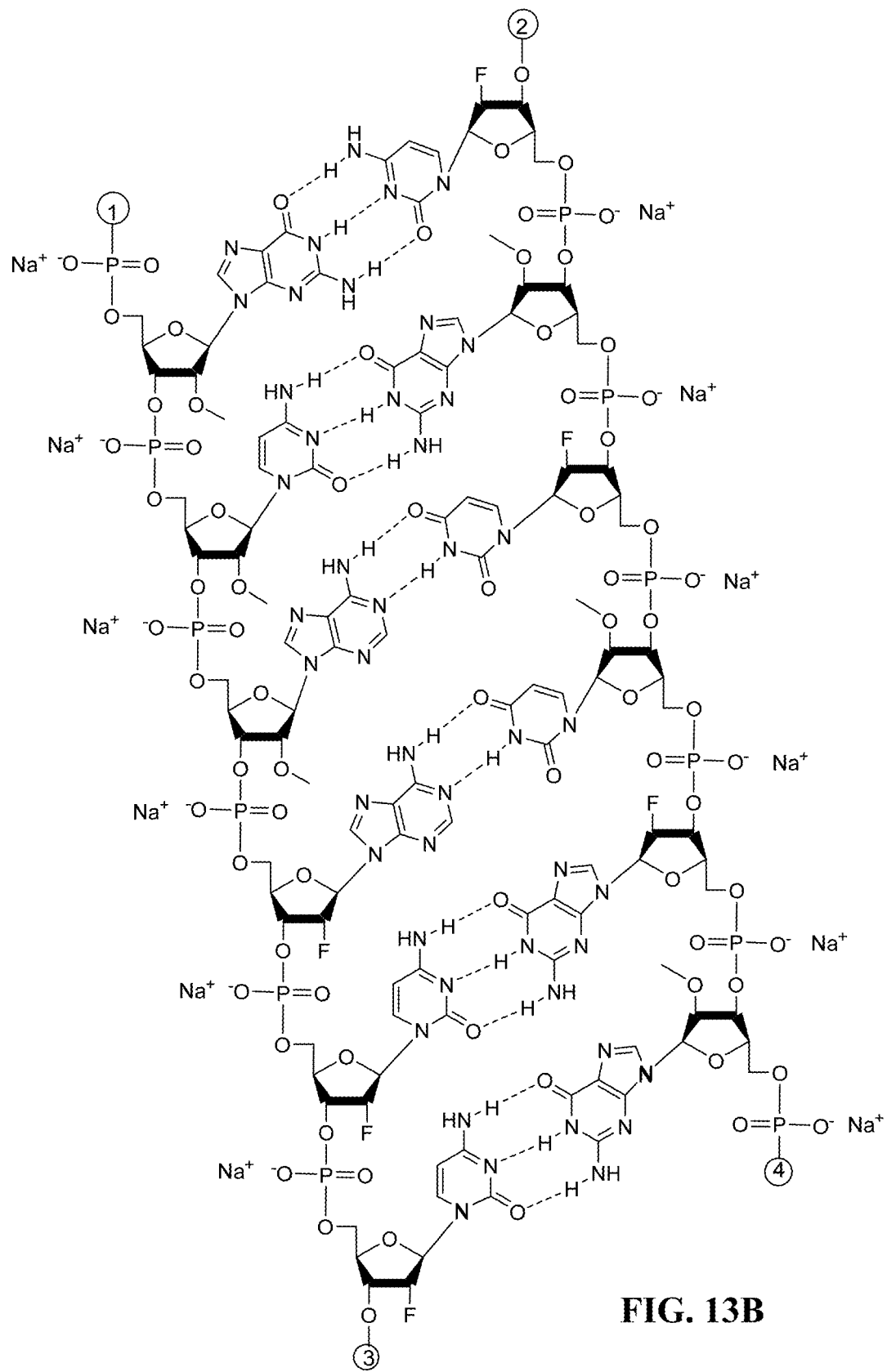
Figure 13C:
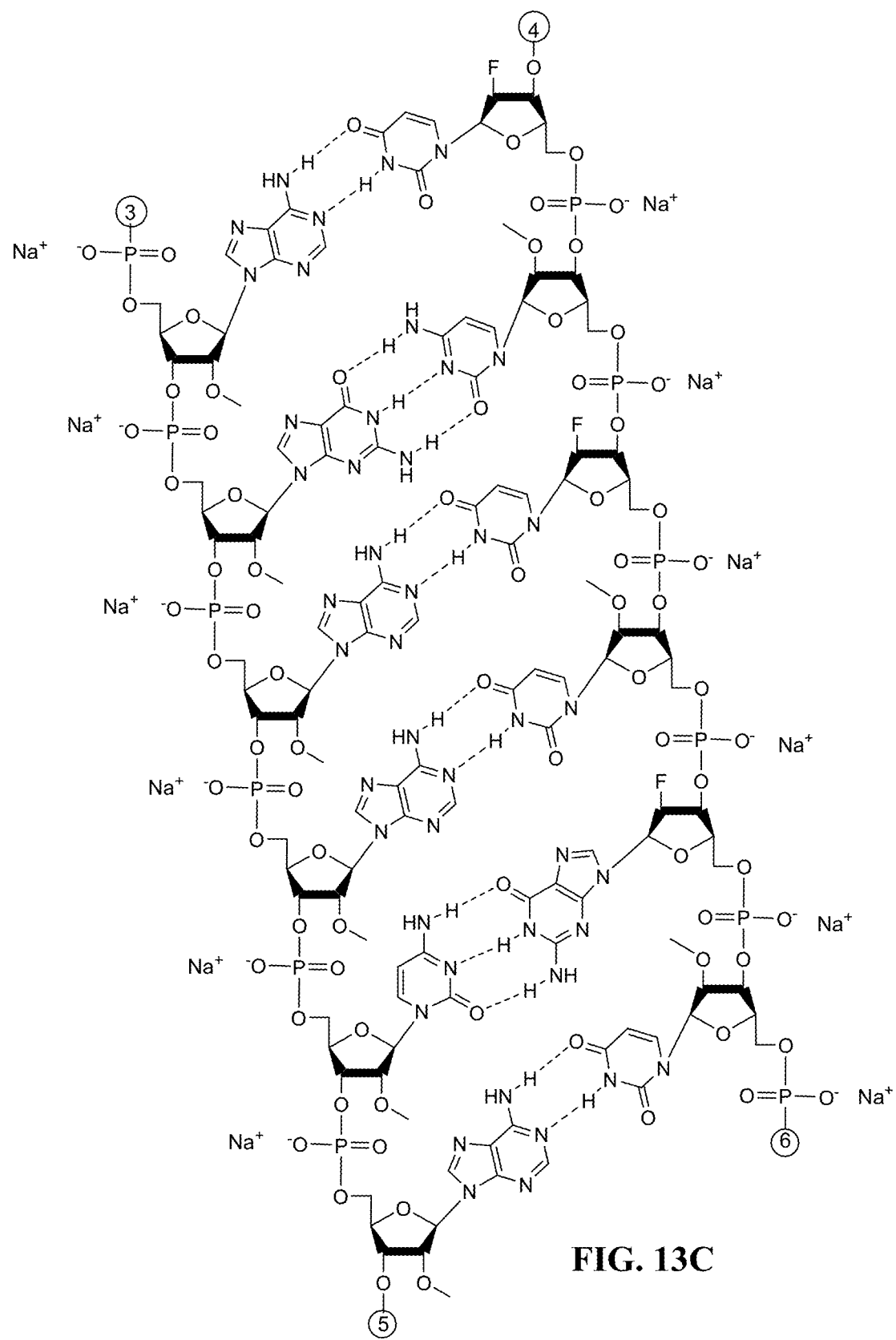
Figure 13D:
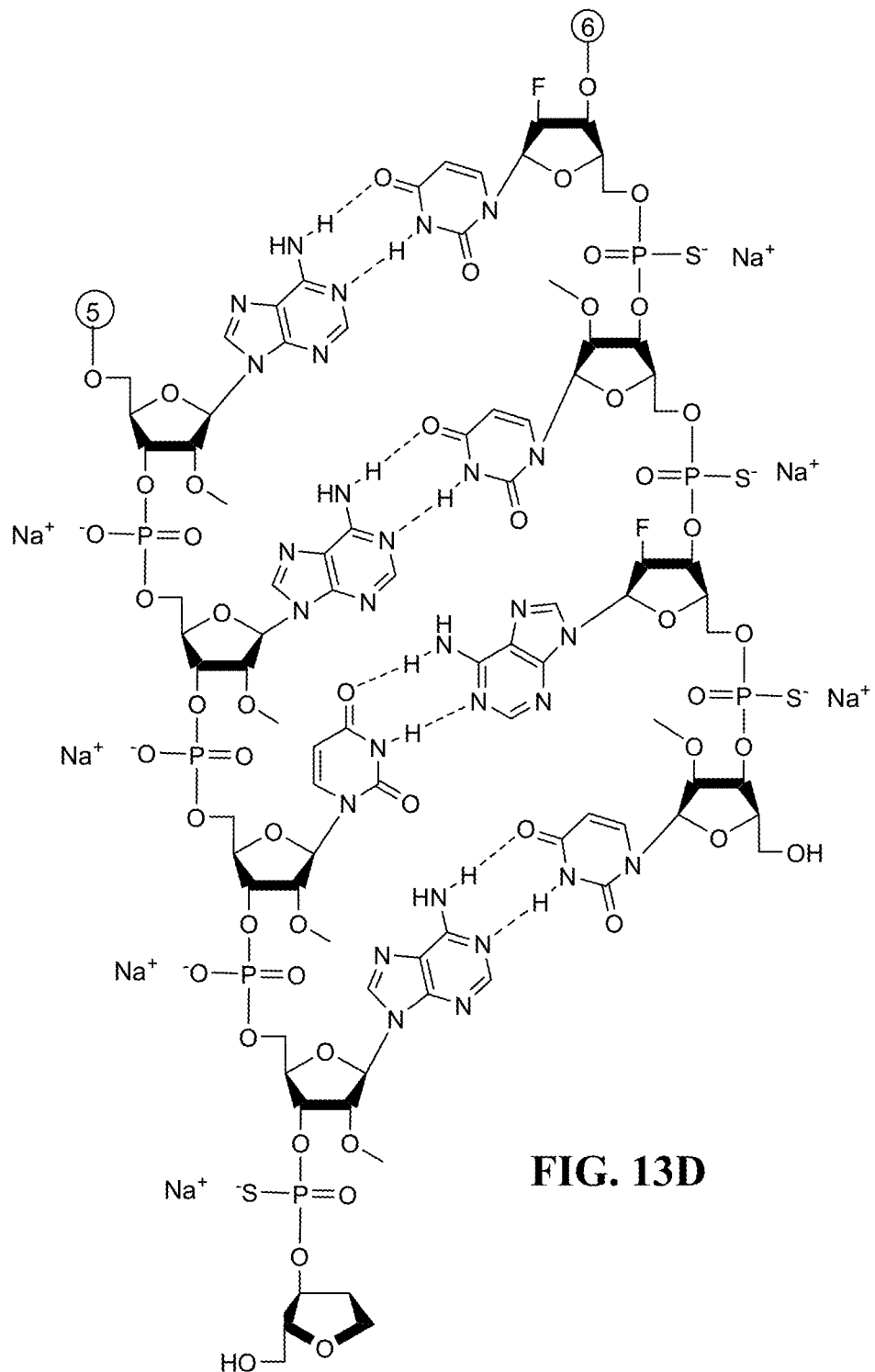
Figure 14A:
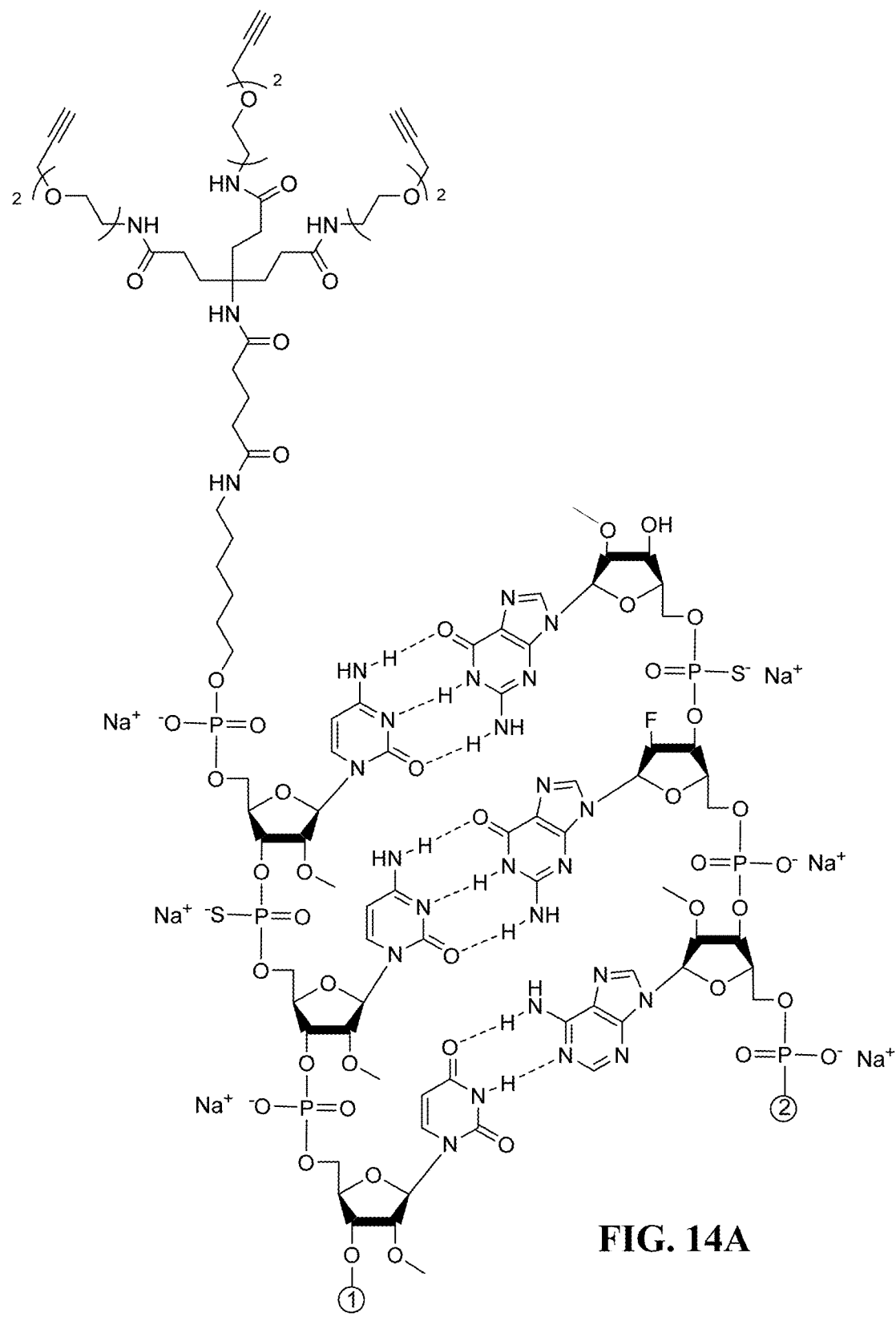
Figure 14B:
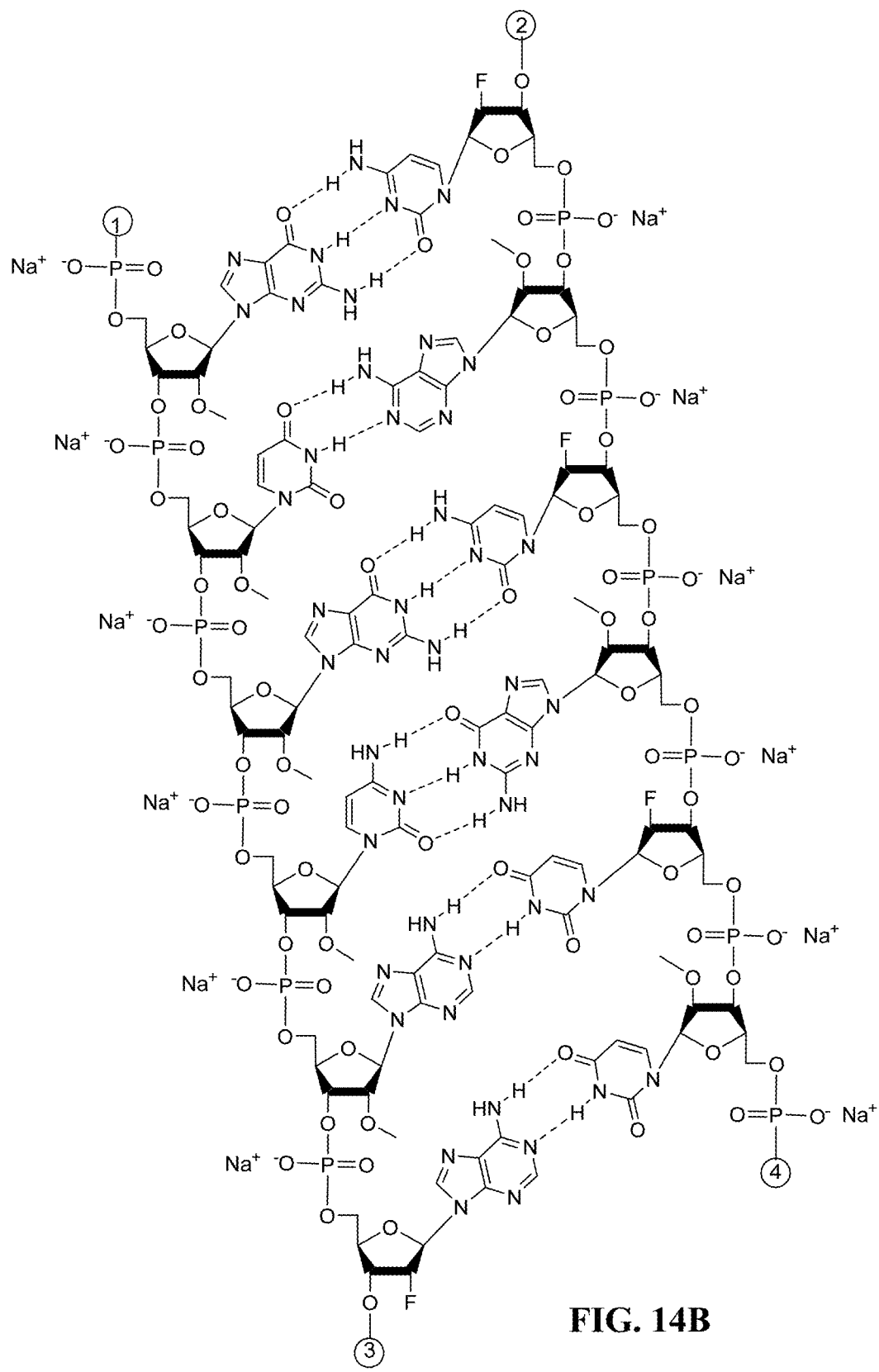
Figure 14C:
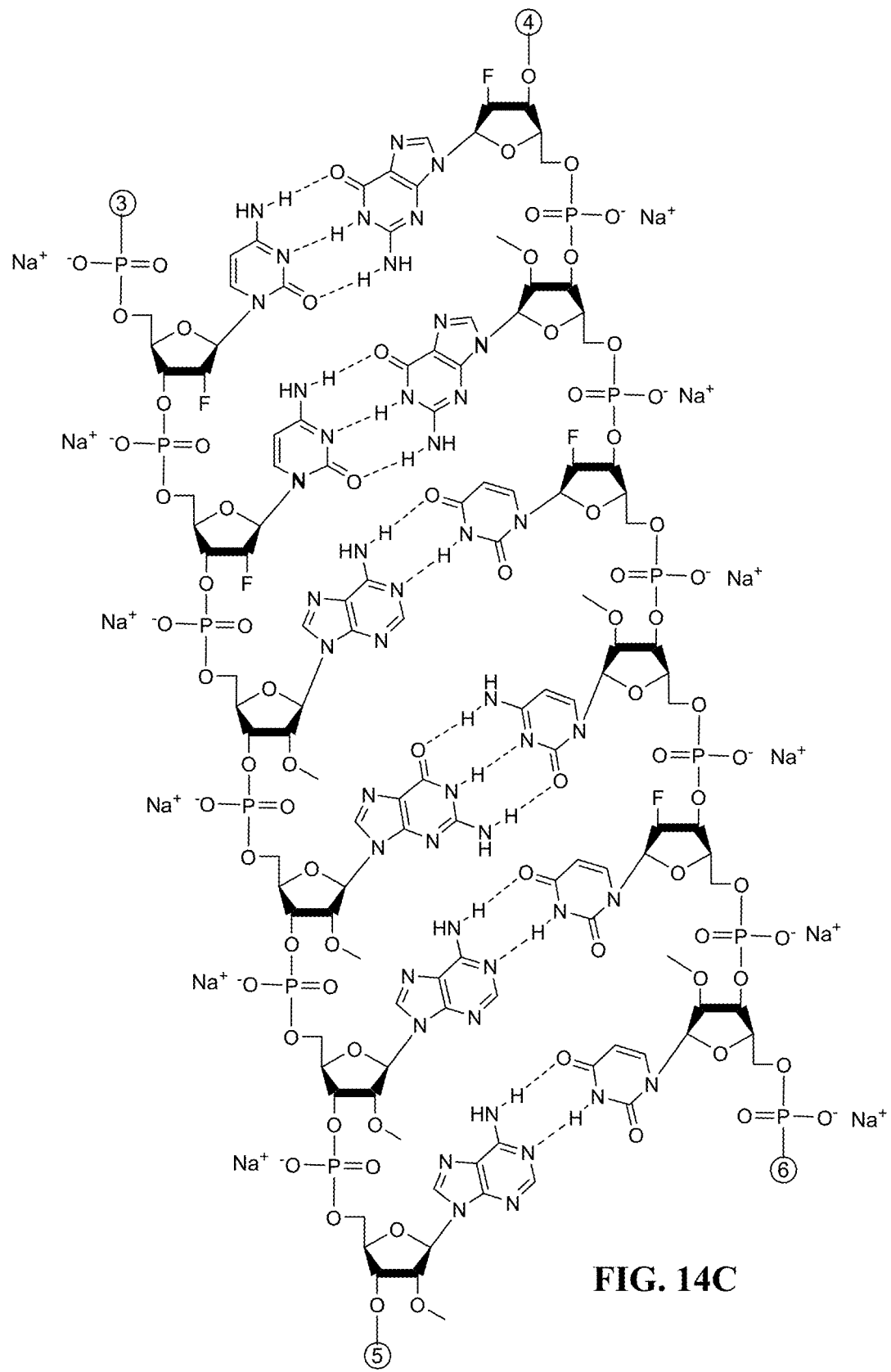
Figure 14D:
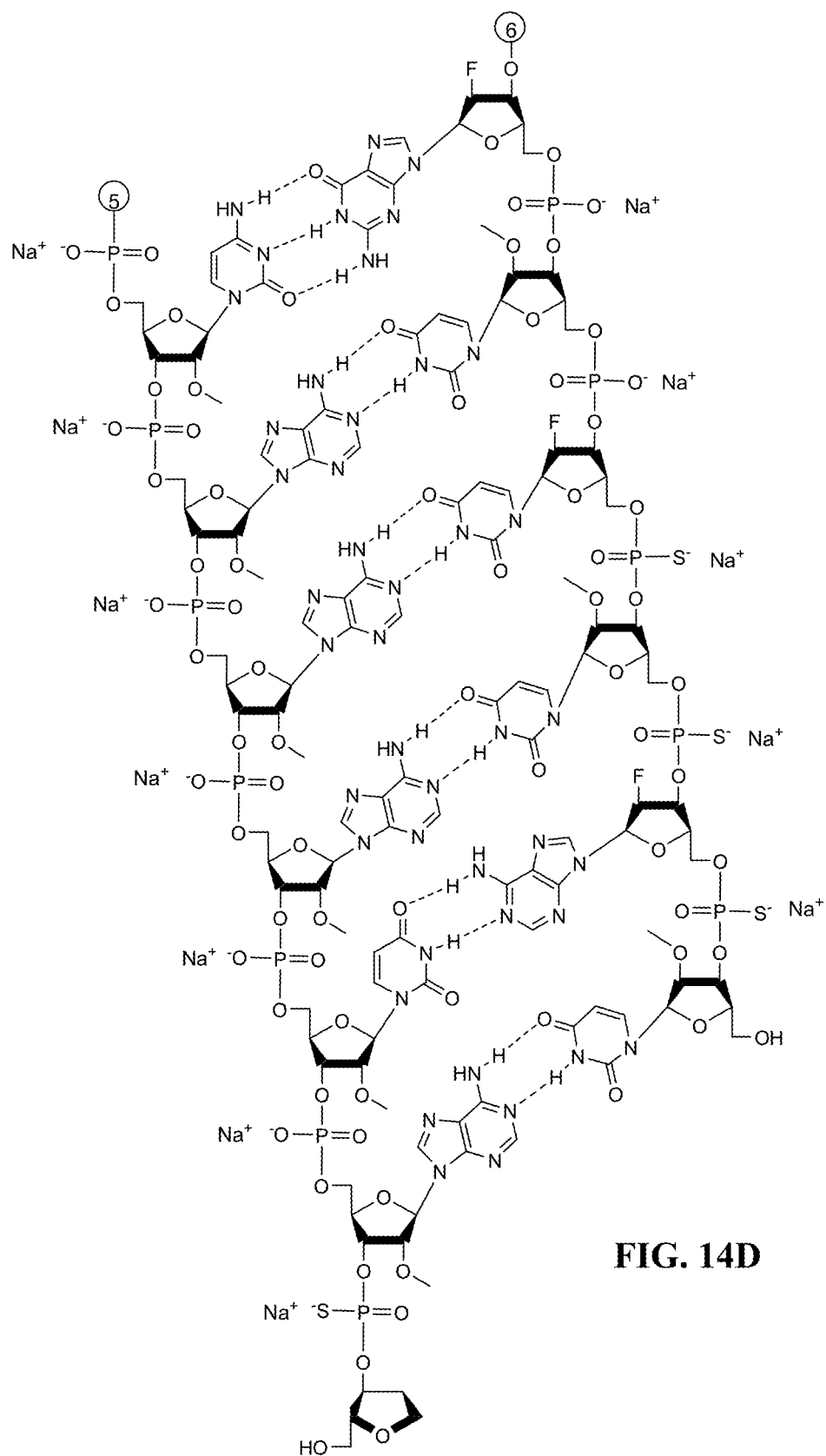
Figure 15A:
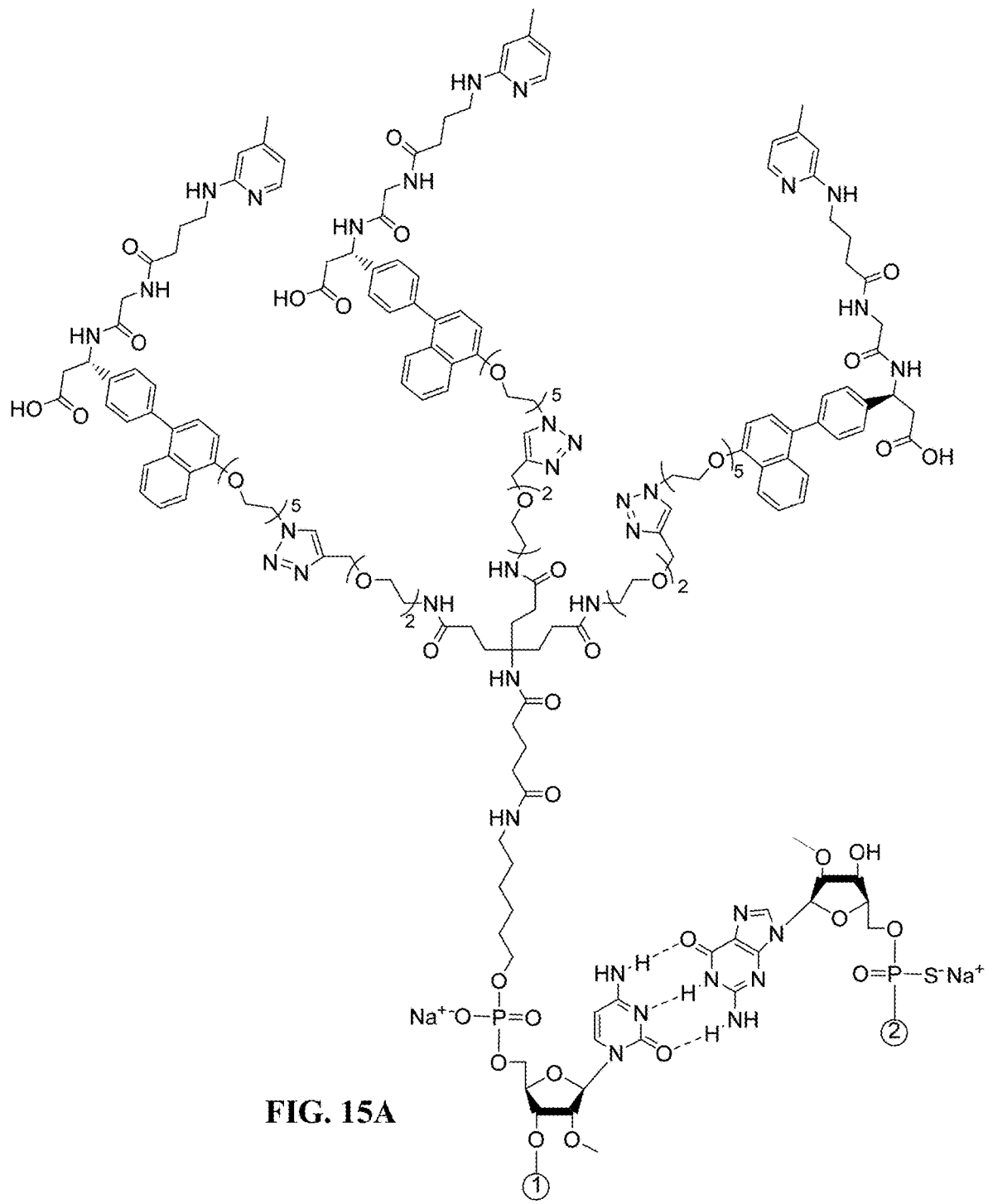
Figure 15B:
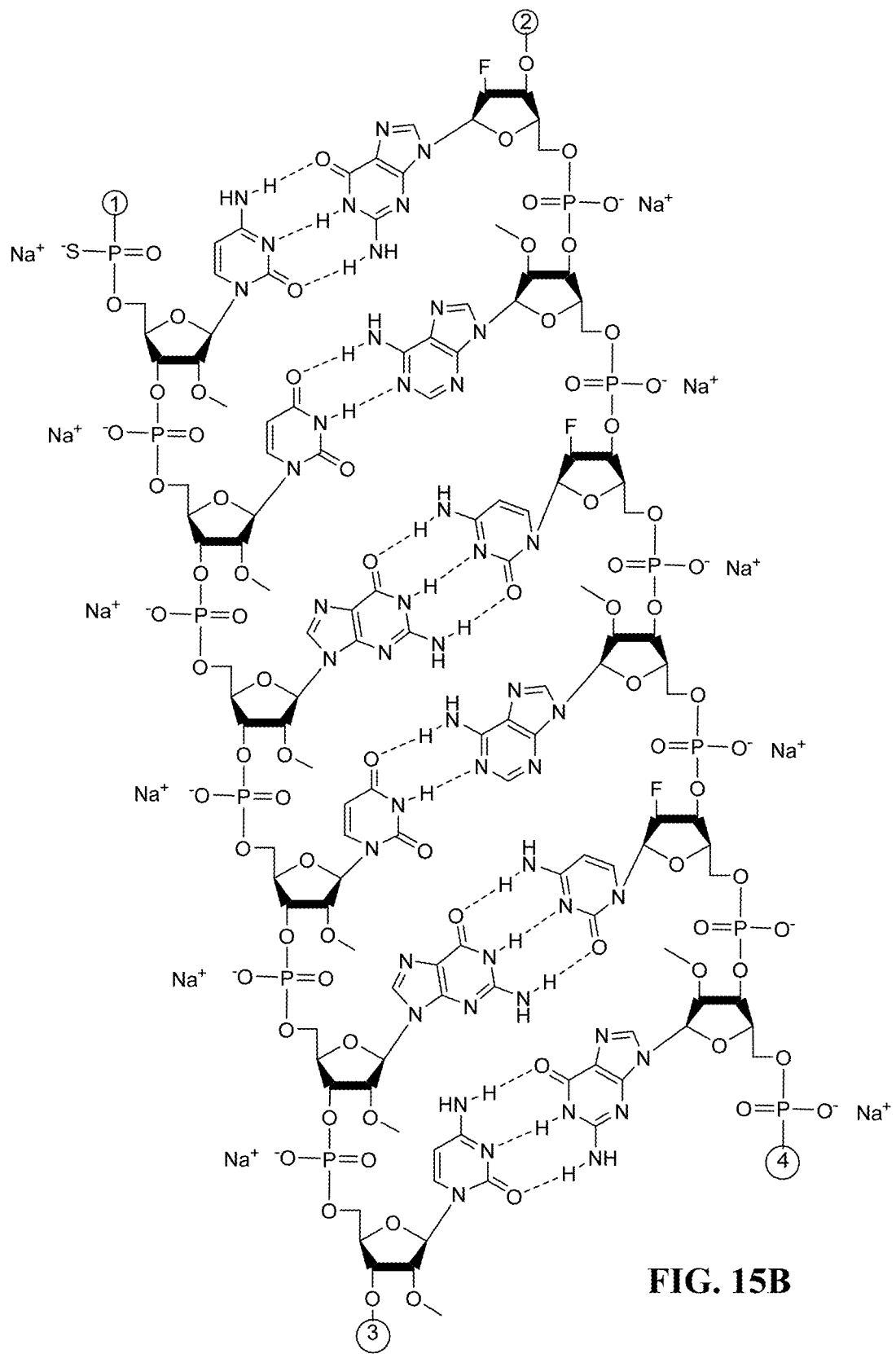
Figure 15C:
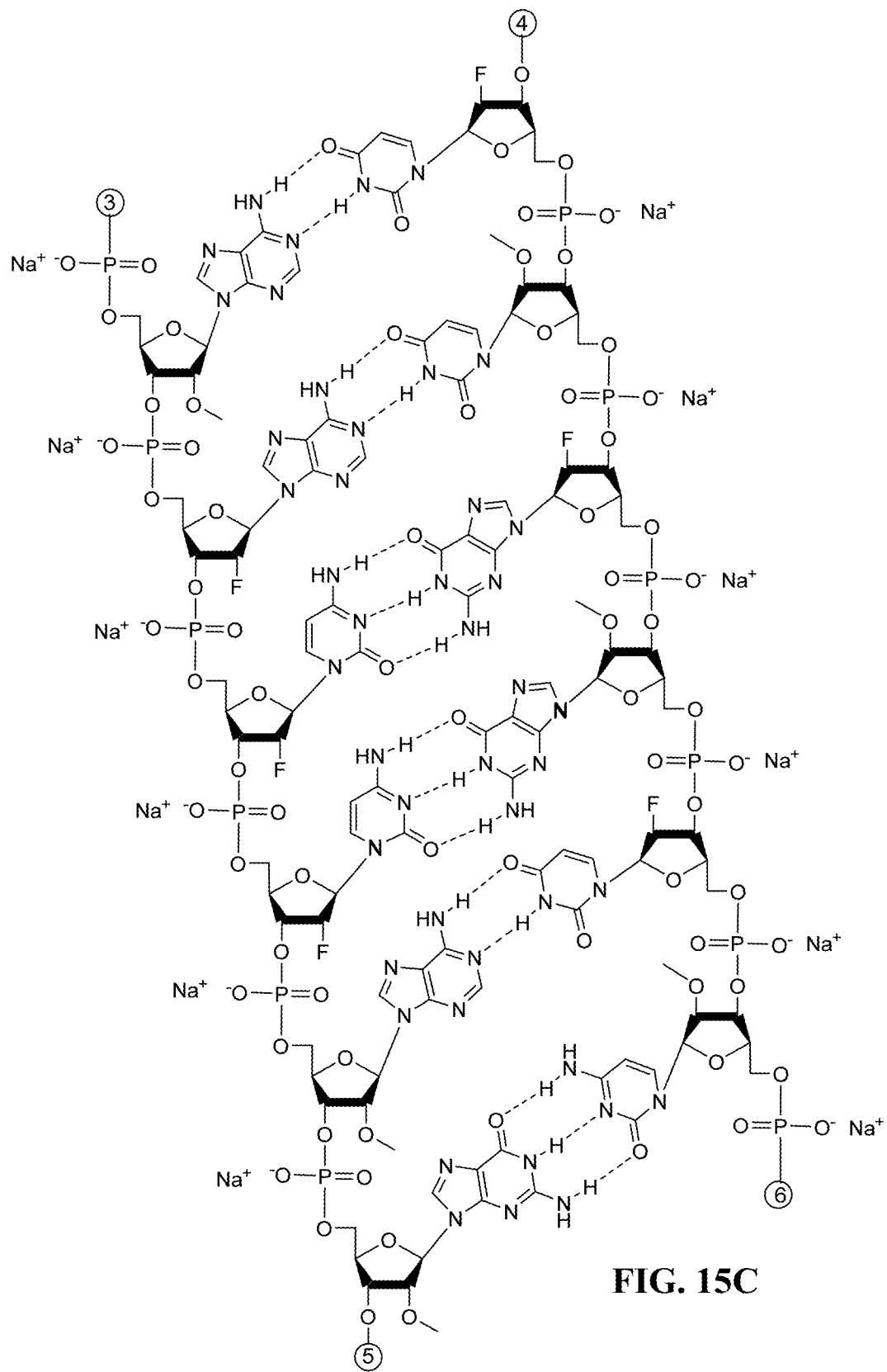
Figure 15D:
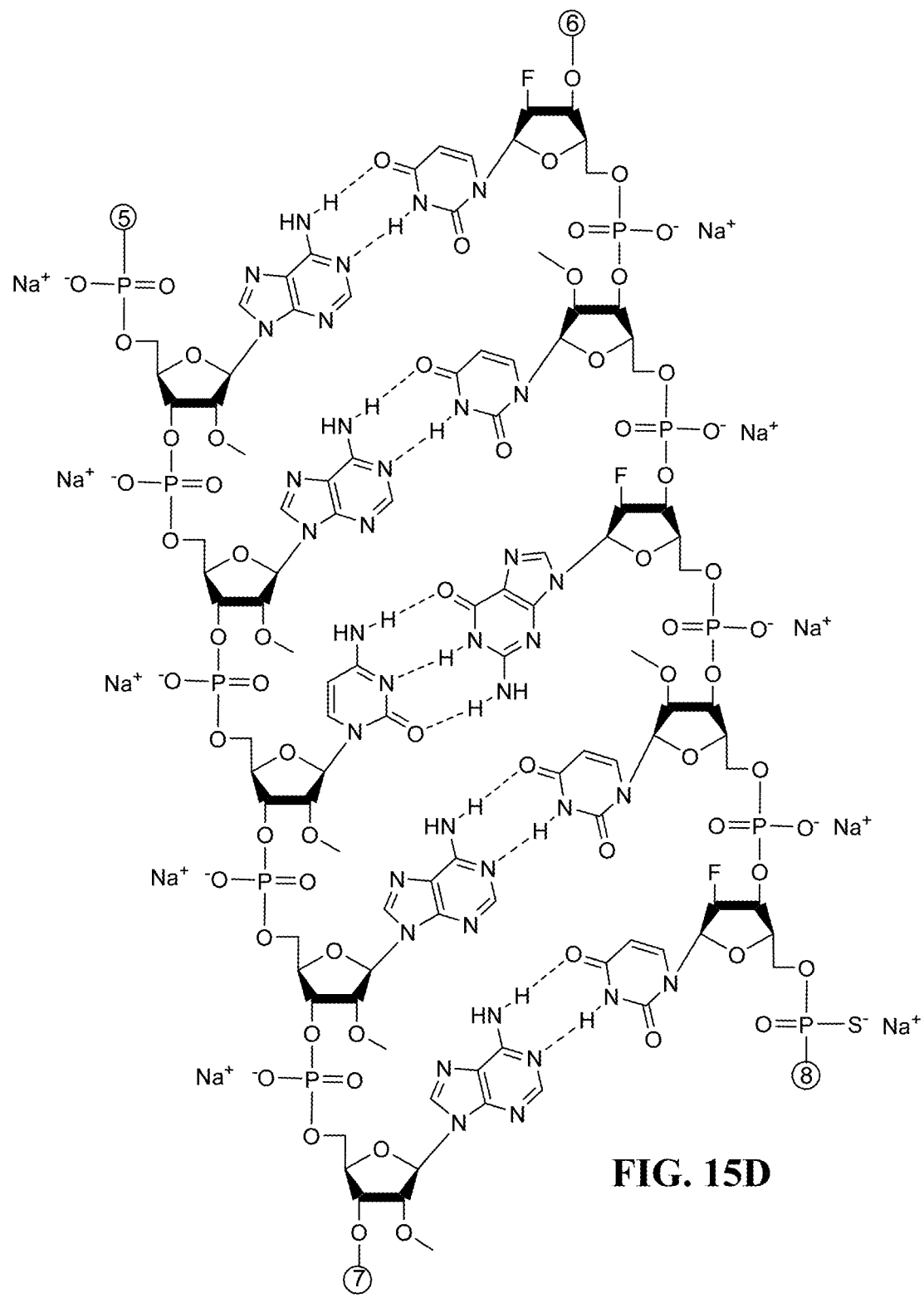
Figure 15E:
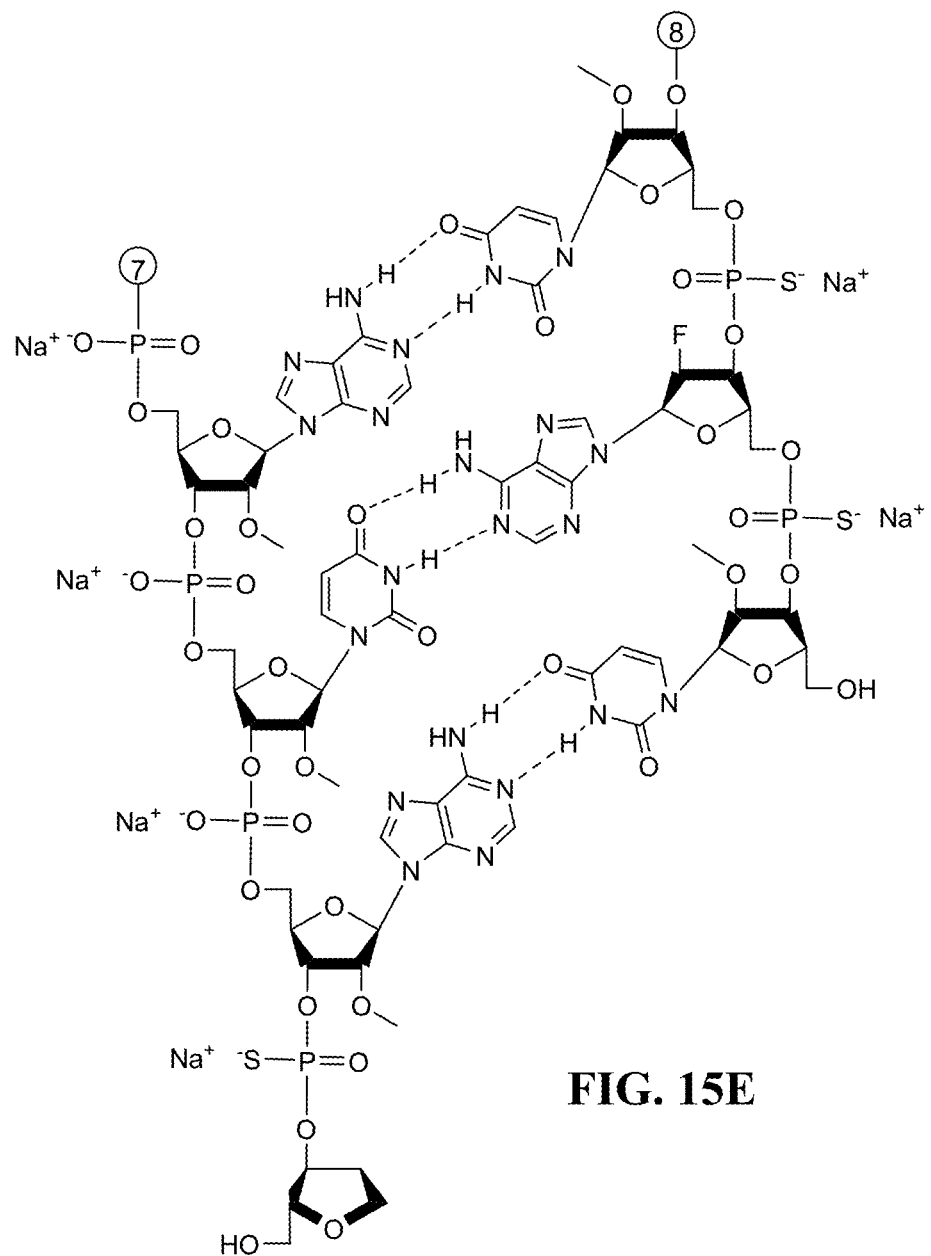
Figure 16A:
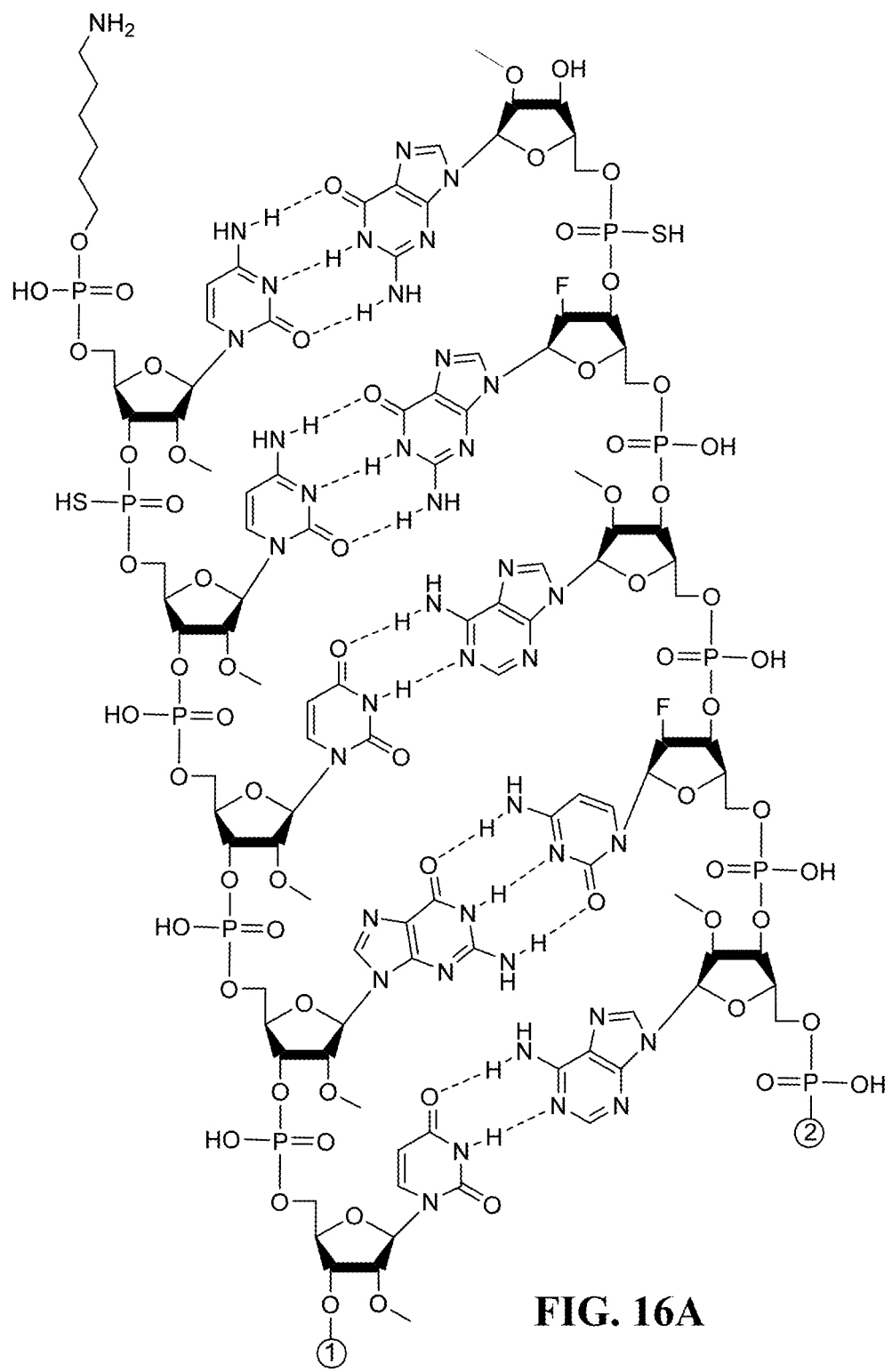
Figure 16B:
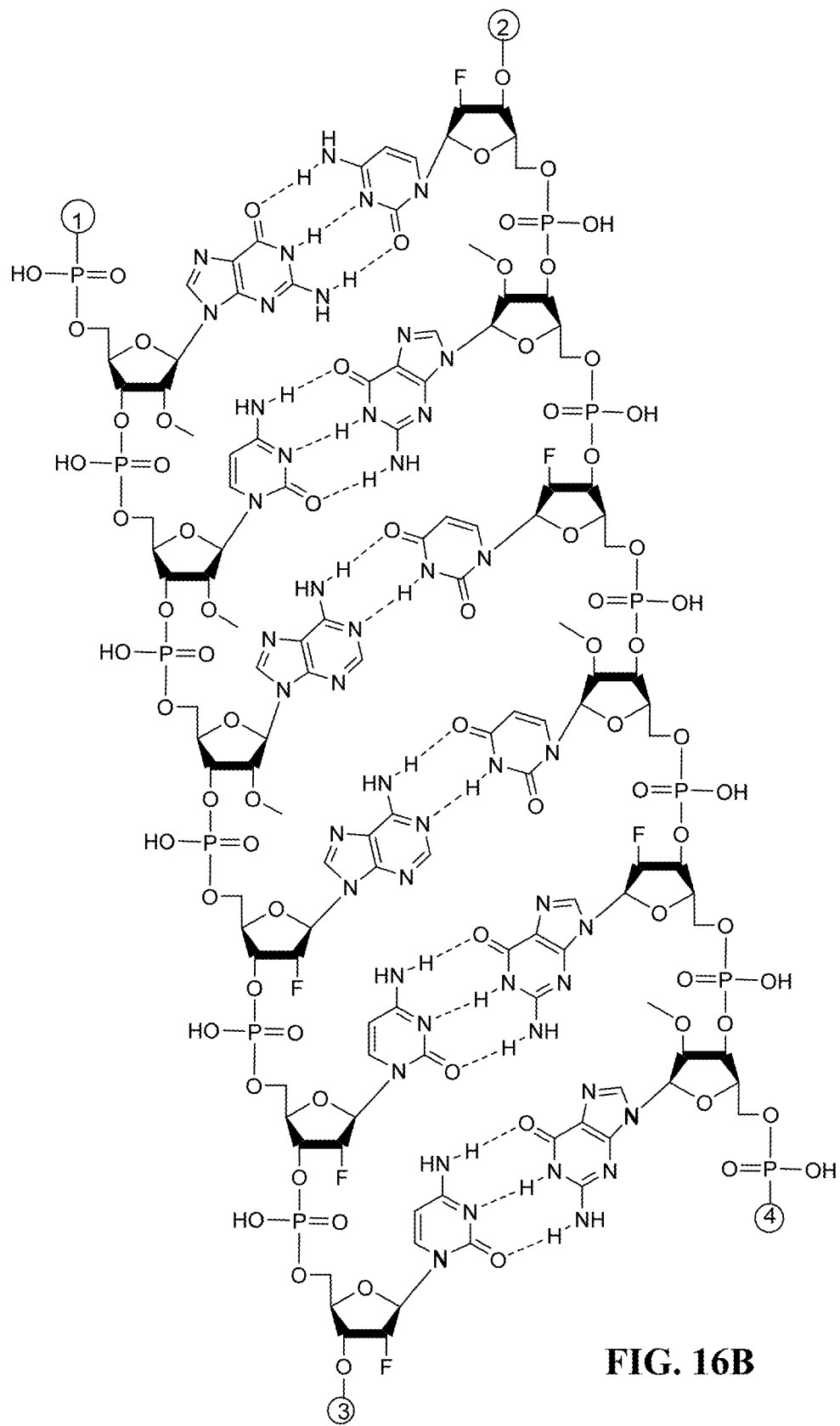
Figure 16C:
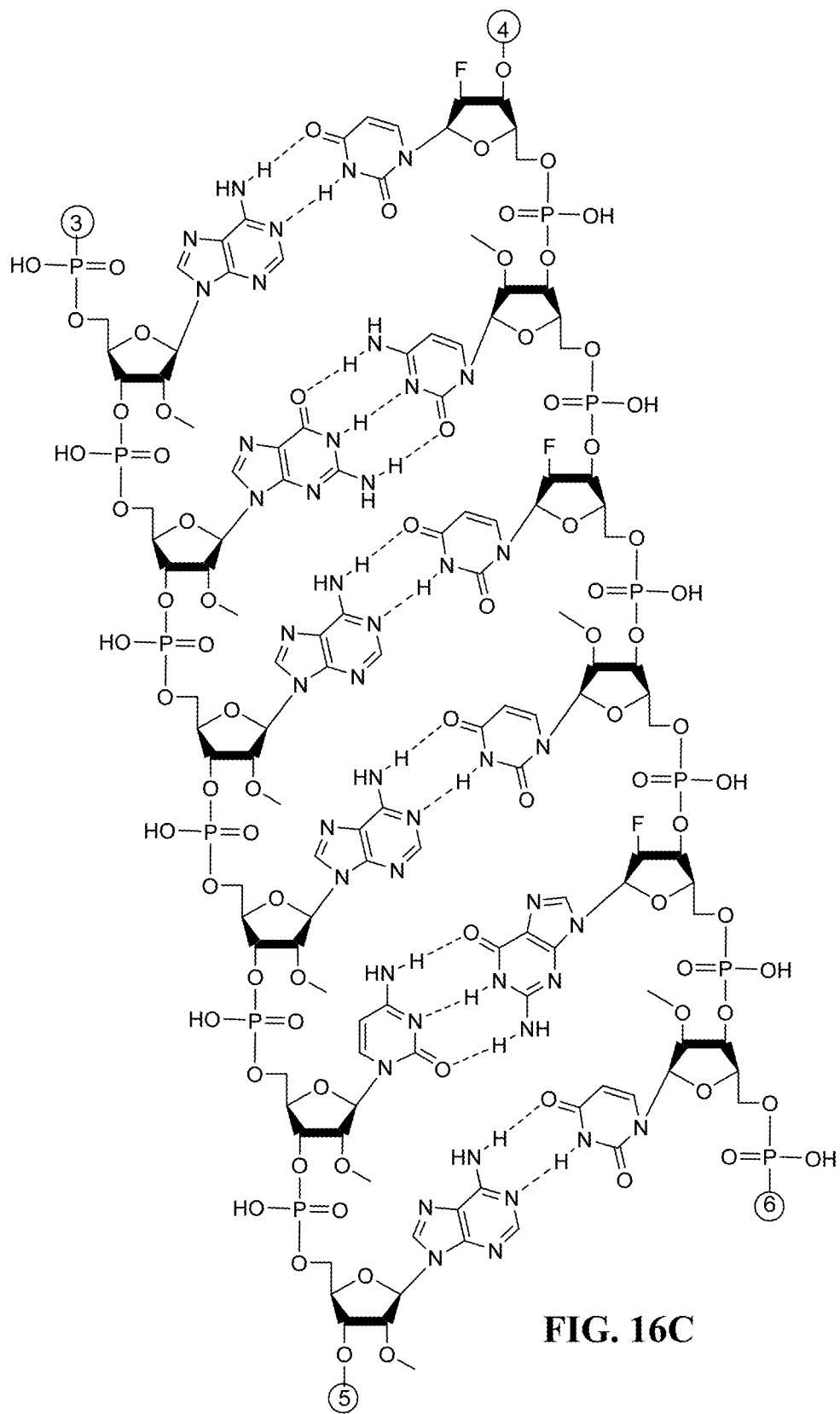
Figure 16D:
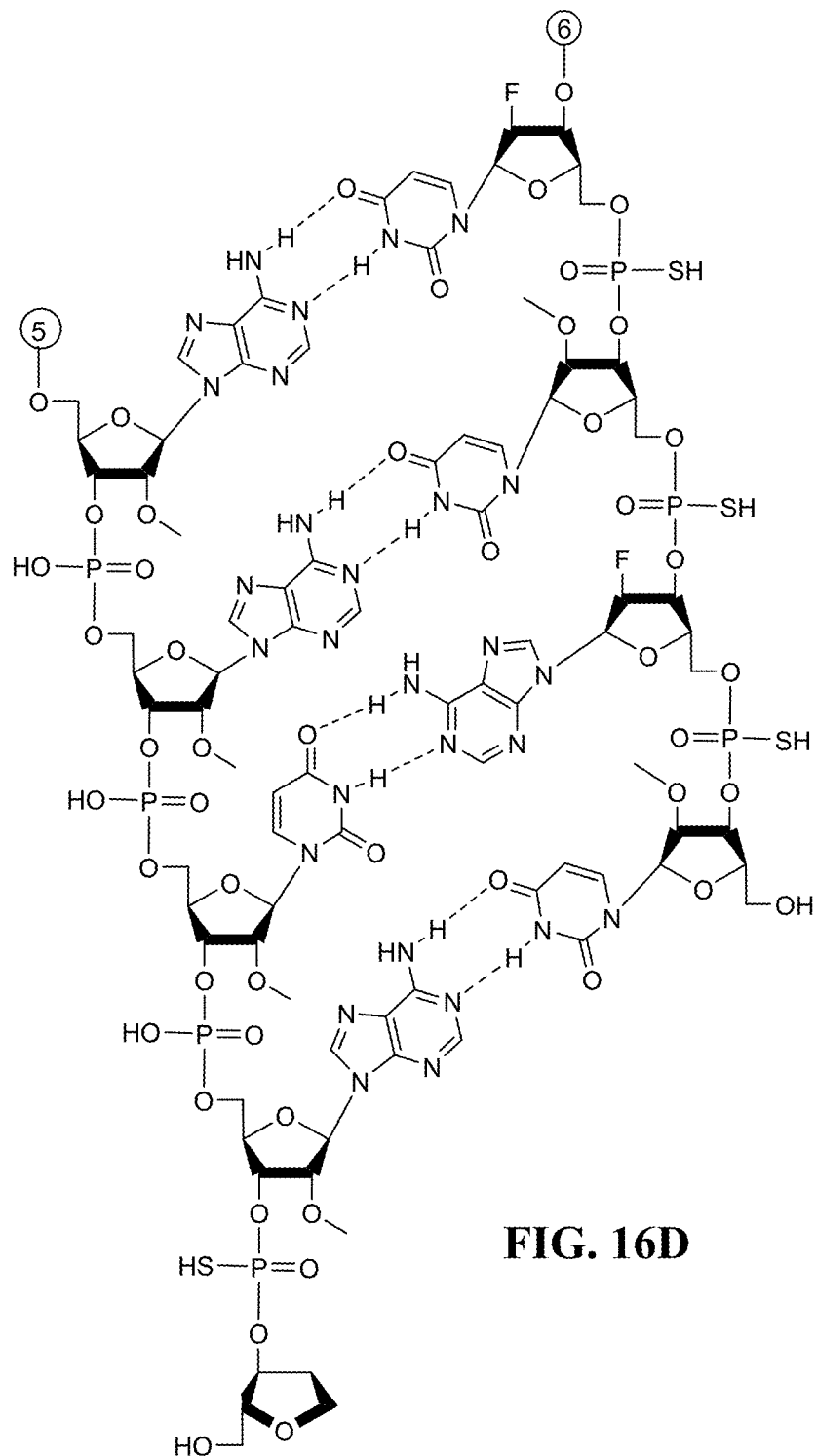

FIG. 12G. Schematic diagram of the modified sense and antisense strands of both alpha-ENaC RNAi agent AD05453 and alpha-ENaC RNAi agent AD05924 (see Tables 3-5), wherein X represents a tridentate αvβ6 integrin targeting ligand (including any linkers).

FIG. 12H. Schematic diagram of an example tridentate αvβ6 integrin targeting ligand-RNAi agent conjugate described herein, wherein a tridentate αvβ6 integrin targeting ligand is conjugated to the 5' terminal end of the sense strand. As shown therein, each αvβ6 represents an αvβ6 integrin targeting compound.

FIG. 13A to 13D. Chemical structure representation of alpha-ENaC RNAi agent AD05453, including an NH2-C6 terminal amino group, shown as a sodium salt.

FIG. 14A to 14D. Chemical structure representation of alpha-ENaC RNAi agent AD05924, including a tri-alkyne functionalized linker group (TriAlk14), shown as a sodium salt.

FIG. 15A to 15E. Chemical structure representation of alpha-ENaC RNAi agent AD05453, shown conjugated to Tri-SM6.1, as a sodium salt. As discussed herein, the same chemical structure can be synthesized using a tri-alkyne functionalized linker group (TriAlk14), which can be added through phosphoramidite synthesis, as set forth in the modified sense strand nucleotide sequence for alpha-ENaC RNAi agent AD05924 (i.e., AM07807-SS in Table 4).

FIG. 16A to 16D. Chemical structure representation of alpha-ENaC RNAi agent AD05453, including a NH2-C6 terminal functionalized amino group, shown as a free acid.

DETAILED DESCRIPTION

RNAi Agents

Described herein are RNAi agents for inhibiting expression of the alpha-ENaC (i.e., SCNN1A) gene (referred to herein as alpha-ENaC RNAi agents or alpha-ENaC RNAi triggers). Each alpha-ENaC RNAi agent comprises a sense strand and an antisense strand. The sense strand and the antisense strand each can be 16 to 30 nucleotides in length. In some embodiments, the sense and antisense strands each can be 17 to 26 nucleotides in length. The sense and antisense strands can be either the same length or they can be different lengths. In some embodiments, the sense and antisense strands are each independently 17 to 26 nucleotides in length. In some embodiments, the sense and antisense strands are each independently 17-21 nucleotides in length. In some embodiments, both the sense and antisense strands are each 21-26 nucleotides in length. In some embodiments, the sense and antisense strands are each 21-24 nucleotides in length. In some embodiments, the sense strand is about 19 nucleotides in length while the antisense strand is about 21 nucleotides in length. In some embodiments, the sense strand is about 21 nucleotides in length while the antisense strand is about 23 nucleotides in length. In some embodiments, both the sense and antisense strands are each 21 nucleotides in length. In some embodiments, the RNAi agent sense and antisense strands are each independently 16, 17, 18, 19, 20, 21, 22, 23, 24, 25, or 26 nucleotides in length. In some embodiments, a double stranded. RNAi agent has a duplex length of about 16, 17, 18, 19, 20, 21, 22, 23 or 24 nucleotides.

In some embodiments, the region of perfect, substantial, or partial complementarily between the sense strand and the antisense strand is 16-26 (e.g., 16, 17, 18, 19, 20, 21, 22, 23, 24, 25, or 26) nucleotides in length and occurs at or near the 5' end of the antisense strand (e.g., this region may be separated from the 5' end of the antisense strand by 0, 1, 2, 3, or 4 nucleotides that are not perfectly, substantially, or partially complementary).

The sense strand and antisense strand each contain a core stretch (also referred to herein as a "core sequence" or a "core stretch sequence")) that is 16 to 23 nucleotides in length. An antisense strand core stretch is 100% (perfectly) complementary or at least 85% (substantially) complementary to a nucleotide sequence (sometimes referred to, e.g., as a target sequence) present in the alpha-ENaC target. A sense strand core stretch is 100% (perfectly) complementary or at least 85% (substantially) complementary to a core stretch in the antisense strand, and thus the sense strand core stretch is typically perfectly identical or at least 85% identical to a nucleotide sequence (target sequence) present in the alpha- ENaC mRNA target. A sense strand core stretch can be the same length as a corresponding antisense core stretch or it can be a different length. In some embodiments, the antisense strand core stretch is 16, 17, 18, 19, 20, 21, 22, or 23 nucleotides in length. In some embodiments, the sense strand core stretch is 16, 17, 18, 19, 20, 21, 22, or 23 nucleotides in length.

Examples of nucleotide sequences used in forming alpha-ENaC RNAi agents are provided in Tables 2, 3, and 4. Examples of RNAi agent duplexes, that include the sense strand and antisense strand nucleotide sequences in Tables 2, 3, and 4, are shown in Table 5.

The alpha-ENaC RNAi agent sense and antisense strands anneal to form a duplex. A sense strand and an antisense strand of an alpha-ENaC RNAi agent can be partially, substantially, or fully complementary to each other. Within the complementary duplex region, the sense strand core stretch sequence is at least 85% complementary or 100% complementary to the antisense core stretch sequence. In some embodiments, the sense strand core stretch sequence contains a sequence of at least 16, at least 17, at least 18, at least 19, at least 20, at least 21, at least 22, or at least 23 nucleotides that is at least 85% or 100% complementary to a corresponding 16, 17, 18, 19, 20, 21, 22, or 23 nucleotide sequence of the antisense strand core stretch sequence (i.e., the sense and antisense core stretch sequences of an alpha-ENaC RNAi agent have a region of at least 16, at least 17, at least 18, at least 19, at least 20, at least 21, at least 22, or at least 23 nucleotides that is at least 85% base paired or 100% base paired.)

In some embodiments, the antisense strand of an alpha-ENaC RNAi agent disclosed herein differs by 0, 1, 2, or 3 nucleotides from any of the antisense strand sequences in Table 2 or Table 3. In some embodiments, the sense strand of an alpha-ENaC RNAi agent disclosed herein differs by 0, 1, 2, or 3 nucleotides from any of the sense strand sequences in Table 2 or Table 4.

The sense strand and/or the antisense strand can optionally and independently contain an additional 1, 2, 3, 4, 5, or 6 nucleotides (extension) at the 3' end, the 5' end, or both the 3' and 5' ends of the core stretch sequences. The antisense strand additional nucleotides, if present, may or may not be complementary to the corresponding sequence in the alpha-ENaC mRNA. The sense strand additional nucleotides, if present, may or may not be identical to the corresponding sequence in the alpha-ENaC mRNA. The antisense strand additional nucleotides, if present, may or may not be complementary to the corresponding sense strand's additional nucleotides, if present.

As used herein, an extension comprises 1, 2, 3, 4, 5, or 6 nucleotides at the 5' and/or 3' end of the sense strand core stretch sequence and/or antisense strand core stretch sequence. The extension nucleotides on a sense strand may or may not be complementary to nucleotides, either core stretch sequence nucleotides or extension nucleotides, in the corresponding antisense strand. Conversely, the extension nucleotides on an antisense strand may or may not be complementary to nucleotides, either core stretch nucleotides or extension nucleotides, in the corresponding sense strand. In some embodiments, both the sense strand and the antisense strand of an RNAi agent contain 3' and 5' extensions. In some embodiments, one or more of the 3' extension nucleotides of one strand base pairs with one or more 5' extension nucleotides of the other strand. In other embodiments, one or more of 3' extension nucleotides of one strand do not base pair with one or more 5' extension nucleotides of the other strand. In some embodiments, an alpha-ENaC RNAi agent has an antisense strand having a 3' extension and a sense strand having a 5' extension. In some embodiments, the extension nucleotide(s) are unpaired and form an overhang. As used herein, an "overhang" refers to a stretch of one or more unpaired nucleotides located at a terminal end of either the sense strand or the antisense strand that does not form part of the hybridized or duplexed portion of an RNAi agent disclosed herein.

In some embodiments, an alpha-ENaC RNAi agent comprises an antisense strand having a 3' extension of 1, 2, 3, 4, 5, or 6 nucleotides in length. In other embodiments, an alpha-ENaC RNAi agent comprises an antisense strand having a 3' extension of 1, 2, or 3 nucleotides in length. In some embodiments, one or more of the antisense strand extension nucleotides comprise uracil or thymidine nucleotides or nucleotides that are complementary to the corresponding alpha-ENaC mRNA sequence.

In some embodiments, the 3' end of the antisense strand can include additional abasic residues (Ab). An "abasic residue" or "abasic site" is a nucleotide or nucleoside that lacks a nucleobase at the 1' position of the sugar moiety. (See, e.g., U.S. Pat. No. 5,998,203). In some embodiments, Ab or AbAb can be added to the 3' end of the antisense strand. In some embodiments, abasic residue(s) can be added as inverted abasic residues (invAb) (see Table 6). (See, e.g., F. Czauderna, Nucleic Acids Res., 2003, 31(11), 2705-16). In some embodiments, the sense strand or the antisense strand may include a "terminal cap," which as used herein is a non-nucleotide compound or other moiety that can be incorporated at one or more termini of a strand of an RNAi agent disclosed herein, and can provide the RNAi agent, in some instances, with certain beneficial properties, such as, for example, protection against exonuclease degradation. Terminal caps are generally known in the art, and include inverted abasic residues, as well as carbon chains such as a terminal C3, C6, or C12 group. In some embodiments, a terminal cap is present at either the 5' terminal end, the 3' terminal end, or both the 5' and 3' terminal ends of the sense strand.

In some embodiments, an alpha-ENaC RNAi agent comprises a sense strand having a 3' extension of 1, 2, 3, 4, or 5 nucleotides in length. In some embodiments, one or more of the sense strand extension nucleotides comprises adenosine, uracil, or thymidine nucleotides, AT dinucleotide, or nucleotides that correspond to nucleotides in the alpha-ENaC mRNA sequence. In some embodiments, the 3' sense strand extension includes or consists of one of the following sequences, but is not limited to: T, UT, TT, UU, UUT, TTT, or TTTT (each listed 5' to 3').

In some embodiments, the 3' end of the sense strand may include additional abasic residues. In some embodiments, UUAb, UAb, or Ab are added to the 3' end of the sense strand.

In some embodiments, one or more inverted abasic residues (invAb) are added to the 3' end of the sense strand. In some embodiments, one or more inverted abasic residues or inverted abasic sites are inserted between the targeting ligand and the nucleobase sequence of the sense strand of the RNAi agent. In some embodiments, the inclusion of one or more inverted abasic residues or inverted abasic sites at or near the terminal end or terminal ends of the sense strand of an RNAi agent allows for enhanced activity or other desired properties of an RNAi agent.

In some embodiments, an alpha-ENaC RNAi agent comprises a sense strand having a 5' extension of 1, 2, 3, 4, 5, or 6 nucleotides in length. In some embodiments, one or more of the sense strand extension nucleotides comprise uracil or adenosine nucleotides or nucleotides that correspond to nucleotides in the alpha-ENaC mRNA sequence. In some embodiments, the sense strand 5' extension is one of the following sequences, but is not limited to: CA, AUAGGC, AUAGG, AUAG, AUA, A, AA, AC, GCA, GGCA, GGC, UAUCA, UAUC, UCA, UAU, U, UU (each listed 5' to 3'). A sense strand can have a 3' extension and/or a 5' extension.

In some embodiments, the 5' end of the sense strand can include one or more additional abasic residues (e.g., (Ab) or (AbAb)). In some embodiments, one or more inverted abasic residues (invAb) are added to the 5' end of the sense strand. In some embodiments, one or more inverted abasic residues can be inserted between the targeting ligand and the nucleobase sequence of the sense strand of the RNAi agent. In some embodiments, the inclusion of one or more inverted abasic residues at or near the terminal end or terminal ends of the sense strand of an RNAi agent may allow for enhanced activity or other desired properties of an RNAi agent. In some embodiments, an abasic (deoxyribose) residue can be replaced with a ribitol (abasic ribose) residue.

In some embodiments, the 3' end of the antisense strand core stretch sequence, or the 3' end of the antisense strand sequence, may include an inverted abasic residue (invAb) (see Table 6)).

Examples of sequences used in forming alpha-ENaC RNAi agents are provided in Tables 2, 3, and 4. In some embodiments, an alpha-ENaC RNAi agent antisense strand includes a sequence of any of the sequences in Tables 2 or 3. In some embodiments, an alpha-ENaC RNAi agent antisense strand includes the sequence of nucleotides (from 5' end 3' end) 1-17, 2-15, 2-17, 1-18, 2-18, 1-19, 2-19, 1-20, 2-20, 1-21, 2-21, 1-22, 2-22, 1-23, 2-23, 1-24, or 2-24, of any of the sequences in Table 2 or Table 3. In certain embodiments, an alpha-ENaC RNAi agent antisense strand comprises or consists of a modified sequence of any one of the modified sequences in Table 3. In some embodiments, an alpha-ENaC RNAi agent sense strand includes the sequence of any of the sequences in Tables 2 or 4. In some embodiments, an alpha-ENaC RNAi agent sense strand includes the sequence of nucleotides (from 5' end→3' end) 1-18, 1-19, 1-20, 1-21, 1-22, 1-23, 1-24, 2-19, 2-20, 2-21, 2-22, 2-23, 2-24, 3-20, 3-21, 3-22, 3-23, 3-24, 4-21, 4-22, 4-23, 4-24, 5-22, 5-23, or 5-24, of any of the sequences in Tables 2 or 4. In certain embodiments, an alpha-ENaC RNAi agent sense strand comprises or consists of a modified sequence of any one of the modified sequences in Table 4.

In some embodiments, the sense and antisense strands of the RNAi agents described herein contain the same number of nucleotides. In some embodiments, the sense and antisense strands of the RNAi agents described herein contain different numbers of nucleotides. In some embodiments, the sense strand 5' end and the antisense strand 3' end of an RNAi agent form a blunt end. In some embodiments, the sense strand 3' end and the antisense strand 5' end of an RNAi agent form a blunt end. In some embodiments, both ends of an RNAi agent form blunt ends. In some embodiments, neither end of an RNAi agent is blunt-ended. As used herein a "blunt end" refers to an end of a double stranded RNAi agent in which the terminal nucleotides of the two annealed strands are complementary (form a complementary base-pair).

In some embodiments, the sense strand 5' end and the antisense strand 3' end of an RNAi agent form a frayed end. In some embodiments, the sense strand 3' end and the antisense strand 5' end of an RNAi agent form a frayed end. In some embodiments, both ends of an RNAi agent form a frayed end. In some embodiments, neither end of an RNAi agent is a frayed end. As used herein, a frayed end refers to an end of a double stranded RNAi agent in which the terminal nucleotides of the two annealed strands from a pair (i.e., do not form an overhang) but are not complementary (i.e. form a non-complementary pair). In some embodiments, one or more unpaired nucleotides at the end of one strand of a double stranded RNAi agent form an overhang. The unpaired nucleotides may be on the sense strand or the antisense strand, creating either 3' or 5' overhangs. In some embodiments, the RNAi agent contains: a blunt end and a frayed end, a blunt end and 5' overhang end, a blunt end and a 3' overhang end, a frayed end and a 5' overhang end, a frayed end and a 3' overhang end, two 5' overhang ends, two 3' overhang ends, a 5' overhang end and a 3' overhang end, two frayed ends, or two blunt ends. Typically, when present, overhangs are located at the 3' terminal ends of the sense strand, the antisense strand, or both the sense strand and the antisense strand.

Modified nucleotides, when used in various polynucleotide or oligonucleotide constructs, can preserve activity of the compound in cells while at the same time increasing the serum stability of these compounds, and can also minimize the possibility of activating interferon activity in humans upon administering of the polynucleotide or oligonucleotide construct.

In some embodiments, an alpha-ENaC RNAi agent is prepared or provided as a salt, mixed salt, or a free-acid. In some embodiments, an alpha-ENaC RNAi agent is prepared as a sodium salt. Such forms that are well known in the art are within the scope of the inventions disclosed herein.

Modified Nucleotides

In some embodiments, an alpha-ENaC RNAi agent contains one or more modified nucleotides. As used herein, a "modified nucleotide" is a nucleotide other than a ribonucleotide (2'-hydroxyl nucleotide). In some embodiments, at least 50% (e.g., at least 60%, at least 70%, at least 80%, at least 90%, at least 95%, at least 97%, at least 98%, at least 99%, or 100%) of the nucleotides are modified nucleotides. As used herein, modified nucleotides can include, but are not limited to, deoxyribonucleotides, nucleotide mimics, abasic nucleotides (represented herein as Ab), 2'-modified nucleotides, 3' to 3' linkages (inverted) nucleotides (represented herein as invdN, invN, invn), modified nucleobase-comprising nucleotides, bridged nucleotides, peptide nucleic acids (PNAs), 2',3'-seco nucleotide mimics (unlocked nucleobase analogues, represented herein as $N_{UNA}$ or NUNA), locked nucleotides (represented herein as $N_{LNA}$ or NLNA), 3'-O-methoxy (2' internucleoside linked) nucleotides (represented herein as 3'-OMen), 2'-F-Arabino nucleotides (represented herein as NfANA or $Nf_{ANA}$), 5'-Me, 2'-fluoro nucleotide (represented herein as 5Me-Nf), morpholino nucleotides, vinyl phosphonate deoxyribonucleotides (represented herein as vpdN), vinyl phosphonate containing nucleotides, and cyclopropyl phosphonate containing nucleotides (cPrpN). 2'-modified nucleotides (i.e., a nucleotide with a group other than a hydroxyl group at the 2' position of the five-membered sugar ring) include, but are not limited to, 2'-O-methyl nucleotides (represented herein as a lower case letter 'n' in a nucleotide sequence), 2'-deoxy-2'-fluoro nucleotides (also referred to herein as 2'-fluoro nucleotide, and represented herein as NO, 2'-deoxy nucleotides (represented herein as dN), 2'-methoxyethyl (2'-O-2-methoxyethyl) nucleotides (also referred to herein as 2'-MOE, and represented herein as NM), 2'-amino nucleotides, and 2'-alkyl nucleotides. It is not necessary for all positions in a given compound to be uniformly modified. Conversely, more than one modification can be incorporated in a single alpha-ENaC RNAi agent or even in a single nucleotide thereof. The alpha-ENaC RNAi agent sense strands and antisense strands can be synthesized and/or modified by methods known in the art. Modification at one nucleotide is independent of modification at another nucleotide.

Modified nucleobases include synthetic and natural nucleobases, such as 5-substituted pyrimidines, 6-azapyrimidines and N-2, N-6 and 0-6 substituted purines, (e.g., 2-aminopropyladenine, 5-propynyluracil, or 5-propynylcytosine), 5-methylcytosine (5-me-C), 5-hydroxymethyl cytosine, inosine, xanthine, hypoxanthine, 2-aminoadenine, 6-alkyl (e.g., 6-methyl, 6-ethyl, 6-isopropyl, or 6-n-butyl) derivatives of adenine and guanine, 2-alkyl (e.g., 2-methyl, 2-ethyl, 2-isopropyl, or 2-n-butyl) and other alkyl derivatives of adenine and guanine, 2-thiouracil, 2-thiothymine, 2-thiocytosine, 5-halouracil, cytosine, 5-propynyl uracil, 5-propynyl cytosine, 6-azo uracil, 6-azo cytosine, 6-azo thymine, 5-uracil (pseudouracil), 4-thiouracil, 8-halo, 8-amino, 8-sulfhydryl, 8-thioalkyl, 8-hydroxyl and other 8-substituted adenines and guanines, 5-halo (e.g., 5-bromo), 5-trifluoromethyl, and other 5-substituted uracils and cytosines, 7-methylguanine and 7-methyladenine, 8-azaguanine and 8-azaadenine, 7-deazaguanine, 7-deazaadenine, 3-deazaguanine, and 3-deazaadenine.

In some embodiments, all or substantially all of the nucleotides of an RNAi agent are modified nucleotides. As used herein, an RNAi agent wherein substantially all of the nucleotides present are modified nucleotides is an RNAi agent having four or fewer (i.e., 0, 1, 2, 3, or 4) nucleotides in both the sense strand and the antisense strand being ribonucleotides (i.e., unmodified). As used herein, a sense strand wherein substantially all of the nucleotides present are modified nucleotides is a sense strand having two or fewer (i.e., 0, 1, or 2) nucleotides in the sense strand being unmodified ribonucleotides. As used herein, an antisense sense strand wherein substantially all of the nucleotides present are modified nucleotides is an antisense strand having two or fewer (i.e., 0, 1, or 2) nucleotides in the sense strand being unmodified ribonucleotides. In some embodiments, one or more nucleotides of an RNAi agent is an unmodified ribonucleotide.

Modified Internucleoside Linkages

In some embodiments, one or more nucleotides of an alpha-ENaC RNAi agent are linked by non-standard linkages or backbones (i.e., modified internucleoside linkages or modified backbones). Modified internucleoside linkages or backbones include, but are not limited to, phosphorothioate groups (represented herein as a lower case "s"), chiral phosphorothioates, thiophosphates, phosphorodithioates, phosphotriesters, aminoalkyl-phosphotriesters, alkyl phosphonates (e.g., methyl phosphonates or 3'-alkylene phosphonates), chiral phosphonates, phosphinates, phosphoramidates (e.g., 3'-amino phosphoramidate, aminoalkylphosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'. In some embodiments, a modified internucleoside linkage or backbone lacks a phosphorus atom. Modified internucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some embodiments, modified internucleoside backbones include, but are not limited to, siloxane backbones, sulfide backbones, sulfoxide backbones, sulfone backbones, formacetyl and thioformacetyl backbones, methylene formacetyl and thioformacetyl backbones, alkene-containing backbones, sulfamate backbones, methyleneimino and methylenehydrazino backbones, sulfonate and sulfonamide backbones, amide backbones, and other backbones having mixed N, O, S, and $CH_2$ components.

In some embodiments, a sense strand of an alpha-ENaC RNAi agent can contain 1, 2, 3, 4, 5, or 6 phosphorothioate linkages, an antisense strand of an alpha-ENaC RNAi agent can contain 1, 2, 3, 4, 5, or 6 phosphorothioate linkages, or both the sense strand and the antisense strand independently can contain 1, 2, 3, 4, 5, or 6 phosphorothioate linkages. In some embodiments, a sense strand of an alpha-ENaC RNAi agent can contain 1, 2, 3, or 4 phosphorothioate linkages, an antisense strand of an alpha-ENaC RNAi agent can contain 1, 2, 3, or 4 phosphorothioate linkages, or both the sense strand and the antisense strand independently can contain 1, 2, 3, or 4 phosphorothioate linkages.

In some embodiments, an alpha-ENaC RNAi agent sense strand contains at least two phosphorothioate internucleoside linkages. In some embodiments, the at least two phosphorothioate internucleoside linkages are between the nucleotides at positions 1-3 from the 3' end of the sense strand. In some embodiments, one phosphorothioate internucleoside linkage is at the 5' end of the sense strand, and another phosphorothioate linkage is at the 3' end of the sense strand. In some embodiments, the at least two phosphorothioate internucleoside linkages are between the nucleotides at positions 1-3, 2-4, 3-5, 4-6, 4-5, or 6-8 from the 5' end of the sense strand. In some embodiments, an alpha-ENaC RNAi agent antisense strand contains four phosphorothioate internucleoside linkages. In some embodiments, the four phosphorothioate internucleoside linkages are between the nucleotides at positions 1-3 from the 5' end of the antisense strand and between the nucleotides at positions 19-21, 20-22, 21-23, 22-24, 23-25, or 24-26 from the 5' end. In some embodiments, an alpha-ENaC RNAi agent contains at least two phosphorothioate internucleoside linkages in the sense strand and three or four phosphorothioate internucleoside linkages in the antisense strand.

In some embodiments, an alpha-ENaC RNAi agent contains one or more modified nucleotides and one or more modified internucleoside linkages. In some embodiments, a 2'-modified nucleoside is combined with modified internucleoside linkage.

Alpha-ENaC RNAi Agents

In some embodiments, the alpha-ENaC RNAi agents disclosed herein target an alpha-ENaC gene at or near the positions of the alpha-ENaC sequence shown in Table 1. In some embodiments, the antisense strand of an alpha-ENaC RNAi agent disclosed herein includes a core stretch sequence that is fully, substantially, or at least partially complementary to a target alpha-ENaC 19-mer sequence disclosed in Table 1.

TABLE 1

Alpha-ENaC 19-mer mRNA Target Sequences (taken from *homo sapiens* sodium channel epithelial 1 alpha subunit (SCNN1A), transcript variant 1, GenBank NM_001038.5 (SEQ ID NO: 1))

| SEQ ID No. | alpha-ENaC 19-mer Target Sequences (5' → 3') | Corresponding Positions on SEQ ID NO: 1 |
|---|---|---|
| 11 | UGUGCAACCAGAACAAAUC | 972-990 |
| 12 | GUGCAACCAGAACAAAUCG | 973-991 |
| 13 | GCAGAGCAGAAUGACUUCA | 1289-1307 |

TABLE 1-continued

Alpha-ENaC 19-mer mRNA Target Sequences (taken from *homo sapiens* sodium channel epithelial 1 alpha subunit (SCNN1A), transcript variant 1, GenBank_NM_001038.5 (SEQ ID NO: 1))

| SEQ ID No. | alpha-ENaC 19-mer Target Sequences (5' → 3') | Corresponding Positions on SEQ ID NO: 1 |
|---|---|---|
| 14 | AGAGCAGAAUGACUUCAUU | 1291-1309 |
| 15 | CUACCAGACAUACUCAUCA | 1000-1018 |
| 16 | UCUACCAGACAUACUCAUC | 999-1017 |
| 17 | CUUUGACCUGUACAAAUAC | 763-781 |
| 18 | UGGAAGGACUGGAAGAUCG | 944-962 |
| 19 | GGAAGGACUGGAAGAUCGG | 945-963 |
| 20 | CUGUGCCUACAUCUUCUAU | 1579-1597 |

In some embodiments, an alpha-ENaC RNAi agent includes an antisense strand wherein position 19 of the antisense strand (5'→3') is capable of forming a base pair with position 1 of a 19-mer target sequence disclosed in Table 1. In some embodiments, an alpha-ENaC agent includes an antisense strand wherein position 1 of the antisense strand (5'→3') is capable of forming a base pair with position 19 of a 19-mer target sequence disclosed in Table 1.

In some embodiments, an alpha-ENaC agent includes an antisense strand wherein position 2 of the antisense strand (5'→3') is capable of forming a base pair with position 18 of a 19-mer target sequence disclosed in Table 1. In some embodiments, an alpha-ENaC agent includes an antisense strand wherein positions 2 through 18 of the antisense strand (5'→3') are capable of forming base pairs with each of the respective complementary bases located at positions 18 through 2 of the 19-mer target sequence disclosed in Table 1.

For the RNAi agents disclosed herein, the nucleotide at position 1 of the antisense strand (from 5' end→3' end) can be perfectly complementary to the alpha-ENaC gene, or can be non-complementary to the alpha-ENaC gene. In some embodiments, the nucleotide at position 1 of the antisense strand (from 5' end→3' end) is a U, A, or dT. In some embodiments, the nucleotide at position 1 of the antisense strand (from 5' end→3' end) forms an A:U or U:A base pair with the sense strand.

In some embodiments, an alpha-ENaC RNAi agent antisense strand comprises the sequence of nucleotides (from 5' end→3' end) 2-18 or 2-19 of any of the antisense strand sequences in Table 2 or Table 3. In some embodiments, an alpha-ENaC RNAi sense strand comprises the sequence of nucleotides (from 5' end→3' end) 1-17, 1-18, or 2-18 of any of the sense strand sequences in Table 2 or Table 4.

In some embodiments, an alpha-ENaC RNAi agent is comprised of (i) an antisense strand comprising the sequence of nucleotides (from 5' end→3' end) 2-18 or 2-19 of any of the antisense strand sequences in Table 2 or Table 3, and (ii) a sense strand comprising the sequence of nucleotides (from 5' end→3' end) 1-17 or 1-18 of any of the sense strand sequences in Table 2 or Table 4.

In some embodiments, the alpha-ENaC RNAi agents include core 19-mer nucleotide sequences shown in the following Table 2.

TABLE 2

Alpha-ENaC RNAi Agent Antisense Strand and Sense Strand Core Stretch Base Sequences (N = any nucleobase)

| SEQ ID NO: | Antisense Strand Base Sequence (5' → 3') (Shown as an Unmodified Nucleotide Sequence) | SEQ ID NO: | Sense Strand Base Sequence (5' → 3') (Shown as an Unmodified Nucleotide Sequence) | Corresponding Positions on SEQ ID NO: 1 |
|---|---|---|---|---|
| 21 | UAUUUGUUCUGGUUGCACA | 60 | UGUGCAACCAGAACAAAUA | 972-990 |
| 22 | AAUUUGUUCUGGUUGCACA | 61 | UGUGCAACCAGAACAAAUU | 972-990 |
| 23 | GAUUUGUUCUGGUUGCACA | 62 | UGUGCAACCAGAACAAAUC | 972-990 |
| 24 | NAUUUGUUCUGGUUGCACA | 63 | UGUGCAACCAGAACAAAUN | 972-990 |
| 25 | NAUUUGUUCUGGUUGCACN | 64 | NGUGCAACCAGAACAAAUN | 972-990 |
| 26 | AAUGAAGUCAUUCUGCUCU | 65 | AGAGCAGAAUGACUUCAUU | 1291-1309 |
| 27 | UAUGAAGUCAUUCUGCUCU | 66 | AGAGCAGAAUGACUUCAUA | 1291-1309 |
| 28 | NAUGAAGUCAUUCUGCUCU | 67 | AGAGCAGAAUGACUUCAUN | 1291-1309 |
| 29 | NAUGAAGUCAUUCUGCUCN | 68 | NGAGCAGAAUGACUUCAUN | 1291-1309 |
| 30 | UGAUGAGUAUGUCUGGUAG | 69 | CUACCAGACAUACUCAUCA | 1000-1018 |
| 31 | NGAUGAGUAUGUCUGGUAG | 70 | CUACCAGACAUACUCAUCN | 1000-1018 |
| 32 | NGAUGAGUAUGUCUGGUAN | 71 | NUACCAGACAUACUCAUCN | 1000-1018 |
| 33 | GAUGAGUAUGUCUGGUAGA | 72 | UCUACCAGACAUACUCAUC | 999-1017 |
| 34 | UAUGAGUAUGUCUGGUAGA | 73 | UCUACCAGACAUACUCAUA | 999-1017 |
| 35 | NAUGAGUAUGUCUGGUAGA | 74 | UCUACCAGACAUACUCAUN | 999-1017 |

TABLE 2-continued

Alpha-ENaC RNAi Agent Antisense Strand and Sense Strand Core Stretch Base Sequences (N = any nucleobase)

| SEQ ID NO: | Antisense Strand Base Sequence (5' → 3') (Shown as an Unmodified Nucleotide Sequence) | SEQ ID NO: | Sense Strand Base Sequence (5' → 3') (Shown as an Unmodified Nucleotide Sequence) | Corresponding Positions on SEQ ID NO: 1 |
|---|---|---|---|---|
| 36 | NAUGAGUAUGUCUGGUAGN | 75 | NCUACCAGACAUACUCAUN | 999-1017 |
| 37 | CGAUUUGUUCUGGUUGCAC | 76 | GUGCAACCAGAACAAAUCG | 973-991 |
| 38 | UGAUUUGUUCUGGUUGCAC | 77 | GUGCAACCAGAACAAAUCA | 973-991 |
| 39 | NGAUUUGUUCUGGUUGCAC | 78 | GUGCAACCAGAACAAAUCN | 973-991 |
| 40 | NGAUUUGUUCUGGUUGCAN | 79 | NUGCAACCAGAACAAAUCN | 973-991 |
| 41 | GUAUUUGUACAGGUCAAAG | 80 | CUUUGACCUGUACAAAUAC | 763-781 |
| 42 | UUAUUUGUACAGGUCAAAG | 81 | CUUUGACCUGUACAAAUAA | 763-781 |
| 43 | NUAUUUGUACAGGUCAAAG | 82 | CUUUGACCUGUACAAAUAN | 763-781 |
| 44 | NUAUUUGUACAGGUCAAAN | 83 | NUUUGACCUGUACAAAUAN | 763-781 |
| 45 | CGAUCUUCCAGUCCUUCCA | 84 | UGGAAGGACUGGAAGAUCG | 944-962 |
| 46 | UGAUCUUCCAGUCCUUCCA | 85 | UGGAAGGACUGGAAGAUCA | 944-962 |
| 47 | NGAUCUUCCAGUCCUUCCA | 86 | UGGAAGGACUGGAAGAUCN | 944-962 |
| 48 | NGAUCUUCCAGUCCUUCCN | 87 | NGGAAGGACUGGAAGAUCN | 944-962 |
| 49 | CCGAUCUUCCAGUCCUUCC | 88 | GGAAGGACUGGAAGAUCGG | 945-963 |
| 50 | UCGAUCUUCCAGUCCUUCC | 89 | GGAAGGACUGGAAGAUCGA | 945-963 |
| 51 | NCGAUCUUCCAGUCCUUCC | 90 | GGAAGGACUGGAAGAUCGN | 945-963 |
| 52 | NCGAUCUUCCAGUCCUUCN | 91 | NGAAGGACUGGAAGAUCGN | 945-963 |
| 53 | UGAAGUCAUUCUGCUCUGC | 92 | GCAGAGCAGAAUGACUUCA | 1289-1307 |
| 54 | NGAAGUCAUUCUGCUCUGC | 93 | GCAGAGCAGAAUGACUUCN | 1289-1307 |
| 55 | NGAAGUCAUUCUGCUCUGN | 94 | NCAGAGCAGAAUGACUUCN | 1289-1307 |
| 56 | AUAGAAGAUGUAGGCACAG | 95 | CUGUGCCUACAUCUUCUAU | 1579-1597 |
| 57 | UUAGAAGAUGUAGGCACAG | 96 | CUGUGCCUACAUCUUCUAA | 1579-1597 |
| 58 | NUAGAAGAUGUAGGCACAG | 97 | CUGUGCCUACAUCUUCUAN | 1579-1597 |
| 59 | NUAGAAGAUGUAGGCACAN | 98 | NUGUGCCUACAUCUUCUAN | 1579-1597 |

The alpha-ENaC RNAi agent sense strands and antisense strands that comprise or consist of the nucleotide sequences in Table 2 can be modified nucleotides or unmodified nucleotides. In some embodiments, the alpha-ENaC RNAi agents having the sense and antisense strand sequences that comprise or consist of any of the nucleotide sequences in Table 2 are all or substantially all modified nucleotides.

In some embodiments, the antisense strand of an alpha-ENaC RNAi agent disclosed herein differs by 0, 1, 2, or 3 nucleotides from any of the antisense strand sequences in Table 2. In some embodiments, the sense strand of an alpha-ENaC RNAi agent disclosed herein differs by 0, 1, 2, or 3 nucleotides from any of the sense strand sequences in Table 2.

As used herein, each N listed in a sequence disclosed in Table 2 may be independently selected from any and all nucleobases (including those found on both modified and unmodified nucleotides). In some embodiments, an N nucleotide listed in a sequence disclosed in Table 2 has a nucleobase that is complementary to the N nucleotide at the corresponding position on the other strand. In some embodiments, an N nucleotide listed in a sequence disclosed in Table 2 has a nucleobase that is not complementary to the N nucleotide at the corresponding position on the other strand. In some embodiments, an N nucleotide listed in a sequence disclosed in Table 2 has a nucleobase that is the same as the N nucleotide at the corresponding position on the other strand. In some embodiments, an N nucleotide listed in a sequence disclosed in Table 2 has a nucleobase that is different from the N nucleotide at the corresponding position on the other strand.

Certain modified alpha-ENaC RNAi agent sense and antisense strands are provided in Table 3 and Table 4. Modified alpha-ENaC RNAi agent antisense strands, as well as their underlying unmodified nucleobase sequences, are provided in Table 3. Modified alpha-ENaC RNAi agent sense strands, as well as their underlying unmodified nucleobase sequences, are provided in Table 4. In forming alpha-ENaC RNAi agents, each of the nucleotides in each of the underlying base sequences listed in Tables 3 and 4, as well as in Table 2, above, can be a modified nucleotide.

The alpha-ENaC RNAi agents described herein are formed by annealing an antisense strand with a sense strand. A sense strand containing a sequence listed in Table 2, or Table 4 can be hybridized to any antisense strand containing a sequence listed in Table 2 or Table 3, provided the two sequences have a region of at least 85% complementarity over a contiguous 16, 17, 18, 19, 20, or 21 nucleotide sequence.

In some embodiments, an alpha-ENaC RNAi agent antisense strand comprises a nucleotide sequence of any of the sequences in Table 2 or Table 3.

In some embodiments, an alpha-ENaC RNAi agent comprises or consists of a duplex having the nucleobase sequences of the sense strand and the antisense strand of any of the sequences in Table 2, Table 3, or Table 4.

Examples of antisense strands containing modified nucleotides are provided in Table 3. Examples of sense strands containing modified nucleotides are provided in Table 4.

As used in Tables 3 and 4, the following notations are used to indicate modified nucleotides, targeting groups, and linking groups:

A=adenosine-3'-phosphate
C=cytidine-3'-phosphate
G=guanosine-3'-phosphate
U=uridine-3'-phosphate
I=inosine-3'-phosphate
a=2'-O-methyladenosine-3'-phosphate
as =2'-O-methyladenosine-3'-phosphorothioate
c=2'-O-methylcytidine-3'-phosphate
cs=2'-O-methylcytidine-3'-phosphorothioate
g=2'-O-methylguanosine-3'-phosphate
gs=2'-O-methylguanosine-3'-phosphorothioate
i=2'-O-methylinosine-3'-phosphate
is=2'-O-methylinosine-3'-phosphorothioate
t=2'-O-methyl-5-methyluridine-3'-phosphate
ts=2'-O-methyl-5-methyluridine-3'-phosphorothioate
u=2'-O-methyluridine-3'-phosphate
us=2'-O-methyluridine-3'-phosphorothioate
Nf=any 2'-fluoro modified nucleotide
Af=2'-fluoroadenosine-3'-phosphate
Afs=2'-fluoroadenosine-3'-phosporothioate
Cf=2'-fluorocytidine-3'-phosphate
Cfs=2'-fluorocytidine-3'-phosphorothioate
Gf=2'-fluoroguanosine-3'-phosphate
Gfs=2'-fluoroguanosine-3'-phosphorothioate
Tf=2'-fluoro-5'-methyluridine-3'-phosphate
Tfs=2'-fluoro-5'-methyluridine-3'-phosphorothioate
Uf=2'-fluorouridine-3'-phosphate
Ufs=2'-fluorouridine-3'-phosphorothioate
dN=any 2'-deoxyribonucleotide
dT=2'-deoxythymidine-3'-phosphate
$N_{UNA}$=2',3'-seco nucleotide mimics (unlocked nucleobase analogs)-3'-Phosphate
$N_{UNAS}$=2',3'-seco nucleotide mimics (unlocked nucleobase analogs)-3'-Phosphorothioate
$A_{UNA}$=2',3'-seco-adenosine-3'-phosphate
$A_{UNAS}$=2',3'-seco-adenosine-3'-phosphorothioate
$C_{UNA}$=2',3'-seco-cytidine-3'-phosphate
$C_{UNAS}$=2',3'-seco-cytidine-3'-phosphorothioate
$G_{UNA}$=2',3'-seco-guanosine-3'-phosphate
$G_{UNAS}$=2',3'-seco-guanosine-3'-phosphorothioate
$U_{UNA}$=2',3'-seco-uridine-3'-phosphate
$U_{UNAS}$=2',3'-seco-uridine-3'-phosphorothioate
a_2N=see Table 7
a_2Ns=see Table 7
pu_2N=see Table 7
pu_2Ns=see Table 7
D2us=see Table 7
Npu=see Table 7
Nus=see Table 7
$N_{LNA}$=locked nucleotide
$Nf_{ANA}$=2'-F-Arabino nucleotide
NM=2'-O-(2-methoxyethyl) nucleotide
AM=2'-O-(2-methoxyethyl)adenosine-3'-phosphate
AMs=2'-O-(2-methoxyethyl)adenosine-3'-phosphorothioate
TM=2'-O-(2-methoxyethyl)thymidine-3'-phosphate
TMs=2'-O-(2-methoxyethyl)thymidine-3'-phosphorothioate
R=ribitol
(invdN)=any inverted deoxyribonucleotide (3'-3' linked nucleotide)
(invAb)=inverted (3'-3' linked) abasic deoxyribonucleotide-5'-phosphate, see Table 7
(invAb)s=inverted (3'-3' linked) abasic deoxyribonucleotide-5'-phosphorothioate, see Table 7
(invn)=any inverted 2'-OMe nucleotide (3'-3' linked nucleotide)
s=phosphorothioate linkage
vpdN=vinyl phosphonate deoxyribonucleotide
(5Me-Nf)=5'-Me, 2'-fluoro nucleotide
cPrp=cyclopropyl phosphonate, see Table 7
epTcPr=see Table 7
epTM=see Table 7
spus=see Table 7
(Chol-TEG)=see Table 7
(TEG-Biotin)=see Table 7
(PEG-C3-SS)=see Table 7
(Alk-SS-C6)=see Table 7
(C6-SS-Alk)=see Table 7
(C6-SS-C6)=see Table 7
(6-SS-6)=see Table 7
(C6-SS-Alk-Me)=see Table 7
(NH2-C6)=see Table 7
(TriAlk #)=see Table 7
(TriAlk #)s=see Table 7

As the person of ordinary skill in the art would readily understand, unless otherwise indicated by the sequence (such as, for example, by a phosphorothioate linkage "s"), when present in an oligonucleotide, the nucleotide monomers are mutually linked by 5'-3'-phosphodiester bonds. Further, the person of ordinary skill in the art would readily understand that the terminal nucleotide at the 3' end of a given oligonucleotide sequence would typically have a hydroxyl (—OH) group at the respective 3' position of the given monomer instead of a phosphate moiety ex vivo. Moreover, as the person of ordinary skill would readily understand and appreciate, while the phosphorothioate chemical structures depicted herein typically show the anion on the sulfur atom, the inventions disclosed herein encompass all phosphorothioate tautomers and/or diastereomers (e.g., where the sulfur atom has a double-bond and the anion is on an oxygen atom). Unless expressly indicated otherwise herein, such understandings of the person of ordinary skill in the art are used when describing the alpha-ENaC RNAi agents and compositions of alpha-ENaC RNAi agents disclosed herein.

Certain examples of targeting groups and linking groups used with the alpha-ENaC RNAi agents disclosed herein are included in the chemical structures provided below in Table 6. Each sense strand and/or antisense strand can have any targeting groups or linking groups listed herein, as well as other targeting or linking groups, conjugated to the 5' and/or 3' end of the sequence.

TABLE 3

Alpha-ENaC RNAi Agent Antisense Strand Sequences

| AS Strand ID | Modified Antisense Strand (5' → 3') | SEQ ID NO. | Underlying Base Sequence (5' → 3') (Shown as an Unmodified Nucleotide Sequence) | SEQ ID NO. |
|---|---|---|---|---|
| AM04730-AS | usAfsusuuGfuUfcUfgGfuUfgCfaCfaGfcusg | 99 | UAUUUGUUCUGGUUGCACAGCUG | 224 |
| AM05080-AS | usAfsusUfuGfuUfcUfgGfuUfgCfaCfaGfcusg | 100 | UAUUUGUUCUGGUUGCACAGCUG | 224 |
| AM05081-AS | usAfsusUfuGfuUfcUfgGfuUfgCfaCfaGfsc | 6 | UAUUUGUUCUGGUUGCACAGC | 7 |
| AM05082-AS | usAfsusUfuGfuUfcUfgGfuUfgCfaCfagsc | 101 | UAUUUGUUCUGGUUGCACAGC | 7 |
| AM05083-AS | usAfsusUfuGfuUfcUfgGfuUfgCfaCfausu | 102 | UAUUUGUUCUGGUUGCACAUU | 226 |
| AM05084-AS | vpusAfsusUfuGfuUfcUfgGfuUfgCfaCfaGfsc | 103 | UAUUUGUUCUGGUUGCACAGC | 7 |
| AM05085-AS | asAfsusUfuGfuUfcUfgGfuUfgCfaCfagsc | 104 | AAUUUGUUCUGGUUGCACAGC | 227 |
| AM05772-AS | usAfsusGfaAfgUfcAfuUfcUfgCfuCfuGfsc | 105 | UAUGAAGUCAUUCUGCUCUGC | 228 |
| AM05773-AS | usGfsasUfgAfgUfaUfgUfcUfgGfuAfgAfsa | 106 | UGAUGAGUAUGUCUGGUAGAA | 229 |
| AM05774-AS | usGfsasUfuGfuUfcUfgGfuUfgCfAfcAfsg | 107 | UGAUUUGUUCUGGUUGCACAG | 230 |
| AM05775-AS | usAfsusGfaGfuAfuGfuCfuGfgUfaGfaAfsg | 108 | UAUGAGUAUGUCUGGUAGAAG | 231 |
| AM05776-AS | usUfsasUfuUfgUfaCfaGfgUfcAfaAfgAfsg | 109 | UUAUUUGUACAGGUCAAAGAG | 232 |
| AM05777-AS | usAfsusGfaAfgUfcFAfuUfcUfgCfuCfuGfsc | 110 | UAUGAAGUCAUUCUGCUCUGC | 228 |
| AM05778-AS | usGfsasUfgAfgUfAfUfgUfcUfgGfuAfgAfsa | 111 | UGAUGAGUAUGUCUGGUAGAA | 229 |
| AM05779-AS | usGfsasUfuUfgUfUfCfuGfgUfuGfcAfcAfsg | 112 | UGAUUUGUUCUGGUUGCACAG | 230 |
| AM05780-AS | usAfsusGfaGfuAfUfGfuCfuGfgUfaGfaAfsg | 113 | UAUGAGUAUGUCUGGUAGAAG | 231 |
| AM05781-AS | usUfsasUfuUfgUfAfCfaGfgUfcAfaAfgAfsg | 114 | UUAUUUGUACAGGUCAAAGAG | 232 |
| AM05782-AS | usAfsusGfaAfgUfcFAfuUfcUfgCfuCfuusu | 115 | UAUGAAGUCAUUCUGCUCUUU | 233 |
| AM05783-AS | usGfsasUfgAfgUfAfUfgUfcUfgGfuAfgusu | 116 | UGAUGAGUAUGUCUGGUAGUU | 234 |
| AM05784-AS | usGfsasUfuUfgUfUfCfuGfgUfuGfcAfcusu | 117 | UGAUUUGUUCUGGUUGCACUU | 235 |
| AM05785-AS | usAfsusGfaGfuAfUfGfuCfuGfgUfaGfausu | 118 | UAUGAGUAUGUCUGGUAGAUU | 236 |
| AM05786-AS | usUfsasUfuUfgUfAfCfaGfgUfcAfaAfgusu | 119 | UUAUUUGUACAGGUCAAAGUU | 237 |
| AM05916-AS | cPrpusAfuUfuGfuUfcUfgGfuUfgCfaCfaGfsc | 120 | UAUUUGUUCUGGUUGCACAGC | 7 |
| AM05917-AS | cPrpusAfsusUfuGfuUfcUfgGfuUfgCfaCfaGfsc | 121 | UAUUUGUUCUGGUUGCACAGC | 7 |
| AM06240-AS | cPrpuAfuUfuGfuUfcUfgGfuUfgCfaCfaGfc | 122 | UAUUUGUUCUGGUUGCACAGC | 7 |
| AM06460-AS | cPrpuAfuUfuGfuUfcUfgGfuUfgCfaCfaGfc(invAb) | 123 | UAUUUGUUCUGGUUGCACAGC | 7 |
| AM06461-AS | cPrpuAfuUfuGfuUfcUfgGfuUfgCfaCfaGfsc | 124 | UAUUUGUUCUGGUUGCACAGC | 7 |
| AM06462-AS | cPrpusAfsuUfuGfuUfcUfgGfuUfgCfaCfaGfsc | 125 | UAUUUGUUCUGGUUGCACAGC | 7 |
| AM06691-AS | usGfsasUfcUfuCfcAfgUfcCfuUfcCfaGfsu | 126 | UGAUCUUCCAGUCCUUCCAGU | 238 |
| AM06693-AS | usCfsgsAfuCfuUfcCfaGfuCfcUfuCfcAfsg | 127 | UCGAUCUUCCAGUCCUUCCAG | 239 |
| AM06695-AS | usGfsasAfgUfcAfuUfcUfgCfuCfuGfcGfsc | 128 | UGAAGUCAUUCUGCUCUGCGC | 240 |
| AM06697-AS | asUfsasGfaAfgAfuAfgGfcAfcAfgCfsc | 129 | AUAGAAGAUGUAGGCACAGCC | 241 |
| AM06699-AS | usAfsusCfgUfgAfcAfgAfgGfgAfgAfcUfsc | 130 | UAUCGUGACAGAGGGAGACUC | 242 |
| AM06701-AS | usUfsgsAfcCfaUfcGfuGfaCfaGfaGfgGfsa | 131 | UUGACCAUCGUGACAGAGGGA | 243 |

TABLE 3-continued

Alpha-ENaC RNAi Agent Antisense Strand Sequences

| AS Strand ID | Modified Antisense Strand (5' → 3') | SEQ ID NO. | Underlying Base Sequence (5' → 3') (Shown as an Unmodified Nucleotide Sequence) | SEQ ID NO. |
| --- | --- | --- | --- | --- |
| AM06765-AS | cPrpuAfuUfuGfuUfcUfgGfuUfgCfaCfaG$_{UNA}$C$_{UNA}$ | 132 | UAUUUGUUCUGGUUGCACAGC | 7 |
| AM06766-AS | cPrpuAfuUfuGfuUfcUfgGfuUfgCfaCfaGfC$_{UNA}$U$_{UNA}$ | 133 | UAUUUGUUCUGGUUGCACAGCU | 244 |
| AM06767-AS | cPrpuAfuUfuGfuUfcUfgGfuUfgCfaCfaGfcU$_{UNA}$U$_{UNA}$ | 134 | UAUUUGUUCUGGUUGCACAGCUU | 245 |
| AM07066-AS | cPrpusAfsusUfuGfuUfcUfgGfuUfgCfaCfaGfsg | 10 | UAUUUGUUCUGGUUGCACAGG | 3 |
| AM07170-AS | cPrpusAfsusUfuGfuU$_{UNA}$UfcUfgGfuUfgCfaCfaGfsg | 135 | UAUUUGUUCUGGUUGCACAGG | 3 |
| AM07174-AS | cPrpusAfsusUfuGfuUfcUfgGfuUfgCfaCfaGfsu | 136 | UAUUUGUUCUGGUUGCACAGU | 247 |
| AM07200-AS | usAfsusUfuGfuUfcUfgGfuUfgCfaCfaGfsg | 2 | UAUUUGUUCUGGUUGCACAGG | 3 |
| AM07204-AS | usAfsusUfuGfuU$_{UNA}$UfcUfgGfuUfgCfaCfaGfsg | 137 | UAUUUGUUCUGGUUGCACAGG | 3 |
| AM07206-AS | usAfsusUfuGfuUfcUfgGfuUfgCfaCfgGfsg | 138 | UAUUUGUUCUGGUUGCACGGG | 248 |
| AM07208-AS | usAfsusUfuGfuUfcUfgGfuUfgCfaCfgGfsu | 139 | UAUUUGUUCUGGUUGCACGGU | 249 |
| AM07333-AS | usAfsusUfuGfuUfcUfgGfuUfgCfaCfcGfsu | 140 | UAUUUGUUCUGGUUGCACCGU | 250 |
| AM07335-AS | usAfsusUfuGfuUfcUfgGfuUfgCfaCfaGfsu | 141 | UAUUUGUUCUGGUUGCACAGU | 247 |
| AM07340-AS | usAfsusUfuGfuUfcUfgGfuUfgCfaCfaGfsa | 142 | UAUUUGUUCUGGUUGCACAGA | 251 |
| AM07409-AS | pusAfsusUfuGfuUfcUfgGfuUfgCfaCfaGfsg | 143 | UAUUUGUUCUGGUUGCACAGG | 3 |
| AM07410-AS | D2usAfsusUfuGfuUfcUfgGfuUfgCfaCfaGfsg | 144 | UAUUUGUUCUGGUUGCACAGG | 3 |
| AM07411-AS | spusAfsusUfuGfuUfcUfgGfuUfgCfaCfaGfsg | 145 | UAUUUGUUCUGGUUGCACAGG | 3 |
| AM07412-AS | epusAfsusUfuGfuUfcUfgGfuUfgCfaCfaGfsg | 146 | UAUUUGUUCUGGUUGCACAGG | 3 |
| AM07484-AS | U$_{UNA}$sAfsusUfuGfuUfcUfgGfuUfgCfaCfaGfsg | 147 | UAUUUGUUCUGGUUGCACAGG | 3 |
| AM07485-AS | isAfsusUfuGfuUfcUfgGfuUfgCfaCfaGfsg | 148 | IAUUUGUUCUGGUUGCACAGG | 252 |
| AM07496-AS | usAfsusUfuguucugGfuUfgCfaCfaGfsu | 149 | UAUUUGUUCUGGUUGCACAGU | 247 |
| AM07497-AS | usAfsusUfuguucUfgGfuUfgcaCfaGfsu | 150 | UAUUUGUUCUGGUUGCACAGU | 247 |
| AM07605-AS | TMsAfsusUfuGfuUfcUfgGfuUfgCfaCfaGfsc | 151 | TAUUUGUUCUGGUUGCACAGC | 253 |
| AM07669-AS | asGfsasAfgUfcAfuUfcUfgCfuCfuGfcusu | 152 | AGAAGUCAUUCUGCUCUGCUU | 254 |

TABLE 4

Alpha-ENaC Agent Sense Strand Sequences

| Strand ID | Modified Sense Strand (5' → 3') | SEQ ID NO. | Underlying Base Sequence (5' → 3') (Shown as an Unmodified Nucleotide Sequence) | SEQ ID NO. |
| --- | --- | --- | --- | --- |
| AM05073-SS | gscugugCfaAfcCfaGfaacaaauas(invAb) | 153 | GCUGUGCAACCAGAACAAAUA | 255 |
| AM05074-SS | gscugugcaAfCfCfagaacaaauas(invAb) | 154 | GCUGUGCAACCAGAACAAAUA | 255 |
| AM05075-SS | asaugugcaAfCfCfagaacaaauas(invAb) | 295 | AAUGUGCAACCAGAACAAAUA | 296 |
| AM05077-SS | gscugugcaAfCfCfagaacaaauus(invAb) | 155 | GCUGUGCAACCAGAACAAAUU | 256 |
| AM05487-SS | (NH2-C6)sgscugugcaAfCfCfagaacaaauas(invAb) | 156 | GCUGUGCAACCAGAACAAAUA | 255 |
| AM05787-SS | gscagagcaGfAfAfugacuucaus(invAb) | 157 | GCAGAGCAGAAUGACUUCAUA | 257 |
| AM05788-SS | usucuaccaGfAfCfaucucaucas(invAb) | 158 | UUCUACCAGACAUCUCAUCA | 258 |
| AM05789-SS | csugugcaaCfCfAfgaacaaaucas(invAb) | 159 | CUGUGCAACCAGAACAAAUCA | 259 |

TABLE 4-continued

Alpha-ENaC Agent Sense Strand Sequences

| Strand ID | Modified Sense Strand (5' → 3') | SEQ ID NO. | Underlying Base Sequence (5' → 3') (Shown as an Unmodified Nucleotide Sequence) | SEQ ID NO. |
|---|---|---|---|---|
| AM05790-SS | csuucuaccAfGfAfcauacucauas(invAb) | 160 | CUUCUACCAGACAUACUCAUA | 260 |
| AM05791-SS | csucuuugaCfCfUfguacaaauaas(invAb) | 161 | CUCUUUGACCUGUACAAAUAA | 261 |
| AM05792-SS | (invAb)AfgAfgCfaGfAfAfuGfaCfuUfcauausu(invAb) | 162 | AGAGCAGAAUGACUUCAUAUU | 262 |
| AM05793-SS | (invAb)CfuAfcCfaGfAfCfaUfaCfuCfcaucausu(invAb) | 163 | CUACCAGACAUACUCAUCAUU | 263 |
| AM05794-SS | (invAb)GfuGfcAfaCfCfAfgAfaCfaAfaucausu(invAb) | 164 | GUGCAACCAGAACAAAUCAUU | 264 |
| AM05795-SS | (invAb)UfcUfaCfcAfGfAfcAfuAfcUfcauausu(invAb) | 165 | UCUACCAGACAUACUCAUAUU | 265 |
| AM05796-SS | (invAb)CfuUfuGfaCfCfUfgUfaCfaAfauaausu(invAb) | 166 | CUUUGACCUGUACAAAUAAUU | 266 |
| AM06162-SS | (invAb)gcugugcaAfCfCfagaacaaaua(invAb) | 167 | GCUGUGCAACCAGAACAAAUA | 255 |
| AM06246-SS | gcugugcaAfCfCfagaacaaau(invdA) | 168 | GCUGUGCAACCAGAACAAAUA | 255 |
| AM06459-SS | gcugugcaAfCfCfagaacaaaua(invAb) | 169 | GCUGUGCAACCAGAACAAAUA | 255 |
| AM06690-SS | (NH2-C6)sascuggaagGfAfCfuggaagaucas(invAb) | 170 | ACUGGAAGGACUGGAAGAUCA | 267 |
| AM06692-SS | (NH2-C6)scsuggaaggAfCfUfggaagaucgas(invAb) | 171 | CUGGAAGGACUGGAAGAUCGA | 268 |
| AM06694-SS | (NH2-C6)sgscgcagagCfAfGfaaugacuucas(invAb) | 172 | GCGCAGAGCAGAAUGACUUCA | 269 |
| AM06696-SS | (NH2-C6)sgsgcugugcCfUfAfcaucuucuaus(invAb) | 173 | GGCUGUGCCUACAUCUUCUAU | 270 |
| AM06698-SS | (NH2-C6)sgsagucuccCfUfCfugucacgauas(invAb) | 174 | GAGUCUCCCUCUGUCACGAUA | 271 |
| AM06700-SS | (NH2-C6)suscccucugUfCfAfcgauggucaas(invAb) | 175 | UCCCUCUGUCACGAUGGUCAA | 272 |
| AM07064-SS | (NH2-C6)gscugugcaAfCfCfagaacaaauas(invAb) | 176 | GCUGUGCAACCAGAACAAAUA | 255 |
| AM07065-SS | (NH2-C6)scscugugcaAfCfCfagaacaaauas(invAb) | 177 | CCUGUGCAACCAGAACAAAUA | 273 |
| AM07067-SS | (NH2-C6)cscugugcaAfCfCfagaacaaauas(invAb) | 178 | CCUGUGCAACCAGAACAAAUA | 273 |
| AM07169-SS | (NH2-C6)scscugugcaAfCfCfaGaacaaauas(invAb) | 179 | CCUGUGCAACCAGAACAAAUA | 273 |
| AM07171-SS | (NH2-C6)scscugugcaAfCfCfaiaacaaauas(invAb) | 180 | CCUGUGCAACCAIAACAAAUA | 274 |
| AM07172-SS | (NH2-C6)scscugugcaAfCfCfagaacaa_2Nauas(invAb) | 181 | CCUGUGCAACCAGAACA(A$^{2n}$)AUA | 275 |
| AM07173-SS | (NH2-C6)sascugugcaAfCfCfagaacaaauas(invAb) | 182 | ACUGUGCAACCAGAACAAAUA | 276 |
| AM07201-SS | (NH2-C6)cscugugcaAfCfCfaGaacaaauas(invAb) | 183 | CCUGUGCAACCAGAACAAAUA | 273 |
| AM07202-SS | (NH2-C6)cscugugcaAfCfCfaiaacaaauas(invAb) | 184 | CCUGUGCAACCAIAACAAAUA | 274 |
| AM07203-SS | (NH2-C6)cscugugcaAfCfCfUfagaacaaauas(invAb) | 185 | CCUGUGCAACUAGAACAAAUA | 277 |
| AM07205-SS | (NH2-C6)csccgugcaAfCfCfagaacaaauas(invAb) | 186 | CCCGUGCAACCAGAACAAAUA | 278 |
| AM07207-SS | (NH2-C6)asccgugcaAfCfCfagaacaaauas(invAb) | 187 | ACCGUGCAACCAGAACAAAUA | 279 |
| AM07217-SS | (NH2-C6)cscugugcaAfCfCfagaacaaauas(invAb)s(C6-SS-C6) | 188 | CCUGUGCAACCAGAACAAAUA | 273 |
| AM07218-SS | (NH2-C6)cscugugcaAfCfCfagaacaaauas(invAb)(C6-SS-C6) | 189 | CCUGUGCAACCAGAACAAAUA | 273 |
| AM07276-SS | (TriAlk1)sgscugugcaAfCfCfagaacaaauas(invAb) | 190 | GCUGUGCAACCAGAACAAAUA | 255 |
| AM07280-SS | (NH2-C6)cscugugcaAfCfCfagaacaaauas(invAb)s(6-SS-6) | 191 | CCUGUGCAACCAGAACAAAUA | 273 |
| AM07281-SS | (NH2-C6)cscugugcaAfCfCfagaacaaauas(invAb)(6-SS-6) | 192 | CCUGUGCAACCAGAACAAAUA | 273 |
| AM07329-SS | (TriAlk1)cscugugcaAfCfCfagaacaaauas(invAb) | 193 | CCUGUGCAACCAGAACAAAUA | 273 |
| AM07330-SS | (TriAlk2)cscugugcaAfCfCfagaacaaauas(invAb) | 194 | CCUGUGCAACCAGAACAAAUA | 273 |

TABLE 4-continued

Alpha-ENaC Agent Sense Strand Sequences

| Strand ID | Modified Sense Strand (5' → 3') | SEQ ID NO. | Underlying Base Sequence (5' → 3') (Shown as an Unmodified Nucleotide Sequence) | SEQ ID NO. |
|---|---|---|---|---|
| AM07331-SS | (TriAlk3)cscugugcaAfCfCfagaacaaauas(invAb) | 195 | CCUGUGCAACCAGAACAAAUA | 273 |
| AM07332-SS | (NH2-C6)ascggugcaAfCfCfagaacaaauas(invAb) | 196 | ACGGUGCAACCAGAACAAAUA | 280 |
| AM07334-SS | (NH2-C6)ascugugcaAfCfCfagaacaaauas(invAb) | 197 | ACUGUGCAACCAGAACAAAUA | 276 |
| AM07336-SS | (NH2-C6)ascugugcaAfCfCfagaacaaa_2Nuas(invAb) | 198 | ACUGUGCAACCAGAACAA(A$^{2n}$)UA | 281 |
| AM07337-SS | (NH2-C6)ascugugcaAfCfCfagaacaa_2Nauas(invAb) | 199 | ACUGUGCAACCAGAACA(A$^{2n}$)AUA | 282 |
| AM07338-SS | (NH2-C6)ascugugcaAfCfCfagaaca_2Naauas(invAb) | 200 | ACUGUGCAACCAGAAC(A$^{2n}$)AAUA | 283 |
| AM07339-SS | (NH2-C6)uscugugcaAfCfCfagaacaaauas(invAb) | 201 | UCUGUGCAACCAGAACAAAUA | 284 |
| AM07341-SS | (NH2-C6)cscugugcaAfCfCfagaaca_2Nauas(invAb) | 202 | CCUGUGCAACCAGAACA(A$^{2n}$)AUA | 285 |
| AM07342-SS | (NH2-C6)cscugugcaAfCfCfaGaacaa_2Nauas(invAb) | 203 | CCUGUGCAACCAGAACA(A$^{2n}$)AUA | 275 |
| AM07343-SS | (NH2-C6)cscugugcaAfCfCfagaacaaa_2Nuas(invAb) | 204 | CCUGUGCAACCAGAACAA(A$^{2n}$)UA | 286 |
| AM07344-SS | (NH2-C6)cscugugcaAfCfCfagaaca_2Naauas(invAb) | 205 | CCUGUGCAACCAGAAC(A$^{2n}$)AAUA | 287 |
| AM07400-SS | (TriAlk4)cscugugcaAfCfCfagaacaaauas(invAb) | 206 | CCUGUGCAACCAGAACAAAUA | 273 |
| AM07401-SS | (TriAlk5)cscugugcaAfCfCfagaacaaauas(invAb) | 207 | CCUGUGCAACCAGAACAAAUA | 273 |
| AM07402-SS | (TriAlk6)cscugugcaAfCfCfagaacaaauas(invAb) | 208 | CCUGUGCAACCAGAACAAAUA | 273 |
| AM07486-SS | (NH2-C6)cscugugcaAfCfCfagaacaaaucs(invAb) | 209 | CCUGUGCAACCAGAACAAAUC | 288 |
| AM07495-SS | (NH2-C6)ascUfgUfgCfaAfCfCfagaacaaauas(invAb) | 210 | ACUGUGCAACCAGAACAAAUA | 276 |
| AM07498-SS | (NH2-C6)ascUfgUfgCfaAfcCfaGfaacaaauas(invAb) | 211 | ACUGUGCAACCAGAACAAAUA | 276 |
| AM07499-SS | (NH2-C6)ascUfgUfgCfaAfCfCfagaacaa_2Nauas(invAb) | 212 | ACUGUGCAACCAGAACA(A$^{2n}$)AUA | 282 |
| AM07594-SS | (TriAlk7)cscugugcaAfCfCfagaacaaauas(invAb) | 213 | CCUGUGCAACCAGAACAAAUA | 273 |
| AM07595-SS | (TriAlk8)cscugugcaAfCfCfagaacaaauas(invAb) | 214 | CCUGUGCAACCAGAACAAAUA | 273 |
| AM07606-SS | (NH2-C6)sgscugugcaAfCfCfagaacaaauas(invAb)(C6-SS-C6)(invAb) | 215 | GCUGUGCAACCAGAACAAAUA | 255 |
| AM07611-SS | (TriAlk9)cscugugcaAfCfCfagaacaaauas(invAb) | 216 | CCUGUGCAACCAGAACAAAUA | 273 |
| AM07612-SS | (TriAlk10)cscugugcaAfCfCfagaacaaauas(invAb) | 217 | CCUGUGCAACCAGAACAAAUA | 273 |
| AM07665-SS | (NH2-C6)ascuggaagGfAfCfuggaagaucas(invAb) | 218 | ACUGGAAGGACUGGAAGAUCA | 267 |
| AM07666-SS | (NH2-C6)scsugugcaaCfCfAfgaacaaaucs(invAb) | 219 | CUGUGCAACCAGAACAAAUCA | 259 |
| AM07667-SS | (NH2-C6)csugugcaaCfCfAfgaacaaaucs(invAb) | 220 | CUGUGCAACCAGAACAAAUCA | 259 |
| AM07668-SS | (NH2-C6)sgscagagCfAfGfaaugacuucuuus(invAb) | 221 | GCAGAGCAGAAUGACUUCUUU | 289 |
| AM07670-SS | (NH2-C6)gscagagCfAfGfaaugacuucuuus(invAb) | 222 | GCAGAGCAGAAUGACUUCUUU | 289 |
| AM07807-SS | (TriAlk14)cscugugcaAfCfCfagaacaaauas(invAb) | 223 | CCUGUGCAACCAGAACAAAUA | 273 |

($A^{2N}$) = 2-aminoadenine nucleotide

The alpha-ENaC RNAi agents disclosed herein are formed by annealing an antisense strand with a sense strand. A sense strand containing a sequence listed in Table 2 or Table 4 can be hybridized to any antisense strand containing a sequence listed in Table 2 or Table 3, provided the two sequences have a region of at least 85% complementarity over a contiguous 16, 17, 18, 19, 20, or 21 nucleotide sequence.

In some embodiments, the antisense strand of an alpha-ENaC RNAi agent disclosed herein differs by 0, 1, 2, or 3 nucleotides from any of the antisense strand sequences in Table 3. In some embodiments, the sense strand of an alpha-ENaC RNAi agent disclosed herein differs by 0, 1, 2, or 3 nucleotides from any of the sense strand sequences in Table 4.

In some embodiments, an alpha-ENaC RNAi agent antisense strand comprises a nucleotide sequence of any of the sequences in Table 2 or Table 3. In some embodiments, an alpha-ENaC RNAi agent antisense strand comprises the sequence of nucleotides (from 5' end→3' end) 1-17, 2-17, 1-18, 2-18, 1-19, 2-19, 1-20, 2-20, 1-21, 2-21, 1-22, 2-22, 1-23, 2-23, 1-24, or 2-24 of any of the sequences in Table 2 or Table 3. In certain embodiments, an alpha-ENaC RNAi agent antisense strand comprises or consists of a modified sequence of any one of the modified sequences in Table 3.

In some embodiments, an alpha-ENaC RNAi agent sense strand comprises the nucleotide sequence of any of the sequences in Table 2 or Table 4. In some embodiments, an alpha-ENaC RNAi agent sense strand comprises the sequence of nucleotides (from 5' end→3' end) 1-17, 2-17, 3-17, 4-17, 1-18, 2-18, 3-18, 4-18, 1-19, 2-19, 3-19, 4-19, 1-20, 2-20, 3-20, 4-20, 1-21, 2-21, 3-21, 4-21, 1-22, 2-22, 3-22, 4-22, 1-23, 2-23, 3-23, 4-23, 1-24, 2-24, 3-24, or 4-24, of any of the sequences in Table 2 or Table 4. In certain embodiments, an alpha-ENaC RNAi agent sense strand comprises or consists of a modified sequence of any one of the modified sequences in Table 3.

For the RNAi agents disclosed herein, the nucleotide at position 1 of the antisense strand (from 5' end→3' end) can be perfectly complementary to the alpha-ENaC gene, or can be non-complementary to the alpha-ENaC gene. In some embodiments, the nucleotide at position 1 of the antisense strand (from 5' end→3' end) is a U, A, or dT (or a modified version of U, A or dT). In some embodiments, the nucleotide at position 1 of the antisense strand (from 5' end→3' end) forms an A:U or U:A base pair with the sense strand.

In some embodiments, an alpha-ENaC RNAi agent antisense strand comprises the sequence of nucleotides (from 5' end→3' end) 2-18 or 2-19 of any of the antisense strand sequences in Table 2 or Table 3. In some embodiments, an alpha-ENaC RNAi sense strand comprises the sequence of nucleotides (from 5' end→3' end) 1-17 or 1-18 of any of the sense strand sequences in Table 2 or Table 4.

In some embodiments, an alpha-ENaC RNAi agent includes (i) an antisense strand comprising the sequence of nucleotides (from 5' end→3' end) 2-18 or 2-19 of any of the antisense strand sequences in Table 2 or Table 3, and (ii) a sense strand comprising the sequence of nucleotides (from 5' end→3' end) 1-17 or 1-18 of any of the sense strand sequences in Table 2 or Table 4.

A sense strand containing a sequence listed in Table 2 or Table 4 can be hybridized to any antisense strand containing a sequence listed in Table 2 or Table 3 provided the two sequences have a region of at least 85% complementarity over a contiguous 16, 17, 18, 19, 20, or 21 nucleotide sequence. In some embodiments, the alpha-ENaC RNAi agent has a sense strand consisting of the modified sequence of any of the modified sequences in Table 4, and an antisense strand consisting of the modified sequence of any of the modified sequences in Table 3. Certain representative sequence pairings are exemplified by the Duplex ID Nos. shown in Table 5.

In some embodiments, an alpha-ENaC RNAi agent comprises, consists of, or consists essentially of a duplex represented by any one of the Duplex ID Nos. presented herein. In some embodiments, an alpha-ENaC RNAi agent consists of any of the Duplex ID Nos. presented herein. In some embodiments, an alpha-ENaC RNAi agent comprises the sense strand and antisense strand nucleotide sequences of any of the Duplex ID Nos. presented herein. In some embodiments, an alpha-ENaC RNAi agent comprises the sense strand and antisense strand nucleotide sequences of any of the Duplex ID Nos. presented herein and a targeting group, linking group, and/or other non-nucleotide group wherein the targeting group, linking group, and/or other non-nucleotide group is covalently linked (i.e., conjugated) to the sense strand or the antisense strand. In some embodiments, an alpha-ENaC RNAi agent includes the sense strand and antisense strand modified nucleotide sequences of any of the Duplex ID Nos. presented herein. In some embodiments, an alpha-ENaC RNAi agent comprises the sense strand and antisense strand modified nucleotide sequences of any of the Duplex ID Nos. presented herein and a targeting group, linking group, and/or other non-nucleotide group, wherein the targeting group, linking group, and/or other non-nucleotide group is covalently linked to the sense strand or the antisense strand.

In some embodiments, an alpha-ENaC RNAi agent comprises an antisense strand and a sense strand having the nucleotide sequences of any of the antisense strand/sense strand duplexes of Table 2 or Table 5, and further comprises a targeting group. In some embodiments, an alpha-ENaC RNAi agent comprises an antisense strand and a sense strand having the nucleotide sequences of any of the antisense strand/sense strand duplexes of Table 2 or Table 5, and further comprises one or more αvβ6 integrin targeting ligands.

In some embodiments, an alpha-ENaC RNAi agent comprises an antisense strand and a sense strand having the nucleotide sequences of any of the antisense strand/sense strand duplexes of Table 2 or Table 5, and further comprises a targeting group that is an integrin targeting ligand. In some embodiments, an alpha-ENaC RNAi agent comprises an antisense strand and a sense strand having the nucleotide sequences of any of the antisense strand/sense strand duplexes of Table 2 or Table 5, and further comprises one or more αvβ6 integrin targeting ligands or clusters of αvβ6 integrin targeting ligands (e.g., a tridentate αvβ6 integrin targeting ligand).

In some embodiments, an alpha-ENaC RNAi agent comprises an antisense strand and a sense strand having the modified nucleotide sequences of any of the antisense strand/sense strand duplexes of Table 5.

In some embodiments, an alpha-ENaC RNAi agent comprises an antisense strand and a sense strand having the modified nucleotide sequences of any of the antisense strand/sense strand duplexes of Table 5, and further comprises an integrin targeting ligand.

In some embodiments, an alpha-ENaC RNAi agent comprises, consists of, or consists essentially of any of the duplexes of Table 5.

TABLE 5

Alpha-ENaC RNAi Agent Duplexes with Corresponding Sense and Antisense Strand ID Numbers

| Duplex ID | Antisense Strand ID | Sense Strand ID |
| --- | --- | --- |
| AD04019 | AM04730-AS | AM05073-SS |
| AD04020 | AM04730-AS | AM05074-SS |
| AD04021 | AM05080-AS | AM05074-SS |
| AD04022 | AM05081-AS | AM05074-SS |
| AD04023 | AM05082-AS | AM05074-SS |
| AD04024 | AM05083-AS | AM05075-SS |
| AD04025 | AM05084-AS | AM05074-SS |
| AD04026 | AM05085-AS | AM05077-SS |
| AD04526 | AM05772-AS | AM05787-SS |
| AD04527 | AM05773-AS | AM05788-SS |
| AD04528 | AM05774-AS | AM05789-SS |
| AD04529 | AM05775-AS | AM05790-SS |
| AD04530 | AM05776-AS | AM05791-SS |
| AD04531 | AM05777-AS | AM05792-SS |
| AD04532 | AM05778-AS | AM05793-SS |

TABLE 5-continued

Alpha-ENaC RNAi Agent Duplexes with Corresponding Sense and Antisense Strand ID Numbers

| Duplex ID | Antisense Strand ID | Sense Strand ID |
|---|---|---|
| AD04533 | AM05779-AS | AM05794-SS |
| AD04534 | AM05780-AS | AM05795-SS |
| AD04535 | AM05781-AS | AM05796-SS |
| AD04536 | AM05782-AS | AM05792-SS |
| AD04537 | AM05783-AS | AM05793-SS |
| AD04538 | AM05784-AS | AM05794-SS |
| AD04539 | AM05785-AS | AM05795-SS |
| AD04540 | AM05786-AS | AM05796-SS |
| AD04835 | AM05917-AS | AM05487-SS |
| AD04858 | AM05917-AS | AM05074-SS |
| AD04859 | AM06240-AS | AM06162-SS |
| AD04976 | AM06460-AS | AM06459-SS |
| AD04977 | AM06461-AS | AM06459-SS |
| AD04978 | AM05916-AS | AM06459-SS |
| AD04979 | AM06462-AS | AM06459-SS |
| AD04980 | AM06462-AS | AM06246-SS |
| AD05116 | AM06691-AS | AM06690-SS |
| AD05117 | AM06693-AS | AM06692-SS |
| AD05118 | AM06695-AS | AM06694-SS |
| AD05119 | AM06697-AS | AM06696-SS |
| AD05120 | AM06699-AS | AM06698-SS |
| AD05121 | AM06701-AS | AM06700-SS |
| AD05160 | AM06240-AS | AM06459-SS |
| AD05161 | AM06765-AS | AM06459-SS |
| AD05162 | AM06766-AS | AM06459-SS |
| AD05163 | AM06767-AS | AM06459-SS |
| AD05345 | AM05917-AS | AM07064-SS |
| AD05346 | AM07066-AS | AM07065-SS |
| AD05347 | AM07066-AS | AM07067-SS |
| AD05426 | AM07066-AS | AM07169-SS |
| AD05427 | AM07170-AS | AM07065-SS |
| AD05428 | AM07066-AS | AM07171-SS |
| AD05429 | AM07066-AS | AM07172-SS |
| AD05430 | AM07174-AS | AM07173-SS |
| AD05453 | AM07200-AS | AM07067-SS |
| AD05454 | AM07200-AS | AM07201-SS |
| AD05455 | AM07200-AS | AM07202-SS |
| AD05456 | AM07200-AS | AM07203-SS |
| AD05457 | AM07204-AS | AM07067-SS |
| AD05458 | AM07206-AS | AM07205-SS |
| AD05459 | AM07208-AS | AM07207-SS |
| AD05471 | AM07066-AS | AM07217-SS |
| AD05472 | AM07066-AS | AM07218-SS |
| AD05473 | AM07200-AS | AM07217-SS |
| AD05474 | AM07200-AS | AM07218-SS |
| AD05515 | AM05081-AS | AM07276-SS |
| AD05548 | AM07200-AS | AM07280-SS |
| AD05549 | AM07200-AS | AM07281-SS |
| AD05558 | AM07200-AS | AM07329-SS |
| AD05559 | AM07200-AS | AM07330-SS |
| AD05560 | AM07200-AS | AM07331-SS |
| AD05561 | AM07333-AS | AM07332-SS |
| AD05562 | AM07335-AS | AM07334-SS |
| AD05563 | AM07335-AS | AM07336-SS |
| AD05564 | AM07335-AS | AM07337-SS |
| AD05565 | AM07335-AS | AM07338-SS |
| AD05566 | AM07340-AS | AM07339-SS |
| AD05567 | AM07200-AS | AM07341-SS |
| AD05568 | AM07200-AS | AM07172-SS |
| AD05569 | AM07200-AS | AM07342-SS |
| AD05570 | AM07200-AS | AM07343-SS |
| AD05571 | AM07200-AS | AM07344-SS |
| AD05611 | AM07200-AS | AM07400-SS |
| AD05612 | AM07200-AS | AM07401-SS |
| AD05613 | AM07200-AS | AM07402-SS |
| AD05618 | AM07409-AS | AM07067-SS |
| AD05619 | AM07410-AS | AM07067-SS |
| AD05622 | AM07411-AS | AM07067-SS |
| AD05623 | AM07412-AS | AM07067-SS |
| AD05625 | AM05081-AS | AM05487-SS |
| AD05671 | AM07484-AS | AM07067-SS |
| AD05672 | AM07485-AS | AM07067-SS |
| AD05673 | AM07485-AS | AM07486-SS |
| AD05683 | AM07174-AS | AM07334-SS |
| AD05684 | AM07335-AS | AM07495-SS |
| AD05685 | AM07496-AS | AM07495-SS |
| AD05686 | AM07497-AS | AM07334-SS |
| AD05687 | AM07496-AS | AM07498-SS |
| AD05688 | AM07174-AS | AM07337-SS |
| AD05689 | AM07335-AS | AM07499-SS |
| AD05690 | AM07496-AS | AM07499-SS |
| AD05691 | AM07497-AS | AM07337-SS |
| AD05757 | AM07200-AS | AM07594-SS |
| AD05758 | AM07200-AS | AM07595-SS |
| AD05772 | AM07605-AS | AM05487-SS |
| AD05773 | AM05081-AS | AM07606-SS |
| AD05778 | AM07200-AS | AM07611-SS |
| AD05779 | AM07200-AS | AM07612-SS |
| AD05829 | AM06691-AS | AM07665-SS |
| AD05830 | AM05774-AS | AM07666-SS |
| AD05831 | AM05774-AS | AM07667-SS |
| AD05832 | AM07669-AS | AM07668-SS |
| AD05833 | AM07669-AS | AM07670-SS |
| AD05924 | AM07200-AS | AM07807-SS |

In some embodiments, an alpha-ENaC RNAi agent is prepared or provided as a salt, mixed salt, or a free-acid. The RNAi agents described herein, upon delivery to a cell expressing an alpha-ENaC gene, inhibit or knockdown expression of one or more alpha-ENaC genes in vivo and/or in vitro.

Targeting Groups, Linking Groups, Pharmacokinetic (PK) Modulators, and Delivery Vehicles In some embodiments, an alpha-ENaC RNAi agent contains or is conjugated to one or more non-nucleotide groups including, but not limited to, a targeting group, a linking group, a pharmacokinetic (PK) modulator, a delivery polymer, or a delivery vehicle. The non-nucleotide group can enhance targeting, delivery, or attachment of the RNAi agent. Examples of targeting groups and linking groups are provided in Table 6. The non-nucleotide group can be covalently linked to the 3' and/or 5' end of either the sense strand and/or the antisense strand. In some embodiments, an alpha-ENaC RNAi agent contains a non-nucleotide group linked to the 3' and/or 5' end of the sense strand. In some embodiments, a non-nucleotide group is linked to the 5' end of an alpha-ENaC RNAi agent sense strand. A non-nucleotide group can be linked directly or indirectly to the RNAi agent via a linker/linking group. In some embodiments, a non-nucleotide group is linked to the RNAi agent via a labile, cleavable, or reversible bond or linker.

In some embodiments, a non-nucleotide group enhances the pharmacokinetic or biodistribution properties of an RNAi agent or conjugate to which it is attached to improve cell- or tissue-specific distribution and cell-specific uptake of the conjugate. In some embodiments, a non-nucleotide group enhances endocytosis of the RNAi agent.

Targeting groups or targeting moieties enhance the pharmacokinetic or biodistribution properties of a conjugate or RNAi agent to which they are attached to improve cell-specific (including, in some cases, organ specific) distribution and cell-specific (or organ specific) uptake of the conjugate or RNAi agent. A targeting group can be monovalent, divalent, trivalent, tetravalent, or have higher valency for the target to which it is directed. Representative targeting groups include, without limitation, compounds with affinity to cell surface molecule, cell receptor ligands, hapten, antibodies, monoclonal antibodies, antibody fragments, and antibody mimics with affinity to cell surface molecules. In some embodiments, a targeting group is linked to an RNAi agent using a linker, such as a PEG linker or one, two, or three abasic and/or ribitol (abasic ribose) residues, which in some instances can serve as linkers. In some embodiments, a targeting group comprises an integrin targeting ligand.

The alpha-ENaC RNAi agents described herein can be synthesized having a reactive group, such as an amino group (also referred to herein as an amine), at the 5'-terminus and/or the 3'-terminus. The reactive group can be used subsequently to attach a targeting moiety using methods typical in the art.

For example, in some embodiments, the alpha-ENaC RNAi agents disclosed herein are synthesized having an NH2-C6 group at the 5'-terminus of the sense strand of the RNAi agent. The terminal amino group subsequently can be reacted to form a conjugate with, for example, a group that includes an αvβ6 integrin targeting ligand. In some embodiments, the alpha-ENaC RNAi agents disclosed herein are synthesized having one or more alkyne groups at the 5'-terminus of the sense strand of the RNAi agent. The terminal alkyne group(s) can subsequently be reacted to form a conjugate with, for example, a group that includes an αvβ6 integrin targeting ligand.

In some embodiments, a targeting group comprises an integrin targeting ligand. In some embodiments, an integrin targeting ligand is an αvβ6 integrin targeting ligand. The use of an αvβ6 integrin targeting ligand facilitates cell-specific targeting to cells having αvβ6 on its respective surface, and binding of the integrin targeting ligand can facilitate entry of the therapeutic agent, such as an RNAi agent, to which it is linked, into cells such as epithelial cells, including pulmonary epithelial cells and renal epithelial cells. Integrin targeting ligands can be monomeric or monovalent (e.g., having a single integrin targeting moiety) or multimeric or multivalent (e.g., having multiple integrin targeting moieties). The targeting group can be attached to the 3' and/or 5' end of the RNAi oligonucleotide using methods known in the art. The preparation of targeting groups, such as αvβ6 integrin targeting ligands, is described, for example, in International Patent Application Publication No. WO 2018/085415 and in U.S. Provisional Patent Application Nos. 62/580,398 and 62/646,739, the contents of each of which are incorporated herein in its entirety.

Embodiments of the present disclosure include pharmaceutical compositions for delivering an alpha-ENaC RNAi agent to a pulmonary epithelial cell in vivo. Such pharmaceutical compositions can include, for example, an alpha-ENaC RNAi agent conjugated to a targeting group that comprises an integrin targeting ligand. In some embodiments, the integrin targeting ligand is comprised of an αvβ6 integrin ligand.

In some embodiments, a linking group is conjugated to the RNAi agent. The linking group facilitates covalent linkage of the agent to a targeting group, pharmacokinetic modulator, delivery polymer, or delivery vehicle. The linking group can be linked to the 3' and/or the 5' end of the RNAi agent sense strand or antisense strand. In some embodiments, the linking group is linked to the RNAi agent sense strand. In some embodiments, the linking group is conjugated to the 5' or 3' end of an RNAi agent sense strand. In some embodiments, a linking group is conjugated to the 5' end of an RNAi agent sense strand. Examples of linking groups, include, but are not limited to: Alk-SMPT-C6, Alk-SS-C6, DBCO-TEG, Me-Alk-SS-C6, and C6-SS-Alk-Me, reactive groups such a primary amines and alkynes, alkyl groups, abasic residues/nucleotides, amino acids, trialkyne functionalized groups, ribitol, and/or PEG groups.

A linker or linking group is a connection between two atoms that links one chemical group (such as an RNAi agent) or segment of interest to another chemical group (such as a targeting group, pharmacokinetic modulator, or delivery polymer) or segment of interest via one or more covalent bonds. A labile linkage contains a labile bond. A linkage can optionally include a spacer that increases the distance between the two joined atoms. A spacer may further add flexibility and/or length to the linkage. Spacers include, but are not be limited to, alkyl groups, alkenyl groups, alkynyl groups, aryl groups, aralkyl groups, aralkenyl groups, and aralkynyl groups; each of which can contain one or more heteroatoms, heterocycles, amino acids, nucleotides, and saccharides. Spacer groups are well known in the art and the preceding list is not meant to limit the scope of the description.

In some embodiments, targeting groups are linked to the alpha-ENaC RNAi agents without the use of an additional linker. In some embodiments, the targeting group is designed having a linker readily present to facilitate the linkage to an alpha-ENaC RNAi agent. In some embodiments, when two or more RNAi agents are included in a composition, the two or more RNAi agents can be linked to their respective targeting groups using the same linkers. In some embodiments, when two or more RNAi agents are included in a composition, the two or more RNAi agents are linked to their respective targeting groups using different linkers.

Any of the alpha-ENaC RNAi agent nucleotide sequences listed in Tables 2, 3, and 4, whether modified or unmodified, can contain 3' and/or 5' targeting group(s), linking group(s), and/or pharmacokinetic modulator(s). Any of the alpha-ENaC RNAi agent sequences listed in Tables 3 and 4, or are otherwise described herein, which contain a 3' or 5' targeting group, linking group, or pharmacokinetic modulator can alternatively contain no 3' or 5' targeting group, linking group, or pharmacokinetic modulator, or can contain a different 3' or 5' targeting group, linking group, or pharmacokinetic modulator including, but not limited to, those depicted in Table 6. Any of the alpha-ENaC RNAi agent duplexes listed in Table 5, whether modified or unmodified, can further comprise a targeting group or linking group, including, but not limited to, those depicted in Table 6, and the targeting group or linking group can be attached to the 3' or 5' terminus of either the sense strand or the antisense strand of the alpha-ENaC RNAi agent duplex.

Examples of certain targeting groups and linking groups are provided in Table 6.

TABLE 6
Structures Representing Various Modified Nucleotides, Targeting Groups, and Linking Groups
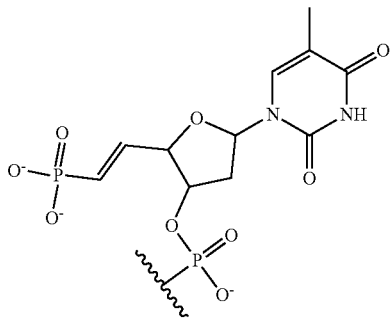 [SMILES: *P(=O)([O-])OC1CC(n2cc(C)c(=O)[nH]c2=O)OC1/C=C/P(=O)([O-])[O-]]
vpdT
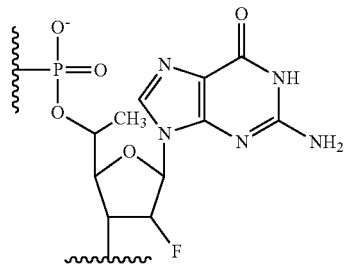 [SMILES: *C1C(F)C(n2cnc3c(=O)[nH]c(N)nc32)OC1C(C)OP(*)(=O)[O-]]
5Me-Gf
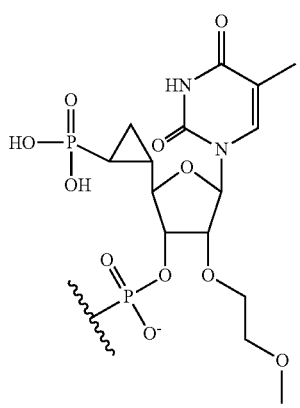 [SMILES: *P(=O)([O-])OC1C(C2CC2P(=O)(O)O)OC(n2cc(C)c(=O)[nH]c2=O)C1OCCOC]
cPrpTM
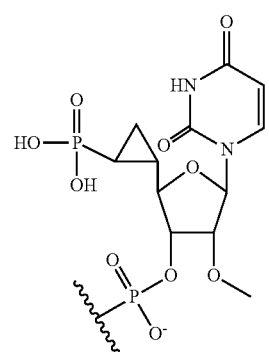 [SMILES: *P(=O)([O-])OC1C(C2CC2P(=O)(O)O)OC(n2ccc(=O)[nH]c2=O)C1OC]
cPrpu
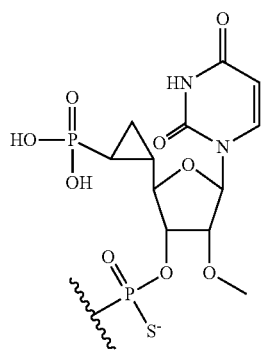
cPrpus
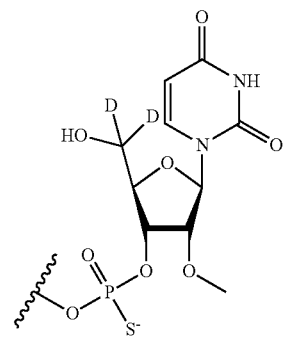
D2us
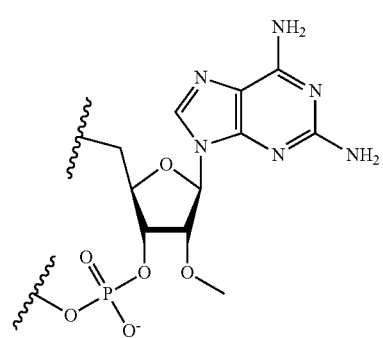
a_2N
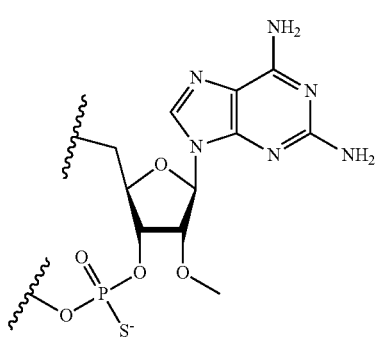
a_2Ns TABLE 6-continued
Structures Representing Various Modified Nucleotides, Targeting Groups, and Linking Groups
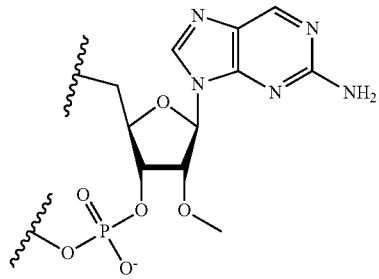
pu_2N
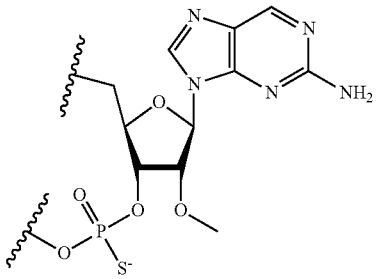
pu_2Ns
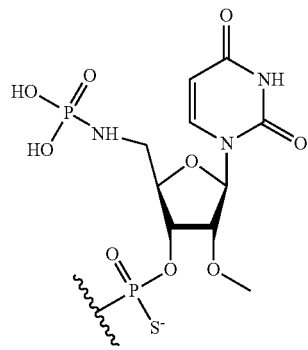
Npus
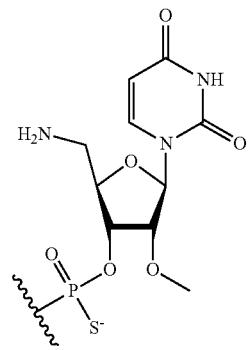
Nus
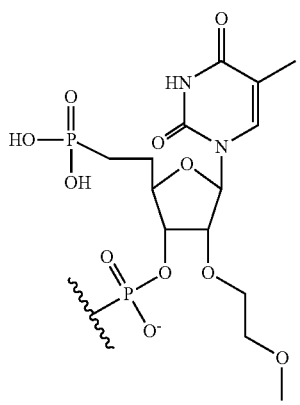 [SMILES: *P(=O)([O-])OC1C(CCP(=O)(O)O)OC(n2cc(C)c(=O)[nH]c2=O)C1OCCOC]
epTM
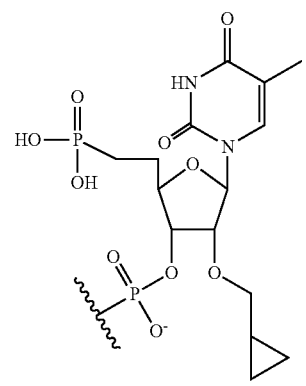 [SMILES: *P(=O)([O-])OC1C(CCP(=O)(O)O)OC(n2cc(C)c(=O)[nH]c2=O)C1OCC1CC1]
epTcPr
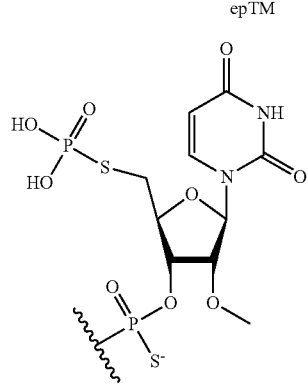
spus
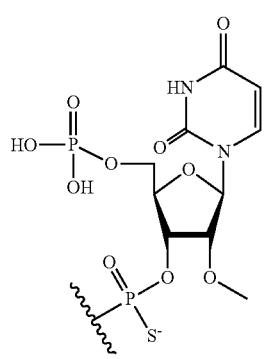
pus
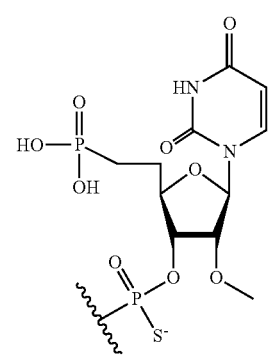
epus TABLE 6-continued
Structures Representing Various Modified Nucleotides, Targeting Groups, and Linking Groups
When positioned internally in oligonucleotide:
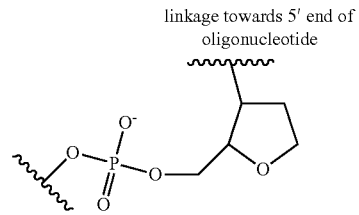
(invAb)
When positioned internally in oligonucleotide:
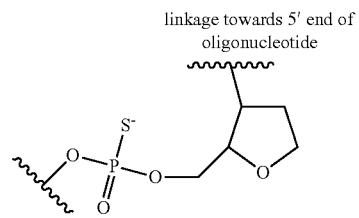
(invAb)s
When positioned at the 3' terminal end of oligonucleotide:
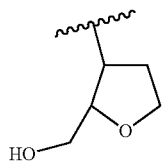
(invAb)
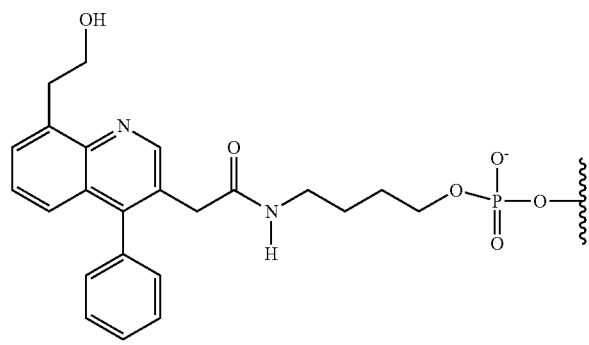 [SMILES: *OP(=O)([O-])OCCCCNC(=O)Cc1cnc2c(CCO)cccc2c1-c1ccccc1]
(PAZ)

TABLE 6-continued

Structures Representing Various Modified Nucleotides, Targeting Groups, and Linking Groups When positioned at the 3' terminal end of oligonucleotide:

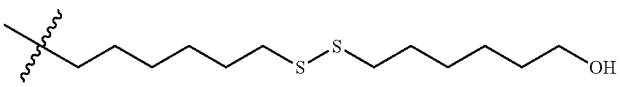 [SMILES: *CCCCCCSSCCCCCCO]

(C6-SS-C6)

When positioned internally in oligonucleotide:

linkage towards 5' end of oligonucleotide      linkage towards 3' end of oligonucleotide

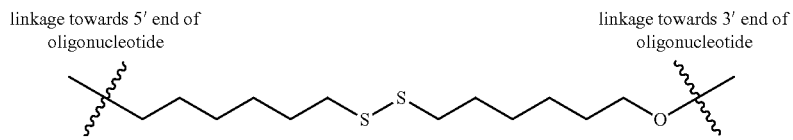 [SMILES: *CCCCCCSSCCCCCCO*]

(C6-SS-C6)

When positioned at the 3' terminal end of oligonucleotide:

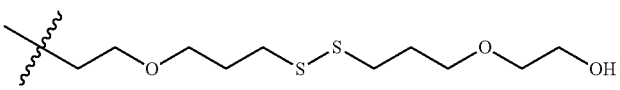 [SMILES: *CCOCCCSSCCCOCCO]

When positioned internally in oligonucleotide:

linkage towards 5' end of oligonucleotide     linkage towards 3' end of oligonucleotide

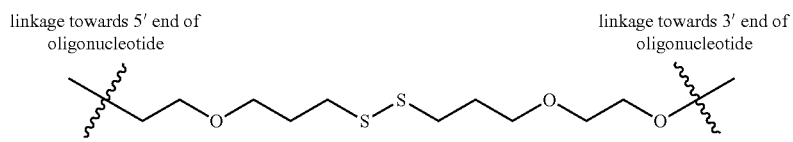 [SMILES: *CCOCCCSSCCCOCCO*]

(6-SS-6)

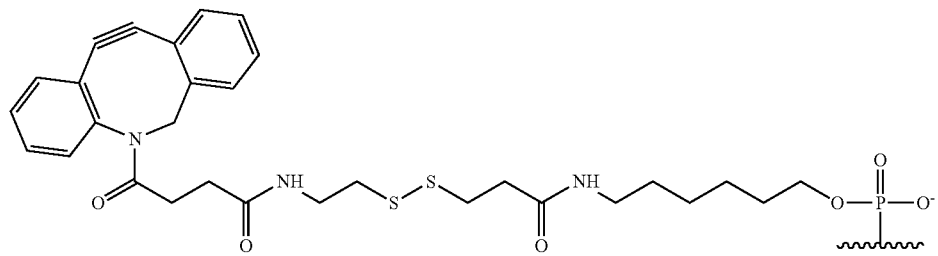 [SMILES: *P(=O)([O-])OCCCCCCNC(=O)CCSSCCNC(=O)CCC(=O)N1Cc2ccccc2C#Cc2ccccc21]

(C6-SS-Alk) or (Alk-SS-C6)

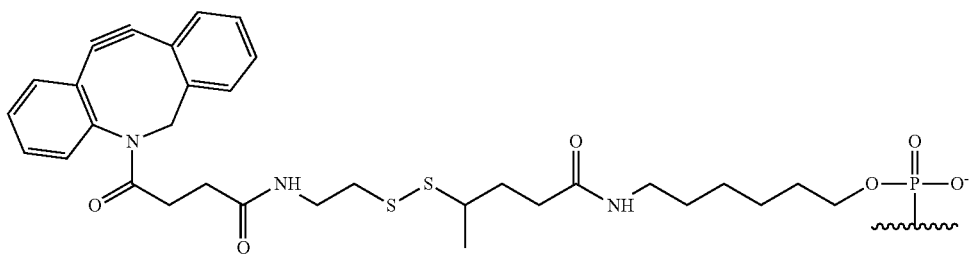 [SMILES: *P(=O)([O-])OCCCCCCNC(=O)CCC(C)SSCCNC(=O)CCC(=O)N1Cc2ccccc2C#Cc2ccccc21]

(C6-SS-Alk-Me)

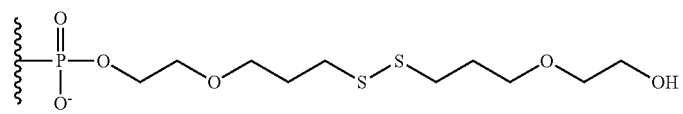 [SMILES: *P(=O)([O-])OCCOCCCSSCCCOCCO]

(PEG-C3-SS)

TABLE 6-continued
Structures Representing Various Modified Nucleotides, Targeting Groups, and Linking Groups
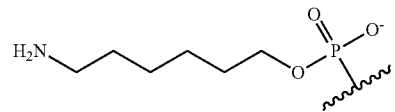 [SMILES: *P(=O)([S-])OCCCCCCN]
(NH2-C6)
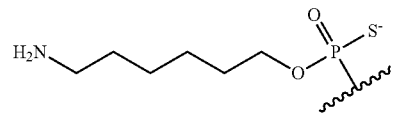
(NH2-C6)s
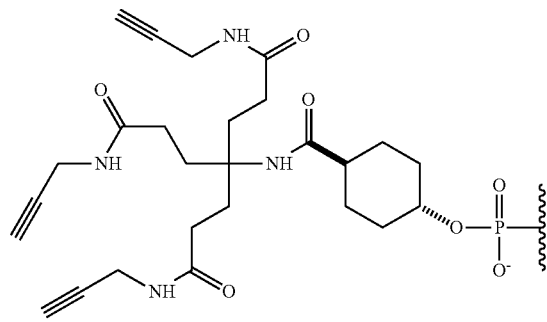 [SMILES: *P(=O)([O-])O[C@H]1CC[C@H](C(=O)NC(CCC(=O)NCC#C)(CCC(=O)NCC#C)CCC(=O)NCC#C)CC1]
(TriAlk1)
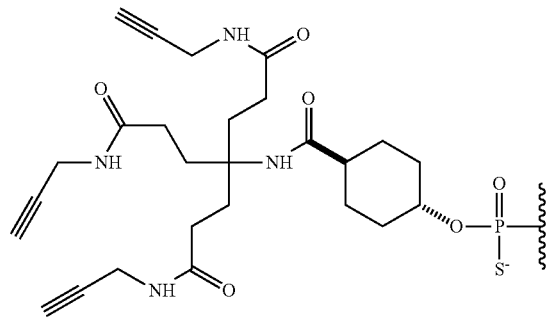 [SMILES: *P(=O)([S-])O[C@H]1CC[C@H](C(=O)NC(CCC(=O)NCC#C)(CCC(=O)NCC#C)CCC(=O)NCC#C)CC1]
(TriAlk1)s
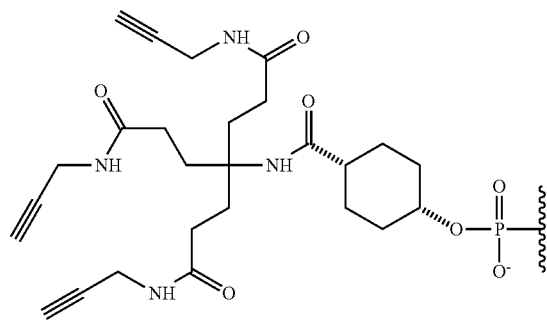 [SMILES: *P(=O)([O-])O[C@H]1CC[C@@H](C(=O)NC(CCC(=O)NCC#C)(CCC(=O)NCC#C)CCC(=O)NCC#C)CC1]
(TriAlk2)

TABLE 6-continued
Structures Representing Various Modified Nucleotides, Targeting Groups, and Linking Groups
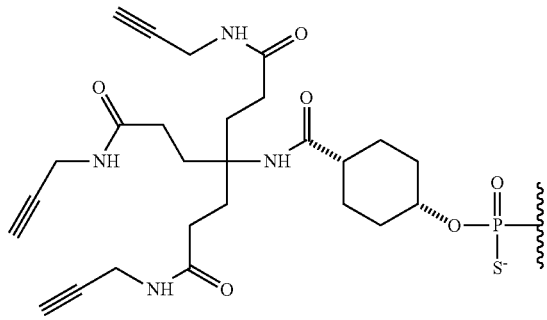 [SMILES: *P(=O)([S-])O[C@H]1CC[C@@H](C(=O)NC(CCC(=O)NCC#C)(CCC(=O)NCC#C)CCC(=O)NCC#C)CC1]
(TriAlk2)s
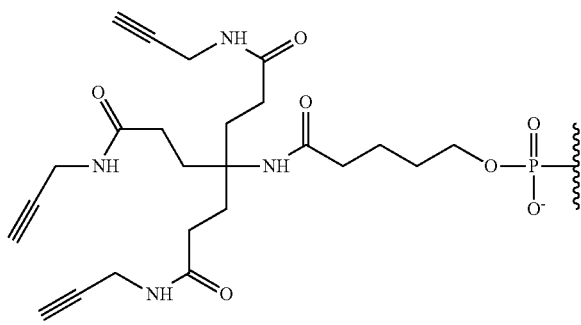 [SMILES: *P(=O)([O-])OCCCCC(=O)NC(CCC(=O)NCC#C)(CCC(=O)NCC#C)CCC(=O)NCC#C]
(TriAlk3)
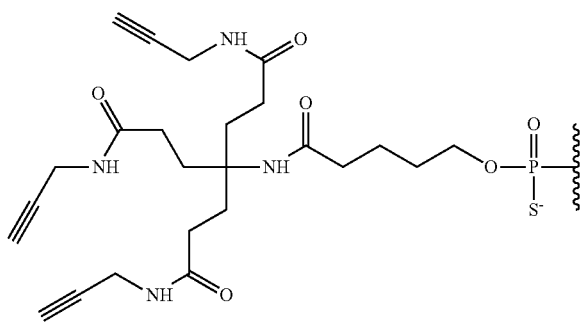 [SMILES: *P(=O)([S-])OCCCCC(=O)NC(CCC(=O)NCC#C)(CCC(=O)NCC#C)CCC(=O)NCC#C]
(TriAlk3)s
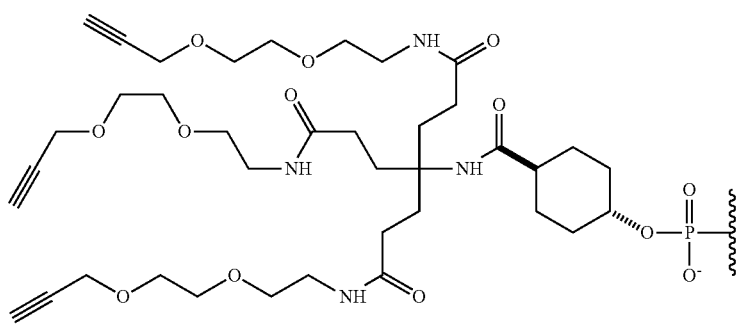
(TriAlk4)

TABLE 6-continued
Structures Representing Various Modified Nucleotides, Targeting Groups, and Linking Groups
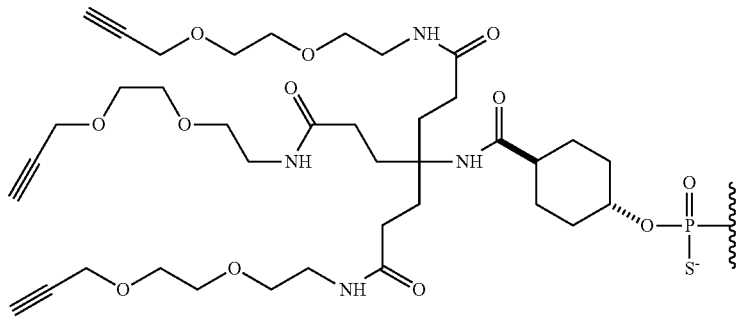
(TriAlk4)s
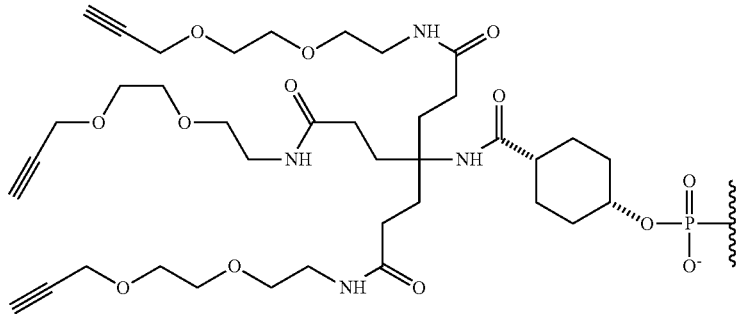
(TriAlk5)
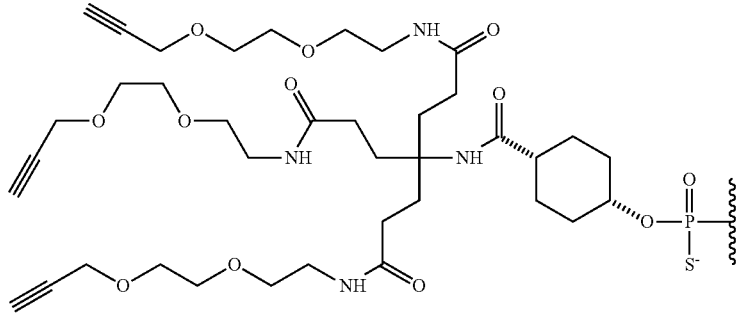
(TriAlk5)s
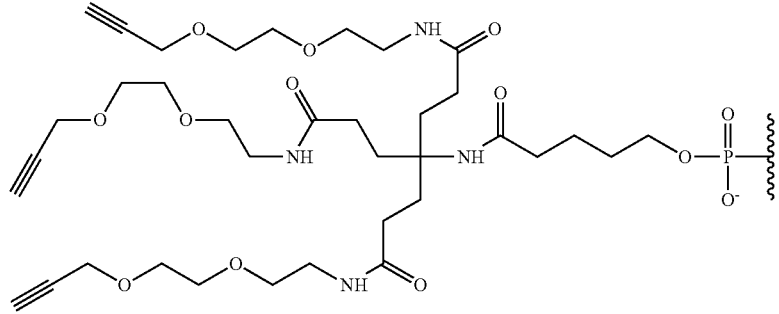
(TriAlk6)

TABLE 6-continued
Structures Representing Various Modified Nucleotides, Targeting Groups, and Linking Groups
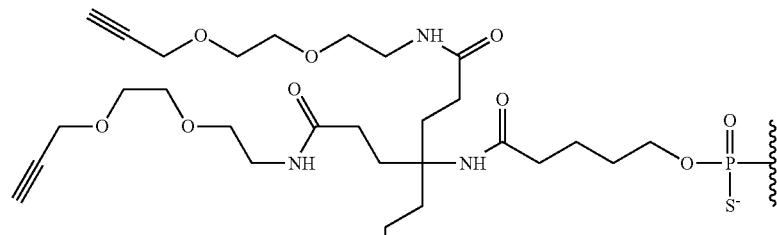
(TriAlk6)s
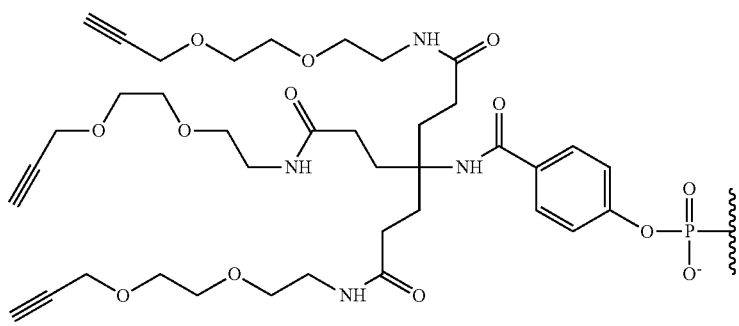
(TriAlk7)
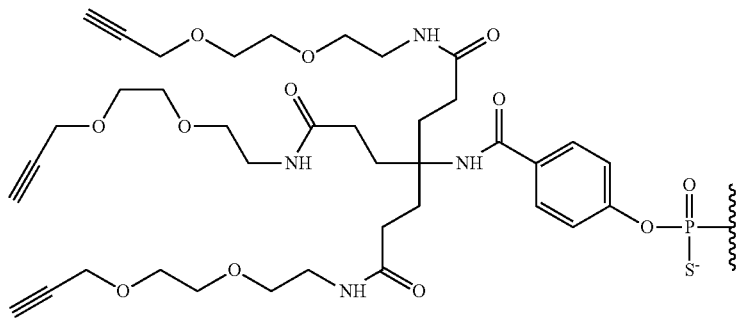
(TriAlk7)s
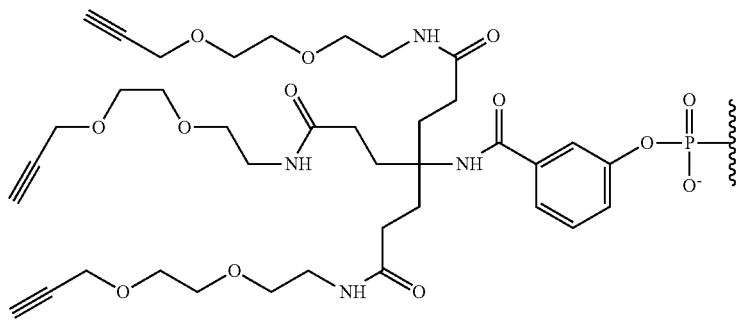
(TriAlk8)

TABLE 6-continued
Structures Representing Various Modified Nucleotides, Targeting Groups, and Linking Groups
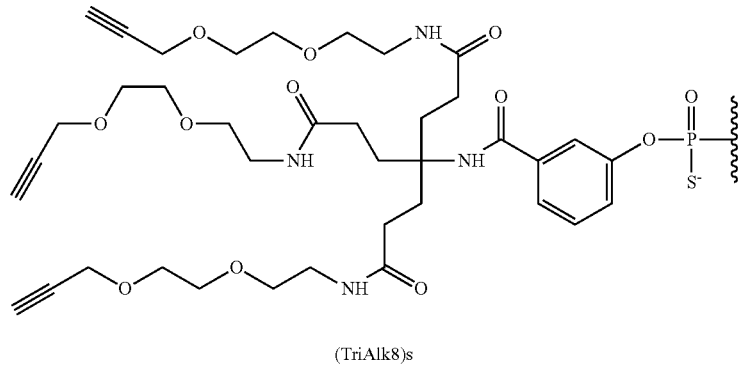
(TriAlk8)s
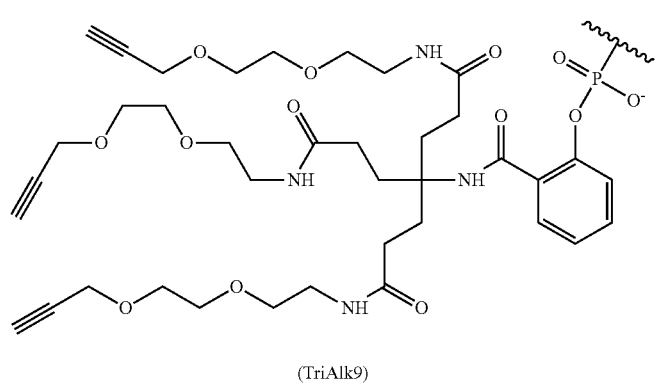
(TriAlk9)
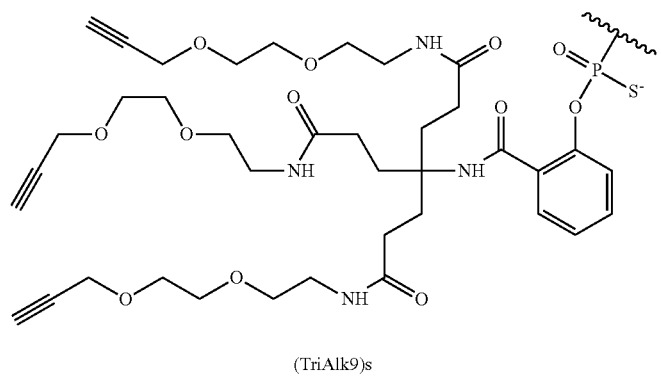
(TriAlk9)s
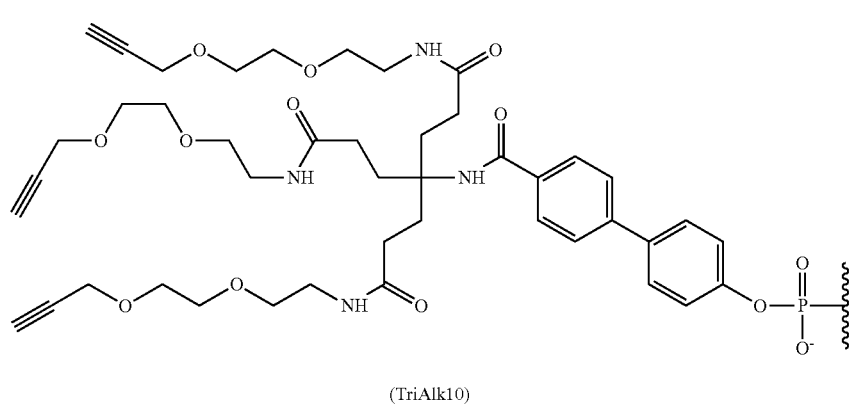
(TriAlk10)

TABLE 6-continued
Structures Representing Various Modified Nucleotides, Targeting Groups, and Linking Groups
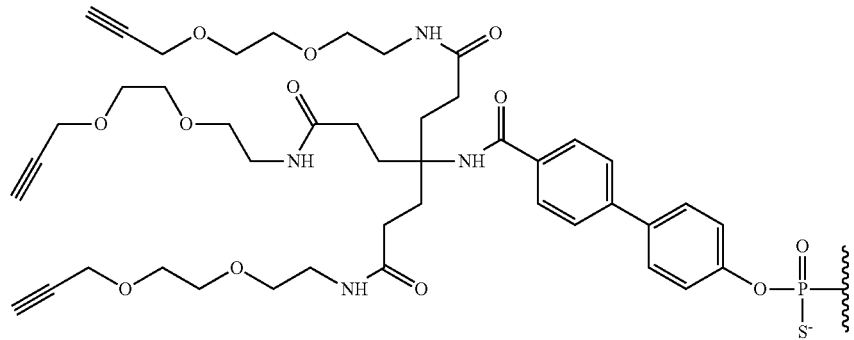
(TriAlk10)s
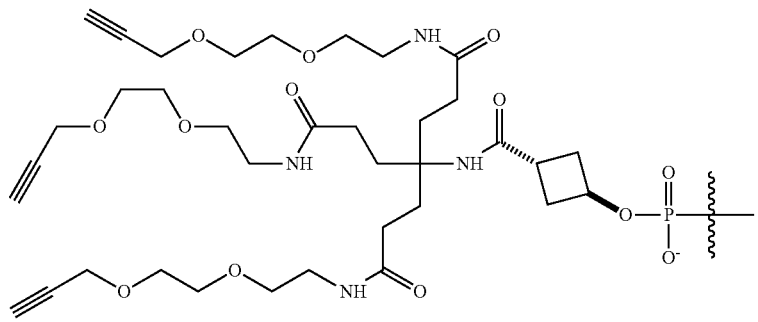 [SMILES: *P(=O)([O-])O[C@H]1C[C@H](C(=O)NC(CCC(=O)NCCOCCOCC#C)(CCC(=O)NCCOCCOCC#C)CCC(=O)NCCOCCOCC#C)C1]
(TriAlk11)
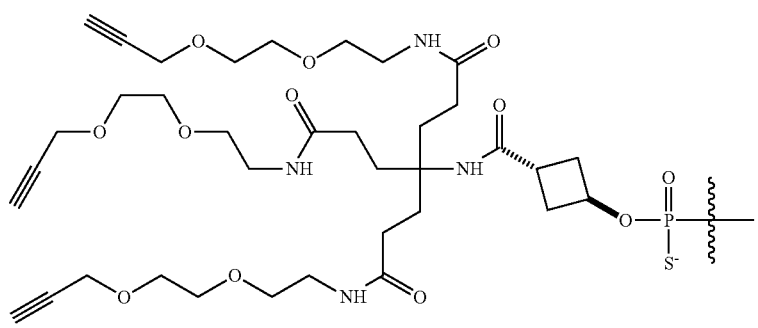
(TriAlk11)s
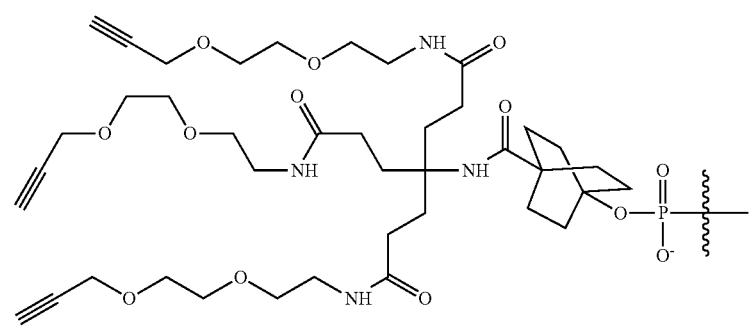
(TriAlk12)

TABLE 6-continued
Structures Representing Various Modified Nucleotides, Targeting Groups, and Linking Groups
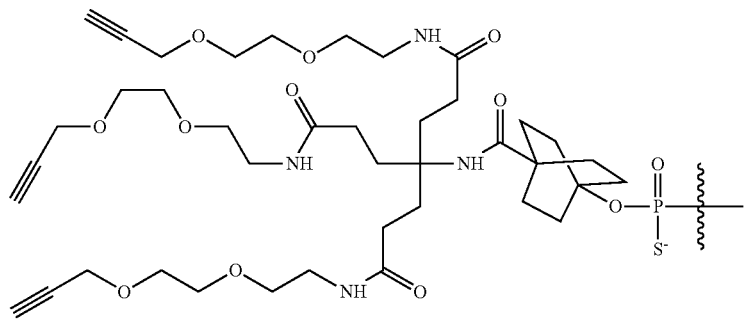 [SMILES: *P(=O)([S-])OC12CCC(C(=O)NC(CCC(=O)NCCOCCOCC#C)(CCC(=O)NCCOCCOCC#C)CCC(=O)NCCOCCOCC#C)(CC1)CC2]
(TriAlk12)s
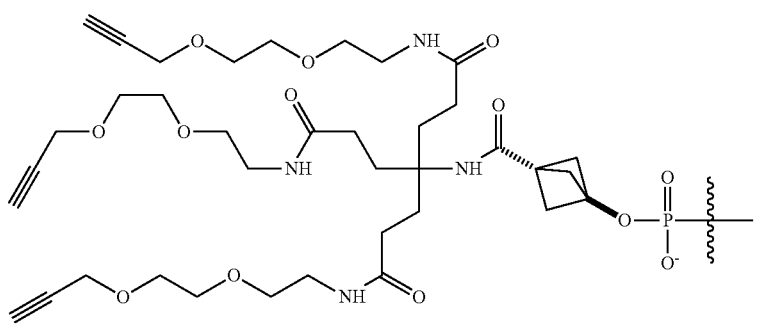 [SMILES: *P(=O)([O-])O[C@]12C[C@@](C(=O)NC(CCC(=O)NCCOCCOCC#C)(CCC(=O)NCCOCCOCC#C)CCC(=O)NCCOCCOCC#C)(C1)C2]
(TriAlk13)
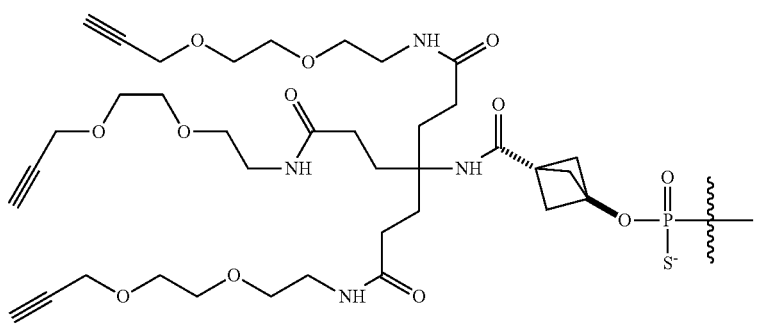 [SMILES: *P(=O)([S-])O[C@]12C[C@@](C(=O)NC(CCC(=O)NCCOCCOCC#C)(CCC(=O)NCCOCCOCC#C)CCC(=O)NCCOCCOCC#C)(C1)C2]
(TriAlk13)s
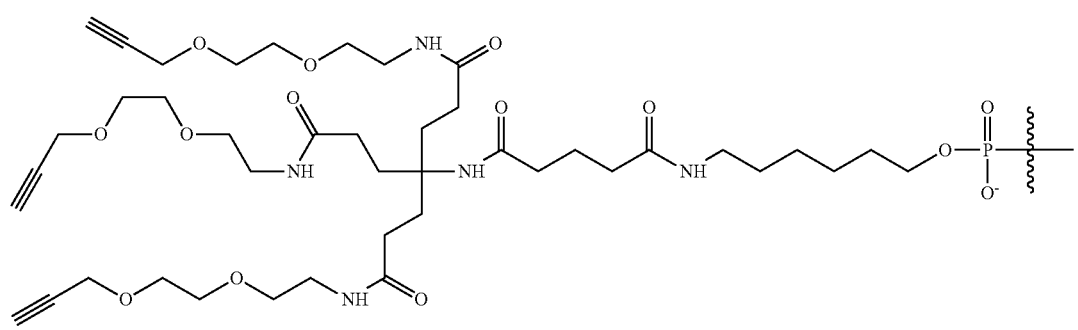 [SMILES: *P(=O)([O-])OCCCCCCNC(=O)CCCC(=O)NC(CCC(=O)NCCOCCOCC#C)(CCC(=O)NCCOCCOCC#C)CCC(=O)NCCOCCOCC#C]
(TriAlk14)

TABLE 6-continued

Structures Representing Various Modified Nucleotides, Targeting Groups, and Linking Groups

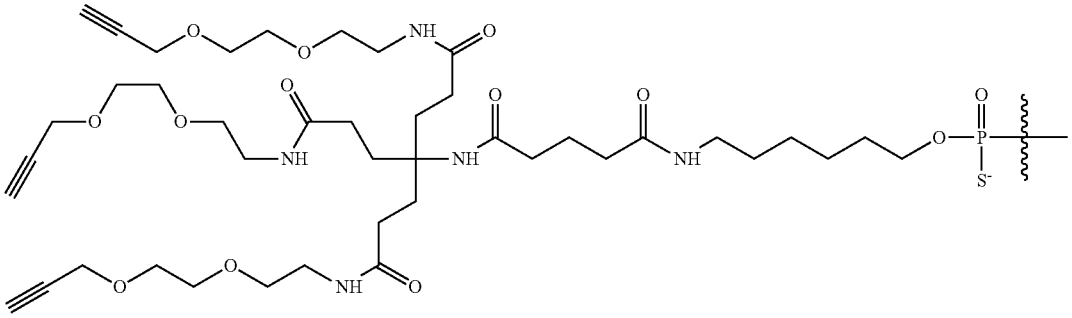 [SMILES: *P(=O)([S-])OCCCCCCNC(=O)CCCC(=O)NC(CCC(=O)NCCOCCOCC#C)(CCC(=O)NCCOCCOCC#C)CCC(=O)NCCOCCOCC#C]

(TriAlk14)s

Alternatively, other linking groups known in the art may be used.

In some embodiments, a delivery vehicle may be used to deliver an RNAi agent to a cell or tissue. A delivery vehicle is a compound that improves delivery of the RNAi agent to a cell or tissue. A delivery vehicle can include, or consist of, but is not limited to: a polymer, such as an amphipathic polymer, a membrane active polymer, a peptide, a melittin peptide, a melittin-like peptide (MLP), a lipid, a reversibly modified polymer or peptide, or a reversibly modified membrane active polyamine.

In some embodiments, the RNAi agents can be combined with lipids, nanoparticles, polymers, liposomes, micelles, DPCs or other delivery systems available in the art. The RNAi agents can also be chemically conjugated to targeting groups, lipids (including, but not limited to cholesteryl and cholesteryl derivatives), nanoparticles, polymers, liposomes, micelles, DPCs (see, for example WO 2000/053722, WO 2008/022309, WO 2011/104169, and WO 2012/083185, WO 2013/032829, WO 2013/158141, each of which is incorporated herein by reference), or other delivery systems available in the art.

Pharmaceutical Compositions and Formulations

The alpha-ENaC RNAi agents disclosed herein can be prepared as pharmaceutical compositions or formulations (also referred to herein as "medicaments"). In some embodiments, pharmaceutical compositions include at least one alpha-ENaC RNAi agent. These pharmaceutical compositions are particularly useful in the inhibition of the expression of alpha-ENaC mRNA in a target cell, a group of cells, a tissue, or an organism. The pharmaceutical compositions can be used to treat a subject having a disease, disorder, or condition that would benefit from reduction in the level of the target mRNA, or inhibition in expression of the target gene. The pharmaceutical compositions can be used to treat a subject at risk of developing a disease or disorder that would benefit from reduction of the level of the target mRNA or an inhibition in expression the target gene. In one embodiment, the method includes administering an alpha-ENaC RNAi agent linked to a targeting ligand as described herein, to a subject to be treated. In some embodiments, one or more pharmaceutically acceptable excipients (including vehicles, carriers, diluents, and/or delivery polymers) are added to the pharmaceutical compositions that include an alpha-ENaC RNAi agent, thereby forming a pharmaceutical formulation or medicament suitable for in vivo delivery to a subject, including a human.

The pharmaceutical compositions that include an alpha-ENaC RNAi agent and methods disclosed herein decrease the level of the target mRNA in a cell, group of cells, group of cells, tissue, organ, or subject, including by administering to the subject a therapeutically effective amount of a herein described alpha-ENaC RNAi agent, thereby inhibiting the expression of alpha-ENaC mRNA in the subject. In some embodiments, the subject has been previously identified or diagnosed as having a disease or disorder that is mediated at least in part by ENaC expression. In some embodiments, the subject has been previously identified or diagnosed as having enhanced. ENaC activity in one or more cells or tissues. In some embodiments, the subject has been previously diagnosed with having one or more respiratory diseases such as cystic fibrosis, chronic bronchitis, non-cystic fibrosis bronchiectasis, chronic obstructive pulmonary disease (COPD), asthma, respiratory tract infections, primary ciliary dyskinesia, and lung carcinoma cystic fibrosis. In some embodiments, the subject has been previously diagnosed with having one or more ocular diseases such as dry eye. In some embodiments, the subject has been suffering from symptoms associated with one or more respiratory diseases that is associated with or caused by enhanced ENaC activity.

In some embodiments, the described pharmaceutical compositions including an alpha-ENaC RNAi agent are used for treating or managing clinical presentations in a subject that would benefit from the inhibition of expression of ENaC. In some embodiments, a therapeutically or prophylactically effective amount of one or more of pharmaceutical compositions is administered to a subject in need of such treatment. In some embodiments, administration of any of the disclosed alpha-ENaC RNAi agents can be used to decrease the number, severity, and/or frequency of symptoms of a disease in a subject.

The described pharmaceutical compositions that include an alpha-ENaC RNAi agent can be used to treat at least one symptom in a subject having a disease or disorder that would benefit from reduction or inhibition in expression of alpha-ENaC mRNA. In some embodiments, the subject is administered a therapeutically effective amount of one or more pharmaceutical compositions that include an alpha-ENaC RNAi agent thereby treating the symptom. In other embodiments, the subject is administered a prophylactically effective amount of one or more alpha-ENaC RNAi agents, thereby preventing or inhibiting the at least one symptom.

The route of administration is the path by which an alpha-ENaC RNAi agent is brought into contact with the body. In general, methods of administering drugs, oligonucleotides, and nucleic acids, for treatment of a mammal are well known in the art and can be applied to administration of the compositions described herein. The alpha-ENaC RNAi agents disclosed herein can be administered via any suitable route in a preparation appropriately tailored to the particular route. Thus, in some embodiments, the herein described pharmaceutical compositions are administered via inhalation, intranasal administration, intratracheal administration, or oropharyngeal aspiration administration. In some embodiments, the pharmaceutical compositions can be administered by injection, for example, intravenously, intramuscularly, intracutaneously, subcutaneously, intraarticularly, or intraperitoneally, or topically.

The pharmaceutical compositions including an alpha-ENaC RNAi agent described herein can be delivered to a cell, group of cells, tissue, or subject using oligonucleotide delivery technologies known in the art. In general, any suitable method recognized in the art for delivering a nucleic acid molecule (in vitro or in vivo) can be adapted for use with the compositions described herein. For example, delivery can be by local administration, (e.g., direct injection, implantation, or topical administering), systemic administration, or subcutaneous, intravenous, intraperitoneal, or parenteral routes, including intracranial (e.g., intraventricular, intraparenchymal and intrathecal), intramuscular, transdermal, airway (aerosol), nasal, oral, rectal, or topical (including buccal and sublingual) administration. In some embodiments, the compositions are administered via inhalation, intranasal administration, oropharyngeal aspiration administration, or intratracheal administration. For example, in some embodiments, it is desired that the alpha-ENaC RNAi agents described herein inhibit the expression of an alpha-ENaC gene in the pulmonary epithelium, for which administration via inhalation (e.g., by an inhaler device, such as a metered-dose inhaler, or a nebulizer such as a jet or vibrating mesh nebulizer, or a soft mist inhaler) is particularly suitable and advantageous.

In some embodiments, the pharmaceutical compositions described herein comprise one or more pharmaceutically acceptable excipients. The pharmaceutical compositions described herein are formulated for administration to a subject.

As used herein, a pharmaceutical composition or medicament includes a pharmacologically effective amount of at least one of the described therapeutic compounds and one or more pharmaceutically acceptable excipients. Pharmaceutically acceptable excipients (excipients) are substances other than the Active Pharmaceutical Ingredient (API, therapeutic product, e.g., alpha-ENaC RNAi agent) that are intentionally included in the drug delivery system. Excipients do not exert or are not intended to exert a therapeutic effect at the intended dosage. Excipients can act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, detergents, dextran, dextrose, diluents, disintegrants, emulsifiers, extenders, fillers, flavors, glidants, humectants, lubricants, oils, polymers, preservatives, saline, salts, solvents, sugars, surfactants, suspending agents, sustained release matrices, sweeteners, thickening agents, tonicity agents, vehicles, water-repelling agents, and wetting agents.

Pharmaceutical compositions suitable for injectable use include sterile aqueous solutions (where water-soluble) or dispersions and sterile powders for the extemporaneous preparation of sterile injectable solutions or dispersion. For intravenous administration, suitable carriers include physiological saline, bacteriostatic water, Cremophor® ELTM (BASF, Parsippany, N.J.) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

Formulations suitable for inhalation administration can be prepared by incorporating the active compound in the desired amount in an appropriate solvent, followed by sterile filtration. In general, formulations for inhalation administration are sterile solutions at physiological pH and have low viscosity (<5 cP). Salts may be added to the formulation to balance tonicity. In some cases, surfactants or co-solvents can be added to increase active compound solubility and improve aerosol characteristics. In some cases, excipients can be added to control viscosity in order to ensure size and distribution of nebulized droplets.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

The alpha-ENaC RNAi agents can be formulated in compositions in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the therapeutic effect to be achieved, and the limitations inherent in the art of compounding such an active compound for the treatment of individuals.

A pharmaceutical composition can contain other additional components commonly found in pharmaceutical compositions. Such additional components include, but are not limited to: anti-pruritics, astringents, local anesthetics, or anti-inflammatory agents (e.g., antihistamine, diphenhydramine, etc.). It is also envisioned that cells, tissues, or isolated organs that express or comprise the herein defined RNAi agents may be used as "pharmaceutical compositions." As used herein, "pharmacologically effective amount," "therapeutically effective amount," or simply "effective amount" refers to that amount of an RNAi agent to produce a pharmacological, therapeutic, or preventive result.

In some embodiments, the methods disclosed herein further comprise the step of administering a second therapeutic or treatment in addition to administering an RNAi agent disclosed herein. In some embodiments, the second therapeutic is another alpha-ENaC RNAi agent (e.g., an alpha-ENaC RNAi agent that targets a different sequence within the alpha-ENaC target). In other embodiments, the second therapeutic can be a small molecule drug, an antibody, an antibody fragment, and/or an aptamer.

Generally, an effective amount of an alpha-ENaC RNAi agent disclosed herein will be in the range of from about 0.0001 to about 20 mg/kg of body weight/day, e.g., from about 0.001 to about 3 mg/kg of body weight/day. In some embodiments, an effective amount of an alpha-ENaC RNAi agent will be in the range of from about 0.001 to about 0.500 mg/kg of body weight per dose. In some embodiments, an effective amount of an alpha-ENaC RNAi agent will be in the range of from about 0.001 to about 0.100 mg/kg of body weight per dose. In some embodiments, an effective amount of an alpha-ENaC RNAi agent will be in the range of from about 0.001 to about 0.050 mg/kg of body weight per dose. The amount administered will also likely depend on such variables as the overall health status of the patient, the relative biological efficacy of the compound delivered, the formulation of the drug, the presence and types of excipients in the formulation, and the route of administration. Also, it is to be understood that the initial dosage administered can be increased beyond the above upper level to rapidly achieve the desired blood-level or tissue level, or the initial dosage can be smaller than the optimum.

For treatment of disease or for formation of a medicament or composition for treatment of a disease, the pharmaceutical compositions described herein including an alpha-ENaC RNAi agent can be combined with an excipient or with a second therapeutic agent or treatment including, but not limited to: a second or other RNAi agent, a small molecule drug, an antibody, an antibody fragment, peptide, and/or an aptamer.

The described alpha-ENaC RNAi agents, when added to pharmaceutically acceptable excipients or adjuvants, can be packaged into kits, containers, packs, or dispensers. The pharmaceutical compositions described herein can be packaged in dry powder or aerosol inhalers, other metered-dose inhalers, nebulizers, pre-filled syringes, or vials.

Methods of Treatment and Inhibition of Expression

The alpha-ENaC RNAi agents disclosed herein can be used to treat a subject (e.g., a human or other mammal) having a disease or disorder that would benefit from administration of the RNAi agent. In some embodiments, the RNAi agents disclosed herein can be used to treat a subject (e.g., a human) that would benefit from a reduction and/or inhibition in expression of alpha-ENaC mRNA.

In some embodiments, the RNAi agents disclosed herein can be used to treat a subject (e.g., a human) having a disease or disorder for which the subject would benefit from reduction in ENaC channel activity, including but not limited to, for example, cystic fibrosis, chronic bronchitis, non-cystic fibrosis bronchiectasis, chronic obstructive pulmonary disease (COPD), asthma, respiratory tract infections, primary ciliary dyskinesia, and/or lung carcinoma cystic fibrosis and/or dry eye. Treatment of a subject can include therapeutic and/or prophylactic treatment. The subject is administered a therapeutically effective amount of any one or more alpha-ENaC RNAi agents described herein. The subject can be a human, patient, or human patient. The subject may be an adult, adolescent, child, or infant. Administration of a pharmaceutical composition described herein can be to a human being or animal.

Increased ENaC activity is known to promote airway surface liquid dehydration and impair mucociliary clearance. In some embodiments, the described alpha-ENaC RNAi agents are used to treat at least one symptom mediated at least in part by ENaC activity levels, in a subject. The subject is administered a therapeutically effective amount of any one or more of the described alpha-ENaC RNAi agents. In some embodiments, the subject is administered a prophylactically effective amount of any one or more of the described RNAi agents, thereby treating the subject by preventing or inhibiting the at least one symptom.

In certain embodiments, the present disclosure provides methods for treatment of diseases, disorders, conditions, or pathological states mediated at least in part by alpha-ENaC gene expression, in a patient in need thereof, wherein the methods include administering to the patient any of the alpha-ENaC RNAi agents described herein.

In some embodiments, the alpha-ENaC RNAi agents are used to treat or manage a clinical presentation or pathological state in a subject, wherein the clinical presentation or pathological state is mediated at least in part by ENaC expression. The subject is administered a therapeutically effective amount of one or more of the alpha-ENaC RNAi agents or alpha-ENaC RNAi agent-containing compositions described herein. In some embodiments, the method comprises administering a composition comprising an alpha-ENaC RNAi agent described herein to a subject to be treated.

In some embodiments, the gene expression level and/or mRNA level of an alpha-ENaC gene in certain epithelial cells of subject to whom a described alpha-ENaC RNAi agent is administered is reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater than 99%, relative to the subject prior to being administered the alpha-ENaC RNAi agent or to a subject not receiving the alpha-ENaC RNAi agent. In some embodiments, the ENaC levels or ENaC channel activity levels in certain epithelial cells of a subject to whom a described alpha-ENaC RNAi agent is administered is reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater than 99%, relative to the subject prior to being administered the alpha-ENaC RNAi agent or to a subject not receiving the alpha-ENaC RNAi agent. The gene expression level, protein level, and/or mRNA level in the subject may be reduced in a cell, group of cells, and/or tissue of the subject. In some embodiments, the alpha-ENaC mRNA levels in certain epithelial cells subject to whom a described alpha-ENaC RNAi agent has been administered is reduced by at least about 30%, 35%, 40%, 45%, 50%, 55%, 60%, 65%, 70%, 75%, 80%, 85%, 90%, 95%, or 98% relative to the subject prior to being administered the alpha-ENaC RNAi agent or to a subject not receiving the alpha-ENaC RNAi agent. In some embodiments, the level of the ENaC heterotrimeric protein complex in certain epithelial cells in a subject to whom a described alpha-ENaC RNAi agent has been administered is reduced by at least about 30%, 35%, 40%, 45%, 50%, 55%, 60%, 65%, 70%, 75%, 80%, 85%, 90%, 95%, or 98% relative to the subject prior to being administered the alpha-ENaC RNAi agent or to a subject not receiving the alpha-ENaC RNAi agent. The ENaC level in the subject may be reduced in a cell, group of cells, tissue, blood, and/or other fluid of the subject. For example, in some embodiments, the level of alpha-ENaC mRNA and/or ENaC heterotrimeric protein complex in pulmonary epithelial cells of a subject to whom a described alpha-ENaC RNAi agent has been administered is reduced by at least about 30%, 35%, 40%, 45%, 50%, 55%, 60%, 65%, 70%, 75%, 80%, 85%, 90%, 95%, or 98% relative to the subject prior to being administered the alpha-ENaC RNAi agent or to a subject not receiving the alpha-ENaC RNAi agent. In some embodiments, the level of alpha-ENaC mRNA and/or ENaC heterotrimeric protein complex and/or ENaC channel activity levels in a subset of pulmonary epithelial cells, such as airway epithelial cells, of a subject to whom a described alpha-ENaC RNAi agent has been administered is reduced by at least about 30%, 35%, 40%, 45%, 50%, 55%, 60%, 65%, 70%, 75%, 80%, 85%, 90%, 95%, or 98% relative to the subject prior to being administered the alpha-ENaC RNAi agent or to a subject not receiving the alpha-ENaC RNAi agent.

A reduction in gene expression, mRNA, and protein levels can be assessed by any methods known in the art. Reduction or decrease in alpha-ENaC mRNA level, ENaC channel activity level, and/or ENaC heterotrimeric protein complex levels, are collectively referred to herein as a reduction or decrease in alpha-ENaC or inhibiting or reducing the expression of the alpha-ENaC gene. The Examples set forth herein illustrate known methods for assessing inhibition of alpha-ENaC gene expression.

Cells, Tissues, Organs, and Non-Human Organisms

Cells, tissues, organs, and non-human organisms that include at least one of the alpha-ENaC RNAi agents described herein are contemplated. The cell, tissue, organ, or non-human organism is made by delivering the RNAi agent to the cell, tissue, organ, or non-human organism.

The above provided embodiments and items are now illustrated with the following, non-limiting examples.

EXAMPLES

Example 1. Synthesis of Alpha-ENaC RNAi Agents

The Alpha-ENaC RNAi agent duplexes shown in Table 5 were synthesized in accordance with the following:

A. Synthesis.

The sense and antisense strands of the alpha-ENaC RNAi agents were synthesized according to phosphoramidite technology on solid phase used in oligonucleotide synthesis. Depending on the scale, a MerMade96E® (Bioautomation), a MerMade12® (Bioautomation), or an OP Pilot 100 (GE Healthcare) was used. Syntheses were performed on a solid support made of controlled pore glass (CPG, 500 Å or 600 Å, obtained from Prime Synthesis, Aston, Pa., USA). All RNA and 2'-modified RNA phosphoramidites were purchased from Thermo Fisher Scientific (Milwaukee, Wis., USA). Specifically, the 2'-O-methyl phosphoramidites that were used included the following: (5'-O-dimethoxytrityl-$N^6$-(benzoyl)-2'-O-methyl-adenosine-3'-O-(2-cyanoethyl-N,N-diisopropylamino) phosphoramidite, 5'-O-dimethoxy-trityl-$N^4$-(acetyl)-2'-O-methyl-cytidine-3'-O-(2-cyanoethyl-N,N-diisopropylamino) phosphoramidite, (5'-O-dimethoxytrityl-$N^2$-(isobutyryl)-2'-O-methyl-guanosine-3'-O-(2-cyanoethyl-N,N-diisopropylamino) phosphoramidite, and 5'-O-dimethoxytrityl-2'-O-methyl-uridine-3'-O-(2-cyanoethyl-N,N-diisopropylamino) phosphoramidite. The 2'-deoxy-2'-fluoro-phosphoramidites carried the same protecting groups as the 2'-O-methyl RNA amidites. 5'-dimethoxytrityl-2'-O-methyl-inosine-3'-O-(2-cyanoethyl-N,N-diisopropylamino) phosphoramidites were purchased from Glen Research (Virginia). The inverted abasic (3'-O-dimethoxytrityl-2'-deoxyribose-5'-O-(2-cyanoethyl-N,N-diisopropylamino) phosphoramidites were purchased from ChemGenes (Wilmington, Mass., USA). The following UNA phosphoramidites were used: 5'-(4,4'-Dimethoxytrityl)-N6-(benzoyl)-2',3'-seco-adenosine, 2'-benzoyl-3'-[(2-cyanoethyl)-(N,N-diisopropyl)]-phosphoramidite, 5'-(4,4'-Dimethoxytrityl)-N-acetyl-2',3'-seco-cytosine, 2'-benzoyl-3'-[(2-cyanoethyl)-(N,N-diiso-propyl)]-phosphoramidite, 5'-(4,4'-Dimethoxytrityl)-N-isobutyryl-2',3'-seco-guanosine, 2'-benzoyl-3'-[(2-cyanoethyl)-(N,N-diisopropyl)]-phosphoramidite, and 5'-(4,4'-Dimethoxy-trityl)-2',3'-seco-uridine, 2'-benzoyl-3'-[(2-cyanoethyl)-(N,N-diiso-propyl)]-phosphoramidite. TFA aminolink phosphoramidites were also commercially purchased (ThermoFisher).

Tri-alkyne-containing phosphoramidites were dissolved in anhydrous dichloromethane or anhydrous acetonitrile (50 mM), while all other amidites were dissolved in anhydrous acetonitrile (50 mM) and molecular sieves (3 Å) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 10 minutes (RNA), 90 seconds (2' OMe), and 60 seconds (2' F). In order to introduce phosphorothioate linkages, a 100 mM solution of 3-phenyl 1,2,4-dithiazoline-5-one (POS, obtained from PolyOrg, Inc., Leominster, Mass., USA) in anhydrous acetonitrile was employed.

Alternatively, tri-alkyne moieties were introduced post-synthetically (see section E, below). For this route, the sense strand was functionalized with a 5' and/or 3' terminal nucleotide containing a primary amine. TFA aminolink phosphoramidite was dissolved in anhydrous acetonitrile (50 mM) and molecular sieves (3 Å) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 10 minutes (RNA), 90 seconds (2' OMe), and 60 seconds (2' F). In order to introduce phosphorothioate linkages, a 100 mM solution of 3-phenyl 1,2,4-dithiazoline-5-one (POS, obtained from PolyOrg, Inc., Leominster, Mass., USA) in anhydrous acetonitrile was employed.

B. Cleavage and Deprotection of Support Hound Oligomer.

After finalization of the solid phase synthesis, the dried solid support was treated with a 1:1 volume solution of 40 wt. 9/0 methylamine in water and 28% to 31% ammonium hydroxide solution (Aldrich) for 1.5 hours at 30° C. The solution was evaporated and the solid residue was reconstituted in water (see below).

C. Purification.

Crude oligomers were purified by anionic exchange HPLC using a TSKgel SuperQ-5PW 13 μm column and Shimadzu LC-8 system. Buffer A was 20 mM Iris, 5 mM EDTA, pH 9.0 and contained 20% Acetonitrile and buffer B was the same as buffer A with the addition of 1.5 M sodium chloride. UV traces at 260 nm were recorded. Appropriate fractions were pooled then run on size exclusion HPLC using a GE Healthcare XK 16/40 column packed with Sephadex G-25 fine with a running buffer of 100 mM ammonium bicarbonate, pH 6.7 and 20% Acetonitrile or filtered water. Alternatively, pooled fractions were desalted and exchanged into an appropriate buffer or solvent system via tangential flow filtration.

D. Annealing.

Complementary strands were mixed by combining equimolar RNA solutions (sense and antisense) in 1×PBS (Phosphate-Buffered Saline, 1×, Corning, Cellgro) to form the RNAi agents. Some RNAi agents were lyophilized and stored at −15 to −25° C. Duplex concentration was determined by measuring the solution absorbance on a UV-Vis spectrometer in 1×PBS. The solution absorbance at 260 nm was then multiplied by a conversion factor and the dilution factor to determine the duplex concentration. Unless otherwise stated, the conversion factor used was 0.037 mg/(mL·cm).

E. Conjugation of Tri-Alkyne Linker.

Either prior to or after annealing, the 5' or 3' amine functionalized sense strand is conjugated to a tri-alkyne linker. An example tri-alkyne linker structure that can be used in forming the constructs disclosed herein is as follows:

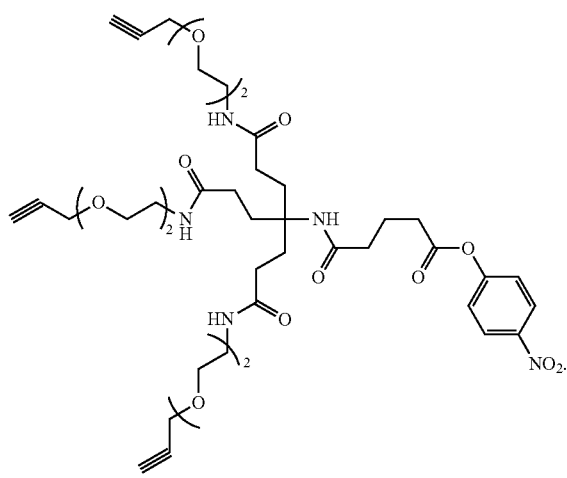

The following describes the conjugation of tri-alkyne linker to the annealed duplex: Amine-functionalized duplex was dissolved in 90% DMSO/10% $H_2O$, at ~50-70 mg/mL. 40 equivalents triethylamine was added, followed by 3 equivalents tri-alkyne-PNP. Once complete, the conjugate was precipitated twice in a solvent system of 1× phosphate buffered saline/acetonitrile (1:14 ratio), and dried.

F. Conjugation of Targeting Ligands.

Either prior to or after annealing, the 5' or 3' tridentate alkyne functionalized sense strand is conjugated to targeting ligands. The following example describes the conjugation of targeting ligands to the annealed duplex: Stock solutions of 0.5M Tris(3-hydroxypropyltriazolylmethyl)amine (THPTA), 0.5M of Cu(II) sulfate pentahydrate (Cu(II) SO4.5H2O) and 2M solution of sodium ascorbate were prepared in deionized water. A 75 mg/mL solution in DMSO of targeting ligand was made. In a 1.5 mL centrifuge tube containing tri-alkyne functionalized duplex (3 mg, 75 μL, 40 mg/mL in deionized water, ~15,000 g/mol), 25 μL of 1M Hepes pH 8.5 buffer is added. After vortexing, 35 μL of DMSO was added and the solution is vortexed. Targeting ligand was added to the reaction (6 equivalents/duplex, 2 equivalents/alkyne, ~15 μL) and the solution is vortexed. Using pH paper, pH was checked and confirmed to be pH~8. In a separate 1.5 mL centrifuge tube, 50 μL of 0.5M THPTA was mixed with 10 uL of 0.5M Cu(II)SO$_4$.5H$_2$O, vortexed, and incubated at room temp for 5 min. After 5 min, THPTA/Cu solution (7.2 μL, 6 equivalents 5:1 THPTA:Cu) was added to the reaction vial, and vortexed. Immediately afterwards, 2M ascorbate (5 μL, 50 equivalents per duplex, 16.7 per alkyne) was added to the reaction vial and vortexed. Once the reaction was complete (typically complete in 0.5-1 h), the reaction was immediately purified by non-denaturing anion exchange chromatography.

Example 2. In Vivo Intratracheal Administration of Alpha-ENaC RNAi Agents in Mice To assess the activity of alpha-ENaC RNAi agents in vivo, male ICR mice were administered 50 microliters via a microsprayer device (Penn Century, Philadelphia, Pa.) suitable for intratracheal (IT) administration on study days 1 and 2, of either isotonic saline vehicle for use as a control, or 5 mg/kg of one of the following alpha-ENaC RNAi agents without conjugate ligand (i.e., "naked RNAi agent") formulated in isotonic saline: AD04019, AD04020, AD04021, AD04022, AD04023, AD04024, AD04025, or AD04026. (See, e.g., Tables 3 through 6 for chemical structure information for the chemically modified duplexes used in this Example).

Either 4 or 5 mice were dosed per group. Mice were sacrificed (sac) on study day 9, and total RNA was isolated from both lungs following collection and homogenization. Alpha-ENaC (SCNN1A) mRNA expression was quantitated by probe-based quantitative PCR, normalized to GAPDH expression, and expressed as fraction of vehicle control group (geometric mean, +/−95% confidence interval).

Figure 1:
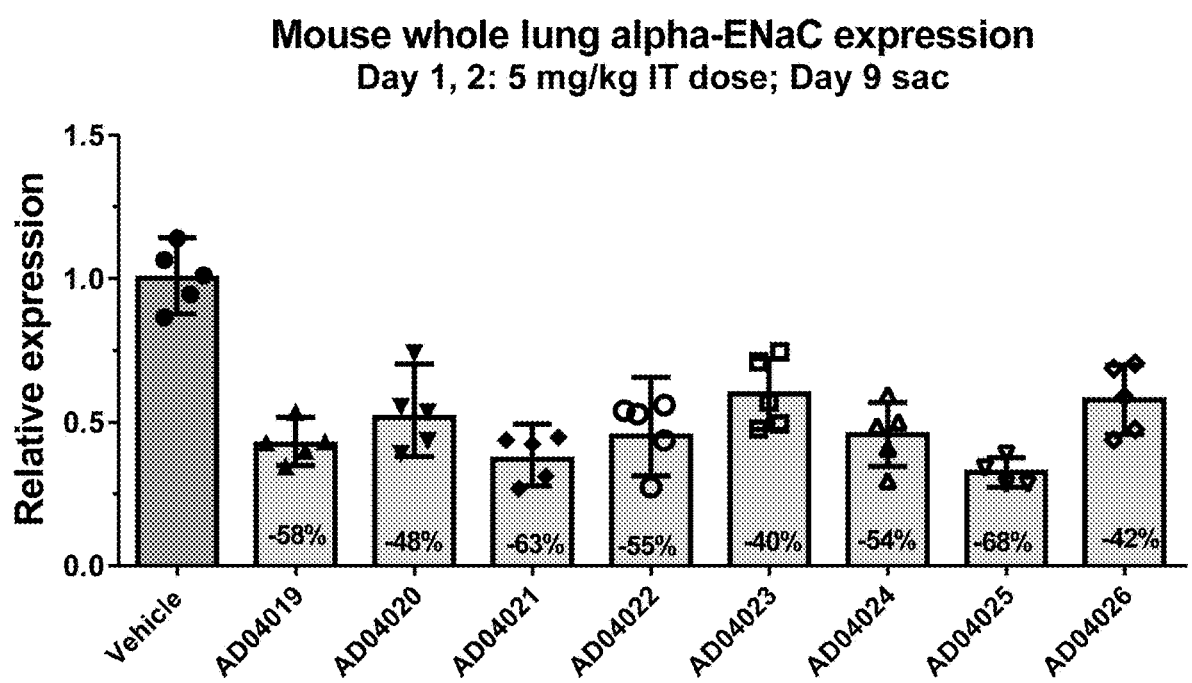
FIG. 1. Histogram showing relative expression of mouse whole lung alpha-ENaC expression after administration of various alpha-ENaC RNAi agents compared to vehicle control.

FIG. 1 shows the relative expression of the identified alpha-ENaC RNAi agent compositions (AD04019, AD04020, AD04021, AD04022, AD04023, AD04024, AD04025, and AD04026), with each RNAi agent showing a significant reduction in lung alpha-ENaC expression compared to the vehicle control.

Example 3. In Vivo Intratracheal Administration of Alpha-ENaC RNAi Agents in Mice On study days 1 and 2, male ICR mice were administered 50 microliters via a microsprayer device (Penn Century, Philadelphia, Pa.) suitable for intratracheal (IT) administration, of either isotonic saline vehicle to use as a control, or 3 mg/kg of an alpha-ENaC RNAi agent (i.e., either AD04025 or AD04858 (see, e.g., Tables 3 through 6 for chemical structure information for the chemically modified duplexes used in this Example)), formulated in isotonic saline. Either 4 or 5 mice were dosed per group. Mice were sacrificed on study day 9, and total RNA was isolated from both lungs following collection and homogenization. Alpha-ENaC (SCNN1 Å) mRNA expression was quantitated by probe-based quantitative PCR, normalized to GAPDH expression, and expressed as fraction of vehicle control group (geometric mean, +/−95% confidence interval).

Figure 2:
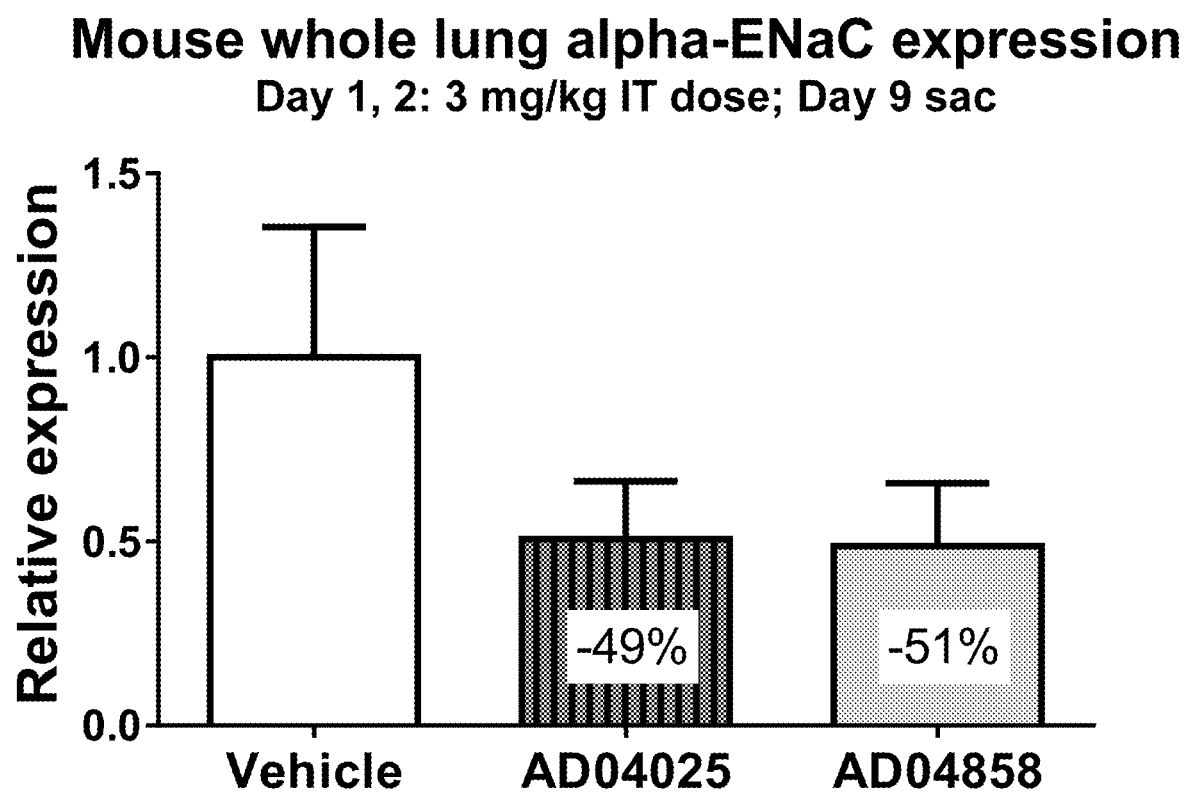
FIG. 2. Histogram showing relative expression of mouse whole lung alpha-ENaC expression after administration of alpha-ENaC RNAi agents AD04025 and AD04858 compared to vehicle control.

FIG. 2 shows the relative expression of alpha-ENaC RNAi agents AD04025 and AD04858, with both RNAi agents showing a significant reduction in lung alpha-ENaC expression compared to control.

Example 4. In Vivo Intratracheal Administration of Alpha-ENaC RNAi Agents with and without Conjugation to Epithelial Cell Targeting Ligands in Rats On study days 1 and 2, male Sprague Dawley rats were administered 200 microliters via a microsprayer device (Penn Century, Philadelphia, Pa.) suitable for intratracheal (IT) administration, of either 0.5 mg/kg, 1.5 mg/kg, or 5 mg/kg of an alpha-ENaC RNAi agent formulated in isotonic saline. Five (5) rats were dosed per group. Rats were sacrificed on study day 9, and total RNA was isolated from both lungs following collection and homogenization. Alpha-ENaC (SCNN1A) mRNA expression was quantitated by probe-based quantitative PCR, normalized to GAPDH expression, and expressed as fraction of vehicle control group (geometric mean, +/−95% confidence interval).

Figure 3:
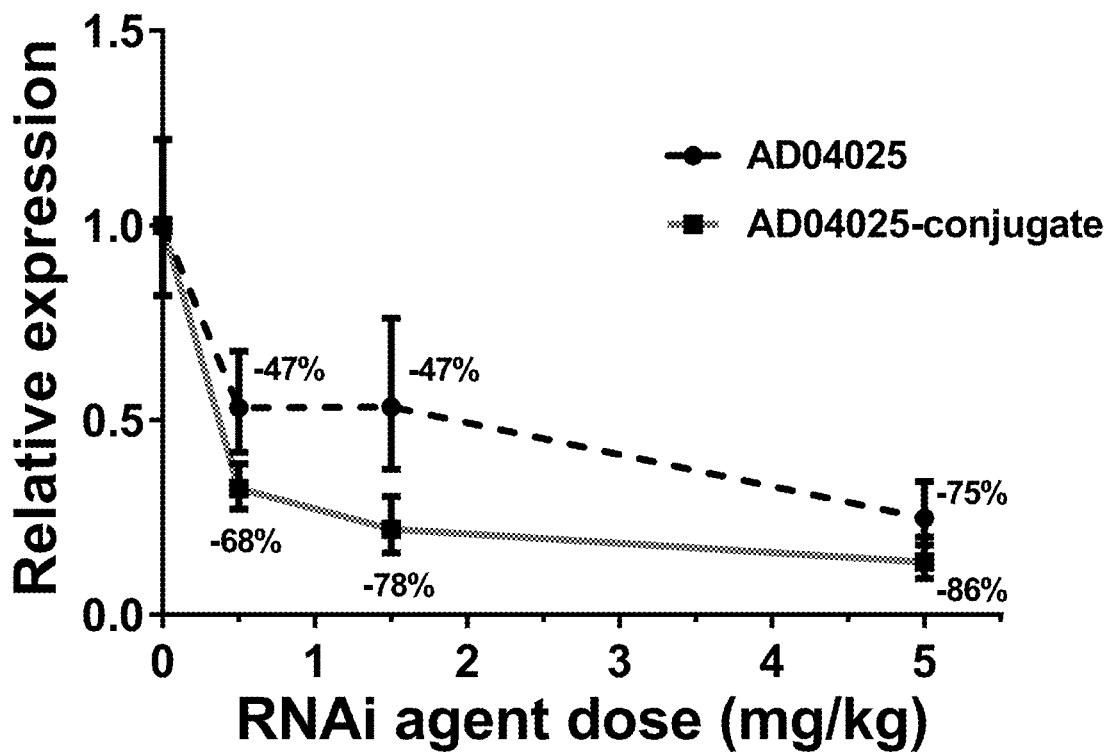
FIG. 3. Graph showing relative expression of rat whole lung alpha-ENaC expression of alpha-ENaC RNAi agents AD04025 and AD04025-conjugate (i.e., AD04025 conjugated to a peptide-based αvβ6 epithelial cell targeting ligand).

FIG. 3 shows the relative expression of alpha-ENaC RNAi agents AD04025 and AD04025-conjugate. AD04025-conjugate was synthesized by post-synthetically linking a peptide-based integrin targeting ligand having affinity for αvβ6 integrin, via a masked poly-L-lysine (PLL) scaffold, to an amino group that was added to 5' terminal end of the sense strand of the RNAi agent. (See, e.g., Tables 3 through 6 for chemical structure information for the chemically modified duplexes used in this Example). While both the naked RNAi agent and the RNAi agent-conjugate showed a substantial reduction in lung alpha-ENaC expression compared to baseline measurements, the AD04025-conjugate showed a numerically improved level of knockdown across each of the three dosage levels measured (0.5 mg/kg, 1.5 mg/kg, and 5 mg/kg), with a particularly noticeable improvement at the 1.5 mg/kg dose (78% knockdown with ligand vs. 47% knockdown without ligand).

Example 5. In Vivo Oropharyngeal Aspiration Administration of Alpha-ENaC RNAi Agents Conjugated to Epithelial Cell Targeting Ligands in Rats On study day 1, male Sprague Dawley rats were dosed via oropharyngeal ("OP") aspiration administration with 200 microliters using a pipette, according to the following dosing groups recited in Table 7:

TABLE 7

Dosing Groups of Rats in Example 5

| Group | RNAi Agent and Dose | Dosing Regimen |
|---|---|---|
| 1 | Isotonic saline (no RNAi agent) | Single OP dose on day 1 |
| 2 | 0.5 mg/kg of AD05347 conjugated to a tridentate small molecule αvβ6 epithelial cell targeting ligand (Tri-SM2) at the 5' terminal end of the sense strand, formulated in isotonic saline. | Single OP dose on day 1 |
| 3 | 0.5 mg/kg of AD05453 conjugated to a tridentate small molecule αvβ6 epithelial cell targeting ligand (Tri-SM2) at the 5' terminal end of the sense strand, formulated in isotonic saline. | Single OP dose on day 1 |
| 4 | 0.5 mg/kg of AD05454 conjugated to a tridentate small molecule αvβ6 epithelial cell targeting ligand (Tri-SM2) at the 5' terminal end of the sense strand, formulated in isotonic saline. | Single OP dose on day 1 |
| 5 | 0.5 mg/kg of AD05455 conjugated to a tridentate small molecule αvβ6 epithelial cell targeting ligand (Tri-SM2) at the 5' terminal end of the sense strand, formulated in isotonic saline. | Single OP dose on day 1 |
| 6 | 0.5 mg/kg of AD05456 conjugated to a tridentate small molecule αvβ6 epithelial cell targeting ligand (Tri-SM2) at the 5' terminal end of the sense strand, formulated in isotonic saline. | Single OP dose on day 1 |
| 7 | 0.5 mg/kg of AD05457 conjugated to a tridentate small molecule αvβ6 epithelial cell targeting ligand (Tri-SM2) at the 5' terminal end of the sense strand, formulated in isotonic saline. | Single OP dose on day 1 |

(See, e.g., Tables 3 through 6 for chemical structure information for the chemically modified duplexes used in this Example).

Figure 4:
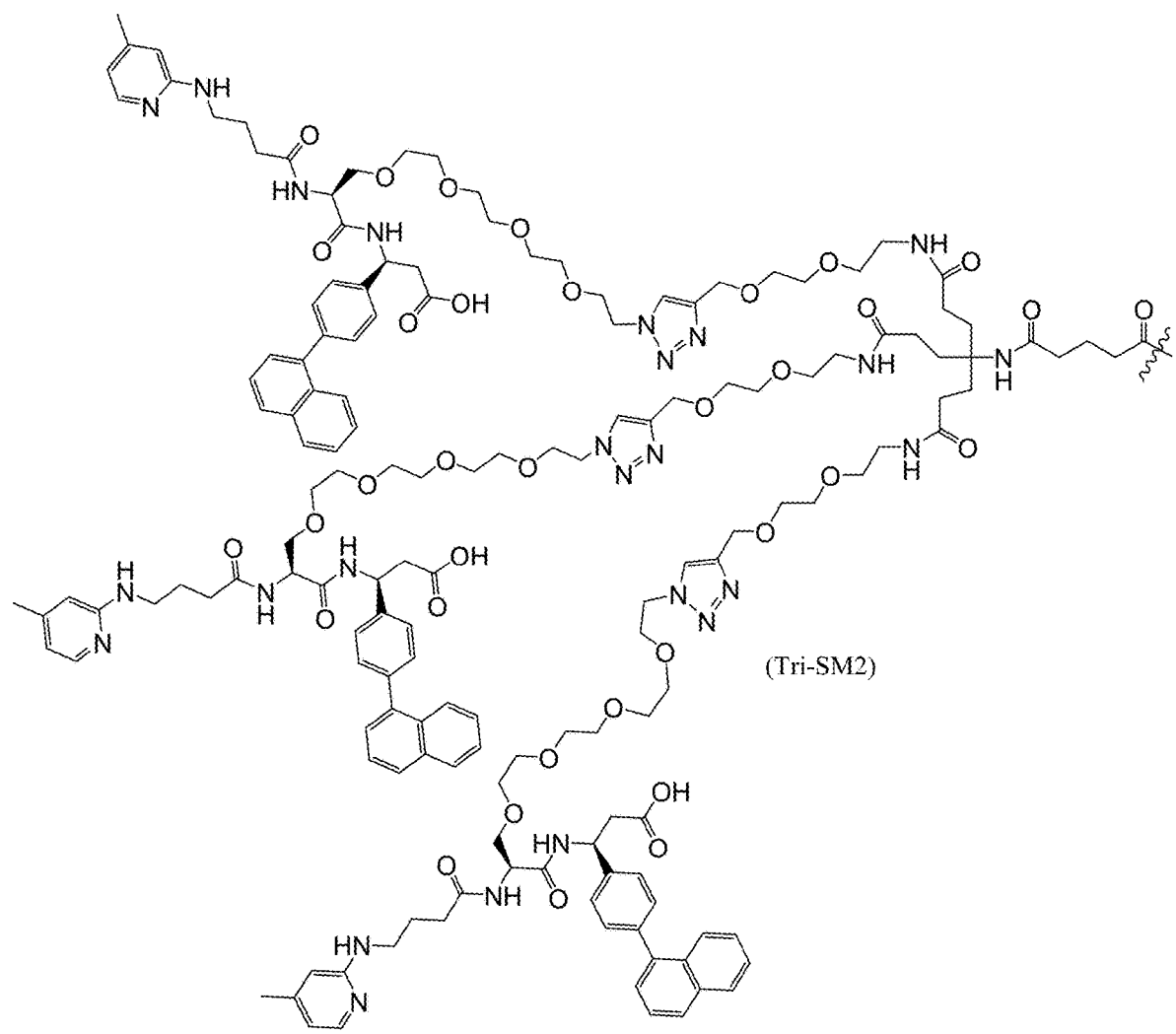
FIG. 4. Chemical structure representation of the tridentate αvβ6 epithelial cell targeting ligand referred to herein as Tri-SM2.

The tridentate small molecule αvβ6 epithelial cell targeting ligand referred to as Tri-SM2 in Groups 2 through 7 has the structure represented in FIG. 4, which was conjugated to the RNAi agent via the terminal amine (i.e., by forming a covalent bond with the terminal $NH_2$-$C_6$ group) on the 5' terminal end of the sense strand.

Five (5) rats were dosed per group (n=5). Rats were sacrificed on study day 9, and total RNA was isolated from both lungs following collection and homogenization. Alpha-ENaC (SCNN1 Å) mRNA expression was quantitated by probe-based quantitative PCR, normalized to GAPDH expression, and expressed as fraction of vehicle control group (geometric mean, +/−95% confidence interval).

TABLE 8

Average Relative rENaC mRNA Expression at Sacrifice (Day 9) in Example 5

| Group ID | Average Relative rENaC mRNA Expression (n = 5 for each group) | Low (error) | High (error) |
|---|---|---|---|
| Group 1 (isotonic saline) | 1.000 | 0.161 | 0.192 |
| Group 2 (0.5 mg/kg AD05347) | 0.411 | 0.039 | 0.042 |
| Group 3 (0.5 mg/kg AD05453) | 0.678 | 0.092 | 0.106 |
| Group 4 (0.5 mg/kg AD05454) | 0.728 | 0.127 | 0.154 |
| Group 5 (0.5 mg/kg AD05455) | 0.663 | 0.075 | 0.084 |
| Group 6 (0.5 mg/kg AD05456) | 0.633 | 0.101 | 0.120 |
| Group 7 (0.5 mg/kg AD05457) | 0.726 | 0.174 | 0.228 |

As shown in Table 8 above, each of the alpha-ENaC RNAi agents showed a reduction in mRNA expression in rats compared to control. For example, AD05347, which includes a cyclopropyl-phosphonate group located at the 5' terminal end of the antisense strand, had an average reduction of approximately 59% (0.411) of mRNA compared to the control group.

Further, each of the other alpha-ENaC RNAi agents showed a reduction of at least approximately 27% of rENaC mRNA compared to control.

Example 6. In Vivo Intratracheal Administration of Alpha-ENaC RNAi Agents Conjugated to Epithelial Cell Targeting Ligands in Rats On study day 1, male Sprague Dawley rats were administered 200 microliters via a microsprayer device (Penn Century, Philadelphia, Pa.) suitable for intratracheal (IT) administration, of either isotonic saline vehicle for use as a control, or one of the following alpha-ENaC RNAi agents according to the following dosing groups recited in Table 9:

(See, e.g., Tables 3 through 6 for chemical structure information for the chemically modified duplexes used in this Example).

Figure 5:
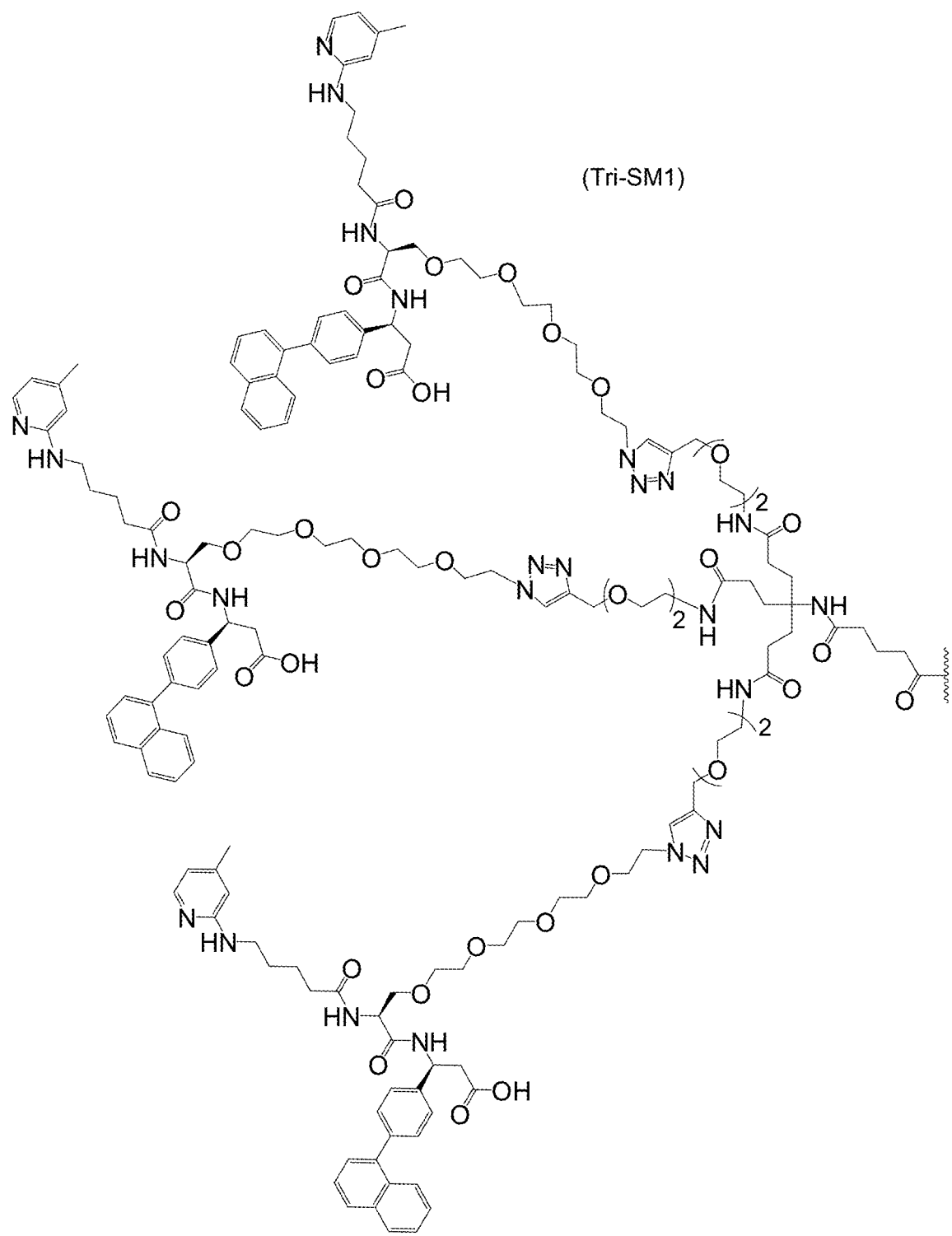
FIG. 5. Chemical structure representation of the tridentate αvβ6 epithelial cell targeting ligand referred to herein as Tri-SM1.

The tridentate small molecule αvβ6 epithelial cell targeting ligand referred to as Tri-SM1 in Groups 2, 5, and 6, has the structure represented in FIG. 5, which was conjugated to the RNAi agent via the terminal amine (i.e., by forming a covalent bond with the terminal NH2-C6 group) on the 5' terminal end of the sense strand. For Groups 3 and 4, the tridentate small molecule ligand in Groups 3 and 4 replaced the glutaric linker shown in FIG. 5 with a linker that included cysteine-PEG$_2$ linkage, represented as follows:

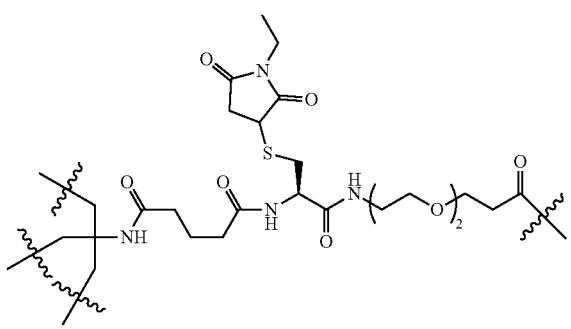

Five (5) rats were dosed in each of Groups 1, 2, 3, 4, 5, and 7 (n=5), and four (4) rats were dosed in Group 6. Rats were sacrificed on study day 9, and total RNA was isolated from both lungs following collection and homogenization. Alpha-ENaC (SCNN1A) mRNA expression was quantitated by probe-based quantitative PCR, normalized to GAPDH expression, and expressed as fraction of vehicle control group (geometric mean, +/−95% confidence interval).

TABLE 9

Dosing Groups of Rats in Example 6

| Group | RNAi Agent and Dose | Dosing Regimen |
|---|---|---|
| 1 | Isotonic saline (no RNAi agent) | Single IT dose on day 1 |
| 2 | 1.5 mg/kg of AD04835 conjugated to a tridentate small molecule αvβ6 epithelial cell targeting ligand (Tri-SM1) at the 5' terminal end of the sense strand, formulated in isotonic saline. | Single IT dose on day 1 |
| 3 | 1.5 mg/kg of AD04835 conjugated to a tridentate small molecule αvβ6 epithelial cell targeting ligand (Tri-SM1) further including a cysteine-PEG2 linkage at the 5' terminal end of the sense strand, formulated in isotonic saline. | Single IT dose on day 1 |
| 4 | 1.5 mg/kg of AD05346 conjugated to a tridentate small molecule αvβ6 epithelial cell targeting ligand (Tri-SM1) at the 5' terminal end of the sense strand, formulated in isotonic saline. | Single IT dose on day 1 |
| 5 | 1.5 mg/kg of AD05345 conjugated to a tridentate small molecule αvβ6 epithelial cell targeting ligand (Tri-SM1) at the 5' terminal end of the sense strand, formulated in isotonic saline. | Single IT dose on day 1 |
| 6 | 1.5 mg/kg of AD05347 conjugated to a tridentate small molecule αvβ6 epithelial cell targeting ligand (Tri-SM1) at the 5' terminal end of the sense strand, formulated in isotonic saline. | Single IT dose on day 1 |
| 7 | 1.5 mg/kg of AD04835 conjugated to a monodentate peptide-based αvβ6 epithelial cell targeting ligand which further included a PEG20 linker, followed by a peptide linker (PheCitPhePro (SEQ ID NO: 290)), a 20 kilodalton (KDa) PEG group, and a cysteine linker, which was then conjugated at the 5' terminal end of the sense strand, formulated in isotonic saline. | Single IT dose on day 1 |

TABLE 10

Average Relative rENaC mRNA Expression at Sacrifice (Day 9) in Example 6

| Group ID | Average Relative rENaC mRNA Expression | Low (error) | High (error) |
|---|---|---|---|
| Group 1 (isotonic saline) | 1.000 | 0.082 | 0.089 |
| Group 2 (1.5 mg/kg AD04835-Tri-SM1) | 0.453 | 0.098 | 0.126 |
| Group 3 (1.5 mg/kg AD04835-PEG$_2$-Cys-Tri-SM1) | 0.365 | 0.076 | 0.095 |
| Group 4 (1.5 mg/kg AD07065-PEG$_2$-Cys-Tri-SM1) | 0.412 | 0.136 | 0.204 |
| Group 5 (1.5 mg/kg AD05345-Tri-SM1) | 0.404 | 0.097 | 0.128 |
| Group 6 (1.5 mg/kg AD05347-Tri-SM1) | 0.311 | 0.048 | 0.057 |
| Group 7 (1.5 mg/kg AD05453-Cys-PEG20 kDa-peptide linker-PEG$_{20}$-Tri-peptide ligand) | 0.354 | 0.078 | 0.101 |

As shown in Table 10 above, each of the alpha-ENaC RNAi agents showed a reduction in mRNA expression in rats compared to control. In addition, the use of a tridentate small molecule αvβ6 epithelial cell targeting ligand shows comparable reduction in mRNA expression when compared to a peptide-based αvβ6 epithelial cell targeting ligand that further included a 20 kDa PEG PK modifier.

Example 7. In Vivo Oropharyngeal Aspiration Administration of Alpha-ENaC RNAi Agents Conjugated to Epithelial Cell Targeting Ligands in Rats On study day 1, male Sprague Dawley rats were dosed via oropharyngeal ("OP") aspiration administration with 200 microliters using a pipette, according to the following dosing groups recited in Table 11:

(See, e.g., Tables 3 through 6 for chemical structure information for the chemically modified duplexes used in this Example).

The tridentate small molecule αvβ6 epithelial cell targeting ligand referred to as Tri-SM2 in each of Groups 2-6 and 8-10, has the structure represented in FIG. 4, which was conjugated to the RNAi agent via the terminal amine (i.e., by forming a covalent bond with the terminal NH2-C6 group) on the 5' terminal end of the sense strand. The ligand for Group 7 included a cysteine linking group (see, e.g., Example 6).

Four (4) rats were dosed in Groups 1, 2, 3, 4, 5, 6, 7, and 9 (n=4), and three (3) rats were dosed in Groups 8 and 10 (n=3). Rats were sacrificed on study day 9, and total RNA was isolated from both lungs following collection and homogenization. Alpha-ENaC (SCNN1A) mRNA expression was quantitated by probe-based quantitative PCR, normalized to GAPDH expression, and expressed as fraction of vehicle control group (geometric mean, +/−95% confidence interval).

TABLE 11

Dosing Groups of Rats in Example 7

| Group | RNAi Agent and Dose | Dosing Regimen |
|---|---|---|
| 1 | Isotonic saline (no RNAi agent) | Single OP dose on day 1 |
| 2 | 0.5 mg/kg of AD05347 conjugated to a tridentate small molecule αvβ6 epithelial cell targeting ligand (Tri-SM2) at the 5' terminal end of the sense strand, formulated in isotonic saline. | Single OP dose on day 1 |
| 3 | 0.5 mg/kg of AD05458 conjugated to a tridentate small molecule αvβ6 epithelial cell targeting ligand (Tri-SM2) at the 5' terminal end of the sense strand, formulated in isotonic saline. | Single OP dose on day 1 |
| 4 | 0.5 mg/kg of AD05459 conjugated to a tridentate small molecule αvβ6 epithelial cell targeting ligand (Tri-SM2) at the 5' terminal end of the sense strand, formulated in isotonic saline. | Single OP dose on day 1 |
| 5 | 0.5 mg/kg of AD05562 conjugated to a tridentate small molecule αvβ6 epithelial cell targeting ligand (Tri-SM2) at the 5' terminal end of the sense strand, formulated in isotonic saline. | Single OP dose on day 1 |
| 6 | 0.5 mg/kg of AD05563 conjugated to a tridentate small molecule αvβ6 epithelial cell targeting ligand (Tri-SM2) at the 5' terminal end of the sense strand, formulated in isotonic saline. | Single OP dose on day 1 |
| 7 | 0.5 mg/kg of AD05564 conjugated to a tridentate small molecule αvβ6 epithelial cell targeting ligand (Tri-SM2) that further includes a cysteine linking group at the 5' terminal end of the sense strand, formulated in isotonic saline. | Single OP dose on day 1 |
| 8 | 0.5 mg/kg of AD05565 conjugated to a tridentate small molecule αvβ6 epithelial cell targeting ligand (Tri-SM2) at the 5' terminal end of the sense strand, formulated in isotonic saline. | Single OP dose on day 1 |
| 9 | 0.5 mg/kg of AD05567 conjugated to a tridentate small molecule αvβ6 epithelial cell targeting ligand (Tri-SM2) at the 5' terminal end of the sense strand, formulated in isotonic saline. | Single OP dose on day 1 |
| 10 | 0.5 mg/kg of AD05570 conjugated to a tridentate small molecule αvβ6 epithelial cell targeting ligand (Tri-SM2) at the 5' terminal end of the sense strand, formulated in isotonic saline. | Single OP dose on day 1 |

TABLE 12

Average Relative rENaC mRNA Expression at Sacrifice (Day 9) in Example 7

| Group ID | Number of rats (n=) | Average Relative rENaC mRNA Expression | Low (error) | High (error) |
|---|---|---|---|---|
| Group 1 (isotonic saline) | 4 | 1.000 | 0.041 | 0.043 |
| Group 2 (0.5 mg/kg AD05347) | 4 | 0.457 | 0.088 | 0.109 |
| Group 3 (0.5 mg/kg AD05458) | 4 | 0.708 | 0.055 | 0.059 |
| Group 4 (0.5 mg/kg AD05459) | 4 | 0.753 | 0.174 | 0.227 |
| Group 5 (0.5 mg/kg AD05562) | 4 | 0.608 | 0.056 | 0.062 |
| Group 6 (0.5 mg/kg AD05563) | 4 | 0.621 | 0.048 | 0.053 |
| Group 7 (0.5 mg/kg AD05564) | 4 | 0.569 | 0.095 | 0.114 |
| Group 8 (0.5 mg/kg AD05565) | 3 | 0.627 | 0.066 | 0.073 |
| Group 9 (0.5 mg/kg AD05567) | 4 | 0.638 | 0.087 | 0.100 |
| Group 10 (0.5 mg/kg AD05570) | 3 | 0.645 | 0.123 | 0.151 |

As shown in Table 12 above, each of the alpha-ENaC RNAi agents showed a reduction in mRNA expression in rats compared to control. For example, AD05347 showed approximately a 54% reduction (0.457) in average rENaC mRNA expression compared to control.

Example 8. In Vivo Oropharyngeal Aspiration Administration of Alpha-ENaC RNAi Agents Conjugated to Epithelial Cell Targeting Ligands in Rats On study day 1, male Sprague Dawley rats were dosed via oropharyngeal ("OP") aspiration administration with 200 microliters using a pipette, according to the following dosing groups recited in Table 13:

(See, e.g., Tables 3 through 6 for chemical structure information for the chemically modified duplexes used in this Example).

Figure 6:
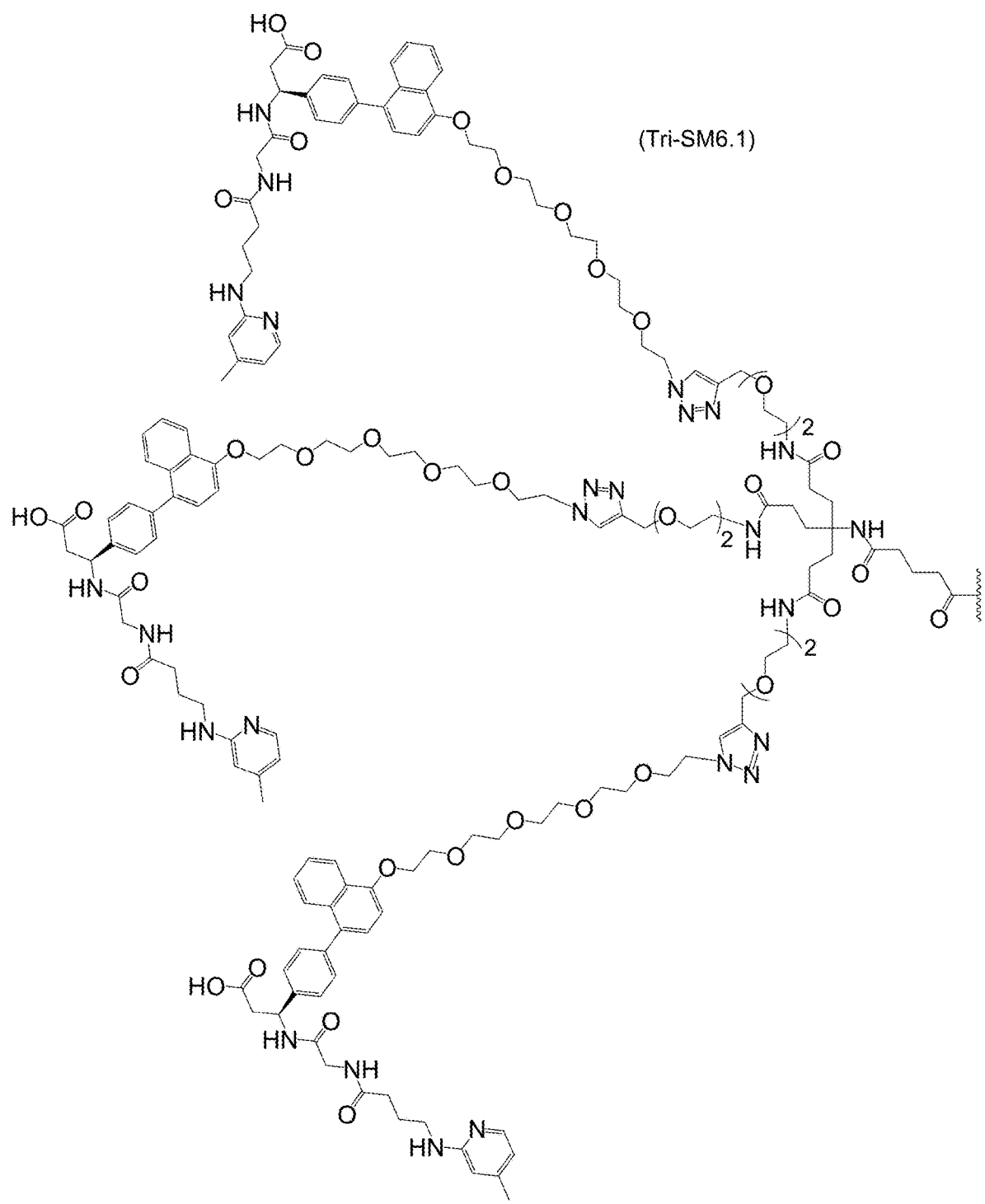
FIG. 6. Chemical structure representation of the tridentate αvβ6 epithelial cell targeting ligand referred to herein as Tri-SM6.1.
Figure 7:
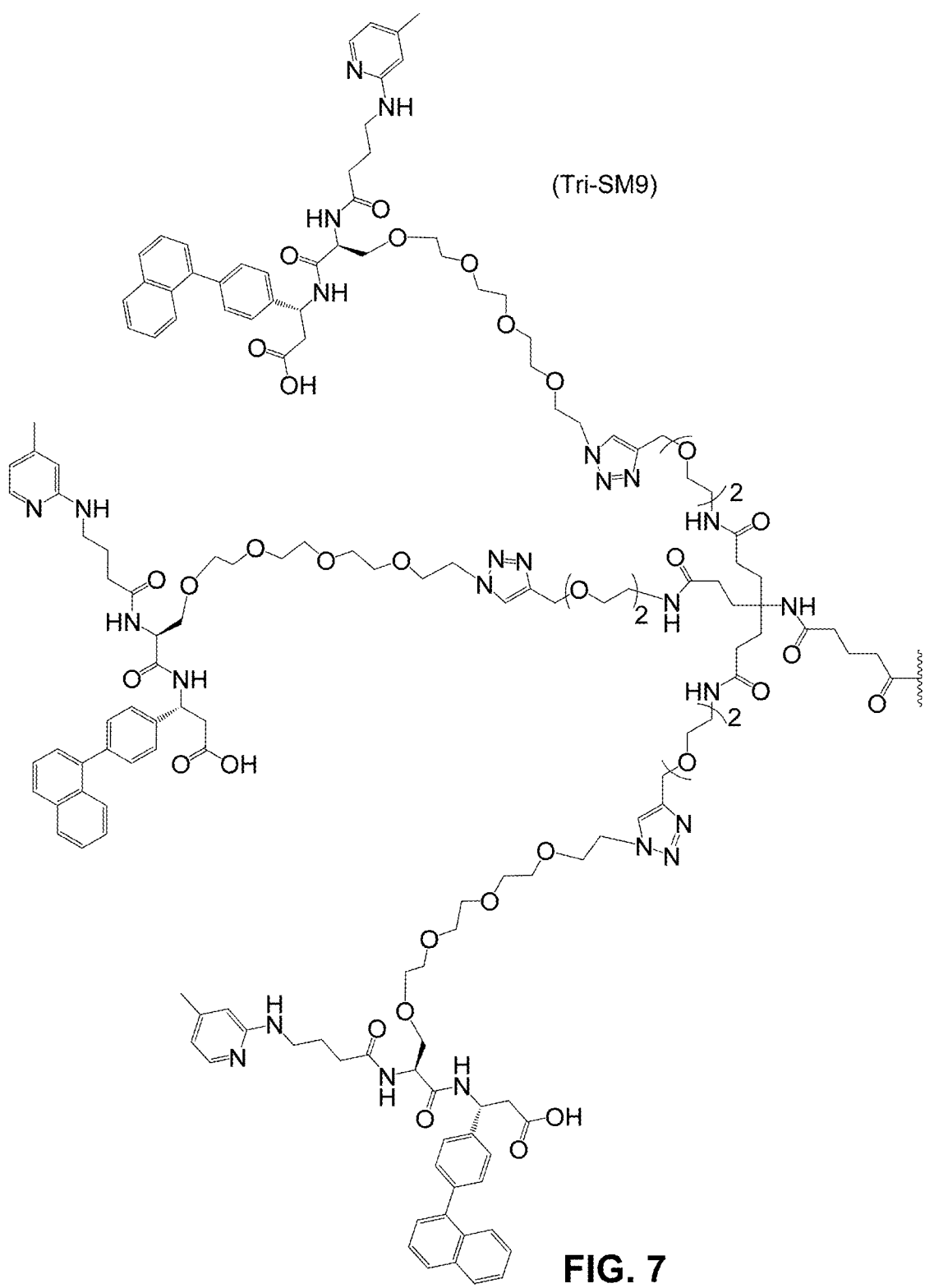
FIG. 7. Chemical structure representation of the tridentate αvβ6 epithelial cell targeting ligand referred to herein as Tri-SM9.
Figure 8:
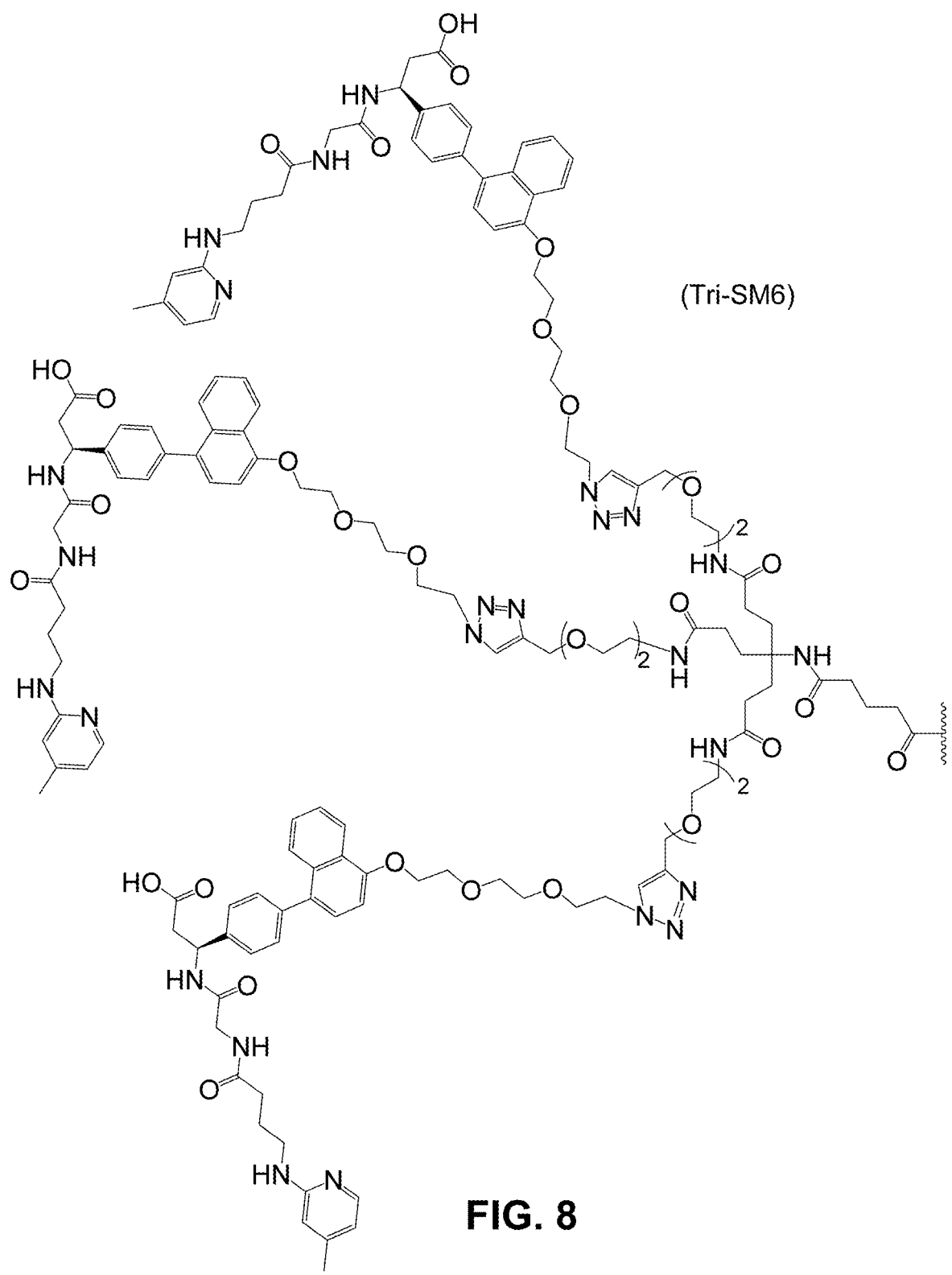
FIG. 8. Chemical structure representation of the tridentate αvβ6 epithelial cell targeting ligand referred to herein as Tri-SM6.
Figure 9:
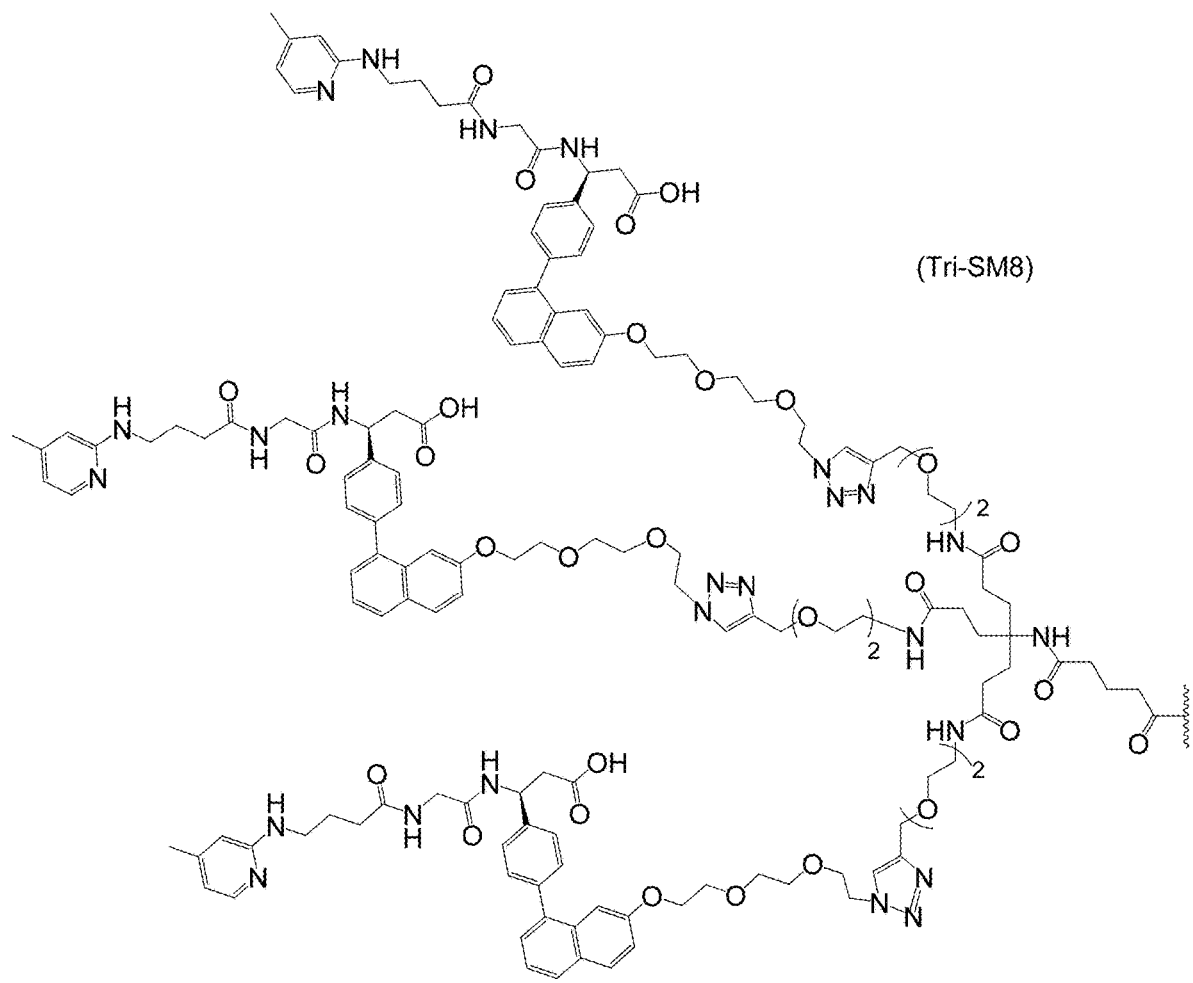
FIG. 9. Chemical structure representation of the tridentate αvβ6 epithelial cell targeting ligand referred to herein as Tri-SM8.

The tridentate small molecule αvβ6 epithelial cell targeting ligand referred to as Tri-SM2 in Group 2 and Group 4 has the structure represented in FIG. 4; the tridentate small molecule αvβ6 epithelial cell targeting ligand referred to as Tri-SM6.1 in Groups 3 and 8 has the structure represented in FIG. 6; the tridentate small molecule αvβ6 epithelial cell targeting ligand referred to as Tri-SM9 in Group 5 has the structure represented in FIG. 7; the tridentate small molecule αvβ6 epithelial cell targeting ligand referred to as Tri-SM6 in Group 6 has the structure represented in FIG. 8; the tridentate small molecule αvβ6 epithelial cell targeting ligand referred to as Tri-SM8 in Group 7 has the structure represented in FIG. 9; the tridentate small molecule αvβ6

TABLE 13

Dosing Groups of Rats in Example 8

Figure 10:
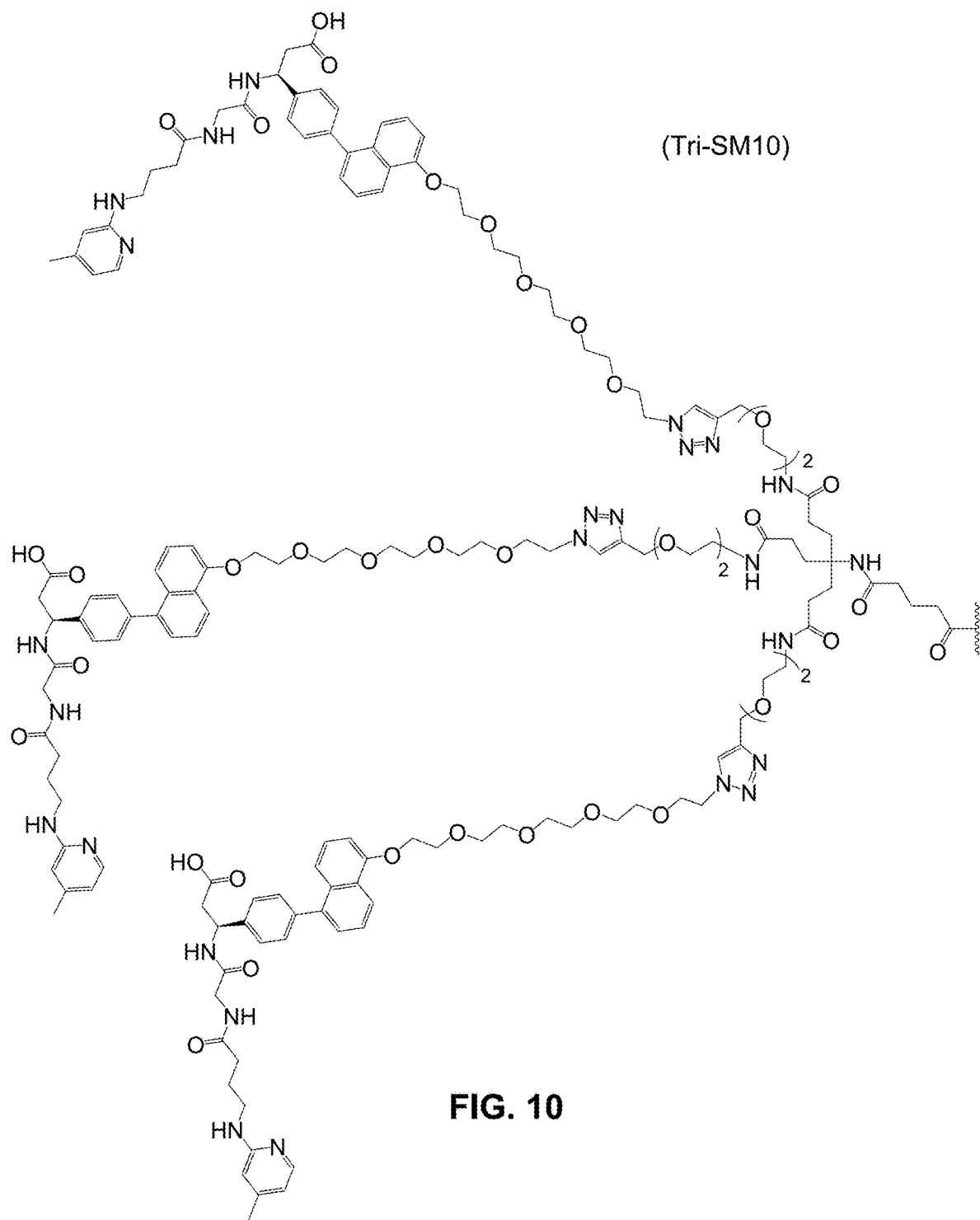
FIG. 10. Chemical structure representation of the tridentate αvβ6 epithelial cell targeting ligand referred to herein as Tri-SM10.
Figure 11:
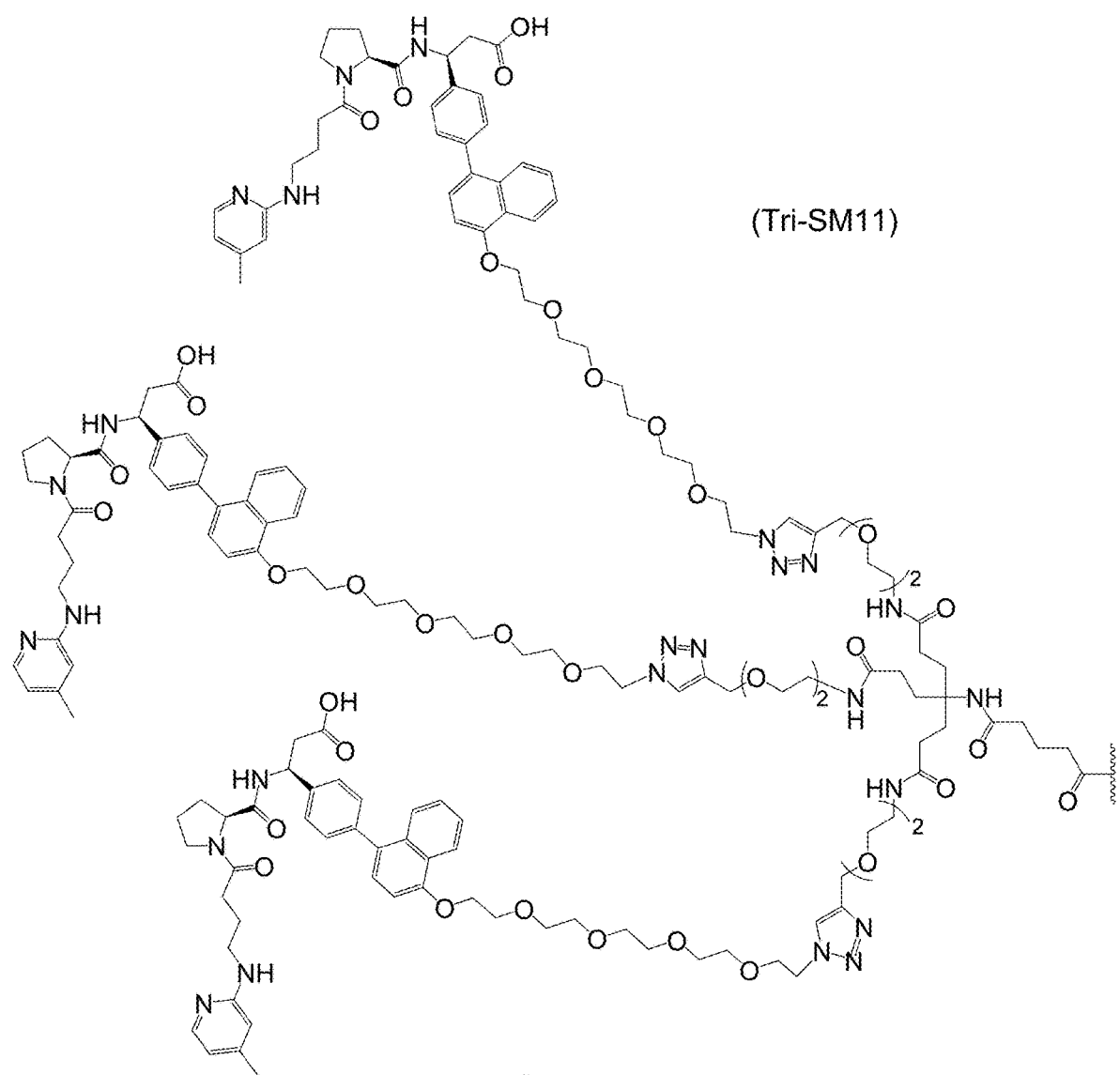
FIG. 11. Chemical structure representation of the tridentate αvβ6 epithelial cell targeting ligand referred to herein as Tri-SM11.

| Group | RNAi Agent and Dose | Dosing Regimen |
|---|---|---|
| 1 | Isotonic saline (no RNAi agent) | Single OP dose on day 1 |
| 2 | 0.5 mg/kg of AD05347 conjugated to a tridentate small molecule αvβ6 epithelial cell targeting ligand (Tri-SM2) at the 5' terminal end of the sense strand, formulated in isotonic saline. | Single OP dose on day 1 |
| 3 | 0.5 mg/kg of AD05347 conjugated to a tridentate small molecule αvβ6 epithelial cell targeting ligand (Tri-SM6.1) at the 5' terminal end of the sense strand, formulated in isotonic saline. | Single OP dose on day 1 |
| 4 | 0.5 mg/kg of AD05453 conjugated to a tridentate small molecule αvβ6 epithelial cell targeting ligand (Tri-SM2) at the 5' terminal end of the sense strand, formulated in isotonic saline. | Single OP dose on day 1 |
| 5 | 0.5 mg/kg of AD05453 conjugated to a tridentate small molecule αvβ6 epithelial cell targeting ligand (Tri-SM9) at the 5' terminal end of the sense strand, formulated in isotonic saline. | Single OP dose on day 1 |
| 6 | 0.5 mg/kg of AD05453 conjugated to a tridentate small molecule αvβ6 epithelial cell targeting ligand (Tri-SM6) at the 5' terminal end of the sense strand, formulated in isotonic saline. | Single OP dose on day 1 |
| 7 | 0.5 mg/kg of AD05453 conjugated to a tridentate small molecule αvβ6 epithelial cell targeting ligand (Tri-SM8) at the 5' terminal end of the sense strand, formulated in isotonic saline. | Single OP dose on day 1 |
| 8 | 0.5 mg/kg of AD05453 conjugated to a tridentate small molecule αvβ6 epithelial cell targeting ligand (Tri-SM6.1) at the 5' terminal end of the sense strand, formulated in isotonic saline. | Single OP dose on day 1 |
| 9 | 0.5 mg/kg of AD05453 conjugated to a tridentate small molecule αvβ6 epithelial cell targeting ligand (Tri-SM10) at the 5' terminal end of the sense strand, formulated in isotonic saline. | Single OP dose on day 1 |
| 10 | 0.5 mg/kg of AD05453 conjugated to a tridentate small molecule αvβ6 epithelial cell targeting ligand (Tri-SM11) at the 5' terminal end of the sense strand, formulated in isotonic saline. | Single OP dose on day 1 |
| 11 | 0.5 mg/kg of AD05453 conjugated to a tridentate peptide-based αvβ6 epithelial cell targeting ligand at the 5' terminal end of the sense strand, formulated in isotonic saline. | Single OP dose on day 1 | epithelial cell targeting ligand referred to as Tri-SM10 in Group 9 has the structure represented in FIG. 10; and the tridentate small molecule αvβ6 epithelial cell targeting ligand referred to as Tri-SM11 in Group 10 has the structure represented in FIG. 11. Each of the respective tridentate small molecule αvβ6 epithelial cell targeting ligands were added by conjugation via the amino group on the 5' terminal end of the respective alpha-ENaC RNAi agent.

Four (4) rats were dosed in each Group (n=4). Rats were sacrificed on study day 9, and total RNA was isolated from both lungs following collection and homogenization. Alpha-ENaC (SCNN1 Å) mRNA expression was quantitated by probe-based quantitative PCR, normalized to GAPDH expression, and expressed as fraction of vehicle control group (geometric mean, +/−95% confidence interval).

TABLE 14

Average Relative rENaC mRNA Expression at Sacrifice (Day 9) in Example 8

| Group ID | Average Relative rENaC mRNA Expression | Low (error) | High (error) |
|---|---|---|---|
| Group 1 (isotonic saline) | 1.000 | 0.162 | 0.193 |
| Group 2 (0.5 mg/kg AD05347-Tri-SM2) | 0.469 | 0.101 | 0.129 |
| Group 3 (0.5 mg/kg AD05347-Tri-SM6.1) | 0.358 | 0.078 | 0.100 |
| Group 4 (0.5 mg/kg AD05453-Tri-SM2) | 0.562 | 0.086 | 0.102 |
| Group 5 (0.5 mg/kg AD05453-Tri-SM9) | 0.620 | 0.168 | 0.230 |
| Group 6 (0.5 mg/kg AD05453-Tri-SM6) | 0.559 | 0.099 | 0.120 |
| Group 7 (0.5 mg/kg AD05453-Tri-SM8) | 0.691 | 0.072 | 0.081 |
| Group 8 (0.5 mg/kg AD05453-Tri-SM6.1) | 0.454 | 0.055 | 0.063 |
| Group 9 (0.5 mg/kg AD05453-Tri-SM10) | 0.454 | 0.080 | 0.097 |
| Group 10 (0.5 mg/kg AD05453-Tri-SM11) | 0.577 | 0.113 | 0.140 |
| Group 11 (0.5 mg/kg AD05453-tridentate peptide ligand) | 0.558 | 0.057 | 0.064 |

As shown in Table 14 above, each of the alpha-ENaC RNAi agents showed a reduction in mRNA expression in rats compared to control. For example, AD05347-Tri-SM6.1 (Group 3) showed approximately a 64% reduction (0.358) in average rENaC mRNA expression compared to control, and AD05453-Tri-SM6.1 (Group 8) showed approximately a 55% reduction (0.454) in average rENaC mRNA expression compared to control. Further, Groups 8 and 9 achieved approximately 55% reduction (0.454) in average rENaC mRNA expression without the use of a 5' terminal cyclopropyl-phosphonate modification on the antisense strand, and showed a comparable inhibitory effect to Group 2, which had approximately 53% reduction (0.469) in average rENaC mRNA expression with 5' antisense cyclopropyl-phosphonate modification. Moreover, as observed in groups 4, 6, 8, 9, and 10, tridentate small molecule αvβ6 epithelial cell targeting ligands were comparable or in some instances numerically superior to Group 11 (e.g., Groups 8 and 9 that included Tri-SM6.1 and Tri-SM10), which utilized a tridentate peptide-based αvβ6 epithelial cell targeting ligand known to have affinity for integrin αvβ6 (See International Patent Application Publication No. WO 2018/085415 at FIG. 11 for chemical structure information).

Example 9. In Vivo Oropharyngeal Aspiration Administration of Alpha-ENaC RNAi Agents Conjugated to Epithelial Cell Targeting Ligands in Rats On study day 1, male Sprague Dawley rats were dosed via oropharyngeal ("OP") aspiration administration with 200 microliters using a pipette, which included the following dosing groups recited in Table 15:

TABLE 15

Dosing Groups of Rats in Example 9

| Group | RNAi Agent and Dose | Dosing Regimen |
|---|---|---|
| 1 | Isotonic saline (no RNAi agent) | Single OP dose on day 1 |
| 2 | 0.5 mg/kg of AD05453 without any targeting ligand (i.e., "naked RNAi agent"), formulated in isotonic saline | Single OP dose on day 1 |
| 3 | 0.5 mg/kg of AD05453 conjugated to a tridentate small molecule αvβ6 epithelial cell targeting ligand (Tri-SM6.1) at the 5' terminal end of the sense strand, formulated in isotonic saline. | Single OP dose on day 1 |
| 4 | 0.5 mg/kg of AD05453 conjugated to a tridentate small molecule αvβ6 epithelial cell targeting ligand (Tri-SM7) at the 5' terminal end of the sense strand, formulated in isotonic saline. | Single OP dose on day 1 |

TABLE 15-continued

Dosing Groups of Rats in Example 9

| Group | RNAi Agent and Dose | Dosing Regimen |
|---|---|---|
| 5 | 0.5 mg/kg of AD05618 conjugated to a tridentate small molecule αvβ6 epithelial cell targeting ligand (Tri-SM6.1) at the 5' terminal end of the sense strand, formulated in isotonic saline. | Single OP dose on day 1 |
| 6 | 0.5 mg/kg of AD05562 conjugated to a tridentate small molecule αvβ6 epithelial cell targeting ligand (Tri-SM6.1) at the 5' terminal end of the sense strand, formulated in isotonic saline. | Single OP dose on day 1 |
| 7 | 0.5 mg/kg of AD05564 conjugated to a tridentate small molecule αvβ6 epithelial cell targeting ligand (Tri-SM6.1) at the 5' terminal end of the sense strand, formulated in isotonic saline. | Single OP dose on day 1 |
| 8 | 0.5 mg/kg of AD05567 conjugated to a tridentate small molecule αvβ6 epithelial cell targeting ligand (Tri-SM6.1) at the 5' terminal end of the sense strand, formulated in isotonic saline. | Single OP dose on day 1 |

(See, e.g., Tables 3 through 6 for chemical structure information for the chemically modified duplexes used in this Example).

The tridentate small molecule αvβ6 epithelial cell targeting ligand referred to as Tri-SM6.1 in Groups 3 and 5-8 has the structure represented in FIG. 6.

Four (4) rats were dosed in each Group (n=4). Rats were sacrificed on study day 9, and total RNA was isolated from both lungs following collection and homogenization. Alpha-ENaC (SCNN1 A) mRNA expression was quantitated by probe-based quantitative PCR, normalized to GAPDH expression, and expressed as fraction of vehicle control group (geometric mean, +/−95% confidence interval).

TABLE 16

Average Relative rENaC mRNA Expression at Sacrifice (Day 9) in Example 9

| Group ID | Average Relative rENaC mRNA Expression | Low (error) | High (error) |
|---|---|---|---|
| Group 1 (isotonic saline) | 1.00 | 0.180 | 0.219 |
| Group 2 (0.5 mg/kg AD05453) | 0.713 | 0.139 | 0.173 |
| Group 3 (0.5 mg/kg AD05453-Tri-SM6.1) | 0.562 | 0.082 | 0.096 |
| Group 4 (0.5 mg/kg AD05453-Tri-SM7) | 0.768 | 0.059 | 0.064 |
| Group 5 (0.5 mg/kg AD05618-Tri-SM6.1) | 0.524 | 0.074 | 0.086 |
| Group 6 (0.5 mg/kg AD05562-Tri-SM6.1) | 0.784 | 0.07 | 0.077 |
| Group 7 (0.5 mg/kg AD05564-Tri-SM6.1) | 0.921 | 0.104 | 0.117 |
| Group 8 (0.5 mg/kg AD05567-Tri-SM6.1) | 0.707 | 0.084 | 0.096 |

As shown in Table 16 above, each of the alpha-ENaC RNAi agents showed a reduction in mRNA expression in rats compared to control. Further, when administered naked, AD05453 showed only approximately 29% inhibition (0.713), while when conjugated to Tri-SM6.1 integrin targeting ligand it showed a 44% reduction (0.562) in average rENaC mRNA expression.

Example 10. In Vivo Oropharyngeal Aspiration Administration of Alpha-ENaC RNAi Agents Conjugated to Epithelial Cell Targeting Ligands in Rats On study day 1, male Sprague Dawley rats were dosed via oropharyngeal ("OP") aspiration administration with 200 microliters using a pipette, which included the following dosing groups recited in Table 17:

TABLE 17

Dosing Groups of Rats in Example 10

| Group | RNAi Agent and Dose | Dosing Regimen |
|---|---|---|
| 1 | Isotonic saline (no RNAi agent) | Single OP dose on day 1 |
| 2 | 0.5 mg/kg of AD05347 conjugated to a tridentate small molecule αvβ6 epithelial cell targeting ligand (Tri-SM6.1) at the 5' terminal end of the sense strand, formulated in isotonic saline. | Single OP dose on day 1 |

TABLE 17-continued

Dosing Groups of Rats in Example 10

| Group | RNAi Agent and Dose | Dosing Regimen |
|---|---|---|
| 3 | 0.5 mg/kg of AD05453 conjugated to a tridentate small molecule αvβ6 epithelial cell targeting ligand (Tri-SM6.1) at the 5' terminal end of the sense strand, formulated in isotonic saline. | Single OP dose on day 1 |
| 4 | 0.5 mg/kg of AD05671 conjugated to a tridentate small molecule αvβ6 epithelial cell targeting ligand (Tri-SM6.1) at the 5' terminal end of the sense strand, formulated in isotonic saline. | Single OP dose on day 1 |
| 5 | 0.5 mg/kg of AD05672 conjugated to a tridentate small molecule αvβ6 epithelial cell targeting ligand (Tri-SM6.1) at the 5' terminal end of the sense strand, formulated in isotonic saline. | Single OP dose on day 1 |
| 6 | 0.5 mg/kg of AD05673 conjugated to a tridentate small molecule αvβ6 epithelial cell targeting ligand (Tri-SM6.1) at the 5' terminal end of the sense strand, formulated in isotonic saline. | Single OP dose on day 1 |
| 7 | 0.5 mg/kg of AD05558 conjugated to a tridentate small molecule αvβ6 epithelial cell targeting ligand (Tri-SM6.1) at the 5' terminal end of the sense strand, formulated in isotonic saline. | Single OP dose on day 1 |
| 8 | 0.5 mg/kg of AD05560 conjugated to a tridentate small molecule αvβ6 epithelial cell targeting ligand (Tri-SM6.1) at the 5' terminal end of the sense strand, formulated in isotonic saline. | Single OP dose on day 1 |
| 9 | 0.5 mg/kg of AD05611 conjugated to a tridentate small molecule αvβ6 epithelial cell targeting ligand (Tri-SM6.1) at the 5' terminal end of the sense strand, formulated in isotonic saline. | Single OP dose on day 1 |
| 10 | 0.5 mg/kg of AD05613 conjugated to a tridentate small molecule αvβ6 epithelial cell targeting ligand (Tri-SM6.1) at the 5' terminal end of the sense strand, formulated in isotonic saline. | Single OP dose on day 1 |

(See, e.g., Tables 3 through 6 for chemical structure information for the chemically modified duplexes used in this Example).

The tridentate small molecule αvβ6 epithelial cell targeting ligand referred to as Tri-SM6.1 in Groups 2-10 has the structure represented in FIG. 6.

Four (4) rats were dosed in each Group (n=4). Rats were sacrificed on study day 9, and total RNA was isolated from both lungs following collection and homogenization. Alpha-ENaC (SCNN1 Å) mRNA expression was quantitated by probe-based quantitative PCR, normalized to GAPDH expression, and expressed as fraction of vehicle control group (geometric mean, +/−95% confidence interval).

TABLE 18

Average Relative rENaC mRNA Expression at Sacrifice (Day 9) in Example 10

| Group ID | Average Relative rENaC mRNA Expression | Low (error) | High (error) |
|---|---|---|---|
| Group 1 (isotonic saline) | 1.000 | 0.084 | 0.092 |
| Group 2 (0.5 mg/kg AD05347-Tri-SM6.1) | 0.375 | 0.128 | 0.194 |
| Group 3 (0.5 mg/kg AD05453-Tri-SM6.1) | 0.597 | 0.163 | 0.224 |
| Group 4 (0.5 mg/kg AD05671-Tri-SM6.1) | 0.663 | 0.062 | 0.068 |
| Group 5 (0.5 mg/kg AD05672-Tri-SM6.1) | 0.808 | 0.114 | 0.133 |
| Group 6 (0.5 mg/kg AD05673-Tri-SM6.1) | 0.623 | 0.100 | 0.119 |
| Group 7 (0.5 mg/kg AD05558-Tri-SM6.1) | 0.533 | 0.043 | 0.047 |
| Group 8 (0.5 mg/kg AD05560-Tri-SM6.1) | 0.647 | 0.122 | 0.150 |
| Group 9 (0.5 mg/kg AD05611-Tri-SM6.1) | 0.477 | 0.067 | 0.078 |
| Group 10 (0.5 mg/kg AD05613-Tri-SM6.1) | 0.640 | 0.165 | 0.223 |

As shown in Table 18 above, each of the alpha-ENaC RNAi agents showed a reduction in mRNA expression in rats compared to control.

Example 11. In Vivo Oropharyngeal Aspiration Administration of Alpha-ENaC RNAi Agents Conjugated to Epithelial Cell Targeting Ligands in Rats On study day 1, male Sprague Dawley rats were dosed via oropharyngeal ("OP") aspiration administration with 200 microliters using a pipette, which included the following dosing groups recited in Table 19:

TABLE 19

Dosing Groups of Rats in Example 11

| Group | RNAi Agent and Dose | Dosing Regimen |
|---|---|---|
| 1 | Isotonic saline (no RNAi agent) | Single OP dose on day 1 |
| 2 | 0.5 mg/kg of AD05347 conjugated to a tridentate small molecule αvβ6 epithelial cell targeting ligand (Tri-SM6.1) at the 5' terminal end of the sense strand, formulated in isotonic saline. | Single OP dose on day 1 |
| 3 | 0.5 mg/kg of AD05453 conjugated to a tridentate small molecule αvβ6 epithelial cell targeting ligand (Tri-SM6.1) at the 5' terminal end of the sense strand, formulated in isotonic saline. | Single OP dose on day 1 |
| 4 | 0.5 mg/kg of AD05618 conjugated to a tridentate small molecule αvβ6 epithelial cell targeting ligand (Tri-SM6.1) at the 5' terminal end of the sense strand, formulated in isotonic saline. | Single OP dose on day 1 |
| 5 | 0.5 mg/kg of AD05619 conjugated to a tridentate small molecule αvβ6 epithelial cell targeting ligand (Tri-SM6.1) at the 5' terminal end of the sense strand, formulated in isotonic saline. | Single OP dose on day 1 |
| 6 | 0.5 mg/kg of AD05622 conjugated to a tridentate small molecule αvβ6 epithelial cell targeting ligand (Tri-SM6.1) at the 5' terminal end of the sense strand, formulated in isotonic saline. | Single OP dose on day 1 |
| 7 | 0.5 mg/kg of AD05623 conjugated to a tridentate small molecule αvβ6 epithelial cell targeting ligand (Tri-SM6.1) at the 5' terminal end of the sense strand, formulated in isotonic saline. | Single OP dose on day 1 |

(See, e.g., Tables 3 through 6 for chemical structure information for the chemically modified duplexes used in this Example).

The tridentate small molecule αvβ6 epithelial cell targeting ligand referred to as Tri-SM6.1 in Groups 2-7 has the structure represented in FIG. 6.

Five (5) rats were dosed in each Group (n=5). Rats were sacrificed on study day 9, and total RNA was isolated from both lungs following collection and homogenization. Alpha-ENaC (SCNN1A) mRNA expression was quantitated by probe-based quantitative PCR, normalized to GAPDH expression, and expressed as fraction of vehicle control group (geometric mean, +/−95% confidence interval).

TABLE 20

Average Relative rENaC mRNA Expression at Sacrifice (Day 9) in Example 11

| Group ID | Average Relative rENaC mRNA Expression | Low (error) | High (error) |
|---|---|---|---|
| Group 1 (isotonic saline) | 1.000 | 0.195 | 0.242 |
| Group 2 (0.5 mg/kg AD05347-Tri-SM6.1) | 0.383 | 0.041 | 0.046 |
| Group 3 (0.5 mg/kg AD05453-Tri-SM6.1) | 0.489 | 0.168 | 0.257 |
| Group 4 (0.5 mg/kg AD05618-Tri-SM6.1) | 0.770 | 0.185 | 0.244 |
| Group 5 (0.5 mg/kg AD05619-Tri-SM6.1) | 0.719 | 0.080 | 0.090 |
| Group 6 (0.5 mg/kg AD05622-Tri-SM6.1) | 0.564 | 0.168 | 0.239 |
| Group 7 (0.5 mg/kg AD05623-Tri-SM6.1) | 0.575 | 0.115 | 0.144 |

As shown in Table 20 above, each of the alpha-ENaC RNAi agents showed a reduction in mRNA expression in rats compared to control.

Example 12. In Vivo Oropharyngeal Aspiration Administration of Alpha-ENaC RNAi Agents Conjugated to Epithelial Cell Targeting Ligands in Rats On study day 1, male Sprague Dawley rats were dosed via oropharyngeal ("OP") aspiration administration with 200 microliters using a pipette, according to the following dosing groups recited in Table 21:

TABLE 21

Dosing Groups of Rats in Example 12

| Group | RNAi Agent and Dose | Dosing Regimen |
|---|---|---|
| 1 | Isotonic saline (no RNAi agent) | Single OP dose on day 1 |
| 2 | 0.5 mg/kg of AD05347 conjugated to a tridentate small molecule αvβ6 epithelial cell targeting ligand (Tri-SM6.1) at the 5' terminal end of the sense strand, formulated in isotonic saline. | Single OP dose on day 1 |
| 3 | 0.5 mg/kg of AD05453 conjugated to a tridentate small molecule αvβ6 epithelial cell targeting ligand (Tri-SM6.1) at the 5' terminal end of the sense strand, formulated in isotonic saline. | Single OP dose on day 1 |
| 4 | 0.5 mg/kg of AD05683 conjugated to a tridentate small molecule αvβ6 epithelial cell targeting ligand (Tri-SM6.1) at the 5' terminal end of the sense strand, formulated in isotonic saline. | Single OP dose on day 1 |
| 5 | 0.5 mg/kg of AD05684 conjugated to a tridentate small molecule αvβ6 epithelial cell targeting ligand (Tri-SM6.1) at the 5' terminal end of the sense strand, formulated in isotonic saline. | Single OP dose on day 1 |
| 6 | 0.5 mg/kg of AD05685 conjugated to a tridentate small molecule αvβ6 epithelial cell targeting ligand (Tri-SM6.1) at the 5' terminal end of the sense strand, formulated in isotonic saline. | Single OP dose on day 1 |
| 7 | 0.5 mg/kg of AD05686 conjugated to a tridentate small molecule αvβ6 epithelial cell targeting ligand (Tri-SM6.1) at the 5' terminal end of the sense strand, formulated in isotonic saline. | Single OP dose on day 1 |
| 8 | 0.5 mg/kg of AD05687 conjugated to a tridentate small molecule αvβ6 epithelial cell targeting ligand (Tri-SM6.1) at the 5' terminal end of the sense strand, formulated in isotonic saline. | Single OP dose on day 1 |
| 9 | 0.5 mg/kg of AD05564 conjugated to a tridentate small molecule αvβ6 epithelial cell targeting ligand (Tri-SM6.1) at the 5' terminal end of the sense strand, formulated in isotonic saline. | Single OP dose on day 1 |
| 10 | 0.5 mg/kg of AD05688 conjugated to a tridentate small molecule αvβ6 epithelial cell targeting ligand (Tri-SM6.1) at the 5' terminal end of the sense strand, formulated in isotonic saline. | Single OP dose on day 1 |
| 11 | 0.5 mg/kg of AD05689 conjugated to a tridentate small molecule αvβ6 epithelial cell targeting ligand (Tri-SM6.1) at the 5' terminal end of the sense strand, formulated in isotonic saline. | Single OP dose on day 1 |
| 12 | 0.5 mg/kg of AD05690 conjugated to a tridentate small molecule αvβ6 epithelial cell targeting ligand (Tri-SM6.1) at the 5' terminal end of the sense strand, formulated in isotonic saline. | Single OP dose on day 1 |
| 13 | 0.5 mg/kg of AD05691 conjugated to a tridentate small molecule αvβ6 epithelial cell targeting ligand (Tri-SM6.1) at the 5' terminal end of the sense strand, formulated in isotonic saline. | Single OP dose on day 1 |

(See, e.g., Tables 3 through 6 for chemical structure information for the chemically modified duplexes used in this Example).

The tridentate small molecule αvβ6 epithelial cell targeting ligand referred to as Tri-SM6.1 in Groups 2-13 has the structure represented in FIG. 6.

Four (4) rats were dosed in each Group (n=4). Rats were sacrificed on study day 9, and total RNA was isolated from both lungs following collection and homogenization. Alpha-ENaC (SCNN1 Å) mRNA expression was quantitated by probe-based quantitative PCR, normalized to GAPDH expression, and expressed as fraction of vehicle control group (geometric mean, +/−95% confidence interval).

TABLE 22

Average Relative rENaC mRNA Expression at Sacrifice (Day 9) in Example 12

| Group ID | Average Relative rENaC mRNA Expression | Low (error) | High (error) |
|---|---|---|---|
| Group 1 (isotonic saline) | 1.000 | 0.157 | 0.186 |
| Group 2 (0.5 mg/kg AD05347-Tri-SM6.1) | 0.534 | 0.066 | 0.075 |
| Group 3 (0.5 mg/kg AD05453-Tri-SM6.1) | 0.573 | 0.086 | 0.101 |
| Group 4 (0.5 mg/kg AD05683-Tri-SM6.1) | 0.547 | 0.052 | 0.057 |

TABLE 22-continued

Average Relative rENaC mRNA Expression at Sacrifice (Day 9) in Example 12

| Group ID | Average Relative rENaC mRNA Expression | Low (error) | High (error) |
| --- | --- | --- | --- |
| Group 5 (0.5 mg/kg AD05684-Tri-SM6.1) | 0.755 | 0.158 | 0.200 |
| Group 6 (0.5 mg/kg AD05685-Tri-SM6.1) | 0.609 | 0.077 | 0.089 |
| Group 7 (0.5 mg/kg AD05686-Tri-SM6.1) | 0.591 | 0.077 | 0.089 |
| Group 8 (0.5 mg/kg AD05687-Tri-SM6.1) | 0.624 | 0.099 | 0.118 |
| Group 9 (0.5 mg/kg AD05564-Tri-SM6.1) | 0.787 | 0.172 | 0.221 |
| Group 10 (0.5 mg/kg AD05688-Tri-SM6.1) | 0.563 | 0.072 | 0.082 |
| Group 11 (0.5 mg/kg AD05689-Tri-SM6.1) | 0.693 | 0.136 | 0.169 |
| Group 12 (0.5 mg/kg AD05590-Tri-SM6.1) | 0.651 | 0.159 | 0.211 |
| Group 13 (0.5 mg/kg AD05691-Tri-SM6.1) | 0.870 | 0.132 | 0.155 |

As shown in Table 22 above, each of the alpha-ENaC RNAi agents showed a reduction in mRNA expression in rats compared to control.

Example 13. Dose Ranging Study of Oropharyngeal Aspiration Administration of Alpha-ENaC RNAi Agents Conjugated to Epithelial Cell Targeting Ligands in Rats On study day 1, male Sprague Dawley rats were dosed via oropharyngeal ("OP") aspiration administration with 200 microliters using a pipette, according to the following dosing groups recited in Table 23:

(See, e.g., Tables 3 through 6 for chemical structure information for the chemically modified duplexes used in this Example).

The tridentate small molecule $\alpha v\beta 6$ epithelial cell targeting ligand referred to as Tri-SM6.1 in Groups 2-8 has the structure represented in FIG. 6.

Six (6) rats were dosed in each of Groups 1, 2, 3, 4, 7, and 8 (n=5). Four rats were dosed in Groups 5 and 6 (n=4). Rats were sacrificed on study day 9, and total RNA was isolated from both lungs following collection and homogenization. Alpha-ENaC (SCNN1 Å) mRNA expression was quantitated by probe-based quantitative PCR, normalized to GAPDH expression, and expressed as fraction of vehicle control group (geometric mean, +/−95% confidence interval).

TABLE 23

Dosing Groups of Rats in Example 13

| Group | RNAi Agent and Dose | Dosing Regimen |
| --- | --- | --- |
| 1 | Isotonic saline (no RNAi agent) | Single OP dose on day 1 |
| 2 | 0.0625 mg/kg of AD05453 conjugated to a tridentate small molecule $\alpha v\beta 6$ epithelial cell targeting ligand (Tri-SM6.1) at the 5' terminal end of the sense strand, formulated in isotonic saline. | Single OP dose on day 1 |
| 3 | 0.125 mg/kg of AD05453 conjugated to a tridentate small molecule $\alpha v\beta 6$ epithelial cell targeting ligand (Tri-SM6.1) at the 5' terminal end of the sense strand, formulated in isotonic saline. | Single OP dose on day 1 |
| 4 | 0.25 mg/kg of AD05453 conjugated to a tridentate small molecule $\alpha v\beta 6$ epithelial cell targeting ligand (Tri-SM6.1) at the 5' terminal end of the sense strand, formulated in isotonic saline. | Single OP dose on day 1 |
| 5 | 0.5 mg/kg of AD05453 conjugated to a tridentate small molecule $\alpha v\beta 6$ epithelial cell targeting ligand (Tri-SM6.1) at the 5' terminal end of the sense strand, formulated in isotonic saline. | Single OP dose on day 1 |
| 6 | 0.75 mg/kg of AD05453 conjugated to a tridentate small molecule $\alpha v\beta 6$ epithelial cell targeting ligand (Tri-SM6.1) at the 5' terminal end of the sense strand, formulated in isotonic saline. | Single OP dose on day 1 |
| 7 | 1.0 mg/kg of AD05453 conjugated to a tridentate small molecule $\alpha v\beta 6$ epithelial cell targeting ligand (Tri-SM6.1) at the 5' terminal end of the sense strand, formulated in isotonic saline. | Single OP dose on day 1 |
| 8 | 3.0 mg/kg of AD05453 conjugated to a tridentate small molecule $\alpha v\beta 6$ epithelial cell targeting ligand (Tri-SM6.1at the 5' terminal end of the sense strand, formulated in isotonic saline. | Single OP dose on day 1 |

TABLE 24

Average Relative rENaC mRNA Expression at Sacrifice (Day 9) in Example 13

| Group ID | Average Relative rENaC mRNA Expression | Low (error) | High (error) |
|---|---|---|---|
| Group 1 (isotonic saline) | 1.000 | 0.111 | 0.125 |
| Group 2 (0.0625 mg/kg AD05453-Tri-SM6.1) | 0.695 | 0.083 | 0.095 |
| Group 3 (0.125 mg/kg AD05453-Tri-SM6.1) | 0.747 | 0.139 | 0.171 |
| Group 4 (0.25 mg/kg AD05453-Tri-SM6.1) | 0.631 | 0.080 | 0.092 |
| Group 5 (0.5 mg/kg AD05453-Tri-SM6.1) | 0.492 | 0.034 | 0.037 |
| Group 6 (0.75 mg/kg AD05453-Tri-SM6.1) | 0.485 | 0.113 | 0.147 |
| Group 7 (1.0 mg/kg AD05453-Tri-SM6.1) | 0.433 | 0.077 | 0.094 |
| Group 8 (3.0 mg/kg AD05453-Tri-SM6.1) | 0.324 | 0.052 | 0.062 |

(See, e.g., Tables 3 through 6 for chemical structure information for the chemically modified duplexes used in this Example).

As shown in Table 24 above, alpha-ENaC RNAi agent AD05453 showed a reduction in mRNA expression in rats compared to control at each of the dosage levels administered.

Example 14. In Vivo Intratracheal Administration of Alpha-ENaC RNAi Agents in Mice On study days 1 and 2, male ICR mice were administered 50 microliters via a microsprayer device (Penn Century, Philadelphia, Pa.) of either isotonic saline vehicle for use as a control, or 5 mg/kg of one of the following alpha-ENaC RNAi agents without a conjugate ligand (i.e., "naked RNAi agent"), formulated in isotonic saline: AD04025, AD04526, AD04527, AD04528, AD04529, AD04530, AD04531, AD04536, or AD04537. 4 mice were dosed per group (n=4). Mice were sacrificed on study day 9, and total RNA was isolated from both lungs following collection and homogenization. Alpha-ENaC (SCNN1A) mRNA expression was quantitated by probe-based quantitative PCR, normalized to GAPDH expression, and expressed as fraction of vehicle control group (geometric mean, +/−95% confidence interval).

TABLE 25

Average Relative mENaC mRNA Expression at Sacrifice (Day 9) in Example 14

| Group ID | Average Relative mENaC mRNA Expression | Low (error) | High (error) |
|---|---|---|---|
| Group 1 (isotonic saline) | 1.000 | 0.117 | 0.132 |
| Group 2 (0.5 mg/kg AD04025) | 0.451 | 0.097 | 0.123 |
| Group 3 (0.5 mg/kg AD04526) | 0.585 | 0.108 | 0.132 |
| Group 4 (0.5 mg/kg AD04527) | 0.403 | 0.101 | 0.134 |
| Group 5 (0.5 mg/kg AD04528) | 0.498 | 0.117 | 0.153 |
| Group 6 (0.5 mg/kg AD04529) | 0.480 | 0.042 | 0.047 |
| Group 7 (0.5 mg/kg AD04530) | 0.670 | 0.006 | 0.006 |
| Group 8 (0.5 mg/kg AD04531) | 0.662 | 0.103 | 0.122 |
| Group 9 (0.5 mg/kg AD04536) | 0.746 | 0.101 | 0.117 |
| Group 10 (0.5 mg/kg AD04537) | 0.409 | 0.021 | 0.022 |

(See, e.g., Tables 3 through 6 for chemical structure information for the chemically modified duplexes used in this Example).

As shown in Table 25 above, each of the alpha-ENaC RNAi agents showed a reduction in mRNA expression in rats compared to control.

Example 15. In Vivo Intratracheal Administration of Alpha-ENaC RNAi Agents in Mice On study days 1 and 2, male ICR mice were administered 50 microliters via a microsprayer device (Penn Century, Philadelphia, Pa.) of either isotonic saline vehicle for use as a control, or 5 mg/kg of one of the following alpha-ENaC RNAi agents without a conjugate ligand (i.e., "naked RNAi agent"), formulated in isotonic saline: AD04025, AD04538, AD04539, AD04532, AD04533, AD04534, AD04535, or AD04540. (See, e.g., Tables 3 through 6 for chemical structure information for the chemically modified duplexes used in this Example).

Four (4) mice were dosed per group (n=4). Mice were sacrificed on study day 9, and total RNA was isolated from both lungs following collection and homogenization. Alpha-ENaC (SCNN1A) mRNA expression was quantitated by probe-based quantitative PCR, normalized to GAPDH expression, and expressed as fraction of vehicle control group (geometric mean, +/−95% confidence interval).

TABLE 26

Average Relative mENaC mRNA Expression at Sacrifice (Day 9) in Example 15

| Group ID | Average Relative mENaC mRNA Expression | Low (error) | High (error) |
|---|---|---|---|
| Group 1 (isotonic saline) | 1.000 | 0.081 | 0.088 |
| Group 2 (0.5 mg/kg AD04025) | 0.448 | 0.097 | 0.125 |
| Group 3 (0.5 mg/kg AD04538) | 0.855 | 0.101 | 0.115 |
| Group 4 (0.5 mg/kg AD04539) | 0.833 | 0.076 | 0.083 |
| Group 5 (0.5 mg/kg AD04532) | 0.581 | 0.127 | 0.162 |
| Group 6 (0.5 mg/kg AD04533) | 0.743 | 0.041 | 0.044 |
| Group 7 (0.5 mg/kg AD04534) | 1.006 | 0.127 | 0.146 |
| Group 8 (0.5 mg/kg AD04535) | 1.042 | 0.119 | 0.134 |
| Group 9 (0.5 mg/kg AD04540) | 0.982 | 0.111 | 0.125 |

(See, e.g., Tables 3 through 6 for chemical structure information for the chemically modified duplexes used in this Example).

As shown in Table 26 above, the underlying sequence of the respective alpha-ENaC RNAi agent impacts the level of ENaC gene inhibition achieved. For example, alpha-ENaC RNAi agent AD04025 includes an antisense strand sequence that is designed to target position 972 of the alpha-ENaC gene (i.e., nucleotides 1-19 of the antisense strand are designed to be at least partially complementary to the alpha-ENaC gene (SEQ ID NO:1) at positions 972-990). AD04525 achieved the highest level of inhibition of the RNAi agents tested in this Example and showed approximately 55% knockdown of gene expression (0.448) compared to control. The remaining Alpha-ENaC RNAi agents were designed to target different positions on the gene, including alpha-ENaC RNAi agents AD04538 (targeting gene position 973), AD04539 (targeting gene position 999), AD04532 (targeting gene position 1000), AD04533 (also targeting gene position 973), AD04534 (also targeting gene position 999), AD04535 (targeting gene position 1291), and AD04540 (targeting gene position 763). As shown above, an alpha-ENaC RNAi agent that is designed to target the gene at a different position can have different inhibitory activity (e.g., compare alpha-ENaC mRNA knockdown levels of AD04025 (position 972) with AD04538 (position 973) and AD04533 (position 973)).

Furthermore, when comparing alpha-ENaC RNAi agents at the same position (e.g., AD04539 and AD04534), despite both sequences having underlying nucleobases designed to inhibit the gene at the same position (e.g., gene position 999), slight modifications of the underlying base sequence and/or the inclusion of different modified nucleotides can lead to at least numerically different inhibition activity.

Example 16. In Vivo Intratracheal Administration of Alpha-ENaC RNAi Agents in Rats On study days 1 and 2, male Sprague Dawley rats were administered 200 microliters via a microsprayer device (Penn Century, Philadelphia, Pa.) of either isotonic saline vehicle for use as a control, or approximately 3 mg/kg of one of the following alpha-ENaC RNAi agents without a conjugate ligand (i.e., "naked RNAi agent"), formulated in isotonic saline: AD04835, AD04022, AD05116, AD05117, AD05118, or AD05119. (See, e.g., Tables 3 through 6 for chemical structure information for the chemically modified duplexes used in this Example).

Five (5) rats were dosed per group (n=5). Rats were sacrificed on study day 9, and total RNA was isolated from both lungs following collection and homogenization. Alpha-ENaC (SCNN1 Å) mRNA expression was quantitated by probe-based quantitative PCR, normalized to GAPDH expression, and expressed as fraction of vehicle control group (geometric mean, +/−95% confidence interval).

TABLE 27

Average Relative rENaC mRNA Expression at Sacrifice (Day 9) in Example 16

| Group ID | Average Relative rENaC mRNA Expression | Low (error) | High (error) |
| --- | --- | --- | --- |
| Group 1 (isotonic saline) | 1.000 | 0.171 | 0.207 |
| Group 2 (0.5 mg/kg AD04835) | 0.281 | 0.043 | 0.050 |
| Group 3 (0.5 mg/kg AD04022) | 0.297 | 0.055 | 0.067 |
| Group 4 (0.5 mg/kg AD05116) | 0.554 | 0.095 | 0.115 |
| Group 5 (0.5 mg/kg AD05117) | 0.532 | 0.097 | 0.119 |
| Group 6 (0.5 mg/kg AD05118) | 0.300 | 0.034 | 0.038 |
| Group 7 (0.5 mg/kg AD05119) | 0.496 | 0.075 | 0.089 |

(See, e.g., Tables 3 through 6 for chemical structure information for the chemically modified duplexes used in this Example).

Table 27, above, provides additional data showing that the underlying sequence of the respective alpha-ENaC RNAi agent impacts the level of ENaC gene inhibition achieved. For example, alpha-ENaC RNAi agents AD04025 and AD04835 each include an antisense strand sequence that is designed to target position 972 of the alpha-ENaC gene (i.e., nucleotides 1-19 of the antisense strand are designed to be at least partially complementary to the alpha-ENaC gene (SEQ ID NO:1) at positions 972-990). Of the alpha-ENaC RNAi agents tested in this Example, these two RNAi agents showed the greatest level of knockdown at greater than 70%. The remaining Alpha-ENaC RNAi agents were designed to target different positions on the gene, including alpha-ENaC RNAi agents AD05116 (targeting gene position 944), AD05117 (targeting gene position 945), AD05118 (targeting gene position 1289), and AD05119 (targeting gene position 1579).

Example 17. Multiple Dose, Dose Ranging Study of Oropharyngeal Aspiration Administration of Alpha-ENaC RNAi Agents Conjugated to Epithelial Cell Targeting Ligands in Rats On study day 1, study day 2, and study day 3, male Sprague Dawley rats were dosed via oropharyngeal ("OP") aspiration administration with 200 microliters using a pipette, according to the following dosing groups recited in Table 28:

TABLE 28

Dosing Groups of Rats in Example 17

| Group | RNAi Agent and Dose | Dosing Regimen |
| --- | --- | --- |
| 1 | Isotonic saline (no RNAi agent) | OP dose on day 1, day 2, and day 3 (three total doses) |
| 2 | 0.005 mg/kg of AD05453 conjugated to a tridentate small molecule αvβ6 epithelial cell targeting ligand (Tri-SM6.1) at the 5' terminal end of the sense strand, formulated in isotonic saline. | OP dose on day 1, day 2, and day 3 (three total doses) |
| 3 | 0.01 mg/kg of AD05453 conjugated to a tridentate small molecule αvβ6 epithelial cell targeting ligand (Tri-SM6.1) at the 5' terminal end of the sense strand, formulated in isotonic saline. | OP dose on day 1, day 2, and day 3 (three total doses) |
| 4 | 0.025 mg/kg of AD05453 conjugated to a tridentate small molecule αvβ6 epithelial cell targeting ligand (Tri-SM6.1) at the 5' terminal end of the sense strand, formulated in isotonic saline. | OP dose on day 1, day 2, and day 3 (three total doses) |
| 5 | 0.05 mg/kg of AD05453 conjugated to a tridentate small molecule αvβ6 epithelial cell targeting ligand (Tri-SM6.1) at the 5' terminal end of the sense strand, formulated in isotonic saline. | OP dose on day 1, day 2, and day 3 (three total doses) |

TABLE 28-continued

Dosing Groups of Rats in Example 17

| Group | RNAi Agent and Dose | Dosing Regimen |
|---|---|---|
| 6 | 0.10 mg/kg of AD05453 conjugated to a tridentate small molecule αvβ6 epithelial cell targeting ligand (Tri-SM6.1) at the 5' terminal end of the sense strand, formulated in isotonic saline. | OP dose on day 1, day 2, and day 3 (three total doses) |
| 7 | 0.50 mg/kg of AD05453 conjugated to a tridentate small molecule αvβ6 epithelial cell targeting ligand (Tri-SM6.1) at the 5' terminal end of the sense strand, formulated in isotonic saline. | OP dose on day 1, day 2, and day 3 (three total doses) |

(See, e.g., Tables 3 through 6 for chemical structure information for the chemically modified duplexes used in this Example). As noted herein, the same RNAi agent-tridentate small molecule αvβ6 epithelial cell targeting ligand conjugate structure (i.e., Tri-SM6.1-AD05453) in this Example may be alternatively synthesized by using the tri-alkyne functionalized linking group (TriAlk14) as shown in AD05924, instead of post-synthetic addition to the terminal amino group, as shown in AD05453. (See also Example 1).

The tridentate small molecule αvβ6 epithelial cell targeting ligand referred to as Tri-SM6.1 in Groups 2-7 has the structure represented in FIG. 6.

Seven (7) rats were dosed in each of Groups 1, 2, 3, 4, 5, and 6 (n=7), and six (6) rats were dosed in Group 7 (n=6). Rats were sacrificed on study day 9, and total RNA was isolated from both lungs following collection and homogenization. Alpha-ENaC (SCNN1A) mRNA expression was quantitated by probe-based quantitative PCR, normalized to GAPDH expression, and expressed as fraction of vehicle control group (geometric mean, +/−95% confidence interval).

TABLE 29

Average Relative rENaC mRNA Expression at Sacrifice (Day 9) in Example 17

| Group ID | Average Relative rENaC mRNA Expression | Low (error) | High (error) |
|---|---|---|---|
| Group 1 (isotonic saline) | 1.000 | 0.127 | 0.146 |
| Group 2 (0.005 mg/kg AD05453-Tri-SM6.1) | 0.852 | 0.097 | 0.109 |
| Group 3 (0.01 mg/kg AD05453-Tri-SM6.1) | 0.663 | 0.103 | 0.121 |
| Group 4 (0.025 mg/kg AD05453-Tri-SM6.1) | 0.589 | 0.131 | 0.168 |
| Group 5 (0.05 mg/kg AD05453-Tri-SM6.1) | 0.480 | 0.058 | 0.066 |
| Group 6 (0.10 mg/kg AD05453-Tri-SM6.1) | 0.432 | 0.056 | 0.064 |
| Group 7 (0.50 mg/kg AD05453-Tri-SM6.1) | 0.279 | 0.034 | 0.039 |

As shown in Table 29 above, alpha-ENaC RNAi agent AD05453 showed a reduction in mRNA expression in rats compared to control at each of the dosage levels administered. Further, multiple OP dose administration showed signs of further knockdown of rENaC mRNA expression compared to single dose when using the same alpha-ENaC RNAi agent (compare, e.g., Group 7 of Example 17 with Group 5 of Example 13).

Example 18. In Vivo Intratracheal Administration of Alpha-ENaC RNAi Agents in Mice and Human COPD Sputum Stability Assessment To assess and compare the activity and stability of a known prior art duplex to the RNAi agents disclosed herein, a duplex having the following modified structure, as disclosed International Patent Application Publication No: WO 2008/152131 to Novartis et al. (see Table 1C therein at ND-9201), was synthesized:

```
Antisense strand sequence (5' → 3'):
                                    (SEQ ID NO: 291)
GAUUUGUUCUGGUUGcAcAdTsdT Sense strand sequence (5' → 3'):
                                    (SEQ ID NO: 292)
uGuGcAAccAGAAcAAAucdTsdT
```

(hereinafter referred to as ND-9201). According to WO 2008/152131, ND-9201 showed comparatively potent in vitro inhibition of alpha-ENaC gene expression.

First, studies were conducted to assess alpha-ENaC inhibition activity in vivo. On study days 1 and 2, male ICR mice were administered via a microsprayer device (Penn Century, Philadelphia, Pa.) either isotonic glucose (D5W) vehicle for use as a control, or approximately 10 mg/kg of ND-9201 formulated in D5W. Mice were sacrificed on day 9, and total RNA was isolated from both lungs following collection and homogenization. Alpha-ENaC (SCNN1A) mRNA expression was quantitated by probe-based quantitative PCR, normalized to GAPDH expression, and expressed as fraction of vehicle control group. For comparison, on study days 1 and 2, male ICR mice were administered via a microsprayer device (Penn Century, Philadelphia, Pa.) either D5W vehicle for use as a control, or approximately 5 mg/kg of the RNAi agent AD04025 disclosed herein formulated in D5W. (See, e.g., Tables 3 through 6 for chemical structure information for the chemically modified duplex of AD04025). Mice were similarly sacrificed on day 9, and total RNA was isolated from both lungs following collection and homogenization. Alpha-ENaC (SCNN1A) mRNA expression was quantitated by probe-based quantitative PCR, normalized to GAPDH expression, and expressed as fraction of vehicle control group.

For ND-9201, at 10 mg/kg dosing on days 1 and 2, approximately 25% inhibition of mENaC mRNA expression was achieved in mice in vivo.

For AD04025, at only 5 mg/kg dosing on days 1 and 2, approximately 65% inhibition of mENaC mRNA expression was achieved in mice in vivo, thus showing a substantial improvement in inhibition activity over the known prior art duplex ND-9201.

Additionally, stability studies were conducted with ND-9201 and AD04858 in human sputum taken from patients diagnosed with COPD (See, e.g., Tables 3 through 6 for chemical structure information for the chemically modified duplex of AD04858). A solution containing 50 μL of sputum and 350 μL of lysis buffer was vortexed, and 12.5 μL of either ND-9201 or AD04858 was added and briefly vortexed each hour. LCMS was conducted on the samples to determine the remaining full-length product of both the sense strand and the antisense strand of each of the molecules over time. After 6 hours, AD04858 showed improved stability, as it had approximately 20 to 30% greater full-length product present for both the sense strand and the antisense strand.

Example 19. In Vivo Study of Oropharyngeal Aspiration Administration of Alpha-ENaC RNAi Agents Conjugated to Epithelial Cell Targeting Ligands in Rats On study day 1 and study day 2, male Sprague Dawley rats were dosed via oropharyngeal ("OP") aspiration administration with 200 microliters using a pipette, which included the following dosing groups recited in Table 30:

TABLE 30

Dosing Groups of Rats in Example 19

| Group | RNAi Agent and Dose | Dosing Regimen |
|---|---|---|
| 1 | Isotonic saline (no RNAi agent) | OP dose on day 1 and day 2 |
| 2 | 0.025 mg/kg of AD05625 conjugated to a tridentate small molecule αvβ6 epithelial cell targeting ligand (Tri-SM6.1) at the 5' terminal end of the sense strand, formulated in isotonic saline. | OP dose on day 1 and day 2 |
| 3 | 0.50 mg/kg of AD05453 conjugated to a tridentate small molecule αvβ6 epithelial cell targeting ligand (Tri-SM6.1) at the 5' terminal end of the sense strand, formulated in isotonic saline. | OP dose on day 1 and day 2 |
| 4 | 0.50 mg/kg of AD05829 conjugated to a tridentate small molecule αvβ6 epithelial cell targeting ligand (Tri-SM6.1) at the 5' terminal end of the sense strand, formulated in isotonic saline. | OP dose on day 1 and day 2 |
| 5 | 0.50 mg/kg of AD05831 conjugated to a tridentate small molecule αvβ6 epithelial cell targeting ligand (Tri-SM6.1) at the 5' terminal end of the sense strand, formulated in isotonic saline. | OP dose on day 1 and day 2 |
| 6 | 0.50 mg/kg of AD05833 conjugated to a tridentate small molecule αvβ6 epithelial cell targeting ligand (Tri-SM6.1) at the 5' terminal end of the sense strand, formulated in isotonic saline. | OP dose on day 1 and day 2 |

(See, e.g., Tables 3 through 6 for chemical structure information for the chemically modified duplexes used in this Example).

The tridentate small molecule αvβ6 epithelial cell targeting ligand referred to as Tri-SM6.1 in Groups 2-7 has the structure represented in FIG. 6.

Four (4) rats were dosed in each Group (n=7). Rats were sacrificed on study day 9, and total RNA was isolated from both lungs following collection and homogenization. Alpha-ENaC (SCNN1A) mRNA expression was quantitated by probe-based quantitative PCR, normalized to GAPDH expression, and expressed as fraction of vehicle control group (geometric mean, +/−95% confidence interval).

TABLE 31

Average Relative rENaC mRNA Expression at Sacrifice (Day 9) in Example 19

| Group ID | Average Relative rENaC mRNA Expression | Low (error) | High (error) |
|---|---|---|---|
| Group 1 (isotonic saline) | 1.000 | 0.196 | 0.243 |
| Group 2 (0.25 mg/kg AD05625-Tri-SM6.1) | 0.663 | 0.107 | 0.127 |
| Group 3 (0.50 mg/kg AD05453-Tri-SM6.1) | 0.490 | 0.091 | 0.111 |
| Group 4 (0.50 mg/kg AD05829-Tri-SM6.1) | 0.767 | 0.163 | 0.207 |

TABLE 31-continued

Average Relative rENaC mRNA Expression at Sacrifice (Day 9) in Example 19

| Group ID | Average Relative rENaC mRNA Expression | Low (error) | High (error) |
| --- | --- | --- | --- |
| Group 5 (0.50 mg/kg AD05831-Tri-SM6.1) | 0.542 | 0.113 | 0.142 |
| Group 6 (0.50 mg/kg AD05833-Tri-SM6.1) | 0.599 | 0.025 | 0.026 |

In Table 31 above, alpha-ENaC RNAi agents AD05625 and AD05453 each included an antisense strand that was designed to target the alpha-ENaC gene beginning at position 972 (see SEQ ID NO:1); AD05829 included an antisense strand that was designed to target the alpha-ENaC gene beginning at position 944; AD05831 included an antisense strand that was designed to target the alpha-ENaC gene beginning at position 973; and AD01289 included an antisense strand that was designed to target the alpha-ENaC gene beginning at position 1289. Each of the alpha-ENaC RNAi agents showed inhibition of gene expression, with RNAi agent AD05453 showing comparatively potent inhibition of alpha-ENaC.

Example 20. In Vivo Topical Ocular Administration of Alpha-ENaC RNAi Agents in Mice To evaluate the ability of alpha-ENaC RNAi agents to inhibit expression of alpha ENaC mRNA in the ocular surface epithelium, CB57Bl/6 mice (n=3/group) received twice daily topical ocular instillations of saline vehicle or 400 micrograms AD04858 (in two microliter volume) in both eyes for five days. (See, e.g., Tables 3 through 6 for chemical structure information for the chemically modified duplex of AD04858). On study day five, mice were sacrificed, samples of the conjunctival epithelium collected and total RNA isolated from tissue homogenate. Alpha-ENaC (SCNN1A) mRNA expression was quantitated by probe-based quantitative PCR, normalized to GAPDH expression, and expressed as fraction of vehicle control group.

After five days of twice daily topical dosing of AD04858, conjunctival samples from treated mice expressed significantly less (approximately 24%) alpha ENaC mRNA than samples from vehicle treated controls Other Embodiments It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. An RNAi agent for inhibiting expression of an alpha-ENaC gene, comprising:
   an antisense strand comprising the nucleotides:
   (i) UAUUUGUUCUGGUUGCACAGG (SEQ ID NO:3); or
   (ii) UAUUUGUUCUGGUUGCACAGC (SEQ ID NO:7); and
   a sense strand comprising a nucleotide sequence that is partially complementary, substantially complementary, or fully complementary to the antisense strand.

2. The RNAi agent of claim 1, wherein the sense strand comprises a nucleotide sequence selected from the group consisting of SEQ ID NOs: 255, 273, 276, 284 and 296.

3. The RNAi agent of claim 1, wherein at least one nucleotide of the alpha-ENaC RNAi agent is a modified nucleotide or includes a modified internucleoside linkage.

4. The RNAi agent of claim 1, wherein all or substantially all of the nucleotides are modified nucleotides.

5. The RNAi agent of claim 3, wherein the modified nucleotide is selected from the group consisting of: 2'-O-methyl nucleotide, 2'-fluoro nucleotide, 2'-deoxy nucleotide, 2',3'-seco nucleotide mimic, locked nucleotide, 2'-F-arabino nucleotide, 2'-methoxyethyl nucleotide, abasic nucleotide, ribitol, inverted nucleotide, inverted 2'-O-methyl nucleotide, inverted 2'-deoxy nucleotide, 2'-amino-modified nucleotide, 2'-alkyl-modified nucleotide, morpholino nucleotide, vinyl phosphonate deoxyribonucleotide, and 3'-O-methyl nucleotide.

6. The RNAi agent of claim 4, wherein all or substantially all of the nucleotides are modified with either 2'-O-methyl nucleotides or 2'-fluoro nucleotides.

7. The RNAi agent of claim 1, wherein the antisense strand comprises the nucleotide sequence of any one of the modified sequences of SEQ ID NOS: 2, 6, 10, 99, 100, 101, 103, 120-125, 132-135, 137, 143, 144, 145, 146, or 147.

8. The RNAi agent of claim 1, wherein the sense strand comprises the nucleotide sequence of any one of SEQ ID NOs: 153, 154, 156, 167, 168, 169, 176-179, 182, 183, 188-195, 197, 201, 206-208, 210, 211, 213-217, 223, or 295.

9. The RNAi agent of claim 1, wherein the RNAi agent is linked to a targeting ligand.

10. The RNAi agent of claim 9, wherein the targeting ligand comprises an integrin targeting ligand.

11. The RNAi agent of claim 10, wherein the integrin targeting ligand is an αvβ6 integrin targeting ligand.

12. The RNAi agent of claim 9, wherein the targeting ligand is conjugated to the sense strand.

13. The RNAi agent of claim 12, wherein the targeting ligand is conjugated to the 5' terminal end of the sense strand.

14. The RNAi agent of claim 1, wherein the sense strand is between 21 and 30 nucleotides in length, and the antisense strand is between 21 and 30 nucleotides in length.

15. The RNAi agent of claim 14, wherein the sense strand and the antisense strand are each between 21 and 27 nucleotides in length.

16. The RNAi agent of claim 15, wherein the sense strand and the antisense strand are each between 21 and 24 nucleotides in length.

17. The RNAi agent of claim 16, wherein the sense strand and the antisense strand are each 21 nucleotides in length.

18. The RNAi agent of claim 17, wherein the RNAi agent has two blunt ends.

19. The RNAi agent of claim 1, wherein the sense strand comprises one or two terminal caps.

20. The RNAi agent of claim 19, wherein the sense strand comprises one or two inverted abasic residues.

21. The RNAi agent of claim 1, wherein the RNAi agent is comprised of a sense strand and an antisense strand that form a duplex having the structure of any one of duplexes of AD04019 (SEQ ID NOs: 99/153), AD04020 (SEQ ID NOs: 99/154), AD04021 (SEQ ID NOs: 100/154), AD04022 (SEQ ID NOs: 6/154), AD05515 (SEQ ID NOs: 6/190), AD05625 (SEQ ID NOs: 6/156), AD05773 (SEQ ID NOs: 6/215), AD04023 (SEQ ID NOs: 101/154), AD04025 (SEQ ID NOs: 103/154), AD04978 (SEQ ID NOs: 120/169), AD04835 (SEQ ID NOs: 121/156), AD04858 (SEQ ID NOs: 121/154), AD05345 (SEQ ID NOs: 121/176), AD04859 (SEQ ID NOs: 122/167), AD05160 (SEQ ID NOs: 122/169), AD04976 (SEQ ID NOs: 123/169), AD04977 (SEQ ID NOs: 124/169), AD04979 (SEQ ID NOs: 125/169), AD04980 (SEQ ID NOs: 125/168), AD5161 (SEQ ID NOs: 132/169), AD05162 (SEQ ID NOs: 133/169), or AD05163 (SEQ ID NOs: 134/169).

22. A composition comprising the RNAi agent of claim 1, wherein the composition comprises a pharmaceutically acceptable excipient.

23. The composition of claim 22, further comprising a second RNAi agent for inhibiting the expression of alpha-ENaC.

24. The composition of claim 23, further comprising one or more additional therapeutics.

25. The composition of claim 24, wherein the composition is formulated for administration by inhalation.

26. The composition of claim 25, wherein the composition is delivered by a metered-dose inhaler, jet nebulizer, vibrating mesh nebulizer, or soft mist inhaler.

27. A method for inhibiting expression of an alpha-ENaC gene in a cell, the method comprising introducing into a cell an effective amount of an RNAi agent of claim 1.

28. The method of claim 27, wherein the cell is within a subject.

29. The method of claim 28, wherein the subject is a human subject.

30. The method of claim 28, wherein the alpha-ENaC gene expression is inhibited by at least about 30%.

31. A method for inhibiting expression of an alpha-ENaC gene in a cell, the method comprising introducing into a cell an effective amount of the composition of claim 22.

32. The method of claim 31, wherein the cell is within a subject.

33. The method of claim 32, wherein the subject is a human subject.

34. The method of claim 31, wherein the alpha-ENaC gene expression is inhibited by at least about 30%.

35. A method of treating one or more symptoms or diseases associated with enhanced or elevated ENaC activity levels, the method comprising administering to a human subject in need thereof a therapeutically effective amount of the composition of claim 22.

36. The method of claim 35, wherein the disease is a respiratory disease.

37. The method of claim 36, wherein the respiratory disease is cystic fibrosis, chronic bronchitis, non-cystic fibrosis bronchiectasis, chronic obstructive pulmonary disease (COPD), asthma, respiratory tract infections, primary ciliary dyskinesia, or lung carcinoma cystic fibrosis.

38. The method of claim 35, wherein the disease is an ocular disease.

39. The method of claim 32, wherein the RNAi agent is administered at a dose of about 0.001 mg/kg to about 0.500 mg/kg of body weight.

40. The method of claim 39, wherein the RNAi agent is administered in two or more doses.

41. The method of claim 35, wherein the RNAi agent is administered at a dose of about 0.001 mg/kg to about 0.500 mg/kg of body weight.

42. The method of claim 41, wherein the RNAi agent is administered in two or more doses.

\* \* \* \* \*

SEQUENCE LISTING

```
<160> NUMBER OF SEQ ID NOS: 296

<210> SEQ ID NO 1
<211> LENGTH: 3345
<212> TYPE: DNA
<213> ORGANISM: Homo sapiens
<220> FEATURE:
<223> OTHER INFORMATION: Sodium channel epithelial 1 alpha subunit
      (SCNN1A), transcript variant 1, GenBank NM_001038.5

<400> SEQUENCE: 1
cttgcctgtc tgcgtctaaa gccctgccc  agagtccgcc ttctcaggtc cagtactccc      60
agttcacctg ccctcgggag ccctccttcc ttcggaaaac tcccggctct gactcctcct     120
cagcccctcc ccccgccctg ctcaccttta attgagatgc taatgagatt cctgtcgctt     180
ccatccctgg ccggccagcg ggcgggctcc ccagccaggc cgctgcacct gtcagggaa      240 caagctggag gagcaggacc ctagacctct gcagcccata ccaggtctca tggagggaa      300 caagctggag gagcaggact ctagccctcc acagtccact ccagggctca tgaaggggaa     360
caagcgtgag gagcagggc  tgggcccga  acctgcggcg ccccagcagc ccacggcgga     420
ggaggaggcc ctgatcgagt tccaccgctc ctaccgagag ctcttcgagt tcttctgcaa     480
caacaccacc atccacggcg ccatccgcct ggtgtgctcc cagcacaacc gcatgaagac     540
ggccttctgg gcagtgctgt ggctctgcac ctttggcatg atgtactggc aattcggcct     600
gcttttcgga gagtacttca gctaccccgt cagcctcaac atcaacctca actcggacaa     660
gctcgtcttc cccgcagtga ccatctgcac cctcaatccc tacaggtacc cggaaattaa     720
```

-continued

```
agaggagctg gaggagctgg accgcatcac agagcagacg ctctttgacc tgtacaaata    780
cagctccttc accactctcg tggccggctc ccgcagccgt cgcgacctgc gggggactct    840
gccgcacccc ttgcagcgcc tgagggtccc gcccccgcct cacggggccc gtcgagcccg    900
tagcgtggcc tccagcttgc gggacaacaa ccccaggtg gactggaagg actggaagat    960
cggcttccag ctgtgcaacc agaacaaatc ggactgcttc taccagacat actcatcagg   1020
ggtggatgcg gtgagggagt ggtaccgctt ccactacatc aacatcctgt cgaggctgcc   1080
agagactctg ccatccctgg aggaggacac gctgggcaac ttcatcttcg cctgccgctt   1140
caaccaggtc tcctgcaacc aggcgaatta ctctcacttc caccacccga tgtatggaaa   1200
ctgctatact ttcaatgaca agaacaactc aacctctgg atgtcttcca tgcctggaat   1260
caacaacggt ctgtccctga tgctgcgcgc agagcagaat gacttcattc ccctgctgtc   1320
cacagtgact ggggcccggg taatggtgca cgggcaggat gaacctgcct ttatggatga   1380
tggtggcttt aacttgcggc ctggcgtgga gacctccatc agcatgagga aggaaaccct   1440
ggacagactt gggggcgatt atggcgactg caccaagaat ggcagtgatg ttcctgttga   1500
gaacctttac ccttcaaagt acacacagca ggtgtgtatt cactcctgct ccaggagag   1560
catgatcaag gagtgtggct gtgcctacat ctttctatccg cggccccaga acgtggagta   1620
ctgtgactac agaaagcaca gttcctgggg gtactgctac tataagctcc aggttgactt   1680
ctcctcagac cacctgggct gtttcaccaa gtgccgaaag ccatgcagcg tgaccagcta   1740
ccagctctct gctggttact cacgatggcc ctcggtgaca tcccaggaat gggtcttcca   1800
gatgctatcg cgacagaaca attacccgt caacaacaag agaaatggag tggccaaagt   1860
caacatcttc ttcaaggagc tgaactacaa aaccaattct gagtctccct ctgtcacgat   1920
ggtcacccta ctgtccaacc tgggcagcca gtggagcctg tggttcggct cctcggtgtt   1980
gtctgtggtg gagatggctg agctcgtctt tgacctgctg gtcatcatgt tcctcatgct   2040
gctccgaagg ttccgaagcc gatactggtc tccaggccga gggggcaggg gtgctcagga   2100
ggtagcctcc accctggcat cctcccctcc ttcccacttc tgcccccacc ccatgtctct   2160
gtccttgtcc cagccaggcc ctgctccctc tccagccttg acagcccctc cccctgccta   2220
tgccacccctg ggcccccgcc catctccagg gggctctgca ggggccagtt cctccacctg   2280
tcctctgggg gggccctgag agggaaggag aggtttctca caccaaggca gatgctcctc   2340
tggtgggagg gtgctggccc tggcaagatt gaaggatgtg cagggcttcc tctcagagcc   2400
gcccaaactg ccgttgatgt gtggagggga agcaagatgg gtaagggctc aggaagttgc   2460
tccaagaaca gtagctgatg aagctgccca gaagtgcctt ggctccagcc ctgtacccct   2520
tggtactgcc tctgaacact ctggtttccc caccccaactg cggctaagtc tcttttttccc   2580
ttggatcagc caagcgaaac ttggagcttt gacaaggaac tttcctaaga aaccgctgat   2640
aaccaggaca aaacacaacc aagggtacac gcaggcatgc acgggtttcc tgcccagcga   2700
cggcttaagc cagccccccga ctggcctggc cacactgctc tccagtagca cagatgtctg   2760
ctcctcctct tgaacttggg tgggaaaccc caccccaaaag ccccctttgt tacttaggca   2820
attcccttc cctgactccc gagggctagg gctagagcag accggggtaa gtaaaggcag   2880
acccagggct cctctagcct catacccgtg ccctcacaga gccatgcccc ggcacctctg   2940
ccctgtgtct ttcataccctc tacatgtctg cttgagatat ttcctcagcc tgaaagtttc   3000
cccaaccatc tgccagagaa ctcctatgca tcccttagaa ccctgctcag acaccattac   3060
ttttgtgaac gcttctgcca catcttgtct tccccaaaat tgatcactcc gccttctcct   3120
```

-continued

```
gggctcccgt agcacactat aacatctgct ggagtgttgc tgttgcacca tactttcttg    3180
tacatttgtg tctcccttcc caactagact gtaagtgcct tgcggtcagg gactgaatct    3240
tgcccgttta tgtatgctcc atgtctagcc catcatcctg cttggagcaa gtaggcagga    3300
gctcaataaa tgtttgttgc atgaaggaaa aaaaaaaaaa aaaaa                    3345
```

```
<210> SEQ ID NO 2
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 2
uauuuguucu gguugcacag g                                              21

<210> SEQ ID NO 3
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 3
uauuuguucu gguugcacag g                                              21

<210> SEQ ID NO 4
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 4
ccugugcaac cagaacaaau a                                              21

<210> SEQ ID NO 5
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 5
ccugugcaac cagaacaaau a                                              21

<210> SEQ ID NO 6
<211> LENGTH: 21
<212> TYPE: RNA
<213> ORGANISM: Artificial sequence
<220> FEATURE:
<223> OTHER INFORMATION: RNAi Agent antisense strand modified sequence

<400> SEQUENCE: 6
uauuuguucu gguugcacag c                                              21

<210> SEQ ID NO 7
<211> LENGTH: 21
<212> TYPE: RNA
<213> ORGANISM: Artificial sequence
<220> FEATURE:
<223> OTHER INFORMATION: RNAi agent antisense strand underlying base
      sequence
```

```
<400> SEQUENCE: 7
uauuuguucu gguugcacag c                                              21

<210> SEQ ID NO 8
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 8
gcugugcaac cagaacaaau a                                              21

<210> SEQ ID NO 9
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 9
gcugugcaac cagaacaaau a                                              21

<210> SEQ ID NO 10
<211> LENGTH: 21
<212> TYPE: RNA
<213> ORGANISM: Artificial sequence
<220> FEATURE:
<223> OTHER INFORMATION: RNAi Agent antisense strand modified sequence

<400> SEQUENCE: 10
uauuuguucu gguugcacag g                                              21

<210> SEQ ID NO 11
<211> LENGTH: 19
<212> TYPE: RNA
<213> ORGANISM: Artificial sequence
<220> FEATURE:
<223> OTHER INFORMATION: Alpha-ENaC gene transcript (mRNA) target
      sequence

<400> SEQUENCE: 11
ugugcaacca gaacaaauc                                                 19

<210> SEQ ID NO 12
<211> LENGTH: 19
<212> TYPE: RNA
<213> ORGANISM: Artificial sequence
<220> FEATURE:
<223> OTHER INFORMATION: Alpha-ENaC gene transcript (mRNA) target
      sequence

<400> SEQUENCE: 12
gugcaaccag aacaaaucg                                                 19

<210> SEQ ID NO 13
<211> LENGTH: 19
<212> TYPE: RNA
<213> ORGANISM: Artificial sequence
<220> FEATURE:
<223> OTHER INFORMATION: Alpha-ENaC gene transcript (mRNA) target
      sequence

<400> SEQUENCE: 13
```

```
gcagagcaga augacuuca                                              19

<210> SEQ ID NO 14
<211> LENGTH: 19
<212> TYPE: RNA
<213> ORGANISM: Artificial sequence
<220> FEATURE:
<223> OTHER INFORMATION: Alpha-ENaC gene transcript (mRNA) target
      sequence

<400> SEQUENCE: 14
agagcagaau gacuucauu                                              19

<210> SEQ ID NO 15
<211> LENGTH: 19
<212> TYPE: RNA
<213> ORGANISM: Artificial sequence
<220> FEATURE:
<223> OTHER INFORMATION: Alpha-ENaC gene transcript (mRNA) target
      sequence

<400> SEQUENCE: 15
cuaccagaca uacucauca                                              19

<210> SEQ ID NO 16
<211> LENGTH: 19
<212> TYPE: RNA
<213> ORGANISM: Artificial sequence
<220> FEATURE:
<223> OTHER INFORMATION: Alpha-ENaC gene transcript (mRNA) target
      sequence

<400> SEQUENCE: 16
ucuaccagac auacucauc                                              19

<210> SEQ ID NO 17
<211> LENGTH: 19
<212> TYPE: RNA
<213> ORGANISM: Artificial sequence
<220> FEATURE:
<223> OTHER INFORMATION: Alpha-ENaC gene transcript (mRNA) target
      sequence

<400> SEQUENCE: 17
cuuugaccug uacaaauac                                              19

<210> SEQ ID NO 18
<211> LENGTH: 19
<212> TYPE: RNA
<213> ORGANISM: Artificial sequence
<220> FEATURE:
<223> OTHER INFORMATION: Alpha-ENaC gene transcript (mRNA) target
      sequence

<400> SEQUENCE: 18
uggaaggacu ggaagaucg                                              19

<210> SEQ ID NO 19
<211> LENGTH: 19
<212> TYPE: RNA
<213> ORGANISM: Artificial sequence
<220> FEATURE:
<223> OTHER INFORMATION: Alpha-ENaC gene transcript (mRNA) target
      sequence

<400> SEQUENCE: 19
ggaaggacug gaagaucgg                                              19
```

<210> SEQ ID NO 20
<211> LENGTH: 19
<212> TYPE: RNA
<213> ORGANISM: Artificial sequence
<220> FEATURE:
<223> OTHER INFORMATION: Alpha-ENaC gene transcript (mRNA) target
      sequence

<400> SEQUENCE: 20
cugugccuac aucuucuau                                              19

<210> SEQ ID NO 21
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 21
uauuuguucu gguugcaca                                              19

<210> SEQ ID NO 22
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 22
aauuuguucu gguugcaca                                              19

<210> SEQ ID NO 23
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 23
gauuuguucu gguugcaca                                              19

<210> SEQ ID NO 24
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleotide

<400> SEQUENCE: 24
nauuuguucu gguugcaca                                              19

<210> SEQ ID NO 25
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:

```
<221> NAME/KEY: modified_base
<222> LOCATION: 1, 19
<223> OTHER INFORMATION: n = any nucleotide

<400> SEQUENCE: 25
nauuuguucu gguugcacn                                                  19

<210> SEQ ID NO 26
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 26
aaugaaguca uucugcucu                                                  19

<210> SEQ ID NO 27
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 27
uaugaaguca uucugcucu                                                  19

<210> SEQ ID NO 28
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleotide

<400> SEQUENCE: 28
naugaaguca uucugcucu                                                  19

<210> SEQ ID NO 29
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleotide

<400> SEQUENCE: 29
naugaaguca uucugcucn                                                  19

<210> SEQ ID NO 30
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 30
```
ugaugaguau gucugguag                                            19

<210> SEQ ID NO 31
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleotide

<400> SEQUENCE: 31
ngaugaguau gucugguag                                            19

<210> SEQ ID NO 32
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleotide

<400> SEQUENCE: 32
ngaugaguau gucugguan                                            19

<210> SEQ ID NO 33
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 33
gaugaguaug ucugguaga                                            19

<210> SEQ ID NO 34
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 34
uaugaguaug ucugguaga                                            19

<210> SEQ ID NO 35
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleotide

<400> SEQUENCE: 35
naugaguaug ucugguaga                                            19

```
<210> SEQ ID NO 36
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleotide

<400> SEQUENCE: 36
naugaguaug ucgguagn                                                    19

<210> SEQ ID NO 37
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 37
cgauuuguuc ugguugcac                                                   19

<210> SEQ ID NO 38
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 38
ugauuuguuc ugguugcac                                                   19

<210> SEQ ID NO 39
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleotide

<400> SEQUENCE: 39
ngauuuguuc ugguugcac                                                   19

<210> SEQ ID NO 40
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleotide

<400> SEQUENCE: 40
ngauuuguuc ugguugcan                                                   19

<210> SEQ ID NO 41
```

```
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 41
guauuuguac aggucaaag                                             19

<210> SEQ ID NO 42
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 42
uuauuuguac aggucaaag                                             19

<210> SEQ ID NO 43
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleotide

<400> SEQUENCE: 43
nuauuuguac aggucaaag                                             19

<210> SEQ ID NO 44
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleotide

<400> SEQUENCE: 44
nuauuuguac aggucaaan                                             19

<210> SEQ ID NO 45
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 45
cgaucuucca guccuucca                                             19

<210> SEQ ID NO 46
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
```

```
<400> SEQUENCE: 46
ugaucuucca guccuucca                                            19

<210> SEQ ID NO 47
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleotide

<400> SEQUENCE: 47
ngaucuucca guccuucca                                            19

<210> SEQ ID NO 48
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleotide

<400> SEQUENCE: 48
ngaucuucca guccuuccn                                            19

<210> SEQ ID NO 49
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 49
ccgaucuucc aguccuucc                                            19

<210> SEQ ID NO 50
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 50
ucgaucuucc aguccuucc                                            19

<210> SEQ ID NO 51
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleotide

<400> SEQUENCE: 51
```
ncgaucuucc aguccuucc                                                       19

<210> SEQ ID NO 52
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleotide

<400> SEQUENCE: 52
ncgaucuucc aguccuucn                                                       19

<210> SEQ ID NO 53
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 53
ugaagucauu cugcucugc                                                       19

<210> SEQ ID NO 54
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleotide

<400> SEQUENCE: 54
ngaagucauu cugcucugc                                                       19

<210> SEQ ID NO 55
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleotide

<400> SEQUENCE: 55
ngaagucauu cugcucugn                                                       19

<210> SEQ ID NO 56
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 56
auagaagaug uaggcacag                                                       19

```
<210> SEQ ID NO 57
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence

<400> SEQUENCE: 57
uuagaagaug uaggcacag                                                  19

<210> SEQ ID NO 58
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleotide

<400> SEQUENCE: 58
nuagaagaug uaggcacag                                                  19

<210> SEQ ID NO 59
<211> LENGTH: 19
<212> TYPE: RNA
<213> ORGANISM: Artificial sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleotide

<400> SEQUENCE: 59
nuagaagaug uaggcacan                                                  19

<210> SEQ ID NO 60
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 60
ugugcaacca gaacaaaua                                                  19

<210> SEQ ID NO 61
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 61
ugugcaacca gaacaaauu                                                  19

<210> SEQ ID NO 62
<211> LENGTH: 19
<212> TYPE: RNA
<213> ORGANISM: Artificial sequence
```

```
<220> FEATURE:
<223> OTHER INFORMATION: RNAi agent sense strand core 19-mer base
      sequence

<400> SEQUENCE: 62
ugugcaacca gaacaaauc                                                19

<210> SEQ ID NO 63
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleotide

<400> SEQUENCE: 63
ugugcaacca gaacaaaun                                                19

<210> SEQ ID NO 64
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleotide

<400> SEQUENCE: 64
ngugcaacca gaacaaaun                                                19

<210> SEQ ID NO 65
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 65
agagcagaau gacuucauu                                                19

<210> SEQ ID NO 66
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 66
agagcagaau gacuucaua                                                19

<210> SEQ ID NO 67
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
```

```
<223> OTHER INFORMATION: n = any nucleotide

<400> SEQUENCE: 67
agagcagaau gacuucaun                                                19

<210> SEQ ID NO 68
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleotide

<400> SEQUENCE: 68
ngagcagaau gacuucaun                                                19

<210> SEQ ID NO 69
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 69
cuaccagaca uacucauca                                                19

<210> SEQ ID NO 70
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleotide

<400> SEQUENCE: 70
cuaccagaca uacucaucn                                                19

<210> SEQ ID NO 71
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleotide

<400> SEQUENCE: 71
nuaccagaca uacucaucn                                                19

<210> SEQ ID NO 72
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
```

```
<400> SEQUENCE: 72
ucuaccagac auacucauc                                                19

<210> SEQ ID NO 73
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 73
ucuaccagac auacucaua                                                19

<210> SEQ ID NO 74
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleotide

<400> SEQUENCE: 74
ucuaccagac auacucaun                                                19

<210> SEQ ID NO 75
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleotide

<400> SEQUENCE: 75
ncuaccagac auacucaun                                                19

<210> SEQ ID NO 76
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 76
gugcaaccag aacaaaucg                                                19

<210> SEQ ID NO 77
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 77
gugcaaccag aacaaauca                                                19

<210> SEQ ID NO 78
```

```
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleotide

<400> SEQUENCE: 78
gugcaaccag aacaaaucn                                                      19

<210> SEQ ID NO 79
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleotide

<400> SEQUENCE: 79
nugcaaccag aacaaaucn                                                      19

<210> SEQ ID NO 80
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 80
cuuugaccug uacaaauac                                                      19

<210> SEQ ID NO 81
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 81
cuuugaccug uacaaauaa                                                      19

<210> SEQ ID NO 82
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleotide

<400> SEQUENCE: 82
cuuugaccug uacaaauan                                                      19

<210> SEQ ID NO 83
<211> LENGTH: 19
<212> TYPE: RNA
```

```
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleotide

<400> SEQUENCE: 83
nuuugaccug uacaaaun                                                    19

<210> SEQ ID NO 84
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 84
uggaaggacu ggaagaucg                                                   19

<210> SEQ ID NO 85
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 85
uggaaggacu ggaagauca                                                   19

<210> SEQ ID NO 86
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleotide

<400> SEQUENCE: 86
uggaaggacu ggaagaucn                                                   19

<210> SEQ ID NO 87
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleotide

<400> SEQUENCE: 87
nggaaggacu ggaagaucn                                                   19

<210> SEQ ID NO 88
<211> LENGTH: 19
<212> TYPE: RNA
<213> ORGANISM: Artificial sequence
<220> FEATURE:
```

```
<223> OTHER INFORMATION: RNAi agent sense strand core 19-mer base
      sequence

<400> SEQUENCE: 88
ggaaggacug gaagaucgg                                              19

<210> SEQ ID NO 89
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 89
ggaaggacug gaagaucga                                              19

<210> SEQ ID NO 90
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleotide

<400> SEQUENCE: 90
ggaaggacug gaagaucgn                                              19

<210> SEQ ID NO 91
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleotide

<400> SEQUENCE: 91
ngaaggacug gaagaucgn                                              19

<210> SEQ ID NO 92
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 92
gcagagcaga augacuuca                                              19

<210> SEQ ID NO 93
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleotide
```

```
<400> SEQUENCE: 93
gcagagcaga augacuucn                                                    19

<210> SEQ ID NO 94
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleotide

<400> SEQUENCE: 94
ncagagcaga augacuucn                                                    19

<210> SEQ ID NO 95
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 95
cugugccuac aucuucuau                                                    19

<210> SEQ ID NO 96
<211> LENGTH: 19
<212> TYPE: RNA
<213> ORGANISM: Artificial sequence
<220> FEATURE:
<223> OTHER INFORMATION: RNAi agent sense strand core 19-mer base
      sequence

<400> SEQUENCE: 96
cugugccuac aucuucuaa                                                    19

<210> SEQ ID NO 97
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleotide

<400> SEQUENCE: 97
cugugccuac aucuucuan                                                    19

<210> SEQ ID NO 98
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleotide

<400> SEQUENCE: 98
```

```
nugugccuac aucuucuan                                               19

```
<213> ORGANISM: Artificial sequence
<220> FEATURE:
<223> OTHER INFORMATION: RNAi agent antisense strand modified sequence

<400> SEQUENCE: 105
uaugaaguca uucugcucug c                                              21

<210> SEQ ID NO 106
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 106
ugaugaguau gucugguaga a                                              21

<210> SEQ ID NO 107
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 107
ugauuuguuc ugguugcaca g                                              21

<210> SEQ ID NO 108
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 108
uaugaguaug ucugguagaa g                                              21

<210> SEQ ID NO 109
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 109
uuauuuguac aggucaaaga g                                              21

<210> SEQ ID NO 110
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 110
uaugaaguca uucugcucug c                                              21

<210> SEQ ID NO 111
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 111
ugaugaguau gucugguaga a                                              21
```

<210> SEQ ID NO 112
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 112
ugauuuguuc ugguugcaca g                                              21

<210> SEQ ID NO 113
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 113
uaugaguaug ucugguagaa g                                              21

<210> SEQ ID NO 114
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 114
uuauuuguac aggucaaaga g                                              21

<210> SEQ ID NO 115
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 115
uaugaaguca uucugcucuu u                                              21

<210> SEQ ID NO 116
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 116
ugaugaguau gucugguagu u                                              21

<210> SEQ ID NO 117
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 117
ugauuuguuc ugguugcacu u                                              21

<210> SEQ ID NO 118
<211> LENGTH: 21
<212> TYPE: RNA
<213> ORGANISM: Artificial sequence
<220> FEATURE:

```
<223> OTHER INFORMATION: RNAi agent antisense strand modified sequence

<400> SEQUENCE: 118
uaugaguaug ucugguagau u                                              21

<210> SEQ ID NO 119
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 119
uuauuuguac aggucaaagu u                                              21

<210> SEQ ID NO 120
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 120
uauuuguucu gguugcacag c                                              21

<210> SEQ ID NO 121
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 121
uauuuguucu gguugcacag c                                              21

<210> SEQ ID NO 122
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 122
uauuuguucu gguugcacag c                                              21

<210> SEQ ID NO 123
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 123
uauuuguucu gguugcacag c                                              21

<210> SEQ ID NO 124
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 124
uauuuguucu gguugcacag c                                              21
```

```
<210> SEQ ID NO 125
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 125
uauuuguucu gguugcacag c                                              21

<210> SEQ ID NO 126
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 126
ugaucuucca guccuuccag u                                              21

<210> SEQ ID NO 127
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 127
ucgaucuucc aguccuucca g                                              21

<210> SEQ ID NO 128
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 128
ugaagucauu cugcucugcg c                                              21

<210> SEQ ID NO 129
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 129
auagaagaug uaggcacagc c                                              21

<210> SEQ ID NO 130
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 130
uaucgugaca gagggagacu c                                              21

<210> SEQ ID NO 131
<211> LENGTH: 21
<212> TYPE: RNA
<213> ORGANISM: Artificial sequence
<220> FEATURE:
<223> OTHER INFORMATION: RNAi agent antisense strand modified sequence
```

-continued

```
<400> SEQUENCE: 131
uugaccaucg ugacagaggg a                                              21

<210> SEQ ID NO 132
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 132
uauuuguucu gguugcacag c                                              21

<210> SEQ ID NO 133
<211> LENGTH: 22
<212> TYPE: RNA
<213> ORGANISM: Artificial sequence
<220> FEATURE:
<223> OTHER INFORMATION: RNAi agent antisense strand modified sequence

<400> SEQUENCE: 133
uauuuguucu gguugcacag cu                                             22

<210> SEQ ID NO 134
<211> LENGTH: 23
<212> TYPE: RNA
<213> ORGANISM: Artificial sequence
<220> FEATURE:
<223> OTHER INFORMATION: RNAi agent antisense strand modified sequence

<400> SEQUENCE: 134
uauuuguucu gguugcacag cuu                                            23

<210> SEQ ID NO 135
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 135
uauuuguucu gguugcacag g                                              21

<210> SEQ ID NO 136
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 136
uauuuguucu gguugcacag u                                              21

<210> SEQ ID NO 137
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 137
uauuuguucu gguugcacag g                                              21

<210> SEQ ID NO 138
<211> LENGTH: 21
```

```
<212> TYPE: RNA
<213> ORGANISM: Artificial sequence
<220> FEATURE:
<223> OTHER INFORMATION: RNAi agent antisense strand modified sequence
<400> SEQUENCE: 138
uauuuguucu gguugcacgg g 21

<210> SEQ ID NO 139
<211> LENGTH: 21
<212> TYPE: RNA
<213> ORGANISM: Artificial sequence
<220> FEATURE:
<223> OTHER INFORMATION: RNAi agent antisense strand modified sequence
<400> SEQUENCE: 139
uauuuguucu gguugcacgg u 21

<210> SEQ ID NO 140
<211> LENGTH: 21
<212> TYPE: RNA
<213> ORGANISM: Artificial sequence
<220> FEATURE:
<223> OTHER INFORMATION: RNAi agent antisense strand modified sequence
<400> SEQUENCE: 140
uauuuguucu gguugcaccg u 21

<210> SEQ ID NO 141
<211> LENGTH: 21
<212> TYPE: RNA
<213> ORGANISM: Artificial sequence
<220> FEATURE:
<223> OTHER INFORMATION: RNAi agent antisense strand modified sequence
<400> SEQUENCE: 141
uauuuguucu gguugcacag u 21

<210> SEQ ID NO 142
<211> LENGTH: 21
<212> TYPE: RNA
<213> ORGANISM: Artificial sequence
<220> FEATURE:
<223> OTHER INFORMATION: RNAi agent antisense strand modified sequence
<400> SEQUENCE: 142
uauuuguucu gguugcacag a 21

<210> SEQ ID NO 143
<211> LENGTH: 21
<212> TYPE: RNA
<213> ORGANISM: Artificial sequence
<220> FEATURE:
<223> OTHER INFORMATION: RNAi agent antisense strand modified sequence
<400> SEQUENCE: 143
uauuuguucu gguugcacag g 21

<210> SEQ ID NO 144
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 144
uauuuguuc ugguugcacag g       21

<210> SEQ ID NO 145
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 145
uauuuguucu gguugcacag g       21

<210> SEQ ID NO 146
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 146
uauuuguucu gguugcacag g       21

<210> SEQ ID NO 147
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 147
uauuuguucu gguugcacag g       21

<210> SEQ ID NO 148
<211> LENGTH: 21
<212> TYPE: RNA
<213> ORGANISM: Artificial sequence
<220> FEATURE:
<223> OTHER INFORMATION: RNAi agent antisense strand modified sequence
<220> FEATURE:
<221> NAME/KEY: modified_base
<222> LOCATION: 1
<223> OTHER INFORMATION: n = 2'-O-methylinosine-3'-phosphate

<400> SEQUENCE: 148
nauuuguucu gguugcacag g       21

<210> SEQ ID NO 149
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 149
uauuuguucu gguugcacag u       21

<210> SEQ ID NO 150
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 150
uauuuguucu gguugcacag u       21

```
<210> SEQ ID NO 151
<211> LENGTH: 21
<212> TYPE: DNA
<213> ORGANISM: Artificial sequence
<220> FEATURE:
<223> OTHER INFORMATION: RNAi agent antisense strand modified sequence

<400> SEQUENCE: 151
tauuuguucu gguugcacag c                                              21

<210> SEQ ID NO 152
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 152
agaagucauu cugcucugcu u                                              21

<210> SEQ ID NO 153
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 153
gcugugcaac cagaacaaau a                                              21

<210> SEQ ID NO 154
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 154
gcugugcaac cagaacaaau a                                              21

<210> SEQ ID NO 155
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 155
gcugugcaac cagaacaaau u                                              21

<210> SEQ ID NO 156
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 156
gcugugcaac cagaacaaau a                                              21

<210> SEQ ID NO 157
<211> LENGTH: 21
<212> TYPE: RNA
<213> ORGANISM: Artificial sequence
<220> FEATURE:
<223> OTHER INFORMATION: RNAi agent sense strand modified sequence
```

```
<400> SEQUENCE: 157
gcagagcaga augacuucau a                                              21

<210> SEQ ID NO 158
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 158
uucuaccaga cauacucauc a                                              21

<210> SEQ ID NO 159
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 159
cugugcaacc agaacaaauc a                                              21

<210> SEQ ID NO 160
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 160
cuucuaccag acauacucau a                                              21

<210> SEQ ID NO 161
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 161
cucuuugacc uguacaaaua a                                              21

<210> SEQ ID NO 162
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 162
agagcagaau gacuucauau u                                              21

<210> SEQ ID NO 163
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 163
cuaccagaca uacucaucau u                                              21

<210> SEQ ID NO 164
<211> LENGTH: 21
```

<212> TYPE: RNA
<213> ORGANISM: Artificial sequence
<220> FEATURE:
<223> OTHER INFORMATION: RNAi agent sense strand modified sequence

<400> SEQUENCE: 164
gugcaaccag aacaaaucau u                                              21

<210> SEQ ID NO 165
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 165
ucuaccagac auacucauau u                                              21

<210> SEQ ID NO 166
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 166
cuuugaccug uacaaauaau u                                              21

<210> SEQ ID NO 167
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 167
gcugugcaac cagaacaaau a                                              21

<210> SEQ ID NO 168
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 168
gcugugcaac cagaacaaau a                                              21

<210> SEQ ID NO 169
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 169
gcugugcaac cagaacaaau a                                              21

<210> SEQ ID NO 170
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 170

```
acuggaagga cuggaagauc a                                          21

<210> SEQ ID NO 171
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 171
cuggaaggac uggaagaucg a                                          21

<210> SEQ ID NO 172
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 172
gcgcagagca gaaugacuuc a                                          21

<210> SEQ ID NO 173
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 173
ggcugugccu acaucuucua u                                          21

<210> SEQ ID NO 174
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 174
gagucucccu cugucacgau a                                          21

<210> SEQ ID NO 175
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 175
ucccucuguc acgaugguca a                                          21

<210> SEQ ID NO 176
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 176
gcugugcaac cagaacaaau a                                          21

<210> SEQ ID NO 177
<211> LENGTH: 21
<212> TYPE: RNA
<213> ORGANISM: Artificial sequence
```

```
<220> FEATURE:
<223> OTHER INFORMATION: RNAi agent sense strand modified sequence

<400> SEQUENCE: 177
ccugugcaac cagaacaaau a                                              21

<210> SEQ ID NO 178
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 178
ccugugcaac cagaacaaau a                                              21

<210> SEQ ID NO 179
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 179
ccugugcaac cagaacaaau a                                              21

<210> SEQ ID NO 180
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 13
<223> OTHER INFORMATION: n = 2'-O-methylinosine-3'-phosphate

<400> SEQUENCE: 180
ccugugcaac canaacaaau a                                              21

<210> SEQ ID NO 181
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methyl-2-aminoadenosine-3'-phosphate

<400> SEQUENCE: 181
ccugugcaac cagaacanau a                                              21

<210> SEQ ID NO 182
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 182
acugugcaac cagaacaaau a                                              21

<210> SEQ ID NO 183
<211> LENGTH: 21
<212> TYPE: RNA
```

<213> ORGANISM: Artificial sequence
<220> FEATURE:
<223> OTHER INFORMATION: RNAi agent sense strand modified sequence

<400> SEQUENCE: 183
ccugugcaac cagaacaaau a                                              21

<210> SEQ ID NO 184
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 13
<223> OTHER INFORMATION: n = 2'-O-methylinosine-3'-phosphate

<400> SEQUENCE: 184
ccugugcaac canaacaaau a                                              21

<210> SEQ ID NO 185
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 185
ccugugcaac uagaacaaau a                                              21

<210> SEQ ID NO 186
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 186
cccgugcaac cagaacaaau a                                              21

<210> SEQ ID NO 187
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 187
accgugcaac cagaacaaau a                                              21

<210> SEQ ID NO 188
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 188
ccugugcaac cagaacaaau a                                              21

<210> SEQ ID NO 189
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 189
ccugugcaac cagaacaaau a                                                    21

<210> SEQ ID NO 190
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 190
gcugugcaac cagaacaaau a                                                    21

<210> SEQ ID NO 191
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 191
ccugugcaac cagaacaaau a                                                    21

<210> SEQ ID NO 192
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 192
ccugugcaac cagaacaaau a                                                    21

<210> SEQ ID NO 193
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 193
ccugugcaac cagaacaaau a                                                    21

<210> SEQ ID NO 194
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 194
ccugugcaac cagaacaaau a                                                    21

<210> SEQ ID NO 195
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 195
ccugugcaac cagaacaaau a                                                    21

<210> SEQ ID NO 196

```
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 196
acggugcaac cagaacaaau a                                              21

<210> SEQ ID NO 197
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 197
acugugcaac cagaacaaau a                                              21

<210> SEQ ID NO 198
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methyl-2-aminoadenosine-3'-phosphate

<400> SEQUENCE: 198
acugugcaac cagaacaanu a                                              21

<210> SEQ ID NO 199
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methyl-2-aminoadenosine-3'-phosphate

<400> SEQUENCE: 199
acugugcaac cagaacanau a                                              21

<210> SEQ ID NO 200
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methyl-2-aminoadenosine-3'-phosphate

<400> SEQUENCE: 200
acugugcaac cagaacnaau a                                              21

<210> SEQ ID NO 201
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 201
```
ucugugcaac cagaacaaau a                                          21

<210> SEQ ID NO 202
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methyl-2-aminoadenosine-3'-phosphate

<400> SEQUENCE: 202
ccugugcaac cagaacanau a                                          21

<210> SEQ ID NO 203
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methyl-2-aminoadenosine-3'-phosphate

<400> SEQUENCE: 203
ccugugcaac cagaacanau a                                          21

<210> SEQ ID NO 204
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methyl-2-aminoadenosine-3'-phosphate

<400> SEQUENCE: 204
ccugugcaac cagaacaanu a                                          21

<210> SEQ ID NO 205
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methyl-2-aminoadenosine-3'-phosphate

<400> SEQUENCE: 205
ccugugcaac cagaacnaau a                                          21

<210> SEQ ID NO 206
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 206
ccugugcaac cagaacaaau a                                          21

```
<210> SEQ ID NO 207
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 207
ccugugcaac cagaacaaau a                                              21

<210> SEQ ID NO 208
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 208
ccugugcaac cagaacaaau a                                              21

<210> SEQ ID NO 209
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 209
ccugugcaac cagaacaaau c                                              21

<210> SEQ ID NO 210
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 210
acugugcaac cagaacaaau a                                              21

<210> SEQ ID NO 211
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 211
acugugcaac cagaacaaau a                                              21

<210> SEQ ID NO 212
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methyl-2-aminoadenosine-3'-phosphate

<400> SEQUENCE: 212
acugugcaac cagaacanau a                                              21

<210> SEQ ID NO 213
<211> LENGTH: 21
```

```
<212> TYPE: RNA
<213> ORGANISM: Artificial sequence
<220> FEATURE:
<223> OTHER INFORMATION: RNAi agent sense strand modified sequence

<400> SEQUENCE: 213
ccugugcaac cagaacaaau a                                              21

<210> SEQ ID NO 214
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 214
ccugugcaac cagaacaaau a                                              21

<210> SEQ ID NO 215
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 215
gcugugcaac cagaacaaau a                                              21

<210> SEQ ID NO 216
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 216
ccugugcaac cagaacaaau a                                              21

<210> SEQ ID NO 217
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 217
ccugugcaac cagaacaaau a                                              21

<210> SEQ ID NO 218
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 218
acuggaagga cuggaagauc a                                              21

<210> SEQ ID NO 219
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 219
```

```
cugugcaacc agaacaaauc a                                              21

<210> SEQ ID NO 220
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 220
cugugcaacc agaacaaauc a                                              21

<210> SEQ ID NO 221
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 221
gcagagcaga augacuucuu u                                              21

<210> SEQ ID NO 222
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 222
gcagagcaga augacuucuu u                                              21

<210> SEQ ID NO 223
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 223
ccugugcaac cagaacaaau a                                              21

<210> SEQ ID NO 224
<211> LENGTH: 23
<212> TYPE: RNA
<213> ORGANISM: Artificial sequence
<220> FEATURE:
<223> OTHER INFORMATION: RNAi agent antisense strand underlying base
      sequence

<400> SEQUENCE: 224
uauuuguucu gguugcacag cug                                            23

<210> SEQ ID NO 225
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 225
uauuuguucu gguugcacag c                                              21

<210> SEQ ID NO 226
<211> LENGTH: 21
```

```
<212> TYPE: RNA
<213> ORGANISM: Artificial sequence
<220> FEATURE:
<223> OTHER INFORMATION: RNAi agent antisense strand underlying base
      sequence

<400> SEQUENCE: 226
uauuuguucu gguugcacau u                                              21

<210> SEQ ID NO 227
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 227
aauuuguucu gguugcacag c                                              21

<210> SEQ ID NO 228
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 228
uaugaaguca uucugcucug c                                              21

<210> SEQ ID NO 229
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 229
ugaugaguau gucugguaga a                                              21

<210> SEQ ID NO 230
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 230
ugauuuguuc ugguugcaca g                                              21

<210> SEQ ID NO 231
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 231
uaugaguaug ucugguagaa g                                              21

<210> SEQ ID NO 232
<211> LENGTH: 21
<212> TYPE: RNA
```

<213> ORGANISM: Artificial sequence
<220> FEATURE:
<223> OTHER INFORMATION: RNAi agent antisense strand underlying base
      sequence

<400> SEQUENCE: 232
uuauuuguac aggucaaaga g                                           21

<210> SEQ ID NO 233
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 233
uaugaaguca uucugcucuu u                                           21

<210> SEQ ID NO 234
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 234
ugaugaguau gucugguagu u                                           21

<210> SEQ ID NO 235
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 235
ugauuuguuc ugguugcacu u                                           21

<210> SEQ ID NO 236
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 236
uaugaguaug ucugguagau u                                           21

<210> SEQ ID NO 237
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 237
uuauuuguac aggucaaagu u                                           21

<210> SEQ ID NO 238
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 238
ugaucuucca guccuuccag u                                              21

<210> SEQ ID NO 239
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 239
ucgaucuucc aguccuucca g                                              21

<210> SEQ ID NO 240
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 240
ugaagucauu cugcucugcg c                                              21

<210> SEQ ID NO 241
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 241
auagaagaug uaggcacagc c                                              21

<210> SEQ ID NO 242
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 242
uaucgugaca gagggagacu c                                              21

<210> SEQ ID NO 243
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 243
uugaccaucg ugacagaggg a                                              21

<210> SEQ ID NO 244
<211> LENGTH: 22
<212> TYPE: RNA
<213> ORGANISM: Artificial sequence
<220> FEATURE:

```
<223> OTHER INFORMATION: RNAi agent antisense strand underlying base
      sequence

<400> SEQUENCE: 244
uauuuguucu gguugcacag cu                                           22

<210> SEQ ID NO 245
<211> LENGTH: 23
<212> TYPE: RNA
<213> ORGANISM: Artificial sequence
<220> FEATURE:
<223> OTHER INFORMATION: RNAi agent antisense strand underlying base
      sequence

<400> SEQUENCE: 245
uauuuguucu gguugcacag cuu                                          23

<210> SEQ ID NO 246
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 246
uauuuguucu gguugcacag g                                            21

<210> SEQ ID NO 247
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 247
uauuuguucu gguugcacag u                                            21

<210> SEQ ID NO 248
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 248
uauuuguucu gguugcacgg g                                            21

<210> SEQ ID NO 249
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 249
uauuuguucu gguugcacgg u                                            21

<210> SEQ ID NO 250
<211> LENGTH: 21
<212> TYPE: RNA
<213> ORGANISM: Artificial sequence
<220> FEATURE:
<223> OTHER INFORMATION: RNAi agent antisense strand underlying base
``` sequence

<400> SEQUENCE: 250
uauuuguucu gguugcaccg u                                              21

<210> SEQ ID NO 251
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 251
uauuuguucu gguugcacag a                                              21

<210> SEQ ID NO 252
<211> LENGTH: 21
<212> TYPE: RNA
<213> ORGANISM: Artificial sequence
<220> FEATURE:
<223> OTHER INFORMATION: RNAi agent antisense strand underlying base
      sequence
<220> FEATURE:
<221> NAME/KEY: modified_base
<222> LOCATION: 1
<223> OTHER INFORMATION: n = inosine (hypoxanthine)

<400> SEQUENCE: 252
nauuuguucu gguugcacag g                                              21

<210> SEQ ID NO 253
<211> LENGTH: 21
<212> TYPE: DNA
<213> ORGANISM: Artificial sequence
<220> FEATURE:
<223> OTHER INFORMATION: RNAi agent antisense strand underlying base
      sequence

<400> SEQUENCE: 253
tauuuguucu gguugcacag c                                              21

<210> SEQ ID NO 254
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 254
agaagucauu cugcucugcu u                                              21

<210> SEQ ID NO 255
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 255
gcugugcaac cagaacaaau a                                              21

<210> SEQ ID NO 256
<211> LENGTH: 21
<212> TYPE: RNA

<213> ORGANISM: Artificial sequence
<220> FEATURE:
<223> OTHER INFORMATION: RNAi agent sense strand underlying base
      sequence

<400> SEQUENCE: 256
gcugugcaac cagaacaaau u                                              21

<210> SEQ ID NO 257
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 257
gcagagcaga augacuucau a                                              21

<210> SEQ ID NO 258
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 258
uucuaccaga cauacucauc a                                              21

<210> SEQ ID NO 259
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 259
cugugcaacc agaacaaauc a                                              21

<210> SEQ ID NO 260
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 260
cuucuaccag acauacucau a                                              21

<210> SEQ ID NO 261
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 261
cucuuugacc uguacaaaua a                                              21

<210> SEQ ID NO 262
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 262
agagcagaau gacuucauau u                                              21

<210> SEQ ID NO 263
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 263
cuaccagaca uacucaucau u                                              21

<210> SEQ ID NO 264
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 264
gugcaaccag aacaaaucau u                                              21

<210> SEQ ID NO 265
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 265
ucuaccagac auacucauau u                                              21

<210> SEQ ID NO 266
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 266
cuuugaccug uacaaauaau u                                              21

<210> SEQ ID NO 267
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 267
acuggaagga cuggaagauc a                                              21

<210> SEQ ID NO 268
<211> LENGTH: 21
<212> TYPE: RNA
<213> ORGANISM: Artificial sequence
<220> FEATURE:

```
<223> OTHER INFORMATION: RNAi agent sense strand underlying base
      sequence

<400> SEQUENCE: 268
cuggaaggac uggaagaucg a                                              21

<210> SEQ ID NO 269
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 269
gcgcagagca gaaugacuuc a                                              21

<210> SEQ ID NO 270
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 270
ggcugugccu acaucuucua u                                              21

<210> SEQ ID NO 271
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 271
gagucucccu cugucacgau a                                              21

<210> SEQ ID NO 272
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 272
ucccucuguc acgaugguca a                                              21

<210> SEQ ID NO 273
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 273
ccugugcaac cagaacaaau a                                              21

<210> SEQ ID NO 274
<211> LENGTH: 21
<212> TYPE: RNA
<213> ORGANISM: Artificial sequence
<220> FEATURE:
<223> OTHER INFORMATION: RNAi agent sense strand underlying base
```

```
            sequence
<220> FEATURE:
<221> NAME/KEY: modified_base
<222> LOCATION: 13
<223> OTHER INFORMATION: n = 2'-O-methylinosine-3'-phosphate

<400> SEQUENCE: 274 ccgugugcaac canaacaaau a                                              21

<210> SEQ ID NO 275
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 18
<223> OTHER INFORMATION: n = 2'-O-methyl-2-aminoadenosine-3'-phosphate

<400> SEQUENCE: 275
ccugugcaac cagaacanau a                                               21

<210> SEQ ID NO 276
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 276
acugugcaac cagaacaaau a                                               21

<210> SEQ ID NO 277
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 277
ccugugcaac uagaacaaau a                                               21

<210> SEQ ID NO 278
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 278
cccgugcaac cagaacaaau a                                               21

<210> SEQ ID NO 279
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 279
accgugcaac cagaacaaau a                                               21
```

<210> SEQ ID NO 280
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 280
acggugcaac cagaacaaau a                                              21

<210> SEQ ID NO 281
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 19
<223> OTHER INFORMATION: n = 2'-O-methyl-2-aminoadenosine-3'-phosphate

<400> SEQUENCE: 281
acugugcaac cagaacaanu a                                              21

<210> SEQ ID NO 282
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 18
<223> OTHER INFORMATION: n = 2'-O-methyl-2-aminoadenosine-3'-phosphate

<400> SEQUENCE: 282
acugugcaac cagaacanau a                                              21

<210> SEQ ID NO 283
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 17
<223> OTHER INFORMATION: n = 2'-O-methyl-2-aminoadenosine-3'-phosphate

<400> SEQUENCE: 283
acugugcaac cagaacnaau a                                              21

<210> SEQ ID NO 284
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 284
ucugugcaac cagaacaaau a                                              21

<210> SEQ ID NO 285

```
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 18
<223> OTHER INFORMATION: n = 2'-O-methyl-2-aminoadenosine-3'-phosphate

<400> SEQUENCE: 285
ccugugcaac cagaacanaua                                              21

<210> SEQ ID NO 286
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 19
<223> OTHER INFORMATION: n = 2'-O-methyl-2-aminoadenosine-3'-phosphate

<400> SEQUENCE: 286
ccugugcaac cagaacaanu a                                             21

<210> SEQ ID NO 287
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 17
<223> OTHER INFORMATION: n = 2'-O-methyl-2-aminoadenosine-3'-phosphate

<400> SEQUENCE: 287
ccugugcaac cagaacnaau a                                             21

<210> SEQ ID NO 288
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 288
ccugugcaac cagaacaaau c                                             21

<210> SEQ ID NO 289
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 289
gcagagcaga augacuucuu u                                             21

<210> SEQ ID NO 290
<211> LENGTH: 4
<212> TYPE: PRT
```

<213> ORGANISM: Artificial Sequence
<220> FEATURE:
<223> OTHER INFORMATION: tetrapeptide linker
<220> FEATURE:
<221> NAME/KEY: MISC_FEATURE
<222> LOCATION: (2)..(2)
<223> OTHER INFORMATION: Xaa = Citrulline

<400> SEQUENCE: 290

Phe Xaa Phe Pro
1

<210> SEQ ID NO 291
<211> LENGTH: 21
<212> TYPE: DNA
<213> ORGANISM: Artificial sequence
<220> FEATURE:
<223> OTHER INFORMATION: ND-9201 modified antisense strand sequence

<400> SEQUENCE: 291
gauuuguucu gguugcacat t                                              21

<210> SEQ ID NO 292
<211> LENGTH: 21
<212> TYPE: DNA
<213> ORGANISM: Artificial sequence
<220> FEATURE:
<223> OTHER INFORMATION: ND-9201 modified antisense strand sequence

<400> SEQUENCE: 292
ugugcaacca gaacaaauct t                                              21

<210> SEQ ID NO 293
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 293
cugugcaacc agaacaaauc a                                              21

<210> SEQ ID NO 294
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 294
gcagagcaga augacuucuu u                                              21

<210> SEQ ID NO 295
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 295
aaugugcaac cagaacaaau a                                              21

<210> SEQ ID NO 296
<211> LENGTH: 21
<212> TYPE: RNA
<213> ORGANISM: Artificial sequence
<220> FEATURE:

<223> OTHER INFORMATION: RNAi agent antisense strand underlying base
      sequence

<400> SEQUENCE: 296
aaugugcaac cagaacaaau a    21